(12) United States Patent
Smith et al.

(10) Patent No.: US 11,866,747 B2
(45) Date of Patent: Jan. 9, 2024

(54) ENGINEERED MEGANUCLEASES THAT TARGET HUMAN MITOCHONDRIAL GENOMES

(71) Applicants: Precision Biosciences, Inc., Durham, NC (US); University of Miami, Miami, FL (US)

(72) Inventors: James Jefferson Smith, Morrisville, NC (US); Ginger Tomberlin, Cary, NC (US); John Morris, Raleigh, NC (US); Wendy Shoop, Durham, NC (US); Carlos T. Moraes, Miami, FL (US)

(73) Assignees: University of Miami, Miami, FL (US); Precision BioSciences, Inc., Durham, NC (US)

( * ) Notice: Subject to any disclaimer, the term of this patent is extended or adjusted under 35 U.S.C. 154(b) by 0 days.

(21) Appl. No.: 18/161,560

(22) Filed: Jan. 30, 2023

(65) Prior Publication Data

US 2023/0295590 A1  Sep. 21, 2023

Related U.S. Application Data

(63) Continuation of application No. PCT/US2022/025947, filed on Apr. 22, 2022.

(60) Provisional application No. 63/318,191, filed on Mar. 9, 2022, provisional application No. 63/318,192, filed on Mar. 9, 2022, provisional application No. 63/178,263, filed on Apr. 22, 2021, provisional application No. 63/178,250, filed on Apr. 22, 2021.

(51) Int. Cl.
*C12N 15/86* (2006.01)
*C12N 9/22* (2006.01)

(52) U.S. Cl.
CPC .............. *C12N 9/22* (2013.01); *C12N 15/86* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

2009/0186816 A1* 7/2009 Minczuk .................. A61P 3/10
435/325

FOREIGN PATENT DOCUMENTS

WO WO 2019/183349 A1 9/2019

OTHER PUBLICATIONS

Yang, Y, et al., "Targeted elimination of mutant mitochondrial DNA in MELAS-iPSCs by mitoTALENS," *Protein Cell*, 2018, vol. 9(3), pp. 283-297.

* cited by examiner

*Primary Examiner* — Nancy J Leith
*Assistant Examiner* — Khaleda B Hasan
(74) *Attorney, Agent, or Firm* — Womble Bond Dickinson (US) LLP

(57) ABSTRACT

Disclosed herein are recombinant meganucleases engineered to recognize and cleave a recognition sequence present in the human mitochondrial DNA (mtDNA). The disclosure further relates to the use of such recombinant meganucleases in methods for producing genetically-modified eukaryotic cells, and to a population of genetically-modified eukaryotic cells wherein the mtDNA has been having modified or edited.

24 Claims, 38 Drawing Sheets

Specification includes a Sequence Listing.

US 11,866,747 B2

ENGINEERED MEGANUCLEASES THAT TARGET HUMAN MITOCHONDRIAL GENOMES

CROSS REFERENCE TO RELATED APPLICATIONS

This application is a continuation of International Application PCT/US2022/025947, filed Apr. 22, 2022, which was published by the International Bureau in English on Oct. 27, 2022, and which claims priority from U.S. Provisional Application Nos. 63/178,250, filed Apr. 22, 2021, 63/178,263, filed Apr. 22, 2021, 63/318,191, filed Mar. 9, 2022, and 63/318,192, filed Mar. 9, 2022, each of which is hereby incorporated in its entirety by reference in this application.

FIELD OF THE INVENTION

The present disclosure relates to the field of molecular biology and recombinant nucleic acid technology. In particular, the present disclosure relates to recombinant meganucleases engineered to recognize and cleave recognition sequences found in the human mitochondrial genome. The present disclosure further relates to the use of such recombinant meganucleases in methods for producing genetically-modified eukaryotic cells, and to a population of genetically-modified eukaryotic cells wherein the mitochondrial DNA has been modified.

REFERENCE TO A SEQUENCE LISTING SUBMITTED AS AN XML (ST.26) FILE VIA USPTO PATENT CENTER

The instant application contains a Sequence Listing which has been submitted in xml (ST.26) format via USPTO Patent Center and is hereby incorporated by reference in its entirety. Said xml (ST.26) copy, created on Mar. 2, 2023 is named P89339_01 39_5 Seq_List 2-21-23, and is 105,674 bytes in size.

BACKGROUND OF THE INVENTION

In all organisms, mitochondria regulate cellular energy and metabolism under normal growth and development as well as in response to stress. Many of the proteins functioning in these roles are coded for in the mitochondrial genome. Thus, editing of the mitochondrial genome has diverse applications in both animals and plants. In humans, deleterious mitochondrial mutations are the source of a number of disorders for which gene editing therapies could be applied.

Pathogenic mitochondrial DNA (mtDNA) mutations include large-scale rearrangements and point mutations in protein coding, transfer RNA (tRNA) or ribosomal RNA (rRNA) genes. Although the prevalence of mtDNA-related disease diagnosis is about 1 in 5,000, the population frequency of the ten most common pathogenic mtDNA mutations is much higher, approaching 1 in 200, implying that many "normal" individuals carry low levels of mutated genomes (Schon et al., Nat Rev Gen 13:878-890 (2012)).

Mutated mtDNA, in most cases, co-exist with wild-type mtDNA in patients' cells (mtDNA heteroplasmy). Several studies showed that the wild-type mtDNA has a strong protective effect, and biochemical abnormalities were observed only when the levels of the mutated mtDNA were higher than 80-90% (Schon et al., Nature Reviews Genetics 13:878-890 (2012)). It has been shown that muscle fibers develop an OXPHOS defect only when the mutation load is above 80% (Sciacco et al., Hum Mol Genet 3:13-19 (1994)). Therefore, any approach that could shift this balance by even a small percentage towards the wild-type would have strong therapeutic potential.

However, mtDNA manipulation remains an underexplored area of science because of the inability to target mtDNA at high efficiencies and generate precise edits. The mitochondrial genome is difficult to edit because it requires predictable repair mechanisms and delivery of an editing technology to this organelle. In view of the difficulty and unpredictability associated with mitochondrial genome editing, there is an unmet need for precise editing of mtDNA, which would open up an entire field of inquiry and opportunity in life sciences. The ability to target and edit a defined region (preferably limited to just one gene) of the mitochondrial genome in a more predictable manner would be a clear benefit over currently available systems.

SUMMARY OF THE INVENTION

Provided herein are compositions and methods for precise editing of mitochondrial genome. Up until now, attempts at mitochondrial genome editing have resulted in large and unpredictable deletions/rearrangements. The present invention demonstrates that engineered meganucleases can result in precise editing of mitochondrial DNA (mtDNA), thereby opening up an entire field of inquiry and opportunity in life sciences. The compositions and methods provided herein can be used for editing one specific mitochondrial gene without impacting surrounding regions.

In one aspect, the invention provides a mitochondria-targeting engineered meganuclease (MTEM) that binds and cleaves a recognition sequence comprising SEQ ID NO: 1 in mitochondrial genomes of a eukaryotic cell, wherein the MTEM comprises an engineered meganuclease attached to a mitochondrial transit peptide (MTP), wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of any one of SEQ ID NOs: 3-12. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 3-12. In some embodiments, the HVR1 region comprises residues corresponding to residues 24, 26, 28, 30, 32, 33, 38, 40, 42, 44, 46, 68, 70, 75, and 77 of any one of SEQ ID NOs: 3-12. In some embodiments, the HVR1 region comprises Y, R, K, or D at a residue corresponding to residue 66 of any one of SEQ ID NOs: 3-12. In some embodiments, the HVR1 region comprises residues 24-79 of any one of SEQ ID NOs: 3-12 with up to 1, 2, 3, 4, 5, 6, 7, 8, 9, 10, or 11 amino acid substitutions. In some embodiments, the HVR1 region comprises residues 24-79 of any one of SEQ ID NOs: 3-12.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of any one of SEQ ID NOs: 3-12. In some embodiments, the first subunit comprises a residue corresponding to residue 19 of any one of SEQ ID NOs: 3-12. In some embodiments, the first subunit comprises a residue corresponding to residue 80 of any one of SEQ ID NOs: 3, 5, 7, 9, 11, or 12. In some embodiments, the first subunit comprises G, S, or A at a residue corresponding to residue 19 of any one of SEQ ID NOs: 3-12. In some embodiments, the first subunit comprises E, Q, or K at a residue corresponding to residue 80 of any one of SEQ ID NOs: 3-12. In some embodiments, the first subunit comprises residues 7-153 of any one of SEQ ID NOs: 3-12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of any one of SEQ ID NOs: 3-12.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of any one of SEQ ID NOs: 3-12. In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 3-12. In some embodiments, the HVR2 region comprises residues corresponding to residues 215, 217, 219, 221, 223, 224, 229, 231, 233, 235, 237, 259, 261, 266, and 268 ofany one of SEQ ID NOs: 3-12. In some embodiments, the HVR2 region comprises a residue corresponding to residue 241 of any one of SEQ ID NOs: 3-12. In some embodiments, the HVR2 region comprises a residue corresponding to residue 263 of any one of SEQ ID NOs: 3 or 5-12. In some embodiments, the HVR2 region comprises a residue corresponding to residue 264 of any one of SEQ ID NOs: 3-6 or 8-12. In some embodiments, the HVR2 region comprises a residue corresponding to residue 265 of SEQ ID NO: 6. In some embodiments, the HVR2 region comprises Y, R, K, or D at a residue corresponding to residue 257 of any one of SEQ ID NOs: 3-12. In some embodiments, the HVR2 region comprises residues 215-270 of any one of SEQ ID NOs: 3-12 with up to 1, 2, 3, 4, 5, 6, 7, 8, 9, 10, or 11 amino acid substitutions. In some embodiments, the HVR2 region comprises residues 215-270 of any one of SEQ ID NOs: 3-12.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of any one of SEQ ID NOs: 3-12. In some embodiments, the second subunit comprises a residue corresponding to residue 276 of any one of SEQ ID NO: 4. In some embodiments, the second subunit comprises a residue corresponding to residue 330 of any one of SEQ ID NOs: 3-12. In some embodiments, the second subunit comprises G, S, or A at a residue corresponding to residue 210 of any one of SEQ ID NOs: 3-12. In some embodiments, the second subunit comprises E, Q, or K at a residue corresponding to residue 271 of any one of SEQ ID NOs: 3-12. In some embodiments, the second subunit comprises residues 198-344 of any one of SEQ ID NOs: 3-12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of any one of SEQ ID NOs: 3-12.

In some embodiments, the engineered meganuclease is a single-chain meganuclease comprising a linker, the linker covalently joins the first subunit and the second subunit. In some embodiments, the engineered meganuclease comprises an amino acid sequence having at least 80%, 85%, 90%, 91%, 92%, 93%, 94%, 95%, 96%, 97%, 98%, 99% or more sequence identity to any one of SEQ ID NOs: 3-12. In some embodiments, the engineered meganuclease comprises an amino acid sequence of any one of SEQ ID NOs: 3-12. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence of any one of SEQ ID NO: 33-42. In some embodiments, the engineered meganuclease is encoded by a nucleic acid sequence of any one of SEQ ID NOs: 33-42.

In some embodiments, the MTP comprises an amino acid sequence having at least 80%, 85%, 90%, 91%, 92%, 93%, 94%, 95%, 96%, 97%, 98%, 99% or more sequence identity to a sequence set forth in any one of SEQ ID NOs: 43-45. In some embodiments, the MTP comprises an amino acid sequence set forth in any one of SEQ ID NOs: 43-45. In some embodiments, the MTP is attached to the C-terminus of the engineered meganuclease. In some embodiments, the MTP is attached to the N-terminus of the engineered meganuclease. In some embodiments, the MTP is fused to the engineered meganuclease. In some embodiments, the MTP is attached to the engineered meganuclease by a polypeptide linker. In some embodiments, the engineered meganuclease is attached to a first MTP and a second MTP. In some embodiments, the first MTP and/or the second MTP comprises an amino acid sequence having at least 80%, 85%, 90%, 91%, 92%, 93%, 94%, 95%, 96%, 97%, 98%, 99% or more sequence identity to a sequence set forth in any one of SEQ ID NOs: 43-45. In some embodiments, the first MTP and/or the second MTP comprises an amino acid sequence set forth in any one of SEQ ID NOs: 43-45. In some embodiments, the first MTP and the second MTP are identical. In some embodiments, the first MTP and the second MTP are not identical. In some embodiments, the first MTP and/or the second MTP is fused to the engineered meganuclease. In some embodiments, the first MTP and/or the second MTP is attached to the engineered meganuclease by a polypeptide linker.

In some embodiments, the MTEM is attached to a nuclear export sequence (NES). In some embodiments, the NES comprises an amino acid sequence having at least 80%, 85%, 90%, 91%, 92%, 93%, 94%, 95%, 96%, 97%, 98%, 99% or more sequence identity to a sequence set forth in SEQ ID NO: 46 or 47. In some embodiments, the NES comprises an amino acid sequence set forth in SEQ ID NO: 46 or 47. In some embodiments, the NES is attached at the N-terminus of the MTEM. In some embodiments, the NES is attached at the C-terminus of the MTEM. In some embodiments, the NES is fused to the MTEM. In some embodiments, the NES is attached to the MTEM by a polypeptide linker. In some embodiments, the MTEM is attached to a first NES and a second NES. In some embodiments, the first NES is attached at the N-terminus of the MTEM, and the second NES is attached at the C-terminus of the MTEM. In some embodiments, the first NES and/or the second NES comprises an amino acid sequence having at least 80%, 85%, 90%, 91%, 92%, 93%, 94%, 95%, 96%, 97%, 98%, 99% or more sequence identity to a sequence set forth in SEQ ID NO: 46 or 47. In some embodiments, the first NES and/or the second NES comprises an amino acid sequence set forth in SEQ ID NO: 46 or 47. In some embodiments, the first NES and the second NES are identical. In some embodiments, the first NES and the second NES are not identical. In some embodiments, the first NES and/or the second NES is fused to the MTEM. In some embodiments, the first NES and/or the second NES is attached to the MTEM by a polypeptide linker.

In another aspect, the invention provides a polynucleotide comprising a nucleic acid sequence encoding an MTEM described herein. In some embodiments, the polynucleotide is an mRNA.

In another aspect, the invention provides a recombinant DNA construct comprising a polynucleotide comprising a nucleic acid sequence encoding an MTEM described herein. In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the MTEM. In some embodiments, the promoter is a constitutive promoter, or the promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter.

In another aspect, the invention provides a plasmid comprising any recombinant DNA construct described herein. In another aspect, the invention provides a recombinant virus comprising a polynucleotide comprising a nucleic acid sequence encoding an MTEM described herein. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the MTEM. In some embodiments, the promoter is a constitutive promoter, or the promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter.

In another aspect, the invention provides a lipid nanoparticle composition comprising lipid nanoparticles comprising a polynucleotide, wherein the polynucleotide comprises a nucleic acid sequence encoding an MTEM described herein. In some embodiments, the polynucleotide is an mRNA.

In another aspect, the invention provides a pharmaceutical composition comprising a pharmaceutically acceptable carrier and an MTEM described herein.

In another aspect, the invention provides a pharmaceutical composition comprising a pharmaceutically acceptable carrier a polynucleotide described herein.

In another aspect, the invention provides a pharmaceutical composition comprising a pharmaceutically acceptable carrier and a recombinant DNA construct described herein.

In another aspect, the invention provides a pharmaceutical composition comprising a pharmaceutically acceptable carrier and a recombinant virus described herein.

In another aspect, the invention provides a pharmaceutical composition comprising a pharmaceutically acceptable carrier and a lipid nanoparticle composition described herein.

In another aspect, the invention provides a genetically-modified eukaryotic cell comprising any polynucleotide described herein. In some embodiments, the genetically-modified eukaryotic cell is a genetically-modified mammalian cell. In some embodiments, the genetically-modified eukaryotic cell is a genetically-modified human cell.

In another aspect, the invention provides a method for producing a genetically-modified eukaryotic cell, the method comprising introducing into a eukaryotic cell: (a) a polynucleotide comprising a nucleic acid sequence encoding an MTEM described herein, wherein the MTEM is expressed in the eukaryotic cell; or (b) an MTEM described herein; wherein the MTEM produces a cleavage site at the recognition sequence comprising SEQ ID NO: 1 in mutant mitochondrial genomes of the eukaryotic cell. In some embodiments, the cleavage site is repaired by non-homologous end joining, such that the recognition sequence comprises an insertion or deletion. In some embodiments, the mutant mitochondrial genomes comprising the recognition sequence are degraded in the genetically-modified eukaryotic cell. In some embodiments, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of mutant mitochondrial genomes comprising the recognition sequence are degraded in the genetically-modified eukaryotic cell. In some embodiments, the ratio of wild-type mitochondrial genomes to mutant mitochondrial genomes comprising the recognition sequence increases in the genetically-modified eukaryotic cell. In some embodiments, the ratio increases to about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 20:1, about 50:1, about 100:1, about 150:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, about 1000:1, or more. In some embodiments, the percentage of wild-type mitochondrial genomes in the genetically-modified eukaryotic cell is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, of the total mitochondrial genomes in the genetically-modified eukaryotic cell. In some embodiments, the percentage of mutant mitochondrial genomes comprising the recognition sequence in the genetically-modified eukaryotic cell decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, cellular respiration in the genetically-modified eukaryotic cell increases by about 30%, about 35%, about 40%, about 45%, about 50%, about 55%, about 60%, about 65%, about 70%, about 75%, about 80%, about 85%, about 90%, about 95%, about 100%, or more. In some embodiments, cellular respiration in the genetically-modified eukaryotic cell increases by about 30-40%, about 40-50%, about 50-60%, about 60-70%, about 70-80%, about 80-90%, about 90-100%, or more.

In another aspect, the invention provides a method for producing a population of eukaryotic cells comprising a plurality of genetically-modified cells, the method comprising introducing into a plurality of eukaryotic cells in the population: (a) a polynucleotide comprising a nucleic acid sequence encoding an MTEM described herein, wherein the MTEM is expressed in the plurality of eukaryotic cells; or (b) an MTEM described herein; wherein the MTEM produces a cleavage site at a recognition sequence comprising SEQ ID NO: 1 in mutant mitochondrial genomes of the plurality of eukaryotic cells. In some embodiments, the cleavage site is repaired by non-homologous end joining, such that the recognition sequence comprises an insertion or deletion. In some embodiments, the mutant mitochondrial genomes comprising the recognition sequence are degraded in the plurality of genetically-modified eukaryotic cells. In some embodiments, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of mutant mitochondrial genomes comprising the recognition sequence are degraded in the plurality of genetically-modified eukaryotic cells. In some embodiments, the ratio of wild-type mitochondrial genomes to mutant mitochondrial genomes comprising the recognition sequence increases in the plurality of genetically-modified eukaryotic cells. In some embodiments, the ratio of wild-type mitochondrial genomes to mutant mitochondrial genomes comprising the recognition sequence increases in the population of eukaryotic cells. In some embodiments, the ratio increases to about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 20:1, about 50:1, about 100:1, about 150:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, about 1000:1, or more. In some embodiments, the percentage of wild-type mitochondrial genomes in the plurality of genetically-modified eukaryotic cells increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, the percentage of wild-type mitochondrial genomes in the population of eukaryotic cells increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, the percentage of mutant mitochondrial genomes comprising the recognition sequence in the plurality of genetically-modified eukaryotic cells decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, the percentage of mutant mitochondrial genomes comprising the recognition sequence in the population of eukaryotic cells decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, cellular respiration in the plurality of genetically-modified eukaryotic cells increases by about 30%, about 35%, about 40%, about 45%, about 50%, about 55%, about 60%, about 65%, about 70%, about 75%, about 80%, about 85%, about 90%, about 95%, about 100%, or more. In some embodiments, cellular respiration in the plurality of genetically-modified eukaryotic cells increases by about 30-40%, about 40-50%, about 50-60%, about 60-70%, about 70-80%, about 80-90%, about 90-100%, or more. In some embodiments, cellular respiration in the population of eukaryotic cells increases by about 30%, about 35%, about 40%, about 45%, about 50%, about 55%, about 60%, about 65%, about 70%, about 75%, about 80%, about 85%, about 90%, about 95%, about 100%, or more. In some embodiments, cellular respiration in the population of eukaryotic cells increases by about 30-40%, about 40-50%, about 50-60%, about 60-70%, about 70-80%, about 80-90%, about 90-100%, or more.

In some embodiments, the recognition sequence is within a region of the mutant mitochondrial genomes associated with a mitochondrial disorder. In some embodiments, the mitochondrial disorder is Mitochondrial Encephalomyopathy, Lactic Acidosis, and Stroke-like episodes (MELAS). In some embodiments, the recognition sequence is located in a region of the mutant mitochondrial genomes corresponding to nucleotide positions 3000-3500 of a wild-type mitochondrial genome. In some embodiments, the MTEM targets an A3243G mutation of the mutant mitochondrial genomes. In some embodiments, the method is performed in vivo. In some embodiments, the method is performed in vitro. In some embodiments, the polynucleotide is an mRNA. In some embodiments, the polynucleotide is any mRNA described herein. In some embodiments, the polynucleotide is a recombinant DNA construct. In some embodiments, the polynucleotide is any recombinant DNA construct described herein. In some embodiments, the polynucleotide is introduced into the eukaryotic cell by a lipid nanoparticle. In some embodiments, the polynucleotide is introduced into the eukaryotic cell by a recombinant virus. In some embodiments, the recombinant virus is any recombinant virus described herein. In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the MTEM. In some embodiments, the promoter is a is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter. In some embodiments, the eukaryotic cell is a mammalian cell. In some embodiments, the eukaryotic cell is a human cell. In some embodiments, the eukaryotic cell is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell.

In another aspect, the invention provides a genetically-modified eukaryotic cell, or a population of genetically-modified eukaryotic cells, produced by any method for producing a genetically-modified eukaryotic cell or any method for producing a population of eukaryotic cells comprising a plurality of genetically-modified cells.

In another aspect, the invention provides a method for degrading mutant mitochondrial genomes in a target cell in a subject, or in a population of target cells in a subject, the method comprising delivering to the target cell or the population of target cells: (a) a polynucleotide comprising a nucleic acid sequence encoding an MTEM described herein, wherein the MTEM is expressed in the target cell or the population of target cells; or (b) an MTEM described herein; wherein the MTEM produces a cleavage site in the mutant mitochondrial genomes at a recognition sequence comprising SEQ ID NO: 1, and wherein the mutant mitochondrial genomes are degraded. In some embodiments, the recognition sequence is located in a region of the mutant mitochondrial genomes corresponding to nucleotide positions 3000-3500 of a wild-type mitochondrial genome. In some embodiments, the MTEM targets an A3243G mutation of the mutant mitochondrial genomes. In some embodiments, the subject is a mammal. In some embodiments, the subject is a human. In some embodiments, the target cell is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells or the population of target cells is a population of muscle cells, a skeletal muscle cells, a myotube cells, a muscle satellite cells, a neuron, an astrocyte, a microglia cells, an eye cells, a retinal cells, a retinal ganglion cells, a retinal pigmentary epithelium cells, a pancreatic cells, or a pancreatic beta cells, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells. In some embodiments, the polynucleotide is an mRNA. In some embodiments, the polynucleotide is any mRNA described herein. In some embodiments, the polynucleotide is a recombinant DNA construct. In some embodiments, the polynucleotide is any recombinant DNA construct described herein. In some embodiments, the polynucleotide is delivered to the target cell, or the population of target cells, by a lipid nanoparticle. In some embodiments, the polynucleotide is delivered to the target cell, or the population of target cells, by a recombinant virus. In some embodiments, the recombinant virus is any recombinant virus described herein. In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the MTEM. In some embodiments, the promoter is a constitutive promoter, or wherein said promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter. In some embodiments, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of mutant mitochondrial genomes comprising the recognition sequence are degraded in the target cell or the population of the target cells. In some embodiments, the ratio of wild-type mitochondrial genomes to mutant mitochondrial genomes comprising the recognition sequence increases in the target cell or the population of target cells. In some embodiments, the ratio increases to about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 20:1, about 50:1, about 100:1, about 150:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, about 1000:1, or more. In some embodiments, the percentage of wild-type mitochondrial genomes in the target cell or the population of target cells is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, of the total mitochondrial genomes in the target cell or the population of target cells. In some embodiments, the percentage of mutant mitochondrial genomes comprising the recognition sequence in the genetically-modified eukaryotic cell decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, cellular respiration in the target cell or the population of target cells increases by about 30%, about 35%, about 40%, about 45%, about 50%, about 55%, about 60%, about 65%, about 70%, about 75%, about 80%, about 85%, about 90%, about 95%, about 100%, or more. In some embodiments, cellular respiration in the target cell or the population of target cells increases by about 30-40%, about 40-50%, about 50-60%, about 60-70%, about 70-80%, about 80-90%, about 90-100%, or more.

In another aspect, the invention provides a method for treating a condition associated with MELAS in a subject, the method comprising administering to the subject: (a) a therapeutically-effective amount of a polynucleotide comprising a nucleic acid sequence encoding an MTEM described herein, wherein the polynucleotide is delivered to a target cell, or a population of target cells, in the subject, wherein the MTEM is expressed in the target cell or the population of target cells; or (b) a therapeutically-effective amount of an MTEM described herein, wherein the MTEM is delivered to a target cell, or a population of target cells, in the subject; wherein the MTEM produces a cleavage site in mutant mitochondrial genomes at a recognition sequence comprising SEQ ID NO: 1, and wherein the mutant mitochondrial genomes are degraded. In some embodiments, the recognition sequence is located in a region of the mutant mitochondrial genomes corresponding to nucleotide positions 3000-3500 of a wild-type mitochondrial genome. In some embodiments, the MTEM targets an A3243G mutation of the mutant mitochondrial genomes. In some embodiments, the method reduces or ameliorates one or more symptoms associated with MELAS. In some embodiments, the method comprises administering any pharmaceutical composition described herein. In some embodiments, the subject is a mammal. In some embodiments, the subject is a human. In some embodiments, the target cell is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells, or the population of target cells is a population of a muscle cells, a skeletal muscle cells, a myotube cells, a muscle satellite cells, a neuron, an astrocyte, a microglia cells, an eye cells, a retinal cells, a retinal ganglion cells, a retinal pigmentary epithelium cells, a pancreatic cells, or a pancreatic beta cells, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells. In some embodiments, the condition is a condition of the muscles, brain, central nervous system, pancreas, or retina. In some embodiments, the condition is Mitochondrial Encephalomyopathy, Lactic Acidosis, and Stroke-like episodes (MELAS), Progressive External Ophthalmoplegia, maternally inherited diabetes, migraines, or ocular myopathy. In some embodiments, the polynucleotide is an mRNA. In some embodiments, the polynucleotide is any mRNA described herein. In some embodiments, the polynucleotide is a recombinant DNA construct. In some embodiments, the polynucleotide is any recombinant DNA construct described herein. In some embodiments, the polynucleotide is delivered to the target cell, or the population of target cells, by a lipid nanoparticle. In some embodiments, the polynucleotide is delivered to the target cell, or the population of target cells, by a recombinant virus. In some embodiments, the recombinant virus is any recombinant virus described herein. In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the MTEM. In some embodiments, the promoter is a constitutive promoter, or the promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter. In some embodiments, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of mutant mitochondrial genomes comprising the recognition sequence are degraded in the target cell or the population of the target cells. In some embodiments, the ratio of wild-type mitochondrial genomes to mutant mitochondrial genomes comprising the recognition sequence increases in the target cell or the population of target cells. In some embodiments, the ratio increases to about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 20:1, about 50:1, about 100:1, about 150:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, about 1000:1, or more. In some embodiments, the percentage of wild-type mitochondrial genomes in the target cell or the population of target cells is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, of the total mitochondrial genomes in the target cell or the population of target cells. In some embodiments, the percentage of mutant mitochondrial genomes comprising the recognition sequence in the genetically-modified eukaryotic cell decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. In some embodiments, cellular respiration in the target cell or the population of target cells increases by about 30%, about 35%, about 40%, about 45%, about 50%, about 55%, about 60%, about 65%, about 70%, about 75%, about 80%, about 85%, about 90%, about 95%, about 100%, or more. In some embodiments, cellular respiration in the target cell or the population of target cells increases by about 30-40%, about 40-50%, about 50-60%, about 60-70%, about 70-80%, about 80-90%, about 90-100%, or more.

In one aspect, the invention provides an engineered meganuclease that binds and cleaves a recognition sequence comprising SEQ ID NO: 1, wherein the engineered meganuclease comprises a first subunit and a second subunit, wherein the first subunit binds to a first recognition half-site of the recognition sequence and comprises a first hypervariable (HVR1) region, wherein the second subunit binds to a second recognition half-site of the recognition sequence and comprises a second hypervariable (HVR2) region, wherein the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of any one of SEQ ID NOs: 3-12, and wherein the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of any one of SEQ ID NOs: 3-12.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 3-12. In some embodiments, the HVR1 region comprises residues corresponding to residues 24, 26, 28, 30, 32, 33, 38, 40, 42, 44, 46, 68, 70, 75, and 77 of any one of SEQ ID NOs: 3-12. In some embodiments, the HVR1 region comprises Y, R, K, or D at a residue corresponding to residue 66 of any one of SEQ ID NOs: 3-12. In some embodiments, the HVR1 region comprises residues 24-79 of any one of SEQ ID NOs: 3-12 with up to 1, 2, 3, 4, 5, 6, 7, 8, 9, 10, or 11 amino acid substitutions. In some embodiments, the HVR1 region comprises residues 24-79 of any one of SEQ ID NOs: 3-12.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of any one of SEQ ID NOs: 3-12. In some embodiments, the first subunit comprises a residue corresponding to residue 19 of any one of SEQ ID NOs: 3-12. In some embodiments, the first subunit comprises a residue corresponding to residue 80 of any one of SEQ ID NOs: 3-12. In some embodiments, the first subunit comprises G, S, or A at a residue corresponding to residue 19 of any one of SEQ ID NOs: 3-12. In some embodiments, the first subunit comprises E, Q, or K at a residue corresponding to residue 80 of any one of SEQ ID NOs: 3-12. In some embodiments, the first subunit comprises residues 7-153 of any one of SEQ ID NOs: 3-12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of any one of SEQ ID NOs: 3-12.

In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 3-12. In some embodiments, the HVR2 region comprises residues corresponding to residues 215, 217, 219, 221, 223, 224, 229, 231, 233, 235, 237, 259, 261, 266, and 268 of any one of SEQ ID NOs: 3-12. In some embodiments, the HVR2 region comprises a residue corresponding to residue 241 of any one of SEQ ID NOs: 3-12. In some embodiments, the HVR2 region comprises a residue corresponding to residue 263 of any one of SEQ ID NOs: 3 or 5-12. In some embodiments, the HVR2 region comprises a residue corresponding to residue 264 of any one of SEQ ID NOs: 3 or 8-12. In some embodiments, the HVR2 region comprises a residue corresponding to residue 265 of SEQ ID NO: 6. In some embodiments, the HVR2 region comprises Y, R, K, or D at a residue corresponding to residue 257 of any one of SEQ ID NOs: 3-12. In some embodiments, the HVR2 region comprises residues 215-270 of any one of SEQ ID NOs: 3-12 with up to 1, 2, 3, 4, 5, 6, 7, 8, 9, 10, or 11 amino acid substitutions. In some embodiments, the HVR2 region comprises residues 215-270 of any one of SEQ ID NOs: 3-12.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of any one of SEQ ID NOs: 3-12. In some embodiments, the second subunit comprises a residue corresponding to residue 276 of any one of SEQ ID NO: 4. In some embodiments, the second subunit comprises a residue corresponding to residue 330 of any one of SEQ ID NOs: 3-12. In some embodiments, the second subunit comprises G, S, or A at a residue corresponding to residue 210 of any one of SEQ ID NOs: 3-12. In some embodiments, the second subunit comprises E, Q, or K at a residue corresponding to residue 271 of any one of SEQ ID NOs: 3-12. In some embodiments, the second subunit comprises residues 198-344 of any one of SEQ ID NOs: 3-12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of any one of SEQ ID NOs: 3-12.

In some embodiments, the engineered meganuclease is a single-chain meganuclease comprising a linker, the linker covalently joins the first subunit and the second subunit. In some embodiments, the engineered meganuclease comprises an amino acid sequence having at least 80%, 85%, 90%, 91%, 92%, 93%, 94%, 95%, 96%, 97%, 98%, 99% or more sequence identity to any one of SEQ ID NOs: 3-12. In some embodiments, the engineered meganuclease comprises an amino acid sequence of any one of SEQ ID NOs: 3-12. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence of any one of SEQ ID NOs: 33-42. In some embodiments, the engineered meganuclease is encoded by a nucleic acid sequence of any one of SEQ ID NOs: 33-42.

In some embodiments, the engineered meganuclease is attached to a nuclear export sequence (NES). In some embodiments, the NES comprises an amino acid sequence having at least 80%, 85%, 90%, 91%, 92%, 93%, 94%, 95%, 96%, 97%, 98%, 99% or more sequence identity to a sequence set forth in SEQ ID NO: 46 or 47. In some embodiments, the NES comprises an amino acid sequence set forth in SEQ ID NO: 46 or 47. In some embodiments, the NES is attached at the N-terminus of the engineered meganuclease. In some embodiments, the NES is attached at the C-terminus of the engineered meganuclease. In some embodiments, the NES is fused to the engineered meganuclease. In some embodiments, the NES is attached to the engineered meganuclease by a polypeptide linker. In some embodiments, the engineered meganuclease comprises a first NES and a second NES. In some embodiments, the first NES is attached at the N-terminus of the engineered meganuclease, and the second NES is attached at the C-terminus of the engineered meganuclease. In some embodiments, the first NES and/or the second NES comprises an amino acid sequence having at least 80%, 85%, 90%, 91%, 92%, 93%, 94%, 95%, 96%, 97%, 98%, 99% or more sequence identity to a sequence set forth in SEQ ID NO: 46 or 47. In some embodiments, the first NES and/or the second NES comprises an amino acid sequence set forth in SEQ ID NO: 46 or 47. In some embodiments, the first NES and the second NES are identical. In some embodiments, the first NES and the second NES are not identical. In some embodiments, the first NES and/or the second NES is fused to the engineered meganuclease. In some embodiments, the first NES and/or the second NES is attached to the engineered meganuclease by a polypeptide linker.

In another aspect, the invention provides a polynucleotide comprising a nucleic acid sequence encoding an engineered meganuclease described herein. In some embodiments, the polynucleotide is an mRNA.

In another aspect, the invention provides a recombinant DNA construct comprising a polynucleotide comprising a nucleic acid sequence encoding an engineered meganuclease described herein. In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the engineered meganuclease. In some embodiments, the promoter is a constitutive promoter, or the promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter.

In another aspect, the invention provides a recombinant virus comprising a polynucleotide comprising a nucleic acid sequence encoding an engineered meganuclease described herein. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV has an AAV9 capsid. In some embodiments, the polynucleotide comprises a promoter operably linked to the nucleic acid sequence encoding the engineered meganuclease. In some embodiments, the promoter is a constitutive promoter, or the promoter is a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter. In some embodiments, the constitutive promoter is a CMV promoter, a CAG promoter, an EF1 alpha promoter, or a UbC promoter.

In another aspect, the invention provides a lipid nanoparticle composition comprising lipid nanoparticles comprising a polynucleotide, wherein the polynucleotide comprises a nucleic acid sequence encoding an engineered meganuclease described herein. In some embodiments, the polynucleotide is an mRNA.

In another aspect, the invention provides a pharmaceutical composition comprising a pharmaceutically acceptable carrier and an engineered meganuclease described herein.

In another aspect, the invention provides a pharmaceutical composition comprising a pharmaceutically acceptable carrier any polynucleotide described herein.

In another aspect, the invention provides a pharmaceutical composition comprising a pharmaceutically acceptable carrier and any recombinant DNA construct described herein.

In another aspect, the invention provides a pharmaceutical composition comprising a pharmaceutically acceptable carrier any recombinant virus described herein.

In another aspect, the invention provides a pharmaceutical composition comprising a pharmaceutically acceptable carrier and any lipid nanoparticle composition described herein.

In another aspect, the invention provides a genetically-modified eukaryotic cell comprising any polynucleotide described herein. In some embodiments, the genetically-modified eukaryotic cell is a genetically-modified mammalian cell. In some embodiments, the genetically-modified eukaryotic cell is a genetically-modified human cell.

In another aspect, the invention provides a method for producing a genetically-modified eukaryotic cell, the method comprising introducing into a eukaryotic cell a polynucleotide comprising a nucleic acid sequence encoding an engineered meganuclease described herein wherein the engineered meganuclease is expressed in the eukaryotic cell, and wherein the engineered meganuclease produces a cleavage site at the recognition sequence comprising SEQ ID NO: 1. In some embodiments, the cleavage site is repaired by non-homologous end joining, such that the recognition sequence comprises an insertion or deletion. In some embodiments, the eukaryotic cell is a mammalian cell. In some embodiments, the mammalian cell is a human cell. In some embodiments, the polynucleotide is an mRNA. In some embodiments, the polynucleotide is introduced into the eukaryotic cell by a lipid nanoparticle or by a recombinant virus. In some embodiments, the recombinant virus is a recombinant AAV.

In another aspect, the invention provides a method for producing a genetically-modified eukaryotic cell, the method comprising introducing into a eukaryotic cell an engineered meganuclease described herein wherein the engineered meganuclease is expressed in the eukaryotic cell, and wherein the engineered meganuclease produces a cleavage site at a recognition sequence comprising SEQ ID NO: 1. In some embodiments, the cleavage site is repaired by non-homologous end joining, such that the recognition sequence comprises an insertion or deletion. In some embodiments, the eukaryotic cell is a mammalian cell. In some embodiments, the mammalian cell is a human cell.

In another aspect, the invention provides a method for producing a genetically-modified eukaryotic cell comprising an exogenous sequence of interest inserted in its genome, the method comprising introducing into a eukaryotic cell one or more polynucleotides comprising: a first nucleic acid sequence encoding an engineered meganuclease described herein wherein the engineered meganuclease is expressed in the eukaryotic cell, and a second nucleic acid sequence comprising the sequence of interest, wherein the engineered meganuclease produces a cleavage site at a recognition sequence comprising SEQ ID NO: 1, and wherein the sequence of interest is inserted into the genome at the cleavage site. In some embodiments, the second nucleic acid sequence further comprises nucleic acid sequences homologous to nucleic acid sequences flanking the cleavage site, and the sequence of interest is inserted at the cleavage site by homologous recombination. In some embodiments, the eukaryotic cell is a mammalian cell. In some embodiments, the mammalian cell is a human cell. In some embodiments, the first nucleic acid sequence is introduced into the eukaryotic cell as an mRNA. In some embodiments, the second nucleic acid sequence is introduced into the eukaryotic cell as a double-stranded DNA (dsDNA). In some embodiments, the first nucleic acid sequence is introduced into the eukaryotic cell by a recombinant virus. In some embodiments, the second nucleic acid sequence is introduced into the eukaryotic cell by a recombinant virus. In some embodiments, the recombinant virus is a recombinant AAV.

In another aspect, the invention provides a method for producing a genetically-modified eukaryotic cell comprising an exogenous sequence of interest inserted in its genome, the method comprising introducing into a eukaryotic cell an engineered meganuclease described herein and a polynucleotide comprising a nucleic acid sequence comprising the sequence of interest, wherein the engineered meganuclease produces a cleavage site at a recognition sequence comprising SEQ ID NO: 1, and wherein the sequence of interest is inserted into the genome at the cleavage site. In some embodiments, the polynucleotide sequence further comprises nucleic acid sequences homologous to nucleic acid sequences flanking the cleavage site, and the sequence of interest is inserted at the cleavage site by homologous recombination. In some embodiments, the eukaryotic cell is a mammalian cell. In some embodiments, the mammalian cell is a human cell. In some embodiments, the polynucleotide is introduced into the eukaryotic cell as a double-stranded DNA (dsDNA). In some embodiments, the polynucleotide is introduced into the eukaryotic cell by a recombinant virus. In some embodiments, the recombinant virus is a recombinant AAV.

In another aspect, the invention provides a genetically-modified eukaryotic cell made by a method described herein.

The foregoing and other aspects and embodiments of the present disclosure can be more fully understood by reference to the following detailed description and claims. Certain features of the disclosure, which are, for clarity, described in the context of separate embodiments, may also be provided in combination in a single embodiment. All combinations of the embodiments are specifically embraced by the present disclosure and are disclosed herein just as if each and every combination was individually and explicitly disclosed. Conversely, various features of the disclosure, which are, for brevity, described in the context of a single embodiment, may also be provided separately or in any suitable sub-combination. All sub-combinations of features listed in the embodiments are also specifically embraced by the present disclosure and are disclosed herein just as if each and every such sub-combination was individually and explicitly disclosed herein. Embodiments of each aspect of the present disclosure disclosed herein apply to each other aspect of the disclosure mutatis mutandis.

BRIEF DESCRIPTION OF THE SEQUENCES

Figure 1:
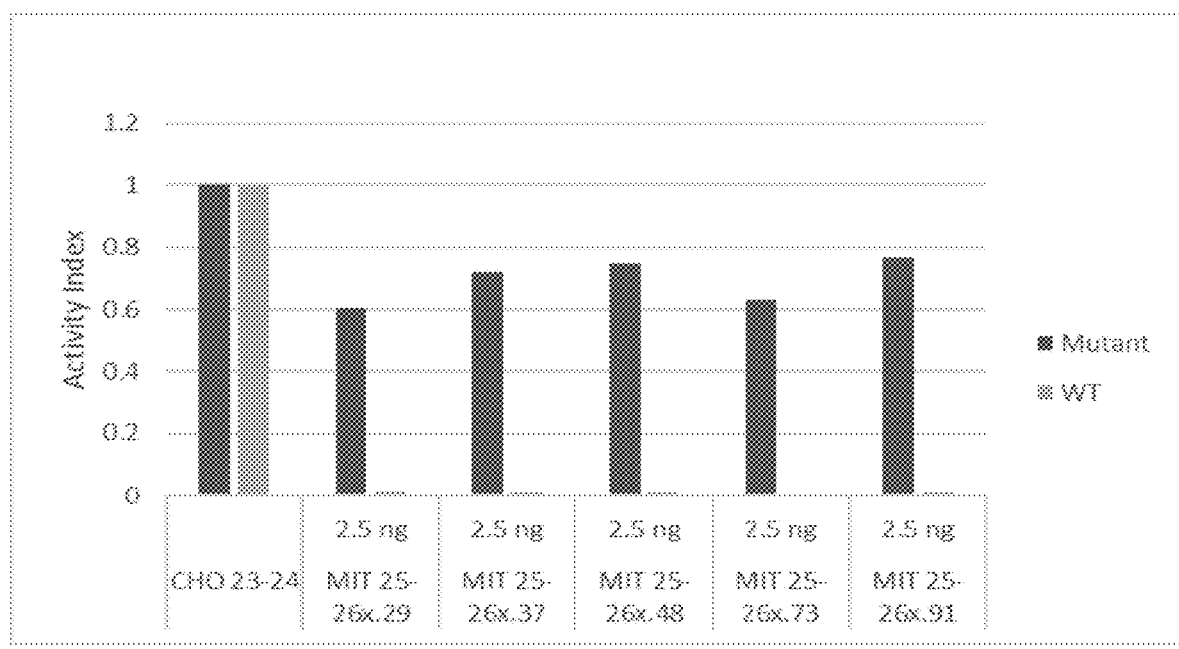
FIG. 1 shows flow cytometry results of CHO reporter cells transfected with mRNA encoding various MIT 25-26 engineered meganucleases, or the CHO 23-24 meganuclease (control) and assayed 48 hours post-transfection for the percentage of GFP+ cells. Data is shown as an activity index, the sum of the activity and toxicity scores.

SEQ ID NO: 1 sets forth the nucleic acid sequence of the MIT 25-26 recognition sequence (sense).

SEQ ID NO: 2 sets forth the nucleic acid sequence of the MIT 25-26 recognition sequence (antisense).

SEQ ID NO: 3 sets forth the amino acid sequence of the MIT 25-26x.91 engineered meganuclease.

SEQ ID NO: 4 sets forth the amino acid sequence of the MIT 25-26x.48 engineered meganuclease.

SEQ ID NO: 5 sets forth the amino acid sequence of the MIT 25-26x.73 engineered meganuclease.

SEQ ID NO: 6 sets forth the amino acid sequence of the MIT 25-26x.29 engineered meganuclease.

SEQ ID NO: 7 sets forth the amino acid sequence of the MIT 25-26x.37 engineered meganuclease.

SEQ ID NO: 8 sets forth the amino acid sequence of the MIT 25-26L.35 engineered meganuclease.

SEQ ID NO: 9 sets forth the amino acid sequence of the MIT 25-26x.91 engineered meganuclease having an H to Q substitution at amino acid position 259 referred to as MIT 25-26x.91 259 H>Q.

SEQ ID NO: 10 sets forth the amino acid sequence of the MIT 25-26L.35 engineered meganuclease having an A to S substitution at amino acid position 19 referred to as MIT 25-26L.35 19A>S.

SEQ ID NO: 11 sets forth the amino acid sequence of the MIT 25-26x.91 engineered meganuclease having a T to R substitution at amino acid position 263 referred to as MIT 25-26x.91 263 T>R.

SEQ ID NO: 12 sets forth the amino acid sequence of the MIT 25-26x.91 engineered meganuclease having an H to W substitution at amino acid position 46 referred to as MIT 25-26x.91 46 H>W.

SEQ ID NO: 13 sets forth the amino acid sequence of the MIT 25-26x.91 meganuclease 25 binding subunit.

SEQ ID NO: 14 sets forth the amino acid sequence of the MIT 25-26x.48 meganuclease 25 binding subunit.

SEQ ID NO: 15 sets forth the amino acid sequence of the MIT 25-26x.73 meganuclease 25 binding subunit.

SEQ ID NO: 16 sets forth the amino acid sequence of the MIT 25-26x.29 meganuclease 25 binding subunit.

SEQ ID NO: 17 sets forth the amino acid sequence of the MIT 25-26x.37 meganuclease 25 binding subunit.

SEQ ID NO: 18 sets forth the amino acid sequence of the MIT 25-26L.35 meganuclease 25 binding subunit.

SEQ ID NO: 19 sets forth the amino acid sequence of the MIT 25-26x.91 259 H>Q meganuclease 25 binding subunit.

SEQ ID NO: 20 sets forth the amino acid sequence of the MIT 25-26L.35 19A>S meganuclease 25 binding subunit.

SEQ ID NO: 21 sets forth the amino acid sequence of the MIT 25-26x.91 263 T>R meganuclease 25 binding subunit.

SEQ ID NO: 22 sets forth the amino acid sequence of the MIT 25-26x.91 46 H>W meganuclease 25 binding subunit.

SEQ ID NO: 23 sets forth the amino acid sequence of the MIT 25-26x.91 meganuclease 26 binding subunit.

SEQ ID NO: 24 sets forth the amino acid sequence of the MIT 25-26x.48 meganuclease 26 binding subunit.

SEQ ID NO: 25 sets forth the amino acid sequence of the MIT 25-26x.73 meganuclease 26 binding subunit.

SEQ ID NO: 26 sets forth the amino acid sequence of the MIT 25-26x.29 meganuclease 26 binding subunit.

SEQ ID NO: 27 sets forth the amino acid sequence of the MIT 25-26x.37 meganuclease 26 binding subunit.

SEQ ID NO: 28 sets forth the amino acid sequence of the MIT 25-26L.35 meganuclease 26 binding subunit.

SEQ ID NO: 29 sets forth the amino acid sequence of the MIT 25-26x.91 259 H>Q meganuclease 26 binding subunit.

SEQ ID NO: 30 sets forth the amino acid sequence of the MIT 25-26L.35 19A>S meganuclease 26 binding subunit.

SEQ ID NO: 31 sets forth the amino acid sequence of the MIT 25-26x.91 263 T>R meganuclease 26 binding subunit.

SEQ ID NO: 32 sets forth the amino acid sequence of the MIT 25-26x.91 46 H>W meganuclease 26 binding subunit.

SEQ ID NO: 33 sets forth the nucleic acid sequence of the MIT 25-26x.91 meganuclease.

SEQ ID NO: 34 sets forth the nucleic acid sequence of the MIT 25-26x.48 meganuclease.

SEQ ID NO: 35 sets forth the nucleic acid sequence of the MIT 25-26x.73 meganuclease.

SEQ ID NO: 36 sets forth the nucleic acid sequence of the MIT 25-26x.29 meganuclease.

SEQ ID NO: 37 sets forth the nucleic acid sequence of the MIT 25-26x.37 meganuclease.

SEQ ID NO: 38 sets forth the nucleic acid sequence of the MIT 25-26L.35 meganuclease.

SEQ ID NO: 39 sets forth the nucleic acid sequence of the MIT 25-26x.91 259 H>Q meganuclease.

SEQ ID NO: 40 sets forth the nucleic acid sequence of the MIT 25-26L.35 19A>S meganuclease.

SEQ ID NO: 41 sets forth the nucleic acid sequence of the MIT 25-26x.91 263 T>R meganuclease.

SEQ ID NO: 42 sets forth the nucleic acid sequence of the MIT 25-26x.91 46 H>W meganuclease.

SEQ ID NO: 43 sets forth the amino acid sequence of the COX VIII MTP.

SEQ ID NO: 44 sets forth the amino acid sequence of the SU9 MTP.

SEQ ID NO: 45 sets forth the amino acid sequence of the COX VIII-SU9 MTP.

SEQ ID NO: 46 sets forth the amino acid sequence of the MVMp NS2 NES sequence.

SEQ ID NO: 47 sets forth the amino acid sequence of the NES sequence.

SEQ ID NO: 48 sets forth the amino acid sequence of the Wild-type I-CreI sequence.

SEQ ID NO: 49 sets forth the nucleic acid sequence of a digital droplet PCR (ddPCR) primer P1 used to determine indel frequency at APC 11-12 binding site.

SEQ ID NO: 50 sets forth the nucleic acid sequence of a ddPCR primer F1 used to determine indel frequency at APC 11-12 binding site.

SEQ ID NO: 51 sets forth the nucleic acid sequence of a ddPCR primer R1 used to determine indel frequency at APC 11-12 binding site.

SEQ ID NO: 52 sets forth the nucleic acid sequence of a ddPCR primer P2 used to determine indel frequency at APC 11-12 binding site; ddPCR primer P3 utilized to determine heteroplasmy level of mtDNA and mtDNA copy number relative to nuclear DNA.

SEQ ID NO: 53 sets forth the nucleic acid sequence of a ddPCR primer F2 used to determine indel frequency at APC 11-12 binding site; ddPCR primer F3 utilized to determine heteroplasmy level of mtDNA and mtDNA copy number relative to nuclear DNA.

SEQ ID NO: 54 sets forth the nucleic acid sequence of a ddPCR primer R2 used to determine indel frequency at APC 11-12 binding site; ddPCR primer R3 utilized to determine heteroplasmy level of mtDNA and mtDNA copy number relative to nuclear DNA.

SEQ ID NO: 55 sets forth the nucleic acid sequence of a ddPCR primer F1 used to identify potential nuclear off-target site editing induced by the MIT 25-26x.91 nuclease.

SEQ ID NO: 56 sets forth the nucleic acid sequence of a ddPCR primer R1 used to identify potential nuclear off-target site editing induced by the MIT 25-26x.91 nuclease.

SEQ ID NO: 57 sets forth the nucleic acid sequence of a ddPCR primer F2 used to identify potential nuclear off-target site editing induced by the MIT 25-26x.91 nuclease.

SEQ ID NO: 58 sets forth the nucleic acid sequence of a ddPCR primer R2 used to identify potential nuclear off-target site editing induced by the MIT 25-26x.91 nuclease.

SEQ ID NO: 59 sets forth the nucleic acid sequence of a ddPCR primer F3 used to identify potential nuclear off-target site editing induced by the MIT 25-26x.91 nuclease.

SEQ ID NO: 60 sets forth the nucleic acid sequence of a ddPCR primer R3 used to identify potential nuclear off-target site editing induced by the MIT 25-26x.91 nuclease.

SEQ ID NO: 61 sets forth the nucleic acid sequence of a ddPCR primer F4 used to identify potential nuclear off-target site editing induced by the MIT 25-26x.91 nuclease.

SEQ ID NO: 62 sets forth the nucleic acid sequence of a ddPCR primer R4 used to identify potential nuclear off-target site editing induced by the MIT 25-26x.91 nuclease.

SEQ ID NO: 63 sets forth the nucleic acid sequence of a ddPCR primer P1 utilized to determine heteroplasmy level of mtDNA, as well as mtDNA copy number relative to nuclear DNA (mutant allele).

SEQ ID NO: 64 sets forth the nucleic acid sequence of a ddPCR primer F1 utilized to determine heteroplasmy level of mtDNA, as well as mtDNA copy number relative to nuclear DNA.

SEQ ID NO: 65 sets forth the nucleic acid sequence of a ddPCR primer R1 utilized to determine heteroplasmy level of mtDNA, as well as mtDNA copy number relative to nuclear DNA.

SEQ ID NO: 66 sets forth the nucleic acid sequence of a ddPCR primer P2 utilized to determine heteroplasmy level of mtDNA, as well as mtDNA copy number relative to nuclear DNA.

SEQ ID NO: 67 sets forth the nucleic acid sequence of a ddPCR primer F2 utilized to determine heteroplasmy level of mtDNA, as well as mtDNA copy number relative to nuclear DNA.

SEQ ID NO: 68 sets forth the nucleic acid sequence of a ddPCR primer R2 utilized to determine heteroplasmy level of mtDNA, as well as mtDNA copy number relative to nuclear DNA.

SEQ ID NO: 69 sets forth the nucleic acid sequence of a ddPCR primer P4 utilized to determine heteroplasmy level of mtDNA, as well as mtDNA copy number relative to nuclear DNA.

SEQ ID NO: 70 sets forth the nucleic acid sequence of a ddPCR primer F4 utilized to determine heteroplasmy level of mtDNA, as well as mtDNA copy number relative to nuclear DNA.

SEQ ID NO: 71 sets forth the nucleic acid sequence of a ddPCR primer R4 utilized to determine heteroplasmy level of mtDNA, as well as mtDNA copy number relative to nuclear DNA.

SEQ ID NO: 72 sets forth the nucleic acid sequence of a ddPCR primer P1 utilized to determine heteroplasmy level of mtDNA, as well as mtDNA copy number relative to nuclear DNA (WT Allele).

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, the term "5' cap" (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, the term "allele" refers to one of two or more variant forms of a gene.

As used herein, the term "allogeneic" or, alternatively, "allogenic," refers to any material derived from a different animal of the same species or different patient as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

As used herein, the term "constitutive promoter" refers to a nucleotide sequence which, when operably linked with a polynucleotide which encodes or specifies a gene product, causes the gene product to be produced in a cell under most or all physiological conditions of the cell.

As used herein, the term "a control" or "a control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. For example, a control or control cell of the instant invention can be a cell or population of cells that does not comprise an MTEM or an engineered meganuclease described herein or a polynucleotide having an amino acid sequence encoding an MTEM or an engineered meganuclease described herein.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "disrupted" or "disrupts" or "disrupts expression" or "disrupting a target sequence" refers to the introduction of a mutation (e.g., frameshift mutation) that interferes with the gene function and prevents expression and/or function of the polypeptide/expression product encoded thereby. For example, nuclease-mediated disruption of a gene can result in the expression of a truncated protein and/or expression of a protein that does not retain its wild-type function. Additionally, introduction of a donor template into a gene can result in no expression of an encoded protein, expression of a truncated protein, and/or expression of a protein that does not retain its wild-type function.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "endogenous" in reference to a nucleotide sequence or protein is intended to mean a sequence or protein that is naturally comprised within or expressed by a cell.

As used herein, the terms "exogenous" or "heterologous" in reference to a nucleotide sequence or amino acid sequence are intended to mean a sequence that is purely synthetic, that originates from a foreign species, or, if from the same species, is substantially modified from its native form in composition and/or genomic locus by deliberate human intervention.

As used herein, the term "expression" refers to the transcription and/or translation of a particular nucleotide sequence driven by a promoter.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic." For example, as used herein, a "genetically-modified" cell may refer to a cell wherein the mitochondrial DNA has been deliberately modified by recombinant technology.

As used herein, the term "homologous recombination" or "HR" refers to the natural, cellular process in which a double-stranded DNA-break is repaired using a homologous DNA sequence as the repair template (see, e.g., Cahill et al. (2006), Front. Biosci. 11:1958-1976). The homologous DNA sequence may be an endogenous chromosomal sequence or an exogenous nucleic acid that was delivered to the cell.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term "in vitro transcribed RNA" refers to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, the term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

As used herein, the term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the term "modification" with respect to recombinant proteins means any insertion, deletion, or substitution of an amino acid residue in the recombinant sequence relative to a reference sequence (e.g., a wild-type or a native sequence).

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, the term "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

As used herein, the term "operably linked" is intended to mean a functional linkage between two or more elements. For example, an operable linkage between a nucleic acid sequence encoding a nuclease as described herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, unless specifically indicated otherwise, the word "or" is used in the inclusive sense of "and/or" and not the exclusive sense of "either/or."

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

As used herein, the term "reduced" or "decreased" refers to a reduction in the percentage of cells or ratio of cells in a population of cells that comprise mutant mitochondrial genomes having the MELAS mutation when compared to a population of control cells. In some embodiments, "reduced" or "decreased" refers to a reduction in the percentage of mutant mitochondrial genomes or ratio of mutant mitochondrial genomes to wild-type mitochondrial genomes in a single cell or in a population of cells. Such a reduction is up to 5%, 10%, 20%, 30%, 40%, 50%, 60%, 70%, 80%, 90%, 95%, or up to 100%. Accordingly, the term "reduced" encompasses both a partial reduction and a complete reduction of mutant mtDNA.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3.

As used herein, the term "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability, or efficiency of translation.

As used herein, the term "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly (A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, the term "promoter" or "regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein but produced by cloning and expression in a heterologous host, is not considered recombinant or engineered.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "tissue-specific promoter" refers to a nucleotide sequence which, when operably linked with a polynucleotide encodes or specified by a gene, causes the gene product to be produced in a cell substantially only if the cell is a cell of the tissue type corresponding to the promoter.

As used herein, the terms "transfected" or "transformed" or "transduced" or "nucleofected" refer to a process by which exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

As used herein, the term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

As used herein, the term "transient" refers to expression of a non-integrated transgene for a period of hours, days, or weeks, wherein the period of time of expression is less than the period of time for expression of the gene if integrated into the genome or contained within a stable plasmid replicon in the host cell.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences described herein. In some embodiments, a "vector" also refers to a viral vector. Viral vectors can include, without limitation, retroviral vectors, lentiviral vectors, adenoviral vectors, and adeno-associated viral vectors (AAV).

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "altered specificity," when referencing to a nuclease, means that a nuclease binds to and cleaves a recognition sequence, which is not bound to and cleaved by a reference nuclease (e.g., a wild-type) under physiological conditions, or that the rate of cleavage of a recognition sequence is increased or decreased by a biologically significant amount (e.g., at least 2×, or 2×-10×) relative to a reference nuclease.

As used herein, the term "center sequence" refers to the four base pairs separating half-sites in the meganuclease recognition sequence. These bases are numbered +1 through +4. The center sequence comprises the four bases that become the 3' single-strand overhangs following meganuclease cleavage. "Center sequence" can refer to the sequence of the sense strand or the antisense (opposite) strand. Meganucleases are symmetric and recognize bases equally on both the sense and antisense strand of the center sequence. For example, the sequence A+1A+2A+3A+4 on the sense strand is recognized by a meganuclease as T+1T+2T+3T+4 on the antisense strand and, thus, A+1A+2A+3A+4 and T+1T+2T+3T+4 are functionally equivalent (e.g., both can be cleaved by a given meganuclease). Thus, the sequence C+1T+2G+3C+4, is equivalent to its opposite strand sequence, G+1C+2A+3G+4 due to the fact that the meganuclease binds its recognition sequence as a symmetric homodimer.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 3-12. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments described herein, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 3-12. In other embodiments, variable residues within a hypervariable region correspond to one or more of positions 215, 217, 219, 221, 223, 224, 229, 231, 233, 235, 237, 259, 261, 266, and 268 of any one of SEQ ID NOs: 3-12.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have an amino acid sequence that sets forth residues 154-195 of any one of SEQ ID NOs: 3-12.

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 48), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the terms "nuclease" and "endonuclease" are used interchangeably to refer to naturally-occurring or engineered enzymes, which cleave a phosphodiester bond within a polynucleotide chain.

As used herein, the term "mitochondria-targeting engineered meganuclease" or "MTEM" refers to an engineered meganuclease attached to a peptide or other molecule that is capable of directing the engineered meganuclease to the mitochondria such that the engineered meganuclease is capable of binding and cleaving mitochondrial DNA within the mitochondrial organelle.

As used herein the term "mitochondrial transit peptide" or "MTP" refers to a peptide or fragment of amino acids that can be attached to a separate molecule in order to transport the molecule in the mitochondria. For example, an MTP can be attached to a nuclease, such as an engineered meganuclease, in order to transport the engineered meganuclease into the mitochondria. MTPs can consist of an alternating pattern of hydrophobic and positively charged amino acids to form what is called amphipathic helix.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the terms "recognition sequence" or "recognition site" refers to a DNA sequence that is bound and cleaved by a nuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "specificity" means the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs but may be degenerate at one or more positions. A highly-specific nuclease is capable of cleaving only one or a very few recognition sequences. Specificity can be determined by any method known in the art.

As used herein, the terms "target site" or "target sequence" refers to a region of the chromosomal DNA of a cell comprising a recognition sequence for a nuclease.

As used herein, a "vector" can also refer to a viral vector (i.e. a recombinant virus). Viral vectors can include, without limitation, retroviral vectors, lentiviral vectors, adenoviral vectors, and adeno-associated viral vectors (AAV).

As used herein, the term "serotype" or "capsid" refers to a distinct variant within a species of virus that is determined based on the viral cell surface antigens. Known serotypes of AAV include, among others, AAV1, AAV2, AAV3, AAV3B, AAV4, AAV5, AAV6, AAV7, AAV8, AAV9, AAV10, AAV11, and AAVHSC (Weitzman and Linden (2011) In Snyder and Moullier Adeno-associated virus methods and protocols. Totowa, NJ: Humana Press).

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions, stimuli, or further genetic modifications that would induce expression of altered genotype or phenotype.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition, and responsiveness of the subject to be treated. In some specific embodiments, an effective amount of the MTEM or an engineered meganuclease described herein comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a nucleic acid encoding the MTEM or an engineered meganuclease described herein or of a template nucleic acid. In specific embodiments, an effective amount of a nucleic acid encoding an MTEM or an engineered meganuclease described herein and/or a template nucleic acid, or a pharmaceutical composition comprising a nucleic acid encoding an MTEM or an engineered meganuclease described herein and/or a template nucleic acid described herein, reduces at least one symptom of a disease in a subject.

As used herein, the term "effective dose", "effective amount", "therapeutically effective dose", or "therapeutically effective amount," as used herein, refers to an amount sufficient to effect beneficial or desirable biological and/or clinical results.

As used herein, the term "gc/kg" or "gene copies/kilogram" refers to the number of copies of a nucleic acid encoding an MTEM or an engineered meganuclease described herein or the number of copies of a template nucleic acid described herein per weight in kilograms of a subject that is administered the nucleic acid encoding the MTEM or an engineered meganuclease described herein and/or the template nucleic acid.

As used herein, the term "preventing" refers to the prevention of the disease or condition in the patient.

As used herein, the term "prophylaxis" means the prevention of or protective treatment for a disease or disease state.

As used herein, the term "reduced" refers to any reduction in the symptoms or severity of a disease. Such a reduction may be up to 5%, 10%, 20%, 30%, 40%, 50%, 60%, 70%, 80%, 90%, 95%, or up to 100%. Accordingly, the term "reduced" encompasses both a partial reduction and a complete reduction of a disease state.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Invention

Mitochondria regulate cellular energy and metabolism under normal growth and development, as well as in response to stress. Thus, editing of the mitochondrial genome has diverse applications in both animals and plants. In humans, deleterious mitochondrial mutations are the source of a number of disorders for which gene editing therapies could be applied. However, even in view of the potential of using mitochondrial genome editing for therapeutic applications, it still remains an underexplored area of science because of the inability to efficiently target mitochondrial DNA (mtDNA) and generate precise edits. The mitochondrial genome is difficult to edit as the editing technology needs to be delivered to this organelle. Moreover, the mitochondria lack predictable repair mechanisms. Previous attempts at editing the mitochondrial genome have resulted in large and unpredictable deletions/rearrangements. Hence, compositions and methods that would allow targeting and editing defined regions (preferably limited to just one gene) of the mitochondrial genome in a more predictable manner are desired.

The present disclosure provides compositions and methods for binding and cleaving a recognition sequence on the mitochondrial genome without impacting the surrounding regions in the mitochondrial genome. Disclosed herein are engineered meganucleases attached to MTPs such that DSBs can be generated in the mtDNA. The present invention demonstrates that engineered meganucleases can be directed into the mitochondria organelle and facilitate precise editing of mtDNA, thus opening up an entire field of prospects and opportunities in life sciences.

2.2 Engineered Meganuclease and Mitochondria-Targeting Engineered Meganuclease for Recognizing and Cleaving Recognition Sequences within the Human Mitochondrial DNA It is known in the art that it is possible to use a site-specific nuclease to make a DNA break in the genome of a living cell, and that such a DNA break can result in permanent modification of the genome via homologous recombination with a transgenic DNA sequence. The use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus.

Mitochondria-targeting engineered meganucleases (MTEM) constructed of an engineered meganuclease attached to a mitochondrial transit peptide (MTP) can effectively traffic from the cytoplasm of a eukaryotic cell into the mitochondria. Once inside the mitochondrial organelle, the MTEM can bind and cleave a recognition sequence in the mitochondrial genome. It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode any sequence or polypeptide of interest. In some embodiments, a site-specific nuclease can cleave a recognition sequence in the mitochondrial genome that results in degradation of the mitochondrial genome from the cleaved ends created by the site-specific nuclease.

The nucleases used to practice the invention are meganucleases. In particular embodiments, the meganucleases used to practice the invention are single-chain meganucleases. A single-chain meganuclease comprises an N-terminal subunit and a C-terminal subunit joined by a linker peptide. Each of the two domains recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some embodiments, an engineered meganuclease described herein has been engineered to bind and cleave an MIT 25-26 recognition sequence (SEQ ID NO: 1). Such an engineered meganuclease is referred to herein as "MIT 25-26 meganuclease" or "MIT 25-26 nucleases". In specific embodiments, the MIT 25-26 meganuclease is attached to an MTP to for an MTEM that cleaves the MIT 25-26 recognition sequence of SEQ ID NO: 1.

Engineered meganucleases described herein can comprise a first subunit, comprising a first hypervariable (HVR1) region, and a second subunit, comprising a second hypervariable (HVR2) region. Further, the first subunit can bind to a first recognition half-site in the recognition sequence (e.g., the MIT 25 half-site), and the second subunit can bind to a second recognition half-site in the recognition sequence (e.g., the MIT 26 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Exemplary MIT 25-26 meganucleases described herein are provided in Table 1 and are further described below.

TABLE 1

| Meganuclease | AA SEQ ID | MIT25 Subunit Residues | MIT25 Subunit SEQ ID | *MIT25 Subunit % | MIT26 Subunit Residues | MIT26 Subunit SEQ ID | *MIT26 Subunit % |
|---|---|---|---|---|---|---|---|
| MIT 25-26x. 91 | 3 | 7-153 | 13 | 100 | 198-344 | 23 | 100 |
| MIT 25-26x. 48 | 4 | 7-153 | 14 | 98.64 | 198-344 | 24 | 97.28 |
| MIT 25-26x. 73 | 5 | 7-153 | 15 | 99.32 | 198-344 | 25 | 98.64 |
| MIT 25-26x. 29 | 6 | 7-153 | 16 | 98.64 | 198-344 | 26 | 98.64 |

TABLE 1-continued

| Meganuclease | AA SEQ ID | MIT25 Subunit Residues | MIT25 Subunit SEQ ID | *MIT25 Subunit % | MIT26 Subunit Residues | MIT26 Subunit SEQ ID | *MIT26 Subunit % |
|---|---|---|---|---|---|---|---|
| MIT 25-26x. 37 | 7 | 7-153 | 17 | 99.32 | 198-344 | 27 | 97.28 |
| MIT 25-26L. 35 | 8 | 7-153 | 18 | 96.6 | 198-344 | 28 | 98.64 |
| MIT 25-26x. 91 259H>Q | 9 | 7-153 | 19 | 100 | 198-344 | 29 | 99.32 |
| MIT 25-26L. 35 19A>S | 10 | 7-153 | 20 | 97.28 | 198-344 | 30 | 98.64 |
| MIT 25-26x. 91 263T>R | 11 | 7-153 | 21 | 100 | 198-344 | 31 | 99.32 |
| MIT 25-26x. 91 46H>W | 12 | 7-153 | 22 | 99.32 | 198-344 | 32 | 100 |

*"MIT25 Subunit %" and "MIT26 Subunit %" represent the amino acid sequence identity between the MIT25-binding and MIT26-binding subunit regions of each meganuclease and the MIT25-binding and MIT26-binding subunit regions, respectively, of the MIT25-26x.91 meganuclease.

In certain embodiments described herein, the engineered meganuclease binds and cleaves a recognition sequence comprising SEQ ID NO: 1 within mitochondrial genome, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of any one of SEQ ID NOs: 3-12. In some such embodiments, the HVR1 region comprises one or more residues corresponding to residues 24, 26, 28, 30, 32, 33, 38, 40, 42, 44, 46, 68, 70, 75, and 77 of any one of SEQ ID NOs: 3-12. In some such embodiments, the HVR1 region comprises residues corresponding to residues 24, 26, 28, 30, 32, 33, 38, 40, 42, 44, 46, 68, 70, 75, and 77 of any one of SEQ ID NOs: 3-12. In some such embodiments, the HVR1 region comprises Y, R, K, or D at a residue corresponding to residue 66 of any one of SEQ ID NOs: 3-12. In some such embodiments, the HVR1 region comprises residues 24-79 of any one of SEQ ID NOs: 3-12. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of any one of SEQ ID NOs: 3-12. In some such embodiments, the HVR2 region comprises one or more residues corresponding to residues 215, 217, 219, 221, 223, 224, 229, 231, 233, 235, 237, 259, 261, 266, and 268 of any one of SEQ ID NOs: 3-12. In some such embodiments, the HVR2 region comprises residues corresponding to residues 215, 217, 219, 221, 223, 224, 229, 231, 233, 235, 237, 259, 261, 266, and 268 of any one of SEQ ID NOs: 3-12. In some such embodiments, the HVR2 region comprises Y, R, K, or D at a residue corresponding to residue 257 of any one of SEQ ID NOs: 3-12. In some such embodiments, the HVR2 region comprises residues 215-270 of any one of SEQ ID NOs: 3-12. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of any one of SEQ ID NOs: 3-12, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of any one of SEQ ID NOs: 3-12. In some such embodiments, the first subunit comprises G, S, or A at a residue corresponding to residue 19 of any one of SEQ ID NOs: 3-12. In some such embodiments, the first subunit comprises E, Q, or K at a residue corresponding to residue 80 of any one of SEQ ID NOs: 3-12. In some such embodiments, the second subunit comprises G, S, or A at a residue corresponding to residue 210 of any one of SEQ ID NOs: 3-12. In some such embodiments, the second subunit comprises E, Q, or K at a residue corresponding to residue 271 of any one of SEQ ID NOs: 3-12. In some such embodiments, the first subunit comprises a residue corresponding to residue 80 of any one of SEQ ID NOs: 3-12. In some such embodiments, the second subunit comprises a residue corresponding to residue 271 of any one of SEQ ID NOs: 3-12. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 3-12. In some such embodiments, the engineered meganuclease comprises the amino acid sequence of any one of SEQ ID NOs: 3-12. In some embodiments, the engineered meganuclease is encoded by a nucleic sequence having at least 80%, at least 85%, at least 90%, at least 91%, at least 92%, at least 93%, at least 94%, at least 95%, at least 96%, at least 97%, at least 98%, or at least 99% sequence identity to the nucleic acid sequence set forth in any one of SEQ ID NOs: 33-42. In some such embodiments, the engineered meganuclease is encoded by the nucleic acid sequence set forth in any one of SEQ ID NOs: 33-42.

MIT 25-26x.91 (SEQ ID NO: 3)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 3. In some embodiments, the HVR1 region comprises one or more residues corresponding to residues 24, 26, 28, 30, 32, 33, 38, 40, 42, 44, 46, 68, 70, 75, and 77 of SEQ ID NO: 3. In some embodiments, the HVR1 region comprises residues corresponding to residues 24, 26, 28, 30, 32, 33, 38, 40, 42, 44, 46, 68, 70, 75, and 77 of SEQ ID NO: 3. In some embodiments, the HVR1 region comprises Y, R, K, or D at a residue corresponding to residue 66 of SEQ ID NO: 3. In some embodiments, the HVR1 region comprises residues 24-79 of SEQ ID NO: 3 with up to 1, 2, 3, 4, 5, 6, 7, 8, 9, 10, or 11 amino acid substitutions. In some embodiments, the HVR1 region comprises residues 24-79 of SEQ ID NO: 3.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 3. In some embodiments, the first subunit comprises G, S, or A at a residue corresponding to residue 19 of SEQ ID NO: 3. In some embodiments, the first subunit comprises a residue corresponding to residue 19 of SEQ ID NO: 3. In some embodiments, the first subunit comprises E, Q, or K at a residue corresponding to residue 80 of SEQ ID NO: 3. In some embodiments, the first subunit comprises residues 7-153 of SEQ ID NO: 3 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 3.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 3. In some embodiments, the HVR2 region comprises one or more residues corresponding to residues 215, 217, 219, 221, 223, 224, 229, 231, 233, 235, 237, 259, 261, 266, and 268 of SEQ ID NO: 3. In some embodiments, the HVR2 region comprises residues corresponding to residues 215, 217, 219, 221, 223, 224, 229, 231, 233, 235, 237, 259, 261, 266, and 268 of SEQ ID NO: 3. In some embodiments, the HVR2 region comprises Y, R, K, or D at a residue corresponding to residue 257 of SEQ ID NO: 3. In some embodiments, the HVR2 region comprises a residue corresponding to residue 241 of SEQ ID NO: 3. In some embodiments, the HVR2 region comprises a residue corresponding to residue 262 of SEQ ID NO: 3. In some embodiments, the HVR2 region comprises a residue corresponding to residue 263 of SEQ ID NO: 3. In some embodiments, the HVR2 region comprises a residue corresponding to residue 264 of SEQ ID NO: 3. In some embodiments, the HVR2 region comprises residues 215-270 of SEQ ID NO: 3 with up to 1, 2, 3, 4, 5, 6, 7, 8, 9, 10, or 11 amino acid substitutions. In some embodiments, the HVR2 region comprises residues 215-270 of SEQ ID NO: 3.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 3. In some embodiments, the second subunit comprises G, S, or A at a residue corresponding to residue 210 of SEQ ID NO: 3. In some embodiments, the second subunit comprises E, Q, or K at a residue corresponding to residue 271 of SEQ ID NO: 3. In some embodiments, the second subunit comprises a residue corresponding to residue 330 of SEQ ID NO: 3. In some embodiments, the second subunit comprises residues 198-344 of SEQ ID NO: 3 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 3.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 3. In some embodiments, the engineered meganuclease comprises an amino acid sequence of SEQ ID NO: 3. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 33. In some embodiments, the engineered meganuclease is encoded by a nucleic acid sequence set forth in SEQ ID NO: 33.

MIT 25-26x.48 (SEQ ID NO: 4)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 4. In some embodiments, the HVR1 region comprises one or more residues corresponding to residues 24, 26, 28, 30, 32, 33, 38, 40, 42, 44, 46, 68, 70, 75, and 77 of SEQ ID NO: 4. In some embodiments, the HVR1 region comprises residues corresponding to residues 24, 26, 28, 30, 32, 33, 38, 40, 42, 44, 46, 68, 70, 75, and 77 of SEQ ID NO: 4. In some embodiments, the HVR1 region comprises Y, R, K, or D at a residue corresponding to residue 66 of SEQ ID NO: 4. In some embodiments, the HVR1 region comprises residues 24-79 of SEQ ID NO: 4 with up to 1, 2, 3, 4, 5, 6, 7, 8, 9, 10, or 11 amino acid substitutions. In some embodiments, the HVR1 region comprises residues 24-79 of SEQ ID NO: 4.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 4. In some embodiments, the first subunit comprises G, S, or A at a residue corresponding to residue 19 of SEQ ID NO: 4. In some embodiments, the first subunit comprises a residue corresponding to residue 19 of SEQ ID NO: 4. In some embodiments, the first subunit comprises E, Q, or K at a residue corresponding to residue 80 of SEQ ID NO: 4. In some embodiments, the first subunit comprises residues 7-153 of SEQ ID NO: 4 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 4.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 4. In some embodiments, the HVR2 region comprises one or more residues corresponding to residues 215, 217, 219, 221, 223, 224, 229, 231, 233, 235, 237, 259, 261, 266, and 268 of SEQ ID NO: 4. In some embodiments, the HVR2 region comprises residues corresponding to residues 215, 217, 219, 221, 223, 224, 229, 231, 233, 235, 237, 259, 261, 266, and 268 of SEQ ID NO: 4. In some embodiments, the HVR2 region comprises Y, R, K, or D at a residue corresponding to residue 257 of SEQ ID NO: 4. In some embodiments, the HVR2 region comprises a residue corresponding to residue 241 of SEQ ID NO: 4. In some embodiments, the HVR2 region comprises residues 215-270 of SEQ ID NO: 4 with up to 1, 2, 3, 4, 5, 6, 7, 8, 9, 10, or 11 amino acid substitutions. In some embodiments, the HVR2 region comprises residues 215-270 of SEQ ID NO: 4.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 4. In some embodiments, the second subunit comprises G, S, or A at a residue corresponding to residue 210 of SEQ ID NO: 4. In some embodiments, the second subunit comprises E, Q, or K at a residue corresponding to residue 271 of SEQ ID NO: 4. In some embodiments, the second subunit comprises a residue corresponding to residue 276 of SEQ ID NO: 4. In some embodiments, the second subunit comprises a residue corresponding to residue 330 of SEQ ID NO: 4. In some embodiments, the second subunit comprises residues 198-344 of SEQ ID NO: 4 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 4.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 4. In some embodiments, the engineered meganuclease comprises an amino acid sequence of SEQ ID NO: 4. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 34. In some embodiments, the engineered meganuclease is encoded by a nucleic acid sequence set forth in SEQ ID NO: 34.

MIT 25-26x. 73 (SEQ ID NO: 5)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 5. In some embodiments, the HVR1 region comprises one or more residues corresponding to residues 24, 26, 28, 30, 32, 33, 38, 40, 42, 44, 46, 68, 70, 75, and 77 of SEQ ID NO: 5. In some embodiments, the HVR1 region comprises residues corresponding to residues 24, 26, 28, 30, 32, 33, 38, 40, 42, 44, 46, 68, 70, 75, and 77 of SEQ ID NO: 5. In some embodiments, the HVR1 region comprises Y, R, K, or D at a residue corresponding to residue 66 of SEQ ID NO: 5. In some embodiments, the HVR1 region comprises residues 24-79 of SEQ ID NO: 5 with up to 1, 2, 3, 4, 5, 6, 7, 8, 9, 10, or 11 amino acid substitutions. In some embodiments, the HVR1 region comprises residues 24-79 of SEQ ID NO: 5.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 5. In some embodiments, the first subunit comprises G, S, or A at a residue corresponding to residue 19 of SEQ ID NO: 5. In some embodiments, the first subunit comprises a residue corresponding to residue 19 of SEQ ID NO: 5. In some embodiments, the first subunit comprises E, Q, or K at a residue corresponding to residue 80 of SEQ ID NO: 5. In some embodiments a residue corresponding to residue 80 of SEQ ID NO: 5. In some embodiments, the first subunit comprises residues 7-153 of SEQ ID NO: 5 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 5.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 5. In some embodiments, the HVR2 region comprises one or more residues corresponding to residues 215, 217, 219, 221, 223, 224, 229, 231, 233, 235, 237, 259, 261, 266, and 268 of SEQ ID NO: 5. In some embodiments, the HVR2 region comprises residues corresponding to residues 215, 217, 219, 221, 223, 224, 229, 231, 233, 235, 237, 259, 261, 266, and 268 of SEQ ID NO: 5. In some embodiments, the HVR2 region comprises Y, R, K, or D at a residue corresponding to residue 257 of SEQ ID NO: 5. In some embodiments, the HVR2 region comprises a residue corresponding to residue 241 of SEQ ID NO: 5. In some embodiments, the HVR2 region comprises a residue corresponding to residue 263 of SEQ ID NO: 5. In some embodiments, the HVR2 region comprises a residue corresponding to residue 264 of SEQ ID NO: 5. In some embodiments, the HVR2 region comprises residues 215-270 of SEQ ID NO: 5 with up to 1, 2, 3, 4, 5, 6, 7, 8, 9, 10, or 11 amino acid substitutions. In some embodiments, the HVR2 region comprises residues 215-270 of SEQ ID NO: 5.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 5. In some embodiments, the second subunit comprises G, S, or A at a residue corresponding to residue 210 of SEQ ID NO: 5. In some embodiments, the second subunit comprises E, Q, or K at a residue corresponding to residue 271 of SEQ ID NO: 5. In some embodiments, the second subunit comprises a residue corresponding to residue 330 of SEQ ID NO: 5. In some embodiments, the second subunit comprises residues 198-344 of SEQ ID NO: 5 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 5.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 5. In some embodiments, the engineered meganuclease comprises an amino acid sequence of SEQ ID NO: 5. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 35. In some embodiments, the engineered meganuclease is encoded by a nucleic acid sequence set forth in SEQ ID NO: 35.

MIT 25-26x.29 (SEQ ID NO: 6)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 6. In some embodiments, the HVR1 region comprises one or more residues corresponding to residues 24, 26, 28, 30, 32, 33, 38, 40, 42, 44, 46, 68, 70, 75, and 77 of SEQ ID NO: 6. In some embodiments, the HVR1 region comprises residues corresponding to residues 24, 26, 28, 30, 32, 33, 38, 40, 42, 44, 46, 68, 70, 75, and 77 of SEQ ID NO: 6. In some embodiments, the HVR1 region comprises Y, R, K, or D at a residue corresponding to residue 66 of SEQ ID NO: 6. In some embodiments, the HVR1 region comprises residues 24-79 of SEQ ID NO: 6 with up to 1, 2, 3, 4, 5, 6, 7, 8, 9, 10, or 11 amino acid substitutions. In some embodiments, the HVR1 region comprises residues 24-79 of SEQ ID NO: 6.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 6. In some embodiments, the first subunit comprises G, S, or A at a residue corresponding to residue 19 of SEQ ID NO: 6. In some embodiments, the first subunit comprises a residue corresponding to residue 19 of SEQ ID NO: 6. In some embodiments, the first subunit comprises E, Q, or K at a residue corresponding to residue 80 of SEQ ID NO: 6. In some embodiments, the first subunit comprises residues 7-153 of SEQ ID NO: 6 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 6.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 6. In some embodiments, the HVR2 region comprises one or more residues corresponding to residues 215, 217, 219, 221, 223, 224, 229, 231, 233, 235, 237, 259, 261, 266, and 268 of SEQ ID NO: 6. In some embodiments, the HVR2 region comprises residues corresponding to residues 215, 217, 219, 221, 223, 224, 229, 231, 233, 235, 237, 259, 261, 266, and 268 of SEQ ID NO: 6. In some embodiments, the HVR2 region comprises Y, R, K, or D at a residue corresponding to residue 257 of SEQ ID NO: 6. In some embodiments, the HVR2 region comprises a residue corresponding to residue 241 of SEQ ID NO: 6. In some embodiments, the HVR2 region comprises a residue corresponding to residue 263 of SEQ ID NO: 6. In some embodiments, the HVR2 region comprises a residue corresponding to residue 264 of SEQ ID NO: 6. In some embodiments, the HVR2 region comprises a residue corresponding to residue 265 of SEQ ID NO: 6. In some embodiments, the HVR2 region comprises residues 215-270 of SEQ ID NO: 6 with up to 1, 2, 3, 4, 5, 6, 7, 8, 9, 10, or 11 amino acid substitutions. In some embodiments, the HVR2 region comprises residues 215-270 of SEQ ID NO: 6.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 6. In some embodiments, the second subunit comprises G, S, or A at a residue corresponding to residue 210 of SEQ ID NO: 6. In some embodiments, the second subunit comprises E, Q, or K at a residue corresponding to residue 271 of SEQ ID NO: 6. In some embodiments, the second subunit comprises a residue corresponding to residue 330 of SEQ ID NO: 6. In some embodiments, the second subunit comprises residues 198-344 of SEQ ID NO: 6 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 6.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 6. In some embodiments, the engineered meganuclease comprises an amino acid sequence of SEQ ID NO: 6. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 36. In some embodiments, the engineered meganuclease is encoded by a nucleic acid sequence set forth in SEQ ID NO: 36.

MIT 25-26x.37 (SEQ ID NO: 7)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 7. In some embodiments, the HVR1 region comprises one or more residues corresponding to residues 24, 26, 28, 30, 32, 33, 38, 40, 42, 44, 46, 68, 70, 75, and 77 of SEQ ID NO: 7. In some embodiments, the HVR1 region comprises residues corresponding to residues 24, 26, 28, 30, 32, 33, 38, 40, 42, 44, 46, 68, 70, 75, and 77 of SEQ ID NO: 7. In some embodiments, the HVR1 region comprises Y, R, K, or D at a residue corresponding to residue 66 of SEQ ID NO: 7. In some embodiments, the HVR1 region comprises residues 24-79 of SEQ ID NO: 7 with up to 1, 2, 3, 4, 5, 6, 7, 8, 9, 10, or 11 amino acid substitutions. In some embodiments, the HVR1 region comprises residues 24-79 of SEQ ID NO: 7.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 7. In some embodiments, the first subunit comprises G, S, or A at a residue corresponding to residue 19 of SEQ ID NO: 7. In some embodiments, the first subunit comprises a residue corresponding to residue 19 of SEQ ID NO: 7. In some embodiments, the first subunit comprises E, Q, or K at a residue corresponding to residue 80 of SEQ ID NO: 7. In some embodiments, the first subunit comprises a residue corresponding to residue 80 of SEQ ID NO: 7.

In some embodiments, the first subunit comprises residues 7-153 of SEQ ID NO: 7 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 7.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 7. In some embodiments, the HVR2 region comprises one or more residues corresponding to residues 215, 217, 219, 221, 223, 224, 229, 231, 233, 235, 237, 259, 261, 266, and 268 of SEQ ID NO: 7. In some embodiments, the HVR2 region comprises residues corresponding to residues 215, 217, 219, 221, 223, 224, 229, 231, 233, 235, 237, 259, 261, 266, and 268 of SEQ ID NO: 7. In some embodiments, the HVR2 region comprises Y, R, K, or D at a residue corresponding to residue 257 of SEQ ID NO: 7. In some embodiments, the HVR2 region comprises a residue corresponding to residue 241 of SEQ ID NO: 7. In some embodiments, the HVR2 region comprises a residue corresponding to residue 263 of SEQ ID NO: 7. In some embodiments, the HVR2 region comprises residues 215-270 of SEQ ID NO: 7 with up to 1, 2, 3, 4, 5, 6, 7, 8, 9, 10, or 11 amino acid substitutions. In some embodiments, the HVR2 region comprises residues 215-270 of SEQ ID NO: 7.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 7. In some embodiments, the second subunit comprises G, S, or A at a residue corresponding to residue 210 of SEQ ID NO: 7. In some embodiments, the second subunit comprises E, Q, or K at a residue corresponding to residue 271 of SEQ ID NO: 7. In some embodiments, the second subunit comprises a residue corresponding to residue 330 of SEQ ID NO: 7. In some embodiments, the second subunit comprises residues 198-344 of SEQ ID NO: 7 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 7.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 7. In some embodiments, the engineered meganuclease comprises an amino acid sequence of SEQ ID NO: 7. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 37. In some embodiments, the engineered meganuclease is encoded by a nucleic acid sequence set forth in SEQ ID NO: 37.

MIT 25-26L.35 (SEQ ID NO: 8)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 8. In some embodiments, the HVR1 region comprises one or more residues corresponding to residues 24, 26, 28, 30, 32, 33, 38, 40, 42, 44, 46, 68, 70, 75, and 77 of SEQ ID NO: 8. In some embodiments, the HVR1 region comprises residues corresponding to residues 24, 26, 28, 30, 32, 33, 38, 40, 42, 44, 46, 68, 70, 75, and 77 of SEQ ID NO: 8. In some embodiments, the HVR1 region comprises Y, R, K, or D at a residue corresponding to residue 66 of SEQ ID NO: 8. In some embodiments, the HVR1 region comprises residues 24-79 of SEQ ID NO: 8 with up to 1, 2, 3, 4, 5, 6, 7, 8, 9, 10, or 11 amino acid substitutions. In some embodiments, the HVR1 region comprises residues 24-79 of SEQ ID NO: 8.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 8. In some embodiments, the first subunit comprises G, S, or A at a residue corresponding to residue 19 of SEQ ID NO: 8. In some embodiments, the first subunit comprises a residue corresponding to residue 19 of SEQ ID NO: 8. In some embodiments, the first subunit comprises E, Q, or K at a residue corresponding to residue 80 of SEQ ID NO: 8. In some embodiments, the first subunit comprises residues 7-153 of SEQ ID NO: 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 8.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 8. In some embodiments, the HVR2 region comprises one or more residues corresponding to residues 215, 217, 219, 221, 223, 224, 229, 231, 233, 235, 237, 259, 261, 266, and 268 of SEQ ID NO: 8. In some embodiments, the HVR2 region comprises residues corresponding to residues 215, 217, 219, 221, 223, 224, 229, 231, 233, 235, 237, 259, 261, 266, and 268 of SEQ ID NO: 8. In some embodiments, the HVR2 region comprises Y, R, K, or D at a residue corresponding to residue 257 of SEQ ID NO: 8. In some embodiments, the HVR2 region comprises a residue corresponding to residue 241 of SEQ ID NO: 8. In some embodiments, the HVR2 region comprises a residue corresponding to residue 263 of SEQ ID NO: 8. In some embodiments, the HVR2 region comprises a residue corresponding to residue 264 of SEQ ID NO: 8. In some embodiments, the HVR2 region comprises residues 215-270 of SEQ ID NO: 8 with up to 1, 2, 3, 4, 5, 6, 7, 8, 9, 10, or 11 amino acid substitutions. In some embodiments, the HVR2 region comprises residues 215-270 of SEQ ID NO: 8.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 8. In some embodiments, the second subunit comprises G, S, or A at a residue corresponding to residue 210 of SEQ ID NO: 8. In some embodiments, the second subunit comprises E, Q, or K at a residue corresponding to residue 271 of SEQ ID NO: 8. In some embodiments, the second subunit comprises a residue corresponding to residue 330 of SEQ ID NO: 8. In some embodiments, the second subunit comprises residues 198-344 of SEQ ID NO: 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 8.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 8. In some embodiments, the engineered meganuclease comprises an amino acid sequence of SEQ ID NO: 8. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 38. In some embodiments, the engineered meganuclease is encoded by a nucleic acid sequence set forth in SEQ ID NO: 38.

MIT 25-26x.91 259H>Q (SEQ ID NO: 9)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 9. In some embodiments, the HVR1 region comprises one or more residues corresponding to residues 24, 26, 28, 30, 32, 33, 38, 40, 42, 44, 46, 68, 70, 75, and 77 of SEQ ID NO: 9. In some embodiments, the HVR1 region comprises residues corresponding to residues 24, 26, 28, 30, 32, 33, 38, 40, 42, 44, 46, 68, 70, 75, and 77 of SEQ ID NO: 9. In some embodiments, the HVR1 region comprises Y, R, K, or D at a residue corresponding to residue 66 of SEQ ID NO: 9. In some embodiments, the HVR1 region comprises residues 24-79 of SEQ ID NO: 9 with up to 1, 2, 3, 4, 5, 6, 7, 8, 9, 10, or 11 amino acid substitutions. In some embodiments, the HVR1 region comprises residues 24-79 of SEQ ID NO: 9.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 9. In some embodiments, the first subunit comprises G, S, or A at a residue corresponding to residue 19 of SEQ ID NO: 9. In some embodiments, the first subunit comprises a residue corresponding to residue 19 of SEQ ID NO: 9. In some embodiments, the first subunit comprises E, Q, or K at a residue corresponding to residue 80 of SEQ ID NO: 9. In some embodiments, the first subunit comprises a residue corresponding to residue 80 of SEQ ID NO: 9.

In some embodiments, the first subunit comprises residues 7-153 of SEQ ID NO: 9 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 9.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 9. In some embodiments, the HVR2 region comprises one or more residues corresponding to residues 215, 217, 219, 221, 223, 224, 229, 231, 233, 235, 237, 259, 261, 266, and 268 of SEQ ID NO: 9. In some embodiments, the HVR2 region comprises residues corresponding to residues 215, 217, 219, 221, 223, 224, 229, 231, 233, 235, 237, 259, 261, 266, and 268 of SEQ ID NO: 9. In some embodiments, the HVR2 region comprises Y, R, K, or D at a residue corresponding to residue 257 of SEQ ID NO: 9. In some embodiments, the HVR2 region comprises a residue corresponding to residue 241 of SEQ ID NO: 9. In some embodiments, the HVR2 region comprises a residue corresponding to residue 263 of SEQ ID NO: 9. In some embodiments, the HVR2 region comprises a residue corresponding to residue 264 of SEQ ID NO: 9. In some embodiments, the HVR2 region comprises residues 215-270 of SEQ ID NO: 9 with up to 1, 2, 3, 4, 5, 6, 7, 8, 9, 10, or 11 amino acid substitutions. In some embodiments, the HVR2 region comprises residues 215-270 of SEQ ID NO: 9.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 9. In some embodiments, the second subunit comprises G, S, or A at a residue corresponding to residue 210 of SEQ ID NO: 9. In some embodiments, the second subunit comprises E, Q, or K at a residue corresponding to residue 271 of SEQ ID NO: 9. In some embodiments, the second subunit comprises a residue corresponding to residue 330 of SEQ ID NO: 9. In some embodiments, the second subunit comprises residues 198-344 of SEQ ID NO: 9 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 9.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 9. In some embodiments, the engineered meganuclease comprises an amino acid sequence of SEQ ID NO: 9. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 39. In some embodiments, the engineered meganuclease is encoded by a nucleic acid sequence set forth in SEQ ID NO: 39.

MIT 25-26L.35 19A>S (SEQ ID NO: 10)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 10. In some embodiments, the HVR1 region comprises one or more residues corresponding to residues 24, 26, 28, 30, 32, 33, 38, 40, 42, 44, 46, 68, 70, 75, and 77 of SEQ ID NO: 10. In some embodiments, the HVR1 region comprises residues corresponding to residues 24, 26, 28, 30, 32, 33, 38, 40, 42, 44, 46, 68, 70, 75, and 77 of SEQ ID NO: 10. In some embodiments, the HVR1 region comprises Y, R, K, or D at a residue corresponding to residue 66 of SEQ ID NO: 10. In some embodiments, the HVR1 region comprises residues 24-79 of SEQ ID NO: 10 with up to 1, 2, 3, 4, 5, 6, 7, 8, 9, 10, or 11 amino acid substitutions. In some embodiments, the HVR1 region comprises residues 24-79 of SEQ ID NO: 10.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 10. In some embodiments, the first subunit comprises G, S, or A at a residue corresponding to residue 19 of SEQ ID NO: 10. In some embodiments, the first subunit comprises a residue corresponding to residue 19 of SEQ ID NO: 10. In some embodiments, the first subunit comprises E, Q, or K at a residue corresponding to residue 80 of SEQ ID NO: 10. In some embodiments, the first subunit comprises residues 7-153 of SEQ ID NO: 10 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 10.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 10. In some embodiments, the HVR2 region comprises one or more residues corresponding to residues 215, 217, 219, 221, 223, 224, 229, 231, 233, 235, 237, 259, 261, 266, and 268 of SEQ ID NO: 10. In some embodiments, the HVR2 region comprises residues corresponding to residues 215, 217, 219, 221, 223, 224, 229, 231, 233, 235, 237, 259, 261, 266, and 268 of SEQ ID NO: 10. In some embodiments, the HVR2 region comprises Y, R, K, or D at a residue corresponding to residue 257 of SEQ ID NO: 10. In some embodiments, the HVR2 region comprises a residue corresponding to residue 241 of SEQ ID NO: 10. In some embodiments, the HVR2 region comprises a residue corresponding to residue 263 of SEQ ID NO: 10. In some embodiments, the HVR2 region comprises a residue corresponding to residue 264 of SEQ ID NO: 10. In some embodiments, the HVR2 region comprises residues 215-270 of SEQ ID NO: 10 with up to 1, 2, 3, 4, 5, 6, 7, 8, 9, 10, or 11 amino acid substitutions. In some embodiments, the HVR2 region comprises residues 215-270 of SEQ ID NO: 10.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 10. In some embodiments, the second subunit comprises G, S, or A at a residue corresponding to residue 210 of SEQ ID NO: 10. In some embodiments, the second subunit comprises E, Q, or K at a residue corresponding to residue 271 of SEQ ID NO: 10. In some embodiments, the second subunit comprises a residue corresponding to residue 330 of SEQ ID NO: 10. In some embodiments, the second subunit comprises residues 198-344 of SEQ ID NO: 10 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 10.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 10. In some embodiments, the engineered meganuclease comprises an amino acid sequence of SEQ ID NO: 10. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 40. In some embodiments, the engineered meganuclease is encoded by a nucleic acid sequence set forth in SEQ ID NO: 40.

MIT 25-26x.91 263T>R (SEQ ID NO: 11)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 11. In some embodiments, the HVR1 region comprises one or more residues corresponding to residues 24, 26, 28, 30, 32, 33, 38, 40, 42, 44, 46, 68, 70, 75, and 77 of SEQ ID NO: 11. In some embodiments, the HVR1 region comprises residues corresponding to residues 24, 26, 28, 30, 32, 33, 38, 40, 42, 44, 46, 68, 70, 75, and 77 of SEQ ID NO: 11. In some embodiments, the HVR1 region comprises Y, R, K, or D at a residue corresponding to residue 66 of SEQ ID NO: 11. In some embodiments, the HVR1 region comprises residues 24-79 of SEQ ID NO: 11 with up to 1, 2, 3, 4, 5, 6, 7, 8, 9, 10, or 11 amino acid substitutions. In some embodiments, the HVR1 region comprises residues 24-79 of SEQ ID NO: 11.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 11. In some embodiments, the first subunit comprises G, S, or A at a residue corresponding to residue 19 of SEQ ID NO: 11. In some embodiments, the first subunit comprises a residue corresponding to residue 19 of SEQ ID NO: 11. In some embodiments, the first subunit comprises E, Q, or K at a residue corresponding to residue 80 of SEQ ID NO: 11. In some embodiments, the first subunit comprises a residue corresponding to residue 80 of SEQ ID NO: 11. In some embodiments, the first subunit comprises residues 7-153 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 11.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 11. In some embodiments, the HVR2 region comprises one or more residues corresponding to residues 215, 217, 219, 221, 223, 224, 229, 231, 233, 235, 237, 259, 261, 266, and 268 of SEQ ID NO: 11. In some embodiments, the HVR2 region comprises residues corresponding to residues 215, 217, 219, 221, 223, 224, 229, 231, 233, 235, 237, 259, 261, 266, and 268 of SEQ ID NO: 11. In some embodiments, the HVR2 region comprises Y, R, K, or D at a residue corresponding to residue 257 of SEQ ID NO: 11. In some embodiments, the HVR2 region comprises a residue corresponding to residue 241 of SEQ ID NO: 11. In some embodiments, the HVR2 region comprises a residue corresponding to residue 263 of SEQ ID NO: 11. In some embodiments, the HVR2 region comprises a residue corresponding to residue 264 of SEQ ID NO: 11. In some embodiments, the HVR2 region comprises residues 215-270 of SEQ ID NO: 11 with up to 1, 2, 3, 4, 5, 6, 7, 8, 9, 10, or 11 amino acid substitutions. In some embodiments, the HVR2 region comprises residues 215-270 of SEQ ID NO: 11.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 11. In some embodiments, the second subunit comprises G, S, or A at a residue corresponding to residue 210 of SEQ ID NO: 11. In some embodiments, the second subunit comprises E, Q, or K at a residue corresponding to residue 271 of SEQ ID NO: 11. In some embodiments, the second subunit comprises a residue corresponding to residue 330 of SEQ ID NO: 11. In some embodiments, the second subunit comprises residues 198-344 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 11.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 11. In some embodiments, the engineered meganuclease comprises an amino acid sequence of SEQ ID NO: 11. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 41. In some embodiments, the engineered meganuclease is encoded by a nucleic acid sequence set forth in SEQ ID NO: 41.

MIT 25-26x.91 46H>W (SEQ ID NO: 12)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 12. In some embodiments, the HVR1 region comprises one or more residues corresponding to residues 24, 26, 28, 30, 32, 33, 38, 40, 42, 44, 46, 68, 70, 75, and 77 of SEQ ID NO: 12. In some embodiments, the HVR1 region comprises residues corresponding to residues 24, 26, 28, 30, 32, 33, 38, 40, 42, 44, 46, 68, 70, 75, and 77 of SEQ ID NO: 12. In some embodiments, the HVR1 region comprises Y, R, K, or D at a residue corresponding to residue 66 of SEQ ID NO: 12. In some embodiments, the HVR1 region comprises residues 24-79 of SEQ ID NO: 12 with up to 1, 2, 3, 4, 5, 6, 7, 8, 9, 10, or 11 amino acid substitutions. In some embodiments, the HVR1 region comprises residues 24-79 of SEQ ID NO: 12.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 12. In some embodiments, the first subunit comprises G, S, or A at a residue corresponding to residue 19 of SEQ ID NO: 12. In some embodiments, the first subunit comprises a residue corresponding to residue 19 of SEQ ID NO: 12. In some embodiments, the first subunit comprises E, Q, or K at a residue corresponding to residue 80 of SEQ ID NO: 12. In some embodiments, the first subunit comprises a residue corresponding to residue 80 of SEQ ID NO: 12. In some embodiments, the first subunit comprises residues 7-153 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 12.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 12. In some embodiments, the HVR2 region comprises one or more residues corresponding to residues 215, 217, 219, 221, 223, 224, 229, 231, 233, 235, 237, 259, 261, 266, and 268 of SEQ ID NO: 12. In some embodiments, the HVR2 region comprises residues corresponding to residues 215, 217, 219, 221, 223, 224, 229, 231, 233, 235, 237, 259, 261, 266, and 268 of SEQ ID NO: 12. In some embodiments, the HVR2 region comprises Y, R, K, or D at a residue corresponding to residue 257 of SEQ ID NO: 12. In some embodiments, the HVR2 region comprises a residue corresponding to residue 241 of SEQ ID NO: 12. In some embodiments, the HVR2 region comprises a residue corresponding to residue 263 of SEQ ID NO: 12. In some embodiments, the HVR2 region comprises a residue corresponding to residue 264 of SEQ ID NO: 12. In some embodiments, the HVR2 region comprises residues 215-270 of SEQ ID NO: 12 with up to 1, 2, 3, 4, 5, 6, 7, 8, 9, 10, or 11 amino acid substitutions. In some embodiments, the HVR2 region comprises residues 215-270 of SEQ ID NO: 12.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 12. In some embodiments, the second subunit comprises G, S, or A at a residue corresponding to residue 210 of SEQ ID NO: 12. In some embodiments, the second subunit comprises E, Q, or K at a residue corresponding to residue 271 of SEQ ID NO: 12. In some embodiments, the second subunit comprises a residue corresponding to residue 330 of SEQ ID NO: 12. In some embodiments, the second subunit comprises residues 198-344 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 12.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 12. In some embodiments, the engineered meganuclease comprises an amino acid sequence of SEQ ID NO: 12. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 42. In some embodiments, the engineered meganuclease is encoded by a nucleic acid sequence set forth in SEQ ID NO: 42.MTPs for directing the engineered meganuclease into the mitochondria can be from 10-100 amino acids in length. In specific embodiments, the MTP is about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, about 65, about 70, about 75, about 80, about 85, about 90, about 95, about 100, or more amino acids long. MTPs can contain additional signals that subsequently target the protein to different regions of the mitochondria, such as the mitochondrial matrix. Non limiting examples of MTPs for use in the compositions and methods disclose herein include, *Neurospora crassa* F0 ATPase subunit 9 (SU9) MTP, human cytochrome c oxidase subunit VIII (CoxVIII or Cox8) MTP, the P1 isoform of subunit c of human ATP synthase MTP, aldehyde dehydrogenase targeting sequence MTP, Glutaredoxin 5 MTP, Pyruvate dehydrogenase MTP, Peptidyl-prolyl isomerase MTP, Acetyltransferase MTP, Isocitrate dehydrogenase MTP, cytochrome oxidase MTP, and the subunits of the FA portion of ATP synthase MTP, CPN60/No GGlinker MTP, Superoxide dismutase (SOD) MTP, Superoxide dismutase doubled (2SOD) MTP, Superoxide dismutase modified (SODmod) MTP, Superoxide dismutase modified (2SODmod) doubled MTP, L29 MTP, gATPase gamma subunit (FAγ51) MTP, CoxIV twin strep (ABM97483) MTP, and CoxIV 10×His MTP.

In specific embodiments, the MTP comprises a combination of at least two MTPs. The combination of MTPs can be a combination of identical MTPs or a combination of different MTPs. In specific embodiments, the MTP comprises the Cox VIII MTP (SEQ ID NO: 43) and the SU9 MTP (SEQ ID NO: 44) into a single MTP represented by SEQ ID NO: 45.

In order to form an MTEM, an MTP can be attached by any appropriate means to an engineered meganuclease described herein. In specific embodiments, the MTP can be attached to the N-terminus of the engineered meganuclease.

In other embodiments the MTP can be attached to the C-terminus of the engineered meganuclease. In some embodiments multiple MTPs can be attached to a single engineered meganuclease to form an MTEM. For example, a first MTP can be attached to the N-terminus of the engineered meganuclease and a second MTP can be attached to the C-terminus of the engineered meganuclease. In some embodiments, the first and second MTP are identical and in other embodiments, the first and second MTP not identical. The MTP(s) can be attached by any means that allows for transport of the engineered meganuclease into the mitochondria of a cell. In specific embodiments, the MTP is attached by fusing the MTP to the N- or C-terminus of the engineered meganuclease. The MTP can also be attached to the engineered meganuclease by a peptide linker. The linker can be, for example, about 1, 2, 3, 4, 5, 6, 7, 8, 9, 10, 11, 12, 15, or 20 amino acids. In specific embodiments the MTP is attached to a peptide linker at the N- or C-terminus of the engineered meganuclease.

In some embodiments, an MTEM or an engineered meganuclease described herein for use in the compositions and methods of the present disclosure is attached to a nuclear export sequence (NES) in order to help prevent the engineered meganuclease from cleaving the nuclear genome. In some such embodiments, the NES comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 46 or 47. For example, the NES may comprise the amino acid sequence of SEQ ID NO: 46 or 47. In certain embodiments, the NES is attached at the N-terminus of the engineered meganuclease. In other embodiments, the NES is attached at the C-terminus of the engineered meganuclease. In certain embodiments, the NES is fused to the engineered meganuclease. In certain embodiments, the NES is attached to the engineered meganuclease by a polypeptide linker.

In specific embodiments, the MTEM or an engineered meganuclease described herein is attached to multiple NESs. For example, an engineered meganuclease described herein can comprise a first NES and a second NES. In some such embodiments, the first NES is attached at the N-terminus of the MTEM or an engineered meganuclease described herein, and the second NES is attached at the C-terminus of the MTEM or an engineered meganuclease described herein. In some such embodiments, the first NES and/or the second NES comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to the amino acid sequence set forth in SEQ ID NO: 46 or 47. For example, the first NES and/or the second NES may comprise the amino acid sequence set forth in SEQ ID NO: 46 or 47. In some embodiments, the first NES and the second NES are identical. In other embodiments, the first NES and the second NES are not identical. The NES can be attached to the MTEM or an engineered meganuclease described herein by any appropriate means known in the art. For example, the first NES and/or the second NES can be fused to the MTEM or an engineered meganuclease described herein. In some embodiments, the first NES and/or the second NES is attached to the MTEM or an engineered meganuclease described herein by a polypeptide linker.

An MTEM or an engineered meganuclease described herein with an NES may have reduced or decreased transport to the nucleus of a target cell or target cell population (e.g., a eukaryotic cell or eukaryotic cell population), compared to an engineered meganuclease without an NES. For example, nuclear transport of an MTEM or an engineered meganuclease described herein with an NES may be less than that of an MTEM or an engineered meganuclease described herein without an NES, by about 5-10%, 10-20%, 20-30%, 30-40%, 40-50%, 50-60%, 60-70%, 70-80%, 80-90%, 90-100%, or more (e.g., by about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100%, or more). In some embodiments, an engineered meganuclease with an NES may induce fewer nuclear indels (i.e., less cleavage and resulting deletion in nuclear genome of a target cell or target cell population) compared to an MTEM or an engineered meganuclease described herein without an NES. For example, nuclear indels induced by an MTEM or an engineered meganuclease described herein with an NES may be less than that induced by an MTEM or an engineered meganuclease described herein without an NES, by about 5-10%, 10-20%, 20-30%, 30-40%, 40-50%, 50-60%, 60-70%, 70-80%, 80-90%, 90-100%, or more.

2.3 Pharmaceutical Compositions

In some embodiments, the invention provides a pharmaceutical composition comprising a pharmaceutically acceptable carrier and an MTEM or an engineered meganuclease described herein, or a pharmaceutically acceptable carrier and an isolated polynucleotide comprising a nucleic acid sequence encoding an MTEM or an engineered meganuclease described herein. In particular, pharmaceutical compositions are provided that comprise a pharmaceutically acceptable carrier and a therapeutically effective amount of a nucleic acid encoding an MTEM or an engineered meganuclease described herein or an MTEM or an engineered meganuclease described herein, wherein the engineered meganuclease of the MTEM or an engineered meganuclease described herein has specificity for a recognition sequence within mtDNA, such as human mtDNA (e.g., the MIT 25-26 recognition sequence of SEQ ID NO: 1).

In other embodiments, the invention provides a pharmaceutical composition comprising a pharmaceutically acceptable carrier and a genetically-modified cell described herein.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, nuclease polypeptides (or DNA/RNA encoding the same or cells expressing the same) are typically admixed with a pharmaceutically acceptable carrier, and the resulting composition is administered to a subject. The carrier must be acceptable in the sense of being compatible with any other ingredients in the formulation and must not be deleterious to the subject. In some embodiments, pharmaceutical compositions described herein can further comprise one or more additional agents or biological molecules useful in the treatment of a disease in the subject. Likewise, the additional agent(s) and/or biological molecule(s) can be co-administered as a separate composition.

In particular embodiments described herein, the pharmaceutical composition comprises a recombinant virus (i.e., a viral vector) comprising a polynucleotide (e.g., a viral genome) comprising a nucleic acid sequence encoding an MTEM or an engineered meganuclease described herein. Such recombinant viruses are known in the art and include recombinant retroviruses, recombinant lentiviruses, recombinant adenoviruses, and recombinant adeno-associated viruses (AAV) (reviewed in Vannucci, et al. (2013 *New Microbiol.* 36:1-22). Recombinant AAVs useful in the invention can have any capsid or serotype that allows for transduction of the virus into a target cell type and expression of the MTEM or an engineered meganuclease described herein by the target cell. For example, in some embodiments, recombinant AAV has a serotype of AAV1, AAV2, AAV3, AAV3B, AAV4, AAV5, AAV6, AAV7, AAV8, AAV9, AAV10, AAV11, or AAVHSC. In some embodiments, the recombinant virus is injected directly into target tissues. In alternative embodiments, the recombinant virus is delivered systemically via the circulatory system. It is known in the art that different AAVs tend to localize to different tissues, and one could select an appropriate AAV capsid/serotype for preferential delivery to a particular tissue. Accordingly, in some embodiments, the AAV serotype is AAV9. AAVs can also be self-complementary such that they do not require second-strand DNA synthesis in the host cell (McCarty, et al. (2001) *Gene Ther.* 8:1248-54). Nucleic acids delivered by recombinant AAVs can include left (5') and right (3') inverted terminal repeats.

In particular embodiments described herein, the pharmaceutical composition comprises one or more mRNAs described herein (e.g., mRNAs encoding an MTEM or an engineered meganuclease described herein) formulated within lipid nanoparticles.

The selection of cationic lipids, non-cationic lipids and/or lipid conjugates which comprise the lipid nanoparticle, as well as the relative molar ratio of such lipids to each other, is based upon the characteristics of the selected lipid(s), the nature of the intended target cells, and the characteristics of the mRNA to be delivered. Additional considerations include, for example, the saturation of the alkyl chain, as well as the size, charge, pH, pKa, fusogenicity and toxicity of the selected lipid(s). Thus, the molar ratios of each individual component may be adjusted accordingly.

The lipid nanoparticles for use in the method described herein can be prepared by various techniques which are presently known in the art. Nucleic acid-lipid particles and their method of preparation are disclosed in, for example, U.S. Patent Publication Nos. 20040142025 and 20070042031, the disclosures of which are herein incorporated by reference in their entirety for all purposes.

Selection of the appropriate size of lipid nanoparticles must take into consideration the site of the target cell and the application for which the lipid nanoparticles is being made. Generally, the lipid nanoparticles will have a size within the range of about 25 to about 500 nm. In some embodiments, the lipid nanoparticles have a size from about 50 nm to about 300 nm or from about 60 nm to about 120 nm. The size of the lipid nanoparticles may be determined by quasi-electric light scattering (QELS) as described in Bloomfield, *Ann. Rev. Biophys. Bioeng.*, 10:421^150 (1981), incorporated herein by reference. A variety of methods are known in the art for producing a population of lipid nanoparticles of particular size ranges, for example, sonication or homogenization. One such method is described in U.S. Pat. No. 4,737,323, incorporated herein by reference.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid comprises from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain particular embodiments, the phospholipid is DPPC, DSPC, or mixtures thereof.

In some embodiments, the non-cationic lipid (e.g., one or more phospholipids and/or cholesterol) comprises from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-di-oxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition comprises amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N', N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (LIPOFECTIN®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (TRANSFECTAM®) (C18) 2Gly+ N,N-dioctadecylamido-glycine, CTAB cetyltrimethylammonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid, or other amino acids or aminodicarboxylic acids. According to the same principle, the esters of hydroxycarboxylic acids or hydroxydicarboxylic acids and PS are also weakly anionic compounds.

In some embodiments, amphoteric liposomes contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Some particular examples are PEG-modified diacylglycerols and dialkylglycerols.

In some embodiments, the neutral lipids comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition that specifically enhances delivery and uptake in a eukaryotic cell, such as a mammalian cell (e.g., a human cell). In certain embodiments, the lipid nanoparticles have a composition that specifically enhances delivery and uptake in the liver or specifically within hepatocytes. In certain embodiments, the lipid nanoparticles have a composition that specifically enhances delivery and uptake in a nerve cell.

2.4 Methods for Producing Recombinant Viruses

In some embodiments, the invention provides recombinant viruses (e.g., recombinant AAVs) for use in the methods described herein. Recombinant AAVs are typically produced in mammalian cell lines such as HEK-293. Because the viral cap and rep genes are removed from the vector to prevent its self-replication to make room for the therapeutic gene(s) to be delivered (e.g. the nuclease gene), it is necessary to provide these in trans in the packaging cell line. In addition, it is necessary to provide the "helper" (e.g., adenoviral) components necessary to support replication (Cots et al. (2013), Curr. Gene Ther. 13(5): 370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAVs are typically produced (manufactured) in cells, precautions must be taken in practicing the current invention to ensure that the MTEM or an engineered meganuclease described herein is not expressed in the packaging cells. Because the viral genomes described herein may comprise a recognition sequence for the nuclease, any nuclease expressed in the packaging cell line may be capable of cleaving the viral genome before it can be packaged into viral particles. This will result in reduced packaging efficiency and/or the packaging of fragmented genomes. Several approaches can be used to prevent nuclease expression in the packaging cells.

The MTEM or an engineered meganuclease described herein can be placed under the control of any promoter suitable for expression of the MTEM or an engineered meganuclease described herein. In some embodiments, the promoter is a constitutive promoter, or the promoter is tissue-specific promoter such as, for example, a stem cell-specific promoter, a CD34+ HSC-specific promoter, a muscle-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, a pancreatic beta cell-specific promoter, a kidney cell-specific promoter, a bone marrow cell-specific promoter, or an ear hair cell-specific promoter. In some embodiments, the ubiquitous promoter is a CMV promoter, a CAG promoter, an EF1 alpha promoter, or a UbC promoter.

In specific embodiments, the MTEM or an engineered meganuclease described herein can be placed under control of a tissue-specific promoter that is not active in the packaging cells. For example, if a viral vector is developed for delivery of a nuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human α1-antitrypsin (such as Pa1AT), and hemopexin (such as Phpx) (Kramer et al., (2003) Mol. Therapy 7:375-85), hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of nuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox et al., (2010), PLoS One v.5(8):e12274).

Alternatively, the recombinant virus can be packaged in cells from a different species in which the nuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao, et al. (Gao et al. (2007), J. Biotechnol. 131(2):138-43). A nuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a nuclease. Because these introns are not spliced efficiently from pre-mRNA transcripts in insect cells, insect cells will not express a functional nuclease and will package the full-length genome. In contrast, mammalian cells to which the resulting recombinant AAV particles are delivered will properly splice the pre-mRNA and will express functional nuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The MTEM or an engineered meganuclease described herein gene can be operably linked to an inducible promoter such that a small-molecule inducer is required for nuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the nuclease gene under the control of a promoter that responds to the corresponding transcription factor, the nuclease gene having (a) binding site(s) for the transcription factor; and 2) including the gene encoding the transcription factor in the packaged viral genome. The latter step is necessary because the nuclease will not be expressed in the target cells or tissues following recombinant AAV delivery if the transcription activator is not also provided to the same cells. The transcription activator then induces nuclease gene expression only in cells or tissues that are treated with the cognate small-molecule activator. This approach is advantageous because it enables nuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAVs are produced in a mammalian cell line that expresses a transcription repressor that prevents expression of the nuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the nuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183: 137-42). The use of a non-human transcription repressor ensures that transcription of the nuclease gene will be repressed only in the packaging cells expressing the repressor and not in target cells or tissues transduced with the resulting recombinant AAV.

2.5 Methods for Producing Genetically-Modified Cells

The invention provides methods for producing genetically-modified cells, both in vitro and in vivo, using an MTEM or an engineered meganuclease described herein that bind and cleave recognition sequences found within mtDNA, such as human mtDNA. Cleavage at such recognition sequences can allow for NHEJ at the cleavage site, insertion of an exogenous sequence via homologous recombination, or degradation of the mtDNA.

The invention includes that an MTEM or an engineered meganuclease described herein, or a nucleic acid encoding the MTEM or an engineered meganuclease described herein, can be delivered (i.e., introduced) into cells, such as eukaryotic cells (e.g., human cells).

MTEMs or engineered meganucleases described herein can be delivered into a cell in the form of protein or, preferably, as a nucleic acid encoding the MTEM or an engineered meganuclease described herein. Such nucleic acid can be DNA (e.g., circular or linearized plasmid DNA or PCR products) or RNA (e.g., mRNA). Accordingly, polynucleotides are provided herein that comprise a nucleic acid sequence encoding an MTEM or an engineered meganuclease described herein. In specific embodiments, the polynucleotide is an mRNA. The polynucleotides encoding an MTEM or an engineered meganuclease described herein can be operably linked to a promoter. In specific embodiments, expression cassettes are provided that comprise a promoter operably linked to a polynucleotide having a nucleic acid sequence encoding a MTEM or an engineered meganuclease described herein.

For embodiments in which the MTEM or an engineered meganuclease coding sequence is delivered in DNA form, it should be operably linked to a promoter to facilitate transcription of the MTEM or an engineered meganuclease-encoding sequence. Mammalian promoters suitable for the invention include constitutive promoters such as the cytomegalovirus early (CMV) promoter (Thomsen et al. (1984), Proc Natl Acad Sci USA. 81(3):659-63), the SV40 early promoter (Benoist and Chambon (1981), Nature. 290(5804): 304-10), a CAG promoter, an EF1 alpha promoter, or a UbC promoter, as well as inducible promoters such as the tetracycline-inducible promoter (Dingermann et al. (1992), Mol Cell Biol. 12(9):4038-45). An MTEM or an engineered meganuclease described herein can also be operably linked to a synthetic promoter. Synthetic promoters can include, without limitation, the JeT promoter (WO 2002/012514). In specific embodiments, a nucleic acid sequence encoding an MTEM or an engineered meganuclease described herein is operably linked to a tissue-specific promoter, such as a muscle cell-specific promoter, a skeletal muscle-specific promoter, a myotube-specific promoter, a muscle satellite cell-specific promoter, a neuron-specific promoter, an astrocyte-specific promoter, a microglia-specific promoter, an eye cell-specific promoter, a retinal cell-specific promoter, a retinal ganglion cell-specific promoter, a retinal pigmentary epithelium-specific promoter, a pancreatic cell-specific promoter, or a pancreatic beta cell-specific promoter.

In specific embodiments, a nucleic acid sequence encoding an MTEM or an engineered meganuclease is delivered on a recombinant DNA construct or expression cassette. For example, the recombinant DNA construct can comprise an expression cassette (i.e., "cassette") comprising a promoter and a polynucleotide having a nucleic acid sequence encoding an MTEM or an engineered meganuclease described herein. The polynucleotides provided herein can be mRNA or DNA. In particular embodiments, the polynucleotides further comprise a sequence encoding a selectable marker. The selectable marker can be any marker that allows selection of cells or organisms (e.g., bacteria, eukaryotic cells, mammalian cells, plant cells, plants, and/or plant parts) that contain a polynucleotide described herein. In specific embodiments, the selectable marker is an antibiotic resistance gene.

In some embodiments, mRNA encoding the METM is delivered to a cell because this reduces the likelihood that the gene encoding the MTEM or an engineered meganuclease described herein will integrate into the genome of the cell.

Such mRNA encoding an METM can be produced using methods known in the art such as in vitro transcription. In some embodiments, the mRNA is 5' capped using 7-methylguanosine, anti-reverse cap analogs (ARCA) (U.S. Pat. No. 7,074,596), CLEANCAP® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded MTEM or an engineered meganuclease described herein and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

Purified MTEMs or an engineered meganucleases described herein can be delivered into cells to cleave mitochondrial DNA by a variety of different mechanisms known in the art, including those further detailed herein.

In another particular embodiment, a nucleic acid encoding an MTEM or an engineered meganuclease described herein is introduced into the cell using a single-stranded DNA template. The single-stranded DNA can further comprise a 5' and/or a 3' AAV inverted terminal repeat (ITR) upstream and/or downstream of the sequence encoding the MTEM or an engineered meganuclease described herein. The single-stranded DNA can further comprise a 5' and/or a 3' homology arm upstream and/or downstream of the sequence encoding the MTEM or an engineered meganuclease described herein.

In another particular embodiment, genes encoding an MTEM or an engineered meganuclease described herein is introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

Purified MTEMs or engineered meganucleases described herein, or nucleic acids encoding MTEMs or engineered meganucleases described herein, can be delivered into cells to cleave mitochondrial DNA by a variety of different mechanisms known in the art, including those further detailed herein below.

In some embodiments, MTEMs or engineered meganucleases described herein, DNA/mRNA encoding MTEMs or engineered meganucleases described herein, or cells expressing MTEMs or engineered meganucleases described herein are formulated for systemic administration, or administration to target tissues, in a pharmaceutically acceptable carrier in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, proteins/RNA/mRNA/cells are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, the MTEMs or engineered meganucleases described herein, or DNA/mRNA encoding the MTEMs or engineered meganucleases described herein, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, MTEMs or engineered meganucleases described herein, or DNA/mRNA encoding MTEMs or engineered meganucleases described herein, are coupled covalently or non-covalently to an antibody that recognizes a specific cell-surface receptor expressed on target cells such that the MTEM protein/DNA/mRNA binds to and is internalized by the target cells. Alternatively, MTEM protein/DNA/mRNA can be coupled covalently or non-covalently to the natural ligand (or a portion of the natural ligand) for such a cell-surface receptor. (McCall, et al. (2014) *Tissue Barriers.* 2(4):e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508).

In some embodiments, MTEMs or engineered meganucleases described herein, or DNA/mRNA encoding MTEMs or engineered meganucleases described herein, are encapsulated within biodegradable hydrogels. Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, MTEMs or engineered meganucleases described herein, or DNA/mRNA encoding MTEMs or engineered meganucleases described herein, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the nuclease proteins, mRNA, or DNA can be attached to or encapsulated with the nanoparticle core. This increases the copy number of the protein/mRNA/DNA that is delivered to each cell and, so, increases the intracellular expression of each MTEM or an engineered meganuclease described herein to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the MTEMs or engineered meganucleases described herein or DNA/mRNA encoding the MTEMs or engineered meganucleases described herein are encapsulated within liposomes or complexed using cationic lipids (see, e.g., LIPOFECTAMINE™, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, MTEMs or engineered meganucleases described herein, or DNA/mRNA encoding MTEMs or engineered meganucleases described herein, are encapsulated within polymeric scaffolds (e.g., PLGA) or complexed using cationic polymers (e.g., PEI, PLL) (Tamboli et al. (2011) *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, MTEMs or engineered meganucleases described herein, or DNA/mRNA encoding nMTEMs or engineered meganucleases described herein, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, MTEMs or engineered meganucleases described herein, or DNA/mRNA encoding MTEMs or engineered meganucleases described herein, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, MTEMs or engineered meganucleases described herein, or DNA/mRNA encoding MTEMs or engineered meganucleases described herein, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability, reduce nonspecific interactions, and enhance cell-specific targeting and drug release.

In some embodiments, polynucleotides having nucleic acid sequences encoding an MTEM are introduced into a cell using a recombinant virus. Such recombinant viruses are known in the art and include recombinant retroviruses, recombinant lentiviruses, recombinant adenoviruses, and recombinant AAVs (reviewed in Vannucci, et al. (2013 *New Microbiol.* 36:1-22). Recombinant AAVs useful in the invention can have any capsid or serotype that allows for transduction of the virus into a target cell type and expression of the MTEM by the target cell. For example, in some embodiments, recombinant AAV has a serotype of AAV1, AAV2, AAV3, AAV3B, AAV4, AAV5, AAV6, AAV7, AAV8, AAV9, AAV10, AAV11, or AAVHSC. In some embodiments, the recombinant virus is injected directly into target tissues. In alternative embodiments, the recombinant virus is delivered systemically via the circulatory system. It is known in the art that different AAVs tend to localize to different tissues, and one could select an appropriate AAV capsid/serotype for preferential delivery to a particular tissue. In some embodiments, the AAV serotype is AAV9. AAVs can also be self-complementary such that they do not require second-strand DNA synthesis in the host cell (McCarty, et al. (2001) *Gene Ther.* 8:1248-54). Nucleic acids delivered by recombinant AAVs can include left (5') and right (3') inverted terminal repeats.

In one embodiment, a recombinant virus used for delivery of a polynucleotide having nucleic acid sequences encoding an MTEM or engineered meganuclease described herein is a self-limiting recombinant virus. A self-limiting recombinant virus can have limited persistence time in a cell or organism due to the presence of a recognition sequence for an engineered meganuclease within the vector. Thus, a self-limiting recombinant virus can be engineered to provide coding for a promoter, an MTEM or engineered meganuclease described herein, and a meganuclease recognition site within the ITRs. The self-limiting recombinant virus delivers the meganuclease gene to a cell, tissue, or organism, such that the MTEM or engineered meganuclease described herein is expressed and able to cut the genome of the cell at an endogenous recognition sequence within the genome. The delivered meganuclease will also find its target site within the self-limiting recombinant virus itself, and cut the vector at this target site. Once cut, the 5' and 3' ends of the viral genome will be exposed and degraded by exonucleases, thus killing the virus and ceasing production of the MTEM or engineered meganuclease described herein.

If the polynucleotides having nucleic acid sequences encoding an MTEM or engineered meganuclease described herein are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or constitutive or tissue-specific promoters described elsewhere herein. In a particular embodiment, polynucleotides having nucleic acid sequences encoding an MTEM or engineered meganuclease described herein are operably linked to a promoter that drives gene expression preferentially in the target cells, such as neurons, glial cells (e.g., astrocytes or oligodendrocytes), muscle cells (e.g., skeletal muscle cells, cardiac muscle cells or smooth muscle cells), etc. In some embodiments, the target cell is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells or the population of target cells is a population of muscle cells, a skeletal muscle cells, a myotube cells, a muscle satellite cells, a neuron, an astrocyte, a microglia cells, an eye cells, a retinal cells, a retinal ganglion cells, a retinal pigmentary epithelium cells, a pancreatic cells, or a pancreatic beta cells, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells.

In some embodiments, provided herein are methods for producing a genetically-modified eukaryotic cell or a genetically-modified eukaryotic cell population by introducing into the eukaryotic cell or eukaryotic cell population a polynucleotide of the present disclosure, such as a polynucleotide containing a nucleic acid sequence that encodes an engineered meganuclease described hereinabove. Upon expression in the eukaryotic cell or eukaryotic cell population, the engineered meganuclease localizes to the mitochondria, binds a recognition sequence in the mitochondrial genome, and generates a cleavage site. The cleavage site generated by the engineered meganuclease can be repaired by NHEJ repair pathway which may result in a nucleic acid insertion or deletion at the cleavage site. Additionally or alternatively, the cleavage site generated by the engineered meganuclease in the mitochondrial genome of the eukaryotic cell or eukaryotic cell population can be repaired by alternative nonhomologous end-joining (Alt-NHEJ) or microhomology-mediated end joining (MMEJ). The NHEJ or Alt-NHEJ/MMEJ can result in insertion and/or deletion of a nucleic acid at the cleavage site. In particular, the NHEJ or Alt-NHEJ/MMEJ can result in insertion and/or deletion of 1-1000 (e.g., 1-10, 10-100, 100-200, 200-300, 300-400, 400-500, 500-600, 600-700, 700-80, 800-900, or 900-1000) nucleotides, such as about 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nucleotides at the cleavage site. In some embodiments, mitochondrial genomes in a genetically-modified eukaryotic cell described herein or a genetically-modified eukaryotic cell population described herein can be degraded. In some such embodiments, the percentage of mitochondrial genomes comprising the recognition sequence is decreased by about 30%, 35%, 40%, 45%, 50%, 55%, 60%, 65%, 70%, 75%, 80%, 85%, 90%, 95%, 96%, 97%, 98%, 99%, or 100%, or can be degraded by about can be degraded by about 30-40%, 40-50%, 50-60%, 60-70%, 70-80%, 80-90%, 90-100%, or more, compared to a control cell.

In specific embodiments, mutant mitochondrial genomes comprising the recognition sequence of SEQ ID NO: 1 are degraded. By degrading mutant mitochondrial genomes having the recognition sequence of SEQ ID NO: 1, the overall ratio of wild-type mitochondrial genomes to mutant mitochondrial genomes will increase following administration or expression of an MTEM or engineered meganuclease described herein. In some embodiments, the ratio of wild-type to mutant mitochondrial genomes in a single genetically-modified eukaryotic cell described herein or a population genetically-modified eukaryotic cells increases to about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 20:1, about 50:1, about 100:1, about 150:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, about 1000:1, or more.

In particular embodiments, the percentage of wild-type genomes in a single genetically-modified eukaryotic cell described herein or a population of genetically-modified eukaryotic cells described herein, can increase as mutant mitochondrial genomes comprising SEQ ID NO: 1 are recognized, cleaved, and degraded by the MTEM or engineered meganuclease described herein. The percentage of wild-type mitochondrial genomes in a genetically-modified eukaryotic cell or genetically modified cell population described herein can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, of the total mitochondrial genomes in the genetically-modified eukaryotic cell or genetically modified cell population when compared to a eukaryotic cell or eukaryotic cell population that does not express an MTEM or engineered meganuclease described herein. Likewise the percentage of mutant mitochondrial genomes comprising the recognition sequence of SEQ ID NO: 1 in the genetically-modified eukaryotic cell or genetically-modified cell population can decrease by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more when compared to a eukaryotic cell or eukaryotic cell population that does not express an MTEM or engineered meganuclease described herein.

In some embodiments, mitochondrial respiration in a genetically-modified eukaryotic cell or a genetically-modified eukaryotic cell population described herein can increase by about 30%, about 35%, about 40%, about 45%, about 50%, about 55%, about 60%, about 65%, about 70%, about 75%, about 80%, about 85%, about 90%, about 95%, about 100%, or more when compared to a eukaryotic cell that does not express an MTEM or engineered meganuclease described herein. Mitochondrial respiration in a genetically-modified eukaryotic cell or a genetically-modified eukaryotic cell population described herein can be increased by about 30-40%, 40-50%, 50-60%, 60-70%, 70-80%, 80-90%, 90-100%, or more when compared to a eukaryotic cell or eukaryotic cell population that does not express an MTEM or engineered meganuclease described herein.

In certain instances, the recognition sequence is within a region of the mitochondrial genome associated with a mitochondrial disorder. For example, the recognition sequence can be within a region of the mitochondrial genome associated with Mitochondrial Encephalomyopathy, Lactic Acidosis, and Stroke-like episodes (MELAS)) Mutations in the mtDNA gene MT-TL1 are associated with MELAS in approximately 80% of cases. Over 80% of MELAS cases is caused by a A3243G point mutation in tRNA-Leu. Mutations in MT-TQ, MT-TH, MT-TK, MT-TS1, MT-ND1, MT-ND5, MT-ND6, and MT-TS2 have also been associated with MELAS syndrome. Some cases of MELAS syndrome appear to occur as the result of a new spontaneous mutation in a mitochondrial gene and are not inherited (Sue et al., J Pediatr 134:696-700 (1999); Singh et al., Indian J Pediatr 66:621-625 (1999); Deschauer et al., Neuromuscul Disord 9:305-307 (1999)). MELAS begins in childhood, usually between two and fifteen years of age, and mostly affects the nervous system and muscles. The most common early symptoms are seizures, recurrent headaches, loss of appetite and recurrent vomiting. Stroke-like episodes with temporary muscle weakness on one side of the body (hemiparesis) may also occur and this can lead to altered consciousness, vision and hearing loss, loss of motor skills and intellectual disability. MELAS is caused by mutations in mtDNA.

Both normal and mutated mtDNA can exist in the same cell, a situation known as heteroplasmy. The number of defective mitochondria may be out-numbered by the number of normal mitochondria. Symptoms may not appear in any given generation until the mutation affects a significant proportion of mtDNA. The uneven distribution of normal and mutant mtDNA in different tissues can affect different organs in members of the same family. This can result in a variety of symptoms in affected family members.

In specific embodiments, the recognition sequence described herein in the mitochondrial genome of the eukaryotic cell or eukaryotic cell population is positioned between nucleotides 3000 and 3500 of the mitochondrial genome. In particular embodiments, the MTEMs or engineered meganucleases described herein target an A3243G mutation of the mitochondrial genomes. As used herein a "MELAS mutation" refers to the A3243G mutation of the mitochondrial genome wherein the A of the wild-type genome is replaced with a G in the mutant mitochondrial genome at position 3243. In particular embodiments, the recognition sequence of SEQ ID NO: 1 is located only on mutant mitochondrial genomes. Upon expression in the genetically-modified eukaryotic cell or genetically-modified eukaryotic cell population, the MTEM or engineered meganuclease can localize to the mitochondria, bind the recognition sequence in the mitochondrial genome, and generate a cleavage site. Thus, by targeting a recognition sequence only located on mutant genomes, the genomes can be cleaved and subsequently degraded. This specific degradation of mutant mitochondrial genomes can be used to help treat or alleviate the symptoms of the MELAS.

Accordingly, methods are provided herein for degrading mutant mitochondrial genomes in a target cell or a population of target cells by delivering to the target cell or population a polynucleotide comprising a nucleic acid sequence encoding an MTEM or engineered meganuclease or an MTEM or engineered meganuclease described herein. In specific embodiments, the target cell or population of target cells comprise mutant mitochondrial genomes having the MELAS mutation (i.e., A3243G mutation), and the MTEM or engineered meganuclease recognizes and cleaves the recognition sequence of SEQ ID NO: 1. The target cell or target cell population can be in a mammalian subject, such as a human subject. In some embodiments, the target cell is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells or the population of target cells is a population of muscle cells, a skeletal muscle cells, a myotube cells, a muscle satellite cells, a neuron, an astrocyte, a microglia cells, an eye cells, a retinal cells, a retinal ganglion cells, a retinal pigmentary epithelium cells, a pancreatic cells, or a pancreatic beta cells, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells.

Methods of treating a condition associated with a MELAS disorder in a subject are described herein. Such methods include administering to a subject a therapeutically-effective amount of a polynucleotide having a nucleic acid sequence encoding an MTEM or engineered meganuclease, or a therapeutically-effective amount of an MTEM or engineered meganuclease described herein, wherein the MTEM or engineered meganuclease produces a cleavage site of the recognition sequence of SEQ ID NO: 1 in mutant mitochondrial genomes having the MELAS mutation. The cleavage site produced in mutant mitochondrial genomes can lead to degradation of the mutant mitochondrial genomes. In specific embodiments, treating comprises reducing or alleviating at least one symptom of MELAS. Symptoms of MELAS include but are not limited to seizures, recurrent headaches, loss of appetite, recurrent vomiting, stroke-like episodes with temporary muscle weakness on one side of the body (hemiparesis), altered consciousness, vision and hearing loss, loss of motor skills, and intellectual disability. In specific embodiments, the methods of treating a condition associated with MELAS in a subject involve administration of a pharmaceutical composition described herein.

In some embodiments, a subject is administered a pharmaceutical composition described herein at a dose of about $1 \times 10^{10}$ gc/kg to about $1 \times 10^{14}$ gc/kg (e.g., $1 \times 10^{10}$ gc/kg, $1 \times 10^{11}$ gc/kg, $1 \times 10^{12}$ gc/kg, $1 \times 10^{13}$ gc/kg, or $1 \times 10^{14}$ gc/kg) of a nucleic acid encoding an MTEM or engineered meganuclease. In some embodiments, a subject is administered a pharmaceutical composition at a dose of at least about $1 \times 10^{10}$ gc/kg, at least about $1 \times 10^{11}$ gc/kg, at least about $1 \times 10^{12}$ gc/kg, at least about $1 \times 10^{13}$ gc/kg, or at least about $1 \times 10^{14}$ gc/kg of a nucleic acid encoding an MTEM or engineered meganuclease. In some embodiments, a subject is administered a pharmaceutical composition at a dose of about $1 \times 10^{10}$ gc/kg to about $1 \times 10^{11}$ gc/kg, about $1 \times 10^{11}$ gc/kg to about $1 \times 10^{12}$ gc/kg, about $1 \times 10^{12}$ gc/kg to about $1 \times 10^{13}$ gc/kg, or about $1 \times 10^{13}$ gc/kg to about $1 \times 10^{14}$ gc/kg of a nucleic acid encoding an MTEM or engineered meganuclease. In certain embodiments, a subject is administered a pharmaceutical composition at a dose of about $1 \times 10^{12}$ gc/kg to about $9 \times 10^{13}$ gc/kg (e.g., about $1 \times 10^{12}$ gc/kg, about $2 \times 10^{12}$ gc/kg, about $3 \times 10^{12}$ gc/kg, about $4 \times 10^{12}$ gc/kg, about $5 \times 10^{12}$ gc/kg, about $6 \times 10^{12}$ gc/kg, about $7 \times 10^{12}$ gc/kg, about $8 \times 10^{12}$ gc/kg, about $9 \times 10^{12}$ gc/kg, about $1 \times 10^{13}$ gc/kg, about $2 \times 10^{13}$ gc/kg, about $3 \times 10^{13}$ gc/kg, about $4 \times 10^{13}$ gc/kg, about $5 \times 10^{13}$ gc/kg, about $6 \times 10^{13}$ gc/kg, about $7 \times 10^{13}$ gc/kg, about $8 \times 10^{13}$ gc/kg, or about $9 \times 10^{13}$ gc/kg) of a nucleic acid encoding an MTEM or engineered meganuclease.

In some embodiments, a subject is administered a lipid nanoparticle formulation at a dose of about 0.1 mg/kg to about 3 mg/kg of mRNA encoding an MTEM or engineered meganuclease. In some embodiments, the subject is administered a lipid nanoparticle formulation at a dose of at least about 0.1 mg/kg, at least about 0.25 mg/kg, at least about 0.5 mg/kg, at least about 0.75 mg/kg, at least about 1.0 mg/kg, at least about 1.5 mg/kg, at least about 2.0 mg/kg, at least about 2.5 mg/kg, or at least about 3.0 mg/kg of mRNA encoding an MTEM or engineered meganuclease. In some embodiments, the subject is administered a lipid nanoparticle formulation at a dose of within about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of mRNA encoding an MTEM or engineered meganuclease.

The target tissue(s) for delivery of MTEMs or engineered meganucleases described herein, or nucleic acids encoding MTEMs or engineered meganucleases described herein, include without limitation, muscle tissue, brain tissue, central nervous system tissue, pancreatic tissue, or ocular/retinal tissue. In some embodiments, the target cell for delivery is a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, or a pancreatic beta cell, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells or the population of target cells is a population of muscle cells, a skeletal muscle cells, a myotube cells, a muscle satellite cells, a neuron, an astrocyte, a microglia cells, an eye cells, a retinal cells, a retinal ganglion cells, a retinal pigmentary epithelium cells, a pancreatic cells, or a pancreatic beta cells, or wherein said population of target cells is a population of muscle cells, skeletal muscle cells, myotube cells, muscle satellite cells, neurons, astrocytes, microglia cells, eye cells, retinal cells, retinal ganglion cells, retinal pigmentary epithelium cells, pancreatic cells, or pancreatic beta cells.

In various embodiments of the methods described herein, the one or more MTEMs or engineered meganucleases described herein, polynucleotides encoding such MTEMs or engineered meganucleases described herein, or recombinant viruses comprising one or more polynucleotides encoding such MTEMs or engineered meganucleases described herein, as described herein, can be administered via any suitable route of administration known in the art. Accordingly, the one or more MTEMs or engineered meganucleases described herein, polynucleotides encoding such MTEMs or engineered meganucleases described herein, or recombinant viruses comprising one or more polynucleotides encoding such MTEMs or engineered meganucleases described herein, as described herein may be administered by an administration route comprising intravenous, intramuscular, intraperitoneal, subcutaneous, intrahepatic, transmucosal, transdermal, intraarterial, and sublingual. In some embodiments, MTEMs or engineered meganucleases described herein, or mRNA, or DNA vectors MTEMs or engineered meganucleases described herein, are supplied to target cells (e.g., nerve cells, muscle cells, pancreatic cells, ocular cells, etc.) via injection directly to the target tissue. In some embodiments, the eukaryotic cell is a stem cell, a CD34+ HSC, a muscle cell, a skeletal muscle cell, a myotube cell, a muscle satellite cell, a neuron, an astrocyte, a microglia cell, an eye cell, a retinal cell, a retinal ganglion cell, a retinal pigmentary epithelium cell, a pancreatic cell, a pancreatic beta cell, a kidney cell, a bone marrow cell, or an ear hair cell. In some embodiments, the condition is a condition of the muscles, brain, central nervous system, pancreas, or retina. In some embodiments, the condition is Mitochondrial Encephalomyopathy, Lactic Acidosis, and Stroke-like episodes (MELAS), Progressive External Ophthalmoplegia, maternally inherited diabetes, migraines, or ocular myopathy.

Other suitable routes of administration of the MTEMs or engineered meganucleases described herein, polynucleotides encoding such MTEMs or engineered meganucleases described herein, or recombinant viruses comprising one or more polynucleotides encoding such engineered nucleases may be readily determined by the treating physician as necessary.

In some embodiments, a therapeutically effective amount of MTEMs or engineered meganucleases described herein is administered to a subject in need thereof. As appropriate, the dosage or dosing frequency of the MTEM or engineered meganuclease may be adjusted over the course of the treatment, based on the judgment of the administering physician. Appropriate doses will depend, among other factors, on the specifics of any AAV chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

Exogenous nucleic acid molecules described herein may be introduced into a cell and/or delivered to a subject by any of the means previously discussed. In a particular embodiment, exogenous nucleic acid molecules are introduced by way of a recombinant virus, such as a lentivirus, retrovirus, adenovirus, or a recombinant AAV. Recombinant AAVs useful for introducing an exogenous nucleic acid molecule can have any serotype that allows for transduction of the virus into the cell and insertion of the exogenous nucleic acid molecule sequence into the cell genome, including those serotypes/capsids previously described herein. The recombinant AAVs can also be self-complementary such that they do not require second-strand DNA synthesis in the host cell. Exogenous nucleic acid molecules introduced using a recombinant AAV can be flanked by a 5' (left) and 3' (right) inverted terminal repeat.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, polynucleotides comprising nucleic acid sequences encoding MTEMs or engineered meganucleases described herein and/or an exogenous nucleic acid molecule described herein can be introduced into a cell by transfection with a linearized DNA template. A plasmid DNA encoding an MTEM or an engineered meganucleases described herein and/or an exogenous nucleic acid molecule can, for example, be digested by one or more restriction enzymes such that the circular plasmid DNA is linearized prior to transfection into the cell.

When delivered to a cell, an exogenous nucleic acid described herein can be operably linked to any promoter suitable for expression of the encoded polypeptide in the cell, including those mammalian promoters and inducible promoters previously discussed. An exogenous nucleic acid described herein can also be operably linked to a synthetic promoter. Synthetic promoters can include, without limitation, the JeT promoter (WO 2002/012514).

2.6 Variants

The present invention encompasses variants of the polypeptide and polynucleotide sequences described herein.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; for example, the ability to bind and cleave recognition sequences found in mtDNA (e.g., human mtDNA), such as MIT 25-26 recognition sequence (SEQ ID NO: 1). Such variants may result, for example, from human manipulation. In some embodiments, biologically active variants of a native polypeptide of the embodiments (e.g., any one of SEQ ID NOs: 3-12), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1, or native HVR2 as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases described herein can comprise variants of the HVR1 and HVR2 regions described herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments described herein, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases described herein comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NOs: 3-12.

In certain embodiments, engineered meganucleases described herein comprise an HVR2 that has 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 3-12.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 2 provides potential substitutions that can be made in an engineered meganuclease monomer or subunit to enhance specificity based on the base present at each half-site position (−1 through −9) of a recognition half-site. Such substitutions are incorporated into variants of the meganucleases described herein.

TABLE 2

Potential substitutions in engineered meganuclease variants

| | | | | Favored Sense-Strand Base | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | | K28* | C28* | | | M66 |
| | | | | | | | | Q42 | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |

TABLE 2-continued

Potential substitutions in engineered meganuclease variants

| | | | | | Favored Sense-Strand Base | | | | | |
|---|---|---|---|---|---|---|---|---|---|---|
| Posn. | A | C | G | T | A/T | A/C | A/G | C/T | G/T | A/G/T | A/C/G/T |
| | | | | C79 | H28* | | | | | |
| | | | | I79 | | | | | | |
| | | | | V79 | | | | | | |
| | | | | Q28* | | | | | | |
| −7 | N30* | E38 | K38 | I38 | | | C38 | | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| | | E32 | R32 | L32 | | | | D32 | | | S32 |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein.
An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 3-12 (WO 2009001159), a Y, R, K, or D at a residue corresponding to position 66 of I-CreI or any one of SEQ ID NOs: 3-12 and/or an E, Q, or K at a residue corresponding to position 80 of I-CreI or any one of SEQ ID NOs: 3-12 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode an engineered meganuclease, or an exogenous nucleic acid molecule, or template nucleic acid of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially bind and cleave recognition sequences found within human mtDNA, such as the MIT 25-26 recognition sequence (SEQ ID NO: 1).

Table 3 is a summary of the sequences disclosed herein.

TABLE 3

| SEQ ID NO: | DESCRIPTION | SEQUENCE |
|---|---|---|
| 1 | MIT 25-26 recognition sequence (sense) | CAGGGCCCGGTAATCGCATAAA |
| 2 | MIT 25-26 recognition sequence (antisense) | GTCCCGGGCCATTAGCGTATTT |
| 3 | MIT 25-26x.91 meganuclease amino acid sequence | MNTKYNKEFLLYLAGFVDSDGSIFARIEPTQSAKFKHK LRLTFRVHQKTQRRWFLDKLVDEIGVGYVYDTGSVSD YTLSQIKPLHNFLTQLQPFLKLKQKQANLVLKIIEQLPS AKESPDKFLEVCTWVDQIAALNDSKTRKTTSETVRAV LDSLPGSVGGLSPSQASSAASSASSSPGSGISEALRAGA GSGTGYNKEFLLYLAGFVDGDGSIYACILPNQGSKFKH ALQLFFTVGQKTCRRWFLDKLVDEIGVGYVHDHGTIS |

TABLE 3-continued

| SEQ ID NO: | DESCRIPTION | SEQUENCE |
|---|---|---|
| | | QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 4 | MIT 25-26x.48 meganuclease amino acid sequence | MNTKYNKEFLLYLAGFVDADGSIFARIEPTQSAKFKHK
LRLTFRVHQKTQRRWFLDKLVDEIGVGYVYDTGSVSD
YTLSEIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVNDFGSISQ
YRLSEIKPLYNFLTQLQPFLKLKQKQANLVLKIIEQLPS
AKESPDKFLEVCTWVDQIAALNDSRTRKTTSETVRAV
LDSLSEKKKSSP |
| 5 | MIT 25-26x. 73 meganuclease amino acid sequence | MNTKYNKEFLLYLAGFVDADGSIFARIEPTQSAKFKHK
LRLTFRVHQKTQRRWFLDKLVDEIGVGYVYDTGSVSD
YTLSQIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVHDFGLIS
QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 6 | MIT 25-26x.29 meganuclease amino acid sequence | MNTKYNKEFLLYLAGFVDADGSIFARIEPTQSAKFKHK
LRLTFRVHQKTQRRWFLDKLVDEIGVGYVYDTGSVSD
YTLSEIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEAPRAGA
GSGTGYNKEFLLYLAGFVDGDGSIYACILPNQGSKFKH
ALQLFFTVGQKTCRRWFLDKLVDEIGVGYVHDHGLIA
QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 7 | MIT 25-26x.37 meganuclease amino acid sequence | MNTKYNKEFLLYLAGFVDADGSIFARIEPTQSAKFKHK
LRLTFRVHQKTQRRWFLDKLVDEIGVGYVYDTGSVSD
YTLSQIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVNDFGPVS
QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 8 | MIT 25-26L.35 meganuclease amino acid sequence | MNTKYNKEFLLYLAGFVDADGSIFARIEPTQSAKFKHK
LRLTFRVWQKTQRRWFLDKLVDEIGVGYVYDEGSVSS
YTLSEIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVQDHGRIS
QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 9 | MIT 25-26x.91 259 H > Q meganuclease amino acid sequence | MNTKYNKEFLLYLAGFVDSDGSIFARIEPTQSAKFKHK
LRLTFRVHQKTQRRWFLDKLVDEIGVGYVYDTGSVSD
YTLSQIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVQDHGTIS
QYRLSEIKPLHNFLTQLQPFLKLKQKQANLVLKIIEQLP
SAKESPDKFLEVCTWVDQIAALNDSRTRKTTSETVRAV
LDSLSEKKKSSP |
| 10 | MIT 25-26L.35 19A > S meganuclease amino acid sequence | MNTKYNKEFLLYLAGFVDSDGSIFARIEPTQSAKFKHK
LRLTFRVWQKTQRRWFLDKLVDEIGVGYVYDEGSVSS
YTLSEIKPLHNFLTQLQPFLKLKQKQANLVLKIIEQLPS
AKESPDKFLEVCTWVDQIAALNDSKTRKTTSETVRAV
LDSLPGSVGGLSPSQASSAASSASSSPGSGISEALRAGA
GSGTGYNKEFLLYLAGFVDGDGSIYACILPNQGSKFKH
ALQLFFTVGQKTCRRWFLDKLVDEIGVGYVQDHGRIS |

TABLE 3-continued

| SEQ ID NO: | DESCRIPTION | SEQUENCE |
|---|---|---|
|  |  | QYRLSEIKPLHNFLTQLQPFLKLKQKQANLVLKIIEQLP SAKESPDKFLEVCTWVDQIAALNDSRTRKTTSETVRAV LDSLSEKKKSSP |
| 11 | MIT 25-26x.91 263 T > R meganuclease amino acid sequence | MNTKYNKEFLLYLAGFVDSDGSIFARIEPTQSAKFKHK LRLTFRVHQKTQRRWFLDKLVDEIGVGYVYDTGSVSD YTLSQIKPLHNFLTQLQPFLKLKQKQANLVLKIIEQLPS AKESPDKFLEVCTWVDQIAALNDSKTRKTTSETVRAV LDSLPGSVGGLSPSQASSAASSASSSPGSGISEALRAGA GSGTGYNKEFLLYLAGFVDGDGSIYACILPNQGSKFKH ALQLFFTVGQKTCRRWFLDKLVDEIGVGYVHDHGRIS QYRLSEIKPLHNFLTQLQPFLKLKQKQANLVLKIIEQLP SAKESPDKFLEVCTWVDQIAALNDSRTRKTTSETVRAV LDSLSEKKKSSP |
| 12 | MIT 25-26x.91 46 H > W meganuclease amino acid sequence | MNTKYNKEFLLYLAGFVDSDGSIFARIEPTQSAKFKHK LRLTFRVWQKTQRRWFLDKLVDEIGVGYVYDTGSVS DYTLSQIKPLHNFLTQLQPFLKLKQKQANLVLKIIEQLP SAKESPDKFLEVCTWVDQIAALNDSKTRKTTSETVRA VLDSLPGSVGGLSPSQASSAASSASSSPGSGISEALRAG AGSGTGYNKEFLLYLAGFVDGDGSIYACILPNQGSKFK HALQLFFTVGQKTCRRWFLDKLVDEIGVGYVHDHGTI SQYRLSEIKPLHNFLTQLQPFLKLKQKQANLVLKIIEQL PSAKESPDKFLEVCTWVDQIAALNDSRTRKTTSETVRA VLDSLSEKKKSSP |
| 13 | MIT 25-26x.91 meganuclease 25 binding subunit | KEFLLYLAGFVDSDGSIFARIEPTQSAKFKHKLRLTFRV HQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |
| 14 | MIT 25-26x.48 meganuclease 25 binding subunit | KEFLLYLAGFVDADGSIFARIEPTQSAKFKHKLRLTFRV HQKTQRRWFLDKLVDEIGVGYVYDTGSVSDYTLSEIK PLHNFLTQLQPFLKLKQKQANLVLKIIEQLPSAKESPDK FLEVCTWVDQIAALNDSKTRKTTSETVRAVLD |
| 15 | MIT 25-26x.73 meganuclease 25 binding subunit | KEFLLYLAGFVDADGSIFARIEPTQSAKFKHKLRLTFRV HQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |
| 16 | MIT 25-26x.29 meganuclease 25 binding subunit | KEFLLYLAGFVDADGSIFARIEPTQSAKFKHKLRLTFRV HQKTQRRWFLDKLVDEIGVGYVYDTGSVSDYTLSEIK PLHNFLTQLQPFLKLKQKQANLVLKIIEQLPSAKESPDK FLEVCTWVDQIAALNDSKTRKTTSETVRAVLD |
| 17 | MIT 25-26x.37 meganuclease 25 binding subunit | KEFLLYLAGFVDADGSIFARIEPTQSAKFKHKLRLTFRV HQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |
| 18 | MIT 25-26L.35 meganuclease 25 binding subunit | KEFLLYLAGFVDADGSIFARIEPTQSAKFKHKLRLTFRV WQKTQRRWFLDKLVDEIGVGYVYDEGSVSSYTLSEIK PLHNFLTQLQPFLKLKQKQANLVLKIIEQLPSAKESPDK FLEVCTWVDQIAALNDSKTRKTTSETVRAVLD |
| 19 | MIT 25-26x.91 259 H > Q meganuclease 25 binding subunit | KEFLLYLAGFVDSDGSIFARIEPTQSAKFKHKLRLTFRV HQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |
| 20 | MIT 25-26L.35 19A > S meganuclease 25 binding subunit | KEFLLYLAGFVDSDGSIFARIEPTQSAKFKHKLRLTFRV WQKTQRRWFLDKLVDEIGVGYVYDEGSVSSYTLSEIK PLHNFLTQLQPFLKLKQKQANLVLKIIEQLPSAKESPDK FLEVCTWVDQIAALNDSKTRKTTSETVRAVLD |
| 21 | MIT 25-26x.91 263 T > R meganuclease 25 binding subunit | KEFLLYLAGFVDSDGSIFARIEPTQSAKFKHKLRLTFRV HQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |
| 22 | MIT 25-26x.91 46 H > W meganuclease 25 binding subunit | KEFLLYLAGFVDSDGSIFARIEPTQSAKFKHKLRLTFRV WQKTQRRWFLDKLVDEIGVGYVYDTGSVSDYTLSQIK PLHNFLTQLQPFLKLKQKQANLVLKIIEQLPSAKESPDK FLEVCTWVDQIAALNDSKTRKTTSETVRAVLD |

TABLE 3-continued

| SEQ ID NO: | DESCRIPTION | SEQUENCE |
|---|---|---|
| 23 | MIT 25-26x.91 meganuclease 26 binding subunit | KEFLLYLAGFVDGDGSIYACILPNQGSKFKHALQLFFT VGQKTCRRWFLDKLVDEIGVGYVHDHGTISQYRLSEI KPLHNFLTQLQPFLKLKQKQANLVLKIIEQLPSAKESPD KFLEVCTWVDQIAALNDSRTRKTTSETVRAVLD |
| 24 | MIT 25-26x.48 meganuclease 26 binding subunit | KEFLLYLAGFVDGDGSIYACILPNQGSKFKHALQLFFT VGQKTCRRWFLDKLVDEIGVGYVNDFGSISQYRLSEIK PLYNFLTQLQPFLKLKQKQANLVLKIIEQLPSAKESPDK FLEVCTWVDQIAALNDSRTRKTTSETVRAVLD |
| 25 | MIT 25-26x.73 meganuclease 26 binding subunit | KEFLLYLAGFVDGDGSIYACILPNQGSKFKHALQLFFT VGQKTCRRWFLDKLVDEIGVGYVHDFGLISQYRLSEIK PLHNFLTQLQPFLKLKQKQANLVLKIIEQLPSAKESPDK FLEVCTWVDQIAALNDSRTRKTTSETVRAVLD |
| 26 | MIT 25-26x.29 meganuclease 26 binding subunit | KEFLLYLAGFVDGDGSIYACILPNQGSKFKHALQLFFT VGQKTCRRWFLDKLVDEIGVGYVHDHGLIAQYRLSEI KPLHNFLTQLQPFLKLKQKQANLVLKIIEQLPSAKESPD KFLEVCTWVDQIAALNDSRTRKTTSETVRAVLD |
| 27 | MIT 25-26x.37 meganuclease 26 binding subunit | KEFLLYLAGFVDGDGSIYACILPNQGSKFKHALQLFFT VGQKTCRRWFLDKLVDEIGVGYVNDFGPVSQYRLSEI KPLHNFLTQLQPFLKLKQKQANLVLKIIEQLPSAKESPD KFLEVCTWVDQIAALNDSRTRKTTSETVRAVLD |
| 28 | MIT 25-26L.35 meganuclease 26 binding subunit | KEFLLYLAGFVDGDGSIYACILPNQGSKFKHALQLFFT VGQKTCRRWFLDKLVDEIGVGYVQDHGRISQYRLSEI KPLHNFLTQLQPFLKLKQKQANLVLKIIEQLPSAKESPD KFLEVCTWVDQIAALNDSRTRKTTSETVRAVLD |
| 29 | MIT 25-26x.91 259 H > Q meganuclease 26 binding subunit | KEFLLYLAGFVDGDGSIYACILPNQGSKFKHALQLFFT VGQKTCRRWFLDKLVDEIGVGYVQDHGTISQYRLSEI KPLHNFLTQLQPFLKLKQKQANLVLKIIEQLPSAKESPD KFLEVCTWVDQIAALNDSRTRKTTSETVRAVLD |
| 30 | MIT 25-26L.35 19A > S meganuclease 26 binding subunit | KEFLLYLAGFVDGDGSIYACILPNQGSKFKHALQLFFT VGQKTCRRWFLDKLVDEIGVGYVQDHGRISQYRLSEI KPLHNFLTQLQPFLKLKQKQANLVLKIIEQLPSAKESPD KFLEVCTWVDQIAALNDSRTRKTTSETVRAVLD |
| 31 | MIT 25-26x.91 263 T > R meganuclease 26 binding subunit | KEFLLYLAGFVDGDGSIYACILPNQGSKFKHALQLFFT VGQKTCRRWFLDKLVDEIGVGYVHDHGTISQYRLSEI KPLHNFLTQLQPFLKLKQKQANLVLKIIEQLPSAKESPD KFLEVCTWVDQIAALNDSRTRKTTSETVRAVLD |
| 32 | MIT 25-26x.91 46 H > W meganuclease 26 binding subunit | KEFLLYLAGFVDGDGSIYACILPNQGSKFKHALQLFFT VGQKTCRRWFLDKLVDEIGVGYVHDHGTISQYRLSEI KPLHNFLTQLQPFLKLKQKQANLVLKIIEQLPSAKESPD KFLEVCTWVDQIAALNDSRTRKTTSETVRAVLD |
| 33 | MIT 25-26x.91 meganuclease nucleic acid sequence | ATGAATACAAAATATAATAAAGAGTTCTTACTCTAC TTAGCAGGGTTTGTAGACTCTGACGGTTCCATCTTTG CCCGTATCGAGCCTACTCAAAGTGCTAAGTTCAAGC ACAAGCTGAGGCTCACGTTCCGGGTCCATCAGAAGA CACAGCGCCGTTGGTTCCTCGACAAGCTGGTGGACG AGATCGGTGTGGGTTACGTGTATGACACTGGCAGCG TCTCCGATTACACTCTGTCCCAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA TTCTTAGAAGTTTGTACATGGGTGGATCAAATTGCA GCTCTGAATGATTCGAAGACGCGTAAAACAACTTCT GAAACCGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACTCAGAGCTGGAGCAGGTTCCGGC ACTGGATACAACAAGGAATTCCTGCTCTACCTGGCG GGCTTCGTCGACGGGGACGGCTCCATCTATGCCTGT ATCCTTCCTAATCAAGGGAGTAAGTTCAAGCACGCT CTGCAGCTCTTTTTCACGGTCGGCCAGAAGACATGC CGCCGTTGGTTCCTCGACAAGCTGGTGGACGAGATC GGTGTGGGTTACGTGCACGACCACGGCACTATCTCG CAGTACCGCCTGTCCGAGATCAAGCCTCTGCACAAC TTCCTGACCCAGCTCCAGCCCTTCCTGAAGCTCAAGC AGAAGCAGGCCAACCTCGTGCTGAAGATCATCGAGC AGCTGCCCTCCGCCAAGGAATCCCCGGACAAGTTCC |

TABLE 3-continued

| SEQ ID NO: | DESCRIPTION | SEQUENCE |
|---|---|---|
| | | TGGAGGTGTGCACCTGGGTGGACCAGATCGCCGCTC TGAACGACTCCAGGACCCGCAAGACCACTTCCGAAA CCGTCCGCGCCGTTCTAGACAGTCTCTCCGAGAAGA AGAAGTCGTCCCCC |
| 34 | MIT 25-26x.48 meganuclease nucleic acid sequence | ATGAATACAAAATATAATAAAGAGTTCTTACTCTAC TTAGCAGGGTTTGTAGACGCTGACGGTTCCATCTTTG CCCGTATCGAGCCTACTCAAAGTGCTAAGTTCAAGC ACAAGCTGAGGCTCACGTTCCGGGTCCATCAGAAGA CACAGCGCCGTTGGTTCCTCGACAAGCTGGTGGACG AGATCGGTGTGGGTTACGTGTATGACACTGGCAGCG TCTCCGATTACACTCTGTCCGAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA TTCTTAGAAGTTTGTACATGGGTGGATCAAATTGCA GCTCTGAATGATTCGAAGACGCGTAAAACAACTTCT GAAACCGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACTCAGAGCTGGAGCAGGTTCCGGC ACTGGATACAACAAGGAATTCCTGCTCTACCTGGCC GGCTTCGTCGACGGGGACGGCTCCATCTATGCCTGT ATCCTTCCTAATCAAGGGAGTAAGTTCAAGCACGCT CTGCAGCTCTTTTTCACGGTCGGCCAGAAGACATGC CGCCGTTGGTTCCTCGACAAGCTGGTGGACGAGATC GGTGTGGGTTACGTGAACGACTTCGGCTCTATCTCG CAGTACCGCCTGTCCGAGATCAAGCCTCTGTACAAC TTCCTGACCCAGCTCCAGCCCTTCCTGAAGCTCAAGC AGAAGCAGGCCAACCTCGTGCTGAAGATCATCGAGC AGCTGCCCTCCGCCAAGGAATCCCCGGACAAGTTCC TGGAGGTGTGCACCTGGGTGGACCAGATCGCCGCTC TGAACGACTCCAGGACCCGCAAGACCACTTCCGAAA CCGTCCGCGCCGTTCTAGACAGTCTCTCCGAGAAGA AGAAGTCGTCCCCC |
| 35 | MIT 25-26x.73 meganuclease nucleic acid sequence | ATGAATACAAAATATAATAAAGAGTTCTTACTCTAC TTAGCAGGGTTTGTAGACGCTGACGGTTCCATCTTTG CCCGTATCGAGCCTACTCAAAGTGCTAAGTTCAAGC ACAAGCTGAGGCTCACGTTCCGGGTCCATCAGAAGA CACAGCGCCGTTGGTTCCTCGACAAGCTGGTGGACG AGATCGGTGTGGGTTACGTGTATGACACTGGCAGCG TCTCCGATTACACTCTGTCCCAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA TTCTTAGAAGTTTGTACATGGGTGGATCAAATTGCA GCTCTGAATGATTCGAAGACGCGTAAAACAACTTCT GAAACCGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACTCAGAGCTGGAGCAGGTTCCGGC ACTGGATACAACAAGGAATTCCTGCTCTACCTGGCG GGCTTCGTCGACGGGGACGGCTCCATCTATGCCTGT ATCCTTCCTAATCAAGGGAGTAAGTTCAAGCACGCT CTGCAGCTCTTTTTCACGGTCGGCCAGAAGACATGC CGCCGTTGGTTCCTCGACAAGCTGGTGGACGAGATC GGTGTGGGTTACGTGCACGACTTCGGCCTGATCTCG CAGTACCGCCTGTCCGAGATCAAGCCTCTGCACAAC TTCCTGACCCAGCTCCAGCCCTTCCTGAAGCTCAAGC AGAAGCAGGCCAACCTCGTGCTGAAGATCATCGAGC AGCTGCCCTCCGCCAAGGAATCCCCGGACAAGTTCC TGGAGGTGTGCACCTGGGTGGACCAGATCGCCGCTC TGAACGACTCCAGGACCCGCAAGACCACTTCCGAAA CCGTCCGCGCCGTTCTAGACAGTCTCTCCGAGAAGA AGAAGTCGTCCCCC |
| 36 | MIT 25-26x.29 meganuclease nucleic acid sequence | ATGAATACAAAATATAATAAAGAGTTCTTACTCTAC TTAGCAGGGTTTGTAGACGCTGACGGTTCCATCTTTG CCCGTATCGAGCCTACTCAAAGTGCTAAGTTCAAGC ACAAGCTGAGGCTCACGTTCCGGGTCCATCAGAAGA CACAGCGCCGTTGGTTCCTCGACAAGCTGGTGGACG AGATCGGTGTGGGTTACGTGTATGACACTGGCAGCG TCTCCGATTACACTCTGTCCGAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA |

TABLE 3-continued

| SEQ ID NO: | DESCRIPTION | SEQUENCE |
|---|---|---|
| | | TTCTTAGAAGTTTGTACATGGGTGGATCAAATTGCA GCTCTGAATGATTCGAAGACGCGTAAAACAACTTCT GAAACCGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACCCAGAGCTGGAGCAGGTTCCGGC ACTGGATACAACAAGGAATTCCTGCTCTACCTGGCG GGCTTCGTCGACGGGACGGCTCCATCTATGCCTGT ATCCTTCCTAATCAAGGGAGTAAGTTCAAGCACGCT CTGCAGCTCTTTTTCACGGTCGGCCAGAAGACATGC CGCCGTTGGTTCCTCGACAAGCTGGTGGACGAGATC GGTGTGGGTTACGTGCACGACCACGGCCTTATCGCG CAGTACCGCCTGTCCGAGATCAAGCCTCTGCACAAC TTCCTGACCCAGCTCCAGCCCTTCCTGAAGCTCAAGC AGAAGCAGGCCAACCTCGTGCTGAAGATCATCGAGC AGCTGCCCTCCGCCAAGGAATCCCCGGACAAGTTCC TGGAGGTGTGCACCTGGGTGGACCAGATCGCCGCTC TGAACGACTCCAGGACCCGCAAGACCACTTCCGAAA CCGTCCGCGCCGTTCTAGACAGTCTCTCCGAGAAGA AGAAGTCGTCCCCC |
| 37 | MIT 25-26x.37 meganuclease nucleic acid sequence | ATGAATACAAAATATAATAAAGAGTTCTTACTCTAC TTAGCAGGGTTTGTAGACGCTGACGGTTCCATCTTTG CCCGTATCGAGCCTACTCAAAGTGCTAAGTTCAAGC ACAAGCTGAGGCTCACGTTCCGGGTCCATCAGAAGA CACAGCGCCGTTGGTTCCTCGACAAGCTGGTGGACG AGATCGGTGTGGGTTACGTGTATGACACTGGCAGCG TCTCCGATTACACTCTGTCCCAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA TTCTTAGAAGTTTGTACATGGGTGGATCAAATTGCA GCTCTGAATGATTCGAAGACGCGTAAAACAACTTCT GAAACTGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACTCAGAGCTGGAGCAGGTTCCGGC ACTGGATACAACAAGGAATTCCTGCTCTACCTGGCG GGCTTCGTCGACGGGACGGCTCCATCTATGCCTGT ATCCTTCCTAATCAAGGGAGTAAGTTCAAGCACGCT CTGCAGCTCTTTTTCACGGTCGGCCAGAAGACATGC CGCCGTTGGTTCCTCGACAAGCTGGTGGACGAGATC GGTGTGGGTTACGTGAACGACTTCGGCCCTGTCTCG CAGTACCGCCTGTCCGAGATCAAGCCTCTGCACAAC TTCCTGACCCAGCTCCAGCCCTTCCTGAAGCTCAAGC AGAAGCAGGCCAACCTCGTGCTGAAGATCATCGAGC AGCTGCCCTCCGCCAAGGAATCCCCGGACAAGTTCC TGGAGGTGTGCACCTGGGTGGACCAGATCGCCGCTC TGAACGACTCCAGGACCCGCAAGACCACTTCCGAAA CCGTCCGCGCCGTTCTAGACAGTCTCTCCGAGAAGA AGAAGTCGTCCCCC |
| 38 | MIT 25-26L.35 meganuclease nucleic acid sequence | ATGAATACAAAATATAATAAAGAGTTCTTACTCTAC TTAGCAGGGTTTGTAGACGCTGACGGTTCCATCTTTG CCCGTATCGAGCCTACTCAAAGTGCTAAGTTCAAGC ACAAGCTGAGGCTCACGTTCCGGGTCTGGCAGAAGA CACAGCGCCGTTGGTTCCTCGACAAGCTGGTGGACG AGATCGGTGTGGGTTACGTGTATGACGAGGGCAGCG TCTCCTCTTACACTCTGTCCGAGATCAAGCCTTTGCA TAATTTTTTAACACAACTACAACCTTTTCTAAAACTA AAACAAAAACAAGCAAATTTAGTTTTAAAAATTATT GAACAACTTCCGTCAGCAAAAGAATCCCCGGACAAA TTCTTAGAAGTTTGTACATGGGTGGATCAAATTGCA GCTCTGAATGATTCGAAGACGCGTAAAACAACTTCT GAAACCGTTCGTGCTGTGCTAGACAGTTTACCAGGA TCCGTGGGAGGTCTATCGCCATCTCAGGCATCCAGC GCCGCATCCTCGGCTTCCTCAAGCCCGGGTTCAGGG ATCTCCGAAGCACTCAGAGCTGGAGCAGGTTCCGGC ACTGGATACAACAAGGAATTCCTGCTCTACCTGGCG GGCTTCGTCGACGGGACGGCTCCATCTATGCCTGT ATCCTTCCTAATCAAGGGAGTAAGTTCAAGCACGCT CTGCAGCTATTCTTCACGGTCGGCCAGAAGACATGC CGCCGTTGGTTCCTCGACAAGCTGGTGGACGAGATC GGTGTGGGTTACGTGCAGGACCACGGCAGGATCTCG CAGTACCGCCTGTCCGAGATCAAGCCTCTGCACAAC TTCCTGACCCAGCTCCAGCCCTTCCTGAAGCTCAAGC AGAAGCAGGCCAACCTCGTGCTGAAGATCATCGAGC |

TABLE 3-continued

| SEQ ID NO: | DESCRIPTION | SEQUENCE |
|---|---|---|
| | | AGCTGCCCTCCGCCAAGGAATCCCCGGACAAGTTCC
TGGAGGTGTGCACCTGGGTGGACCAGATCGCCGCTC
TGAACGACTCCAGGACCCGCAAGACCACTTCCGAAA
CCGTCCGCGCCGTTCTAGACAGTCTCTCCGAGAAGA
AGAAGTCGTCCCCC |
| 39 | MIT 25-26x.91 259 H > Q meganuclease nucleic acid sequence | ATGAATACAAAATATAATAAAGAGTTCTTACTCTAC
TTAGCAGGGTTTGTAGACTCTGACGGTTCCATCTTTG
CCCGTATCGAGCCTACTCAAAGTGCTAAGTTCAAGC
ACAAGCTGAGGCTCACGTTCCGGGTCCATCAGAAGA
CACAGCGCCGTTGGTTCCTCGACAAGCTGGTGGACG
AGATCGGTGTGGGTTACGTGTATGACACTGGCAGCG
TCTCCGATTACACTCTGTCCCAGATCAAGCCTTTGCA
TAATTTTTTAACACAACTACAACCTTTTCTAAAACTA
AAACAAAAACAAGCAAATTTAGTTTTAAAAATTATT
GAACAACTTCCGTCAGCAAAAGAATCCCCGGACAAA
TTCTTAGAAGTTTGTACATGGGTGGATCAAATTGCA
GCTCTGAATGATTCGAAGACGCGTAAAACAACTTCT
GAAACCGTTCGTGCTGTGCTAGACAGTTTACCAGGA
TCCGTGGGAGGTCTATCGCCATCTCAGGCATCCAGC
GCCGCATCCTCGGCTTCCTCAAGCCCGGGTTCAGGG
ATCTCCGAAGCACTCAGAGCTGGAGCAGGTTCCGGC
ACTGGATACAACAAGGAATTCCTGCTCTACCTGGCG
GGCTTCGTCGACGGGGACGGCTCCATCTATGCCTGT
ATCCTTCCTAATCAAGGGAGTAAGTTCAAGCACGCT
CTGCAGCTCTTTTTCACGGTCGGCCAGAAGACATGC
CGCCGTTGGTTCCTCGACAAGCTGGTGGACGAGATC
GGTGTGGGTTACGTGCAGGACCACGGCACTATCTCG
CAGTACCGCCTGTCCGAGATCAAGCCTCTGCACAAC
TTCCTGACCCAGCTCCAGCCCTTCCTGAAGCTCAAGC
AGAAGCAGGCCAACCTCGTGCTGAAGATCATCGAGC
AGCTGCCCTCCGCCAAGGAATCCCCGGACAAGTTCC
TGGAGGTGTGCACCTGGGTGGACCAGATCGCCGCTC
TGAACGACTCCAGGACCCGCAAGACCACTTCCGAAA
CCGTCCGCGCCGTTCTAGACAGTCTCTCCGAGAAGA
AGAAGTCGTCCCCC |
| 40 | MIT 25-26L.35 19A > S meganuclease nucleic acid sequence | ATGAATACAAAATATAATAAAGAGTTCTTACTCTAC
TTAGCAGGGTTTGTAGACTCTGACGGTTCCATCTTTG
CCCGTATCGAGCCTACTCAAAGTGCTAAGTTCAAGC
ACAAGCTGAGGCTCACGTTCCGGGTCTGGCAGAAGA
CACAGCGCCGTTGGTTCCTCGACAAGCTGGTGGACG
AGATCGGTGTGGGTTACGTGTATGACGAGGGCAGCG
TCTCCTCTTACACTCTGTCCGAGATCAAGCCTTTGCA
TAATTTTTTAACACAACTACAACCTTTTCTAAAACTA
AAACAAAAACAAGCAAATTTAGTTTTAAAAATTATT
GAACAACTTCCGTCAGCAAAAGAATCCCCGGACAAA
TTCTTAGAAGTTTGTACATGGGTGGATCAAATTGCA
GCTCTGAATGATTCGAAGACGCGTAAAACAACTTCT
GAAACCGTTCGTGCTGTGCTAGACAGTTTACCAGGA
TCCGTGGGAGGTCTATCGCCATCTCAGGCATCCAGC
GCCGCATCCTCGGCTTCCTCAAGCCCGGGTTCAGGG
ATCTCCGAAGCACTCAGAGCTGGAGCAGGTTCCGGC
ACTGGATACAACAAGGAATTCCTGCTCTACCTGGCG
GGCTTCGTCGACGGGGACGGCTCCATCTATGCCTGT
ATCCTTCCTAATCAAGGGAGTAAGTTCAAGCACGCT
CTGCAGCTATTCTTCACGGTCGGCCAGAAGACATGC
CGCCGTTGGTTCCTCGACAAGCTGGTGGACGAGATC
GGTGTGGGTTACGTGCAGGACCACGGCAGGATCTCG
CAGTACCGCCTGTCCGAGATCAAGCCTCTGCACAAC
TTCCTGACCCAGCTCCAGCCCTTCCTGAAGCTCAAGC
AGAAGCAGGCCAACCTCGTGCTGAAGATCATCGAGC
AGCTGCCCTCCGCCAAGGAATCCCCGGACAAGTTCC
TGGAGGTGTGCACCTGGGTGGACCAGATCGCCGCTC
TGAACGACTCCAGGACCCGCAAGACCACTTCCGAAA
CCGTCCGCGCCGTTCTAGACAGTCTCTCCGAGAAGA
AGAAGTCGTCCCCC |
| 41 | MIT 25-26x.91 263 T > R meganuclease nucleic acid sequence | ATGAATACAAAATATAATAAAGAGTTCTTACTCTAC
TTAGCAGGGTTTGTAGACTCTGACGGTTCCATCTTTG
CCCGTATCGAGCCTACTCAAAGTGCTAAGTTCAAGC
ACAAGCTGAGGCTCACGTTCCGGGTCCATCAGAAGA
CACAGCGCCGTTGGTTCCTCGACAAGCTGGTGGACG
AGATCGGTGTGGGTTACGTGTATGACACTGGCAGCG
TCTCCGATTACACTCTGTCCCAGATCAAGCCTTTGCA
TAATTTTTTAACACAACTACAACCTTTTCTAAAACTA
AAACAAAAACAAGCAAATTTAGTTTTAAAAATTATT |

TABLE 3-continued

| SEQ ID NO: | DESCRIPTION | SEQUENCE |
|---|---|---|
| | | GAACAACTTCCGTCAGCAAAAGAATCCCCGGACAAA<br>TTCTTAGAAGTTTGTACATGGGTGGATCAAATTGCA<br>GCTCTGAATGATTCGAAGACGCGTAAAACAACTTCT<br>GAAACCGTTCGTGCTGTGCTAGACAGTTTACCAGGA<br>TCCGTGGGAGGTCTATCGCCATCTCAGGCATCCAGC<br>GCCGCATCCTCGGCTTCCTCAAGCCCGGGTTCAGGG<br>ATCTCCGAAGCACTCAGAGCTGGAGCAGGTTCCGGC<br>ACTGGATACAACAAGGAATTCCTGCTCTACCTGGCG<br>GGCTTCGTCGACGGGGACGGCTCCATCTATGCCTGT<br>ATCCTTCCTAATCAAGGGAGTAAGTTCAAGCACGCT<br>CTGCAGCTCTTTTTCACGGTCGGCCAGAAGACATGC<br>CGCCGTTGGTTCCTCGACAAGCTGGTGGACGAGATC<br>GGTGTGGGTTACGTGCACGACCACGGCAGGATCTCG<br>CAGTACCGCCTGTCCGAGATCAAGCCTCTGCACAAC<br>TTCCTGACCCAGCTCCAGCCCTTCCTGAAGCTCAAGC<br>AGAAGCAGGCCAACCTCGTGCTGAAGATCATCGAGC<br>AGCTGCCCTCCGCCAAGGAATCCCCGGACAAGTTCC<br>TGGAGGTGTGCACCTGGGTGGACCAGATCGCCGCTC<br>TGAACGACTCCAGGACCCGCAAGACCACTTCCGAAA<br>CCGTCCGCGCCGTTCTAGACAGTCTCTCCGAGAAGA<br>AGAAGTCGTCCCCC |
| 42 | MIT 25-26x.91 46<br>H > W meganuclease<br>nucleic acid<br>sequence | ATGAATACAAAATATAATAAAGAGTTCTTACTCTAC<br>TTAGCAGGGTTTGTAGACTCTGACGGTTCCATCTTTG<br>CCCGTATCGAGCCTACTCAAAGTGCTAAGTTCAAGC<br>ACAAGCTGAGGCTCACGTTCCGGGTCTGGCAGAAGA<br>CACAGCGCCGTTGGTTCCTCGACAAGCTGGTGGACG<br>AGATCGGTGTGGGTTACGTGTATGACACTGGCAGCG<br>TCTCCGATTACACTCTGTCCCAGATCAAGCCTTTGCA<br>TAATTTTTTAACACAACTACAACCTTTTCTAAAACTA<br>AAACAAAAACAAGCAAATTTAGTTTTAAAAATTATT<br>GAACAACTTCCGTCAGCAAAAGAATCCCCGGACAAA<br>TTCTTAGAAGTTTGTACATGGGTGGATCAAATTGCA<br>GCTCTGAATGATTCGAAGACGCGTAAAACAACTTCT<br>GAAACCGTTCGTGCTGTGCTAGACAGTTTACCAGGA<br>TCCGTGGGAGGTCTATCGCCATCTCAGGCATCCAGC<br>GCCGCATCCTCGGCTTCCTCAAGCCCGGGTTCAGGG<br>ATCTCCGAAGCACTCAGAGCTGGAGCAGGTTCCGGC<br>ACTGGATACAACAAGGAATTCCTGCTCTACCTGGCG<br>GGCTTCGTCGACGGGGACGGCTCCATCTATGCCTGT<br>ATCCTTCCTAATCAAGGGAGTAAGTTCAAGCACGCT<br>CTGCAGCTCTTTTTCACGGTCGGCCAGAAGACATGC<br>CGCCGTTGGTTCCTCGACAAGCTGGTGGACGAGATC<br>GGTGTGGGTTACGTGCACGACCACGGCACTATCTCG<br>CAGTACCGCCTGTCCGAGATCAAGCCTCTGCACAAC<br>TTCCTGACCCAGCTCCAGCCCTTCCTGAAGCTCAAGC<br>AGAAGCAGGCCAACCTCGTGCTGAAGATCATCGAGC<br>AGCTGCCCTCCGCCAAGGAATCCCCGGACAAGTTCC<br>TGGAGGTGTGCACCTGGGTGGACCAGATCGCCGCTC<br>TGAACGACTCCAGGACCCGCAAGACCACTTCCGAAA<br>CCGTCCGCGCCGTTCTAGACAGTCTCTCCGAGAAGA<br>AGAAGTCGTCCCCC |
| 43 | COX VIII MTP | MSVLTPLLLRGLTGSARRLPVPRAKIHSLPPEGKL |
| 44 | SU9 MTP | MASTRVLASRLASQMAASAKVARPAVRVAQVSKRTIQ<br>TGSPLQTLKRTQMTSIVNATTRQAFQ |
| 45 | COX VIII-SU9<br>MTP | MSVLTPLLLRGLTGSARRLPVPRAKIHSLPPEGKLMAS<br>TRVLASRLASQMAASAKVARPAVRVAQVSKRTIQTGS<br>PLQTLKRTQMTSIVNATTRQAFQ |
| 46 | MVMp NS2 NES<br>sequence | VDEMTKKFGTLTIHDTEK |
| 47 | NES sequence | LGAGLGALGL |
| 48 | Wild-type I-CreI<br>sequence | MNTKYNKEFLLYLAGFVDGDGSIIAQIKPNQSYKFKHQ<br>LSLAFQVTQKTQRRWFLDKLVDEIGVGYVRDRGSVSD<br>YILSEIKPLHNFLTQLQPFLKLKQKQANLVLKIIWRLPS<br>AKESPDKFLEVCTWVDQIAALNDSKTRKTTSETVRAV<br>LDSLSEKKKSSP |

TABLE 3-continued

| SEQ ID NO: | DESCRIPTION | SEQUENCE |
|---|---|---|
| 49 | digital droplet PCR (ddPCR) primer P1 used to determine indel frequency at APC 11-12 binding site | AGCCCCGGGTACTCCTTGTT |
| 50 | ddPCR primer F1 used to determine indel frequency at APC 11-12 binding site | TTCCTTGCAGGAACAGAG |
| 51 | ddPCR primer R1 used to determine indel frequency at APC 11-12 binding site | CTGCTTGACCACCCATT |
| 52 | ddPCR primer P2 used to determine indel frequency at APC 11-12 binding site; ddPCR primer P3 utilized to determine heteroplasmy level of mtDNA and mtDNA copy number relative to nuclear DNA | CCAGCAGGCCAGGTACACC |
| 53 | ddPCR primer F2 used to determine indel frequency at APC 11-12 binding site; ddPCR primer F3 utilized to determine heteroplasmy level of mtDNA and mtDNA copy number relative to nuclear DNA | ACCGCCAAGGATGCAC |
| 54 | ddPCR primer R2 used to determine indel frequency at APC 11-12 binding site; ddPCR primer R3 utilized to determine heteroplasmy level of mtDNA and mtDNA copy number relative to nuclear DNA | GCGGGTGGGAATGGAG |
| 55 | ddPCR primer F1 used to identify potential nuclear off-target site editing induced by the MIT 25-26x.91 nuclease | GCTGGCTAGCGTTTAAACTTAAGCTTG |
| 56 | ddPCR primer R1 used to identify potential nuclear off-target site editing induced by the MIT 25-26x.91 nuclease | GGGTATGTTGTTAAGAAGAGGAATTGAACCTCTG |

TABLE 3-continued

| SEQ ID NO: | DESCRIPTION | SEQUENCE |
|---|---|---|
| 57 | ddPCR primer F2 used to identify potential nuclear off-target site editing induced by the MIT 25-26x.91 nuclease | TGTGAGTGCATATAATGAAATGGGATGACAG |
| 58 | ddPCR primer R2 used to identify potential nuclear off-target site editing induced by the MIT 25-26x.91 nuclease | CAGTCCCCACCTCTTAAGTTTCAAATGAC |
| 59 | ddPCR primer F3 used to identify potential nuclear off-target site editing induced by the MIT 25-26x.91 nuclease | CCGCAAGCCCCTTGGTACTG |
| 60 | ddPCR primer R3 used to identify potential nuclear off-target site editing induced by the MIT 25-26x.91 nuclease | GTCTGCACTCAAGGAAGGAGCTC |
| 61 | ddPCR primer F4 used to identify potential nuclear off-target site editing induced by the MIT 25-26x.91 nuclease | GACCTTATGCTGAGGAAAAGCTGTCATTCTAG |
| 62 | ddPCR primer R4 used to identify potential nuclear off-target site editing induced by the MIT 25-26x.91 nuclease | GGCCATTTATTTCAGAGTTTAGATCGCTATGC |
| 63 | ddPCR primer P1 utilized to determine heteroplasmy level of mtDNA, as well as mtDNA copy number relative to nuclear DNA | TGGCAGGGCCCGGT |
| 64 | ddPCR primer F1 utilized to determine heteroplasmy level of mtDNA, as well as mtDNA copy number relative to nuclear DNA | CCCAAGAACAGGGTTTGTTAAG |
| 65 | ddPCR primer R1 utilized to determine heteroplasmy level of mtDNA, as well as mtDNA copy number relative to nuclear DNA | GGAATGCCATTGCGATTAG |
| 66 | ddPCR primer P2 utilized to determine heteroplasmy level of mtDNA, as well as mtDNA copy number relative to nuclear DNA | AGCAGTTCTACCGTACAACCCTAACA |

TABLE 3-continued

| SEQ ID NO: | DESCRIPTION | SEQUENCE |
|---|---|---|
| 67 | ddPCR primer F2 utilized to determine heteroplasmy level of mtDNA, as well as mtDNA copy number relative to nuclear DNA | GGCAGTTGAGGTGGATTA |
| 68 | ddPCR primer R2 utilized to determine heteroplasmy level of mtDNA, as well as mtDNA copy number relative to nuclear DNA | GGAATGCGGTAGTAGTTAGG |
| 69 | ddPCR primer P4 utilized to determine heteroplasmy level of mtDNA, as well as mtDNA copy number relative to nuclear DNA | AACCAGACAAATCGCTCCACCAAC |
| 70 | ddPCR primer F4 utilized to determine heteroplasmy level of mtDNA, as well as mtDNA copy number relative to nuclear DNA | CGGACAGGATTGACAGATT |
| 71 | ddPCR primer R4 utilized to determine heteroplasmy level of mtDNA, as well as mtDNA copy number relative to nuclear DNA | CCAGAGTCTCGTTCGTTATC |
| 72 | ddPCR primer P2 utilized to determine heteroplasmy level of mtDNA, as well as mtDNA copy number relative to nuclear DNA (WT Allele) | ACCGGGCTCTGCCAT |

EXAMPLES

This disclosure is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1. Reporter Assay for MIT 25-26 Nuclease Activity

The purpose of this experiment was to determine whether various MIT 25-26 meganucleases could bind and cleave the human MIT 25-26 recognition sequence in mammalian cells, and to determine whether the various MIT 25-26 meganucleases could discriminate against the wild-type allele. To do this, the engineered meganucleases were evaluated using the CHO cell reporter assay previously described (see, WO/2012/167192). To perform the assays, two CHO cell reporter lines were produced, which carried a non-functional Green Fluorescent Protein (GFP) gene expression cassette integrated into the genome of the cells. The GFP gene in each cell line contains a direct sequence duplication separated by a pair of recognition sequences such that intracellular cleavage of either recognition sequence by an engineered meganuclease would stimulate a homologous recombination event resulting in a functional GFP gene.

In the CHO reporter cell lines developed for this study, two recognition sequences were inserted into the GFP gene. One recognition sequence was for the human MIT 25-26 recognition sequence (either the mutant or wild-type sequence, which only differ by one base). Cell line number 1 (mutant) contained the mutant allele, while cell line number 2 (wild-type) contained the wild-type allele. The second recognition sequence inserted into both lines was a CHO-23/24 recognition sequence, which is recognized and cleaved by a control engineered meganuclease called "CHO-23/24." The CHO-23/24 recognition sequence is used as a positive control and standard measure of activity.

The CHO reporter cells detailed above were transfected with mRNA encoding various MIT 25-26 nucleases. A control sample of CHO reporter cells were transfected with mRNA encoding the CHO-23/24 meganuclease. In each assay, 5e4 CHO reporter cells were transfected with 2.5 ng (low dose) of mRNA in a 96-well plate using LIPOFECTAMINE® MESSENGERMAX (ThermoFisher) according to the manufacturer's instructions. The transfected CHO cells were evaluated by image cytometry at 2 days post transfection to determine the percentage of GFP-positive cells compared to a non-transfected negative control. Cells transfected with the low dose of mRNA in the mutant reporter cell line were also evaluated by image cytometry at 5 days and 7 days. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines ("normalized activity index"). This was done for both the wild-type and mutant cell lines to determine specificity of the nuclease for the mutant sequence.

Following nuclease optimization, the same reporter cell lines were transfected with MIT 25-26 engineered meganucleases. The same transfection and evaluation protocol was followed, with the following exception: the mutant cell line was transfected with 90 ng (high dose) or 2.5 ng (low dose) of mRNA, while the wild-type cell line was transfected only with the 90 ng dose.

Figure 2:
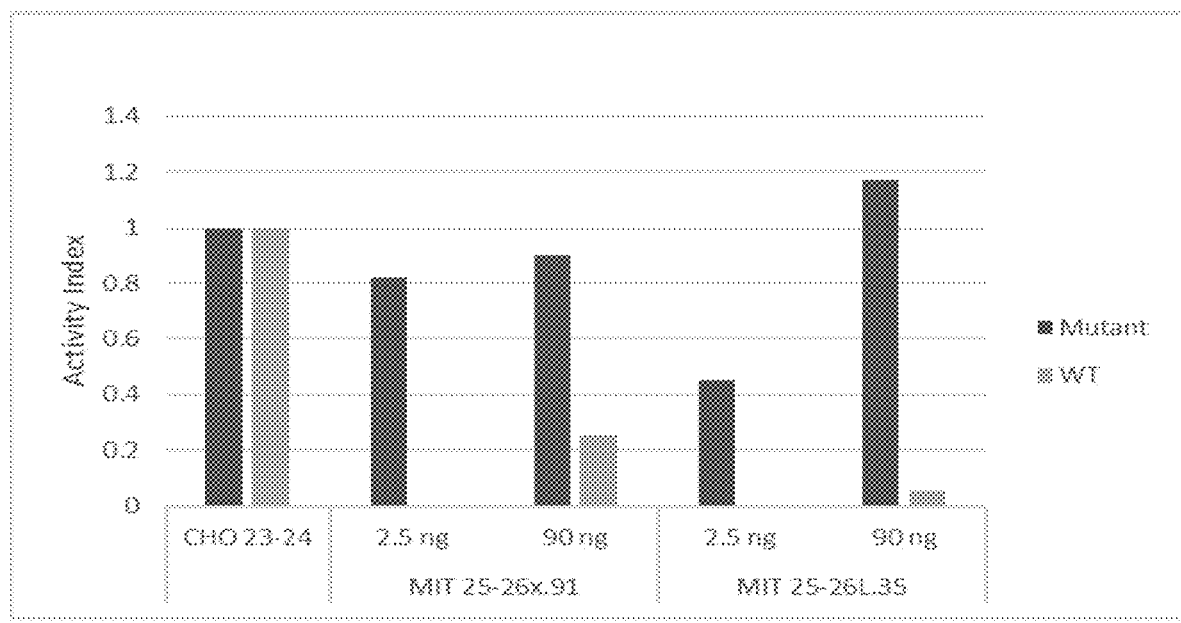
FIG. 2 demonstrates discrimination of the MIT 25-26L.35 engineered meganuclease against the wild-type sequence. Flow cytometry results are shown of CHO reporter cells transfected with mRNA encoding MIT 25-26x.91 or MIT 25-26L.35 engineered meganucleases, or the CHO 23-24 meganuclease (control) and assayed 48 hours post-transfection for the percentage of GFP+ cells. Data is shown as an activity index, the sum of the activity and toxicity scores.

The various MIT 25-26 engineered meganucleases tested were able to bind and cleave the MIT 25-26 recognition sequence in the mutant reporter line (FIG. 1). Additionally, none of the engineered meganucleases were able to bind and cleave the wild-type reporter line, indicating a high level of specificity for the mutant sequence. Furthermore, the optimized MIT 25-26 nuclease (MIT 25-26L.35) shows additional discrimination against the wild-type sequence, notably at higher mRNA dose (FIG. 2).

These studies demonstrated that engineered MIT 25-26 meganucleases described herein could efficiently and selectively bind and cleave their human recognition sequence (e.g., MIT 25-26) in cells.

Example 2. Evaluation of MIT 25-26 Meganucleases in FlpIn CHO Cell Line

The purpose of this experiment was to evaluate several MIT 25-26 meganucleases for (1) activity against the mutant target site and (2) specificity against the corresponding wild-type sequence in an in vitro model. This was done using two FlpIn CHO cell lines that contain a portion of the human mitochondrial genome integrated onto the nuclear chromosome. The integrated sequence contains either the wild-type or mutant MIT 25-26 binding site, as well as surrounding mtDNA sequence. The mutant and wild-type binding sites only differ by one nucleotide and therefore meganuclease specificity is paramount, as the objective is to generate an engineered meganuclease that can cleave the mutant sequence at high efficiency while not cleaving the wild-type sequence. Specificity and potency were evaluated by droplet digital PCR (ddPCR) by calculating insertion/deletion (indel) formation at each site.

Figure 3:
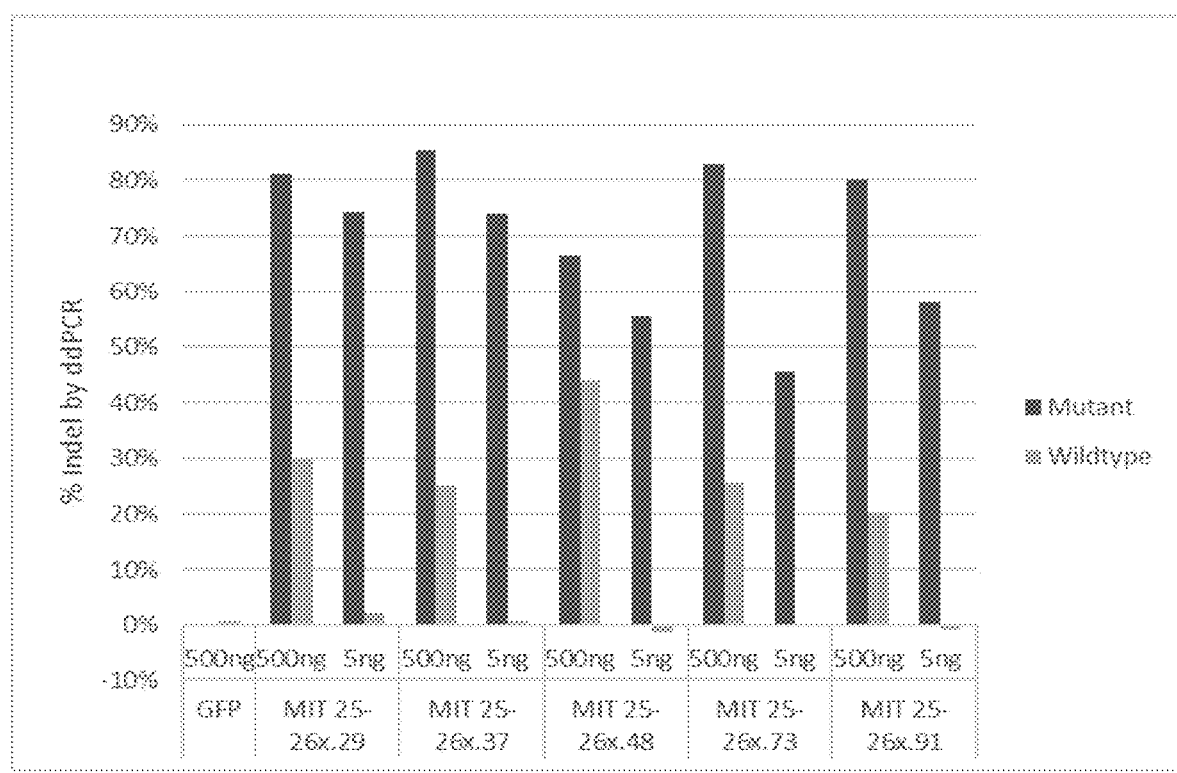
FIG. 3 shows indel formation for various MIT 25-26 engineered meganucleases in FlpIn CHO cells comprising a portion of the human mitochondrial genome with either the wild-type or mutant MIT 25-26 binding site integrated onto the nuclear chromosome. The FlpIn CHO cells were nucleofected with the MIT 25-26 engineered meganuclease and cells were analyzed 2 days later for indel frequency at both the MIT 25-26 mutant and wild-type sites.

The engineered meganucleases compared in the experiment shown in FIG. 3 were as follows: MIT 25-26x.29, MIT 25-26x.37, MIT 25-26x.48, MIT 25-26x.73, and MIT 25-26x.91. The engineered meganucleases compared in the experiment shown in FIG. 4 were the MIT 25-26x.91 and MIT 25-26L.35 meganucleases.

FlpIn CHO lines were made using the Flp-In™ system from ThermoFisher Scientific. The integration cassette contained either the MIT 25-26 mutant or wild-type sequence, as well as surrounding mtDNA sequence. To compare specificity and potency of the various MIT 25-26 meganucleases, 6e5 FlpIn CHO cells were nucleofected using the Lonza 4D-Nucleofector™ at MIT 25-26 meganuclease mRNA doses of either 500 ng or 5 ng (SF buffer, condition EN-138). Cells were collected at two days post-nucleofection for gDNA extraction and evaluated for transfection efficiency using a Beckman Coulter CytoFlex S cytometer. Transfection efficiency exceeded 95% for both cell lines. gDNA was isolated using the Macherey Nagel NucleoSpin Blood QuickPure kit.

Droplet digital PCR (ddPCR) was utilized to determine indel frequency at both the MIT 25-26 mutant and wild-type sites using P1/P2, F1, and R1 to generate an amplicon surrounding the binding site, as well as P3, F2, R2 to generate a reference amplicon that acts as a genomic counter. The ratio of the two amplicons should be equal in an un-treated population and drop relative to indel formation at the binding site in treated samples. Amplifications were multiplexed in a 24 µL reaction containing 1×ddPCR Supermix for Probes (no dUTP, BioRad), 250 nM of each probe, 900 nM of each primer, 20 U/µL Kpn-I HF (NEB), and 150 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute 30 seconds, 1 cycle of 98° C. for 10 minutes, 4° C. hold. Droplets were analyzed using a QX200 droplet reader (BioRad) and QuantaSoft analysis software (BioRad) was used to acquire and analyze data.

```
P1 (mutant allele):
                                        (SEQ ID NO: 63)
TGGCAGGGCCCGGT P2 (wild-type allele):
                                        (SEQ ID NO: 72)
ACCGGGCTCTGCCAT F1:
                                        (SEQ ID NO: 64)
CCCAAGAACAGGGTTTGTTAAG

R1:
                                        (SEQ ID NO: 65)
GGAATGCCATTGCGATTAG

P3:
                                        (SEQ ID NO: 66)
AGCAGTTCTACCGTACAACCCTAACA

F2:
                                        (SEQ ID NO: 67)
GGCAGTTGAGGTGGATTA

R2:
                                        (SEQ ID NO: 68)
GGAATGCGGTAGTAGTTAGG
```

Engineered meganucleases were designed against the MIT 25-26 mutant sequence and were evaluated for indel formation in both the mutant and wild-type sequences at two mRNA doses. All 5 of the engineered meganucleases tested exhibited activity at the wild-type site at a very high mRNA dose (500 ng) (FIG. 3). MIT 25-26x.91 generated the fewest wild-type indels at 20%, whereas MIT 25-26x.48 generated the most wild-type indels at 44%. In terms of mutant recognition site cleavage, both MIT 25-26x.29 and MIT 25-26x.37 were highly active at a low mRNA dose (5 ng), with both generating 74% indels. From the set evaluated here, MIT 25-26x.91 seems to be the most specific.

Figure 4:
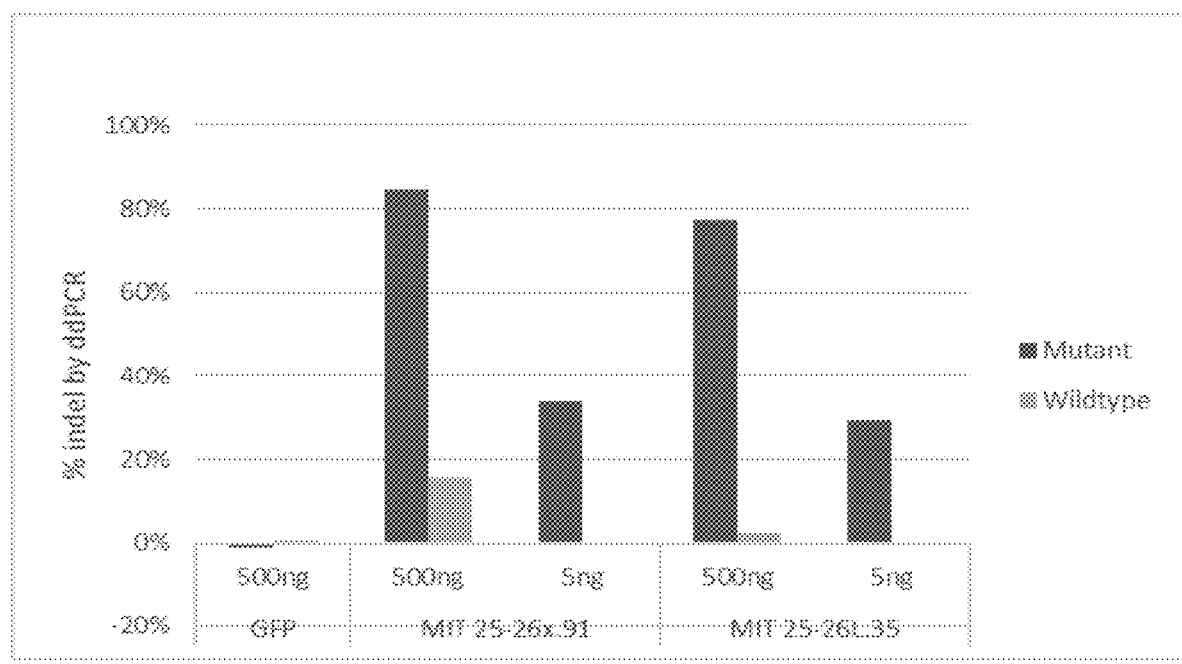
FIG. 4 shows indel formation for the optimized MIT 25-26L.35 engineered meganuclease in comparison to the MIT 25-26x.91 engineered meganuclease in FlpIn CHO cells comprising a portion of the human mitochondrial genome with either the wild-type or mutant MIT 25-26 binding site integrated onto the nuclear chromosome. The FlpIn CHO cells were nucleofected with the MIT 25-26 engineered meganuclease and cells were analyzed 2 days later for indel frequency at both the MIT 25-26 mutant and wild-type sites.

An optimized meganuclease was designed against the MIT 25-26 mutant sequence and was evaluated for indel formation in both the mutant and wild-type sequences along with MIT 25-26x.91 at two mRNA doses. While efficacy against the mutant sequence seemed relatively unchanged between MIT 25-26x.91 and MIT 25-26L.35, specificity against the wild-type sequence greatly improved with MIT 25-26L.35. MIT 25-26x.91 exhibited 16% wild-type indels with 500 ng MIT 25-26x.91 mRNA, whereas MIT 25-26L.35 exhibited only 2% indels (FIG. 4).

Together these data indicate that the collection of MIT 25-26 meganucleases are highly active against and specific for the mutant MIT 25-26 site. Additionally, they are capable of being optimized to reduce any remaining off-target (wild-type) editing.

Example 3: Mitochondrial Localization

The purpose of this experiment was to visualize engineered meganuclease localization when the nuclear localization signal (NLS) on the protein was replaced with a mitochondrial transit peptide (MTP).

6e5 MRC-5 cells were nucleofected with 600 ng engineered meganuclease mRNA using the Lonza 4D-Nucleofector™ (SE buffer, condition CM-150). Two engineered meganuclease constructs were compared: one with an NLS and one with an MTP, both at the N-terminus of the protein. At 24 hours post-nucleofection the cells were stained with 50 nM MitoTracker™ Deep Red FM (ThermoFisher Scientific, M22426) for 30 minutes and then washed with PBS. Cells were then fixed with 4% PFA with HIER for 15 minutes and stained using DAPI and a monoclonal engineered meganuclease antibody (V34 Hu). Cells were imaged using the Zeiss microscope using 20× Z-stack images.

Figure 5:
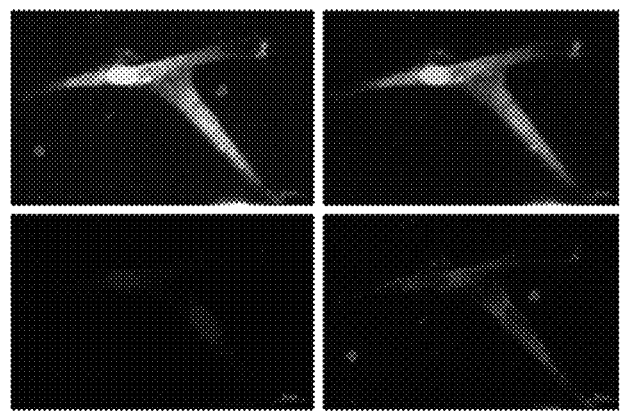
FIG. 5 demonstrates nuclear targeting of an engineered meganuclease. MRC-5 cells were transfected with a plasmid coding for an engineered meganuclease with a nuclear localization sequence. Immunocytological staining was achieved with DAPI and a monoclonal engineered meganuclease antibody, and Mitotracker Red, which stains mitochondria. Cells were viewed under 20× magnification with a Zeiss LSM710 confocal microscope. The top left picture is an overlay of all stains. The top right picture shows the location of the engineered meganuclease. The bottom left picture shows nuclear staining with DAPI and the bottom right picture shows mitochondria.
Figure 6:
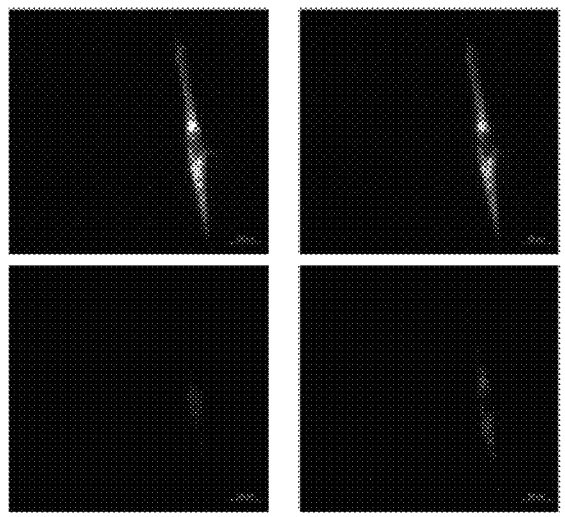
FIG. 6 demonstrates mitochondrial targeting of an engineered meganuclease. MRC-5 cells were transfected with a plasmid coding for an engineered meganuclease with a mitochondrial transit peptide (MTP). Immunocytological staining was achieved with DAPI and a monoclonal engineered meganuclease antibody, and Mitotracker Red, which stains mitochondria. Cells were viewed under 20× magnification with a Zeiss LSM710 confocal microscope. The top left picture is an overlay of all stains. The top right picture shows the location of the engineered meganuclease. The bottom left picture shows nuclear staining with DAPI and the bottom right picture shows mitochondria.

When fused with a nuclear localization sequence, engineered meganuclease staining appears diffuse throughout the cytoplasm and the nucleus (FIG. 5). However, when fused with a mitochondrial transit peptide, engineered meganuclease staining appears punctate and overlays with the MitoTracker staining (FIG. 6). There does not appear to be any nuclear localization of the engineered meganuclease when attached to the MTP.

When the NLS is swapped out for an MTP, engineered meganucleases are effectively localized away from the nucleus and to the mitochondria.

Example 4: Nuclease Activity with Mitochondrial Localization Data

The purpose of this experiment was to determine if any mitochondria-targeting engineered meganuclease (MTEM) protein was making it into the nucleus and causing double-strand breaks (DSBs) following mRNA nucleofection. The staining and imaging data in Example 1 suggested that should not be happening, but this experiment looked deeper at the molecular level to determine if any indels are being generated.

The engineered meganuclease used in this experiment was APC 11-12L.330, which has a nuclear target site (i.e., APC 11-12).

6e5 MRC-5 cells were nucleofected with an equal number of engineered meganuclease mRNA copies using the Lonza 4D-Nucleofector™ (SE buffer, condition CM-150). Three engineered meganuclease constructs were compared: one with an NLS, one with no targeting sequence, and one with a mitochondrial transit peptide (MTP). Since these different constructs yield different length mRNAs, the mRNA copy number was kept consistent across transfections (5.8e11 copies). Cells were collected at two days post-nucleofection for gDNA extraction and evaluated for transfection efficiency using a Beckman Coulter CytoFlex S cytometer. Transfection efficiency exceeded 95%. gDNA was isolated using the Macherey Nagel NucleoSpin Blood QuickPure kit.

Digital droplet PCR (ddPCR) was utilized to determine indel frequency at the APC 11-12 binding site using P1, F1, and R1 to generate an amplicon surrounding the binding site, as well as P2, F2, R2 to generate a reference amplicon that acts as a genomic counter. The ratio of the two amplicons should be equal in an un-treated population and drop relative to indel formation at the binding site in treated samples. Amplifications were multiplexed in a 24 uL reaction containing 1×ddPCR Supermix for Probes (no dUTP, BioRad), 250 nM of each probe, 900 nM of each primer, 20 U/uL Hind-III HF (NEB), and 120 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 57.5° C. (2° C./s ramp) for 30 seconds, 72 C (2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

P1:
(SEQ ID NO: 49)
AGCCCCGGGTACTCCTTGTT

F1:
(SEQ ID NO: 50)
TTCCTTGCAGGAACAGAG

R1:
(SEQ ID NO: 51)
CTGCTTGACCACCCATT

P2:
(SEQ ID NO: 52)
CCAGCAGGCCAGGTACACC

F2:
(SEQ ID NO: 53)
ACCGCCAAGGATGCAC

R2:
(SEQ ID NO: 54)
GCGGGTGGGAATGGAG

Figure 7:
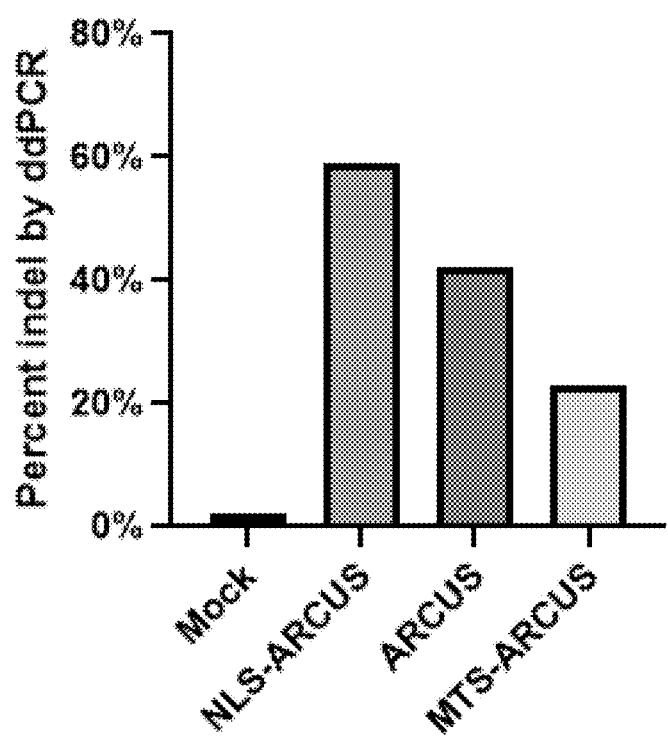
FIG. 7 shows indel formation by an engineered meganuclease fused to a nuclear localization signal (NLS) or a mitochondrial transit peptide (MTP). MRC-5 cells were nucleofected with an engineered meganuclease construct and indel formation at the APC 11-12 binding site was analyzed 2 days later.

As shown in FIG. 7, with an NLS fused to the N-terminus, APC 11-12L.330 is able to generate 59% indels at its intended (nuclear) target site. With no targeting sequence present at all, it is able to generate 42% indels at its intended target site. With an MTP fused to an engineered meganuclease, it is still able to generate 23% indels at its intended target site.

Engineered meganucleases are small proteins that may be able to diffuse into and out of the nucleus, resulting in indel formation even without the presence of a NLS on the protein. This effect may be exacerbated by the nucleofection of the cells and permeabilization of the cell membrane but could potentially be mitigated by the addition of a nuclear export signal (NES).

Example 5: Nuclease Activity with Mitochondrial Localization and Addition of Nuclear Export Sequence The purpose of this experiment was to determine if the addition of a nuclear export signal (NES) onto engineered meganucleases would eliminate nuclear indels.

Figure 8:
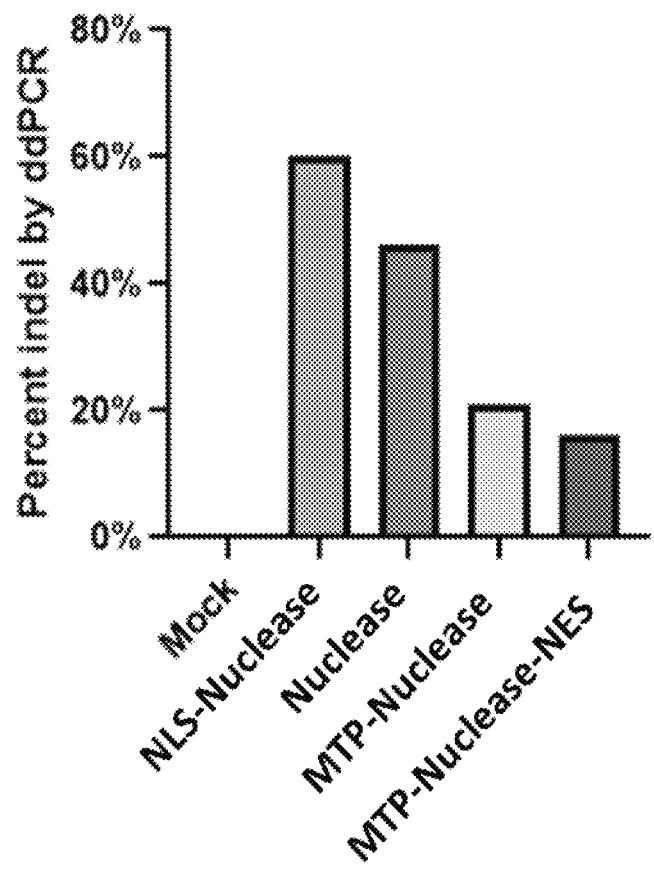
FIG. 8 shows indel formation by an engineered meganuclease fused to a nuclear localization signal (NLS), a mitochondrial transit peptide (MTP), or an MTP and the nuclear export sequence (NES) of SEQ ID NO: 47. MRC-5 cells were nucleofected with an engineered meganuclease construct and indel formation at the APC 11-12 binding site was analyzed 2 days later.

The NES used in FIG. 8 was rationally designed based on data from Kosugi et al 2008 *Traffic* 12:2053-62. The NES amino acid sequence, fused to the C-terminus of the engineered meganuclease, was: LGAGLGALGL (SEQ ID NO: 47). The NES used in FIGS. 9 and 10 was taken from Minczuk et al 2006 *Proc Natl Acad Sci USA* 103(52):19689-19694. The NES amino acid sequence, fused to the C-terminus of the engineered meganuclease, was: VDEMTKKFGTLTIHDTEK (SEQ ID NO: 46).

Figure 9:
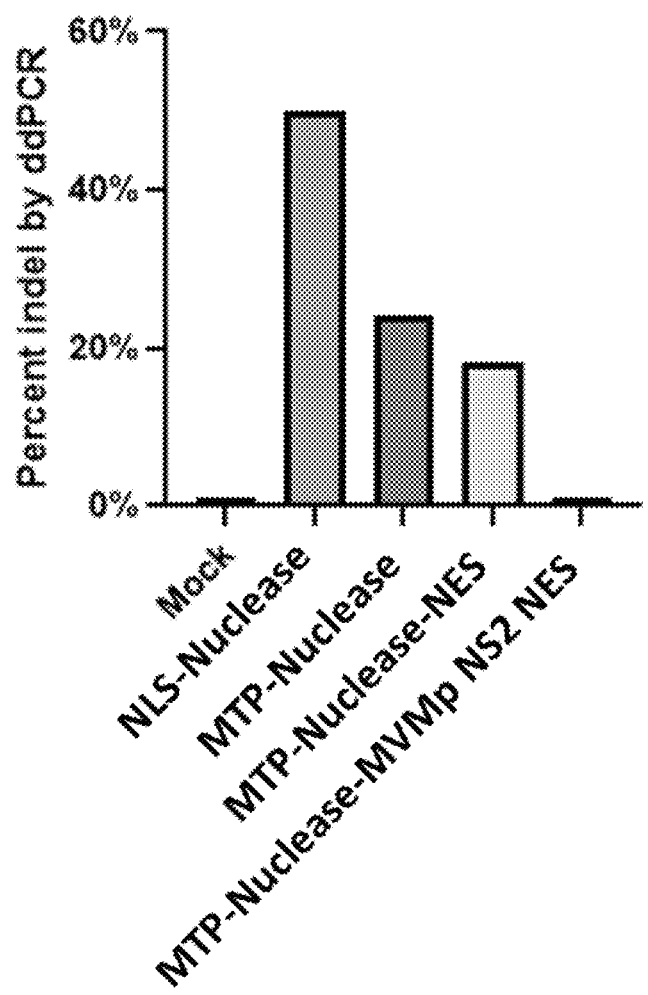
FIG. 9 shows indel formation by an engineered meganuclease fused to a nuclear localization signal (NLS), a mitochondrial transit peptide (MTP), or an MTP and the MVMp NS2 nuclear export sequence (NES) of SEQ ID NO: 46. MRC-5 cells were nucleofected with an engineered meganuclease construct and indel formation at the APC 11-12 binding site was analyzed 2 days later.

The engineered meganuclease used in FIGS. 8 and 9 was APC 11-12L.330, which has a nuclear target site. The engineered meganuclease used in FIG. 10 was MIT 25-26x.91, which does not have an endogenous nuclear target site. However, the mitochondrial sequence containing the binding site was introduced onto the nuclear chromosome of FlpIn 293 cells, and those are the cells being evaluated in FIG. 10 (site 0 is the nuclease binding site).

For experiments involving APC 11-12L.330, 6e5 MRC-5 cells were nucleofected with an equal number of engineered meganuclease mRNA copies using the Lonza 4D-Nucleofector™ (SE buffer, condition CM-150). Four meganuclease constructs were compared in FIG. 8: one with an NLS, one with no targeting sequence, one with a mitochondrial transit peptide (MTP), and one with an MTP and NES. Four engineered meganuclease constructs were compared in FIG. 9: one with an NLS, one with an MTP, one with an MTP and NES, and one with an MTP and MVMp NS2 NES. The NLS and MTP were both fused to the N-terminus of their respective proteins, and the NES was fused to the C-terminus. Since these different constructs yield different length mRNAs, the mRNA copy number was kept consistent across transfections (5.8e11 copies for the data in FIG. 8, 2.88e11 copies for the data in FIG. 9). Cells were collected at two days post-nucleofection for gDNA extraction and evaluated for transfection efficiency using a Beckman Coulter CytoFlex S cytometer. Transfection efficiency exceeded 95%. gDNA was isolated using the Macherey Nagel NucleoSpin Blood QuickPure kit.

Digital droplet PCR (ddPCR) was utilized to determine indel frequency at the APC 11-12 binding site using P1, F1, and R1 to generate an amplicon surrounding the binding site, as well as P2, F2, R2 to generate a reference amplicon that acts as a genomic counter. The ratio of the two amplicons should be equal in an un-treated population and drop relative to indel formation at the binding site in treated samples. Amplifications were multiplexed in a 24 µL reaction containing 1xddPCR Supermix for Probes (no dUTP, BioRad), 250 nM of each probe, 900 nM of each primer, 20 U/µL Hind-III HF (NEB), and 120 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 57.5° C. (2° C./s ramp) for 30 seconds, 72 C (2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

P1:
AGCCCCGGGTACTCCTTGTT (SEQ ID NO: 49)

F1:
TTCCTTGCAGGAACAGAG (SEQ ID NO: 50)

R1:
CTGCTTGACCACCCATT (SEQ ID NO: 51)

P2:
CCAGCAGGCCAGGTACACC (SEQ ID NO: 52)

F2:
ACCGCCAAGGATGCAC (SEQ ID NO: 53)

R2:
GCGGGTGGGAATGGAG (SEQ ID NO: 54)

For experiments involving MIT 25-26x.91, a FlpIn 293 line was made using the Flp-In™ system from ThermoFisher Scientific. The integration cassette contained the MIT 25-26 mutant binding site and surrounding mtDNA sequence. 1.5e6 FlpIn 293 cells were electroporated using the Neon electroporator with 1.8e12 copies of engineered meganuclease mRNA (Neon condition #11, 100 uL tips). Cells were collected at two days post-electroporation for gDNA extraction and evaluated for transfection efficiency using a Beckman Coulter CytoFlex S cytometer. Transfection efficiency exceeded 95%. gDNA was isolated using the Macherey Nagel NucleoSpin Blood QuickPure kit.

To identify potential nuclear off-target site editing induced by the MIT 25-26x.91 nuclease, targeted amplicon sequencing was performed on a selection of the sites that were identified from an in vitro, genome-wide, unbiased off-targeting assay. Three nuclear genomic sequences were identified as putative off-target sites for this nuclease (site 1, site 2, and site 3). gDNA collected from cells treated with either NLS-MIT 25-26x.91, MTP-MIT 25-26x.91, or MTP-MIT 25-26x.91-MVMpNS2 NES was evaluated by targeted amplicon sequencing at the introduced nuclear on-target site (site 0) as well as the three endogenous putative off-target sites (sites 1, 2, and 3) using primers F1><R1, F2><R2, F3><R3, and F4><R4.

F1:
GCTGGCTAGCGTTTAAACTTAAGCTTG (SEQ ID NO: 55)

R1:
GGGTATGTTGTTAAGAAGAGGAATTGAACCTCTG (SEQ ID NO: 56)

F2:
TGTGAGTGCATATAATGAAATGGGATGACAG (SEQ ID NO: 57)

R2:
CAGTCCCCACCTCTTAAGTTTCAAATGAC (SEQ ID NO: 58)

F3:
CCGCAAGCCCCTTGGTACTG (SEQ ID NO: 59)

R3:
GTCTGCACTCAAGGAAGGAGCTC (SEQ ID NO: 60)

```
F4:
                                                   (SEQ ID NO: 61)
GACCTTATGCTGAGGAAAAGCTGTCATTCTAG

R4:
                                                   (SEQ ID NO: 62)
GGCCATTTATTTCAGAGTTTAGATCGCTATGC
```

Amplifications were generated in a 50 μL reaction containing 1× buffer Q5, 1× enhancer Q5, 200 μM dNTP, 0.5 μM of each primer, 1.0 u of Q5 polymerase, and 300 ng cellular gDNA. Cycling conditions were as follows: 1 cycle of 98° C. for 4 minutes, 35 cycles of 98° C. for 30 seconds, 68° C. for 20 seconds, 72° C. for 15 seconds, 1 cycle of 72° C. for 2 minutes, 4° C. hold.

Raw PCR products were amplified using PicoGreen (ThermoFisher Scientific, P7589) and then pooled across each sample. The pooled PCR products were then analyzed for indels by NGS.

The addition of the NES to APC 11-12L.330 appeared to decrease the prevalence of nuclear indels slightly (FIG. 8), and the addition of the MVMp NS2 NES appeared to eliminate nuclear indels entirely (FIG. 9).

Figure 10:
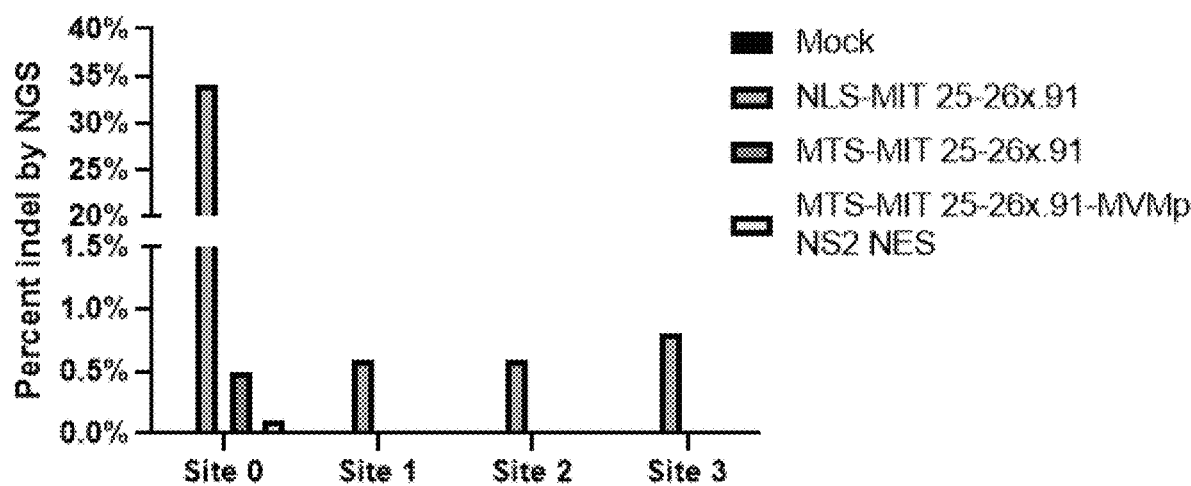
FIG. 10 shows indel formation by the engineered MIT 25-26x.91 meganuclease fused to a nuclear localization signal (NLS), mitochondrial transit peptide (MTP), or an MTP and the MVMp NS2 nuclear export sequence (NES) of SEQ ID NO: 46. MRC-5 cells were nucleofected with an engineered meganuclease construct and indel formation at each of the three MIT 25-26x.91 binding sites was analyzed 2 days later.

In the context of a human genome that contains a segment of the mtDNA sequence on the nuclear chromosome, the on-target (nuclear) indel efficacy of the MIT 25-26x.91 nuclease is 34.1% with the NLS, 0.5% with the MTP, and 0.1% with the MTP and MVMp NS2 NES (FIG. 10). Nuclear off-target editing was only detected (<1%) with the NLS; there was no detectable level of off-target editing with either the MTP or MTP and MVMp NS2 NES.

The MVMp NS2 NES is a highly effective addition to mitochondrial-targeted engineered meganucleases that mitigates potentially problematic nuclear off-target editing.

Example 6: Nuclease Efficacy and Function in Cybrid Cells

The purpose of this experiment was to show efficacy of the MIT 25-26x.91 nuclease in a cell line that harbors the heteroplasmic MELAS mutation (m.3243A>G). The cell line used is a cybrid (cytoplasmic hybrid) that contains both wildtype and mutant mtDNA. The cell line in particular is 91% mutant—that is, 91% of the mtDNA population contains the mutant allele and 9% contains the wildtype allele.

8e5 MELAS cybrid cells were nucleofected with engineered meganuclease mRNA across a dose titration using the Lonza 4D-Nucleofector™ (SF buffer, condition CA-137). The engineered meganuclease mRNA doses started at 1e5 RNA copies/cell; this translates to 8e10 RNA copies total, or 94.8 ng of RNA. The mRNA was then serially diluted 1:10 down to 1e2 RNA copies/cell. Cells were collected at one day post-nucleofection for gDNA extraction and evaluated for transfection efficiency using a Beckman Coulter CytoFlex S cytometer. Transfection efficiency exceeded 95%. gDNA was isolated using the Macherey Nagel NucleoSpin Blood QuickPure kit. The cells were carried for additional timepoints (day 4, day 7, and day 11) for gDNA extraction and functional analysis.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P3, F3, and R3 to generate a nuclear reference amplicon that acts as an nuDNA counter (assay 3).

The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells. This ratio was then normalized based on the MTS-GFP (control) condition, and the resulting normalized copy number was multiplied by the heteroplasmy level to generate the data shown in FIGS. 11-14. In these graphs, the height of the bars is indicative of mtDNA loss, relative to the MTS-GFP cells. Within the bar, the relative percentage of gray corresponds to the relative percentage of wildtype mtDNA present, and the relative percentage of black corresponds to the relative percentage of mutant mtDNA present.

```
P1:
                                                   (SEQ ID NO: 63)
TGGCAGGGCCCGGT

F1:
                                                   (SEQ ID NO: 64)
CCCAAGAACAGGGTTTGTTAAG

R1:
                                                   (SEQ ID NO: 65)
GGAATGCCATTGCGATTAG

P2:
                                                   (SEQ ID NO: 66)
AGCAGTTCTACCGTACAACCCTAACA

F2:
                                                   (SEQ ID NO: 67)
GGCAGTTGAGGTGGATTA

R2:
                                                   (SEQ ID NO: 68)
GGAATGCGGTAGTAGTTAGG

P3:
                                                   (SEQ ID NO: 52)
CCAGCAGGCCAGGTACACC

F3:
                                                   (SEQ ID NO: 53)
ACCGCCAAGGATGCAC

R3:
                                                   (SEQ ID NO: 54)
GCGGGTGGGAATGGAG
```

Assays 1 and 2 were multiplexed in a 24 μL reaction containing 1×ddPCR Supermix for Probes (no dUTP, Bio-Rad), 250 nM of each probe, 900 nM of each primer, 20 U/μL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assay 3 was run as a singleplex in a 24 μL reaction containing 1×ddPCR Supermix for Probes (no dUTP, Bio-Rad), 250 nM of each probe, 900 nM of each primer, 20 U/μL Hind-III HF (NEB), and 90 ng cellular gDNA. Droplets were generated using a QX100 droplet generator (Bio-Rad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98°

C. for 10 minutes, 4° C. hold. Droplets were analyzed using a QX200 droplet reader (BioRad) and QuantaSoft analysis software (BioRad) was used to acquire and analyze data.

At day 11 post-transfection, 5e3 cells were plated into a 96 well Seahorse cell culture microplate for analysis on the Seahorse XFe96 Analyzer (Agilent). An XF Sensor Cartridge was also hydrated with 200 µL/well Seahorse XF Calibrant overnight in a non-$CO_2$ incubator. The following day (day 12), 97 mL of Seahorse Assay Medium (DMEM) was combined with 1 mL 1 mM Sodium Pyruvate, 1 mL 2 mM Glutamine, and 1 mL 10 mM Glucose. Cells were washed two times with the prepared media and then placed in a non-$CO_2$ incubator for 1 hour. One Cell Mito Stress Test Kit was reconstituted according to manufacturer directions. Solutions were made up of Oligomycin (15 uM), FCCP (5 uM), and Rotenone/Antimycin A (5 uM). For the Cell Mito Stress Test, 20 µL Oligomycin solution was added to all Port As of the hydrated cartridge, 22 µL FCCP solution was added to all Port Bs, and 24 µL of Rotenone/Antimycin A was added to all Port Cs. For the ATP Rate Assay, the same stock solutions were used. For this assay, 20 µL Oligomycin solution was added to all Port As, 22 µL of Rotenone/Antimycin A solution was added to all port Bs, and 24 µL of Seahorse Assay Medium was added to all Port Cs. The assay was run with 4 measurement cycles (03:00 mix, 00:00 wait, 03:00 measure) for baseline, Oligomycin, FCCP, and Rotenone/Antimycin A. OCR and PER values were analyzed using Wave software (Agilent). The Cell Mito Stress Test and ATP Rate Assay Reports were generated using Wave software (Agilent).

After completion of the assay, the cells were stained with Hoechst 33342 Solution (ThermoFisher, H3570) at a 1:5000 dilution in standard media. The cells were incubated at 37 C for 20 minutes and then analyzed by image cytometry using ImageXpress Pico Automated Cell Imaging System (Molecular Devices). OCR and PER values were then normalized to cell count using Wave software (Agilent).

Figure 11:
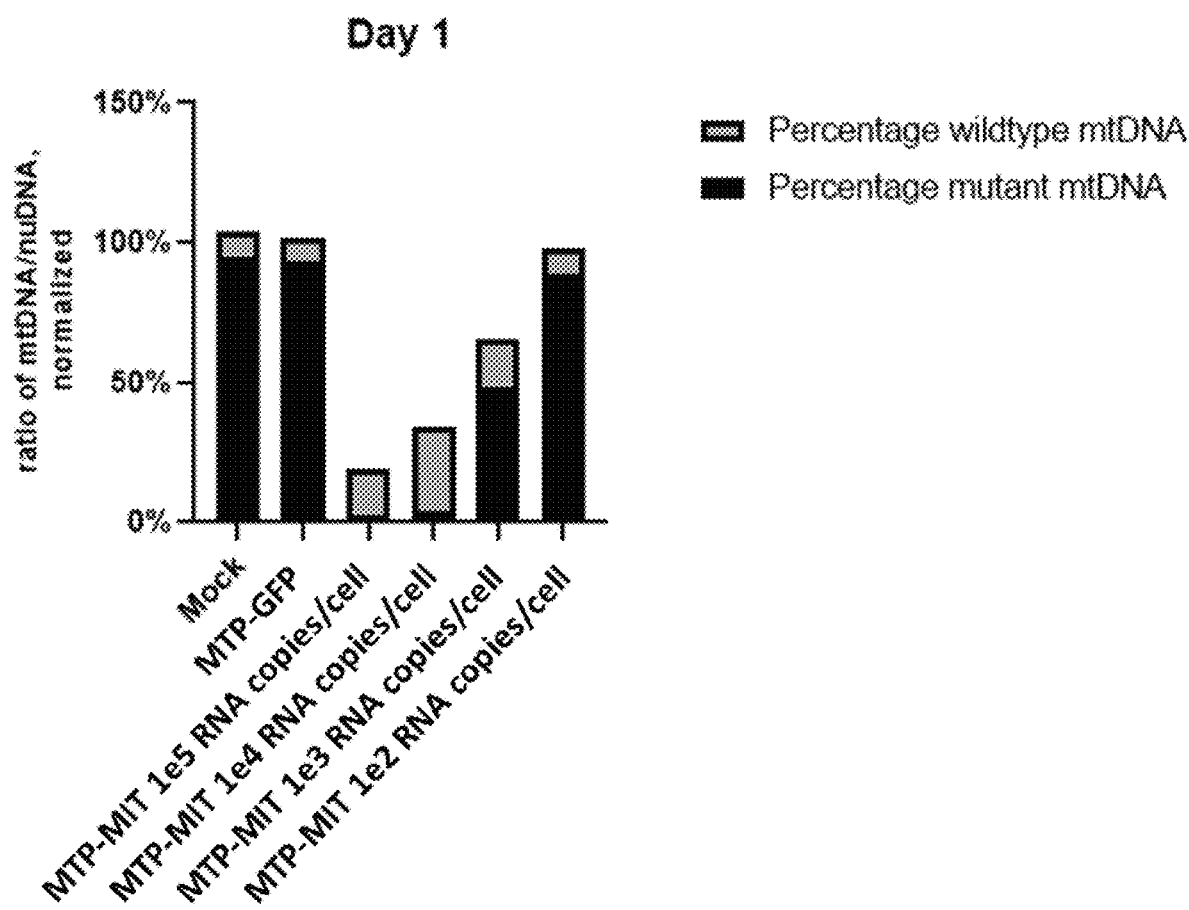
FIG. 11 shows the efficacy of the mitochondria-targeting engineered meganuclease (MTEM) MIT 25-26x.91 in a cybrid cell line that harbors the heteroplasmic MELAS mutation at day 1 post-nucleofection. These data are represented as mtDNA loss relative to the MTS-GFP cells.
Figure 12:
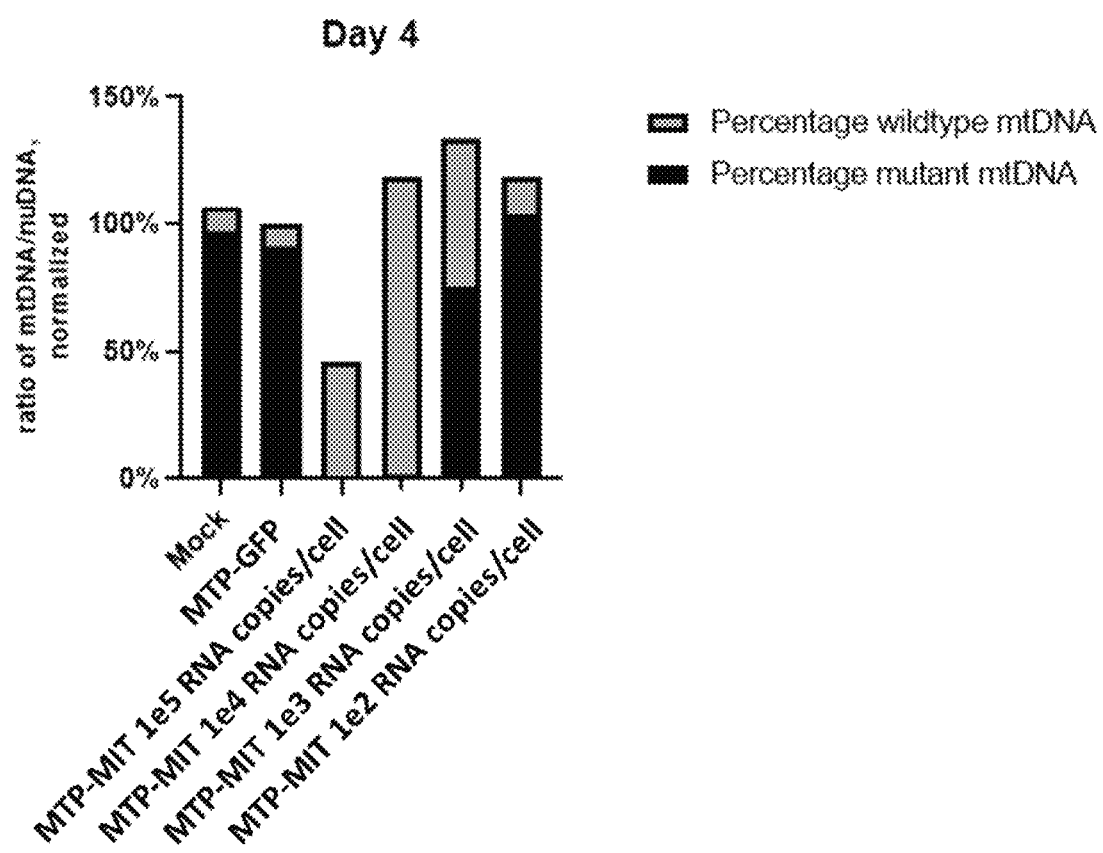
FIG. 12 shows the efficacy of the mitochondria-targeting engineered meganuclease (MTEM) MIT 25-26x.91 in a cybrid cell line that harbors the heteroplasmic MELAS mutation at day 4 post-nucleofection. These data are represented as mtDNA loss relative to the MTS-GFP cells.
Figure 13:
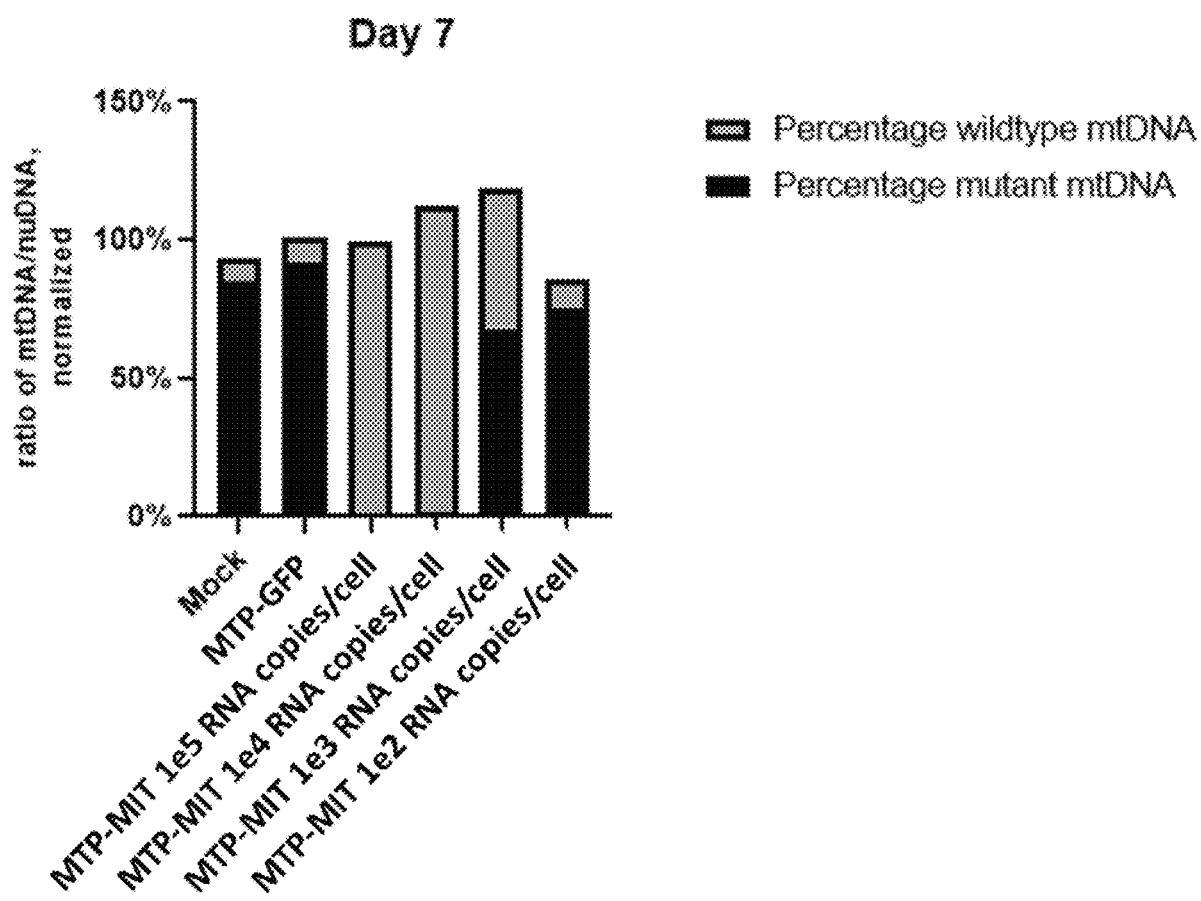
FIG. 13 shows the efficacy of the mitochondria-targeting engineered meganuclease (MTEM) MIT 25-26x.91 in a cybrid cell line that harbors the heteroplasmic MELAS mutation at day 7 post-nucleofection. These data are represented as mtDNA loss relative to the MTS-GFP cells.
Figure 14:
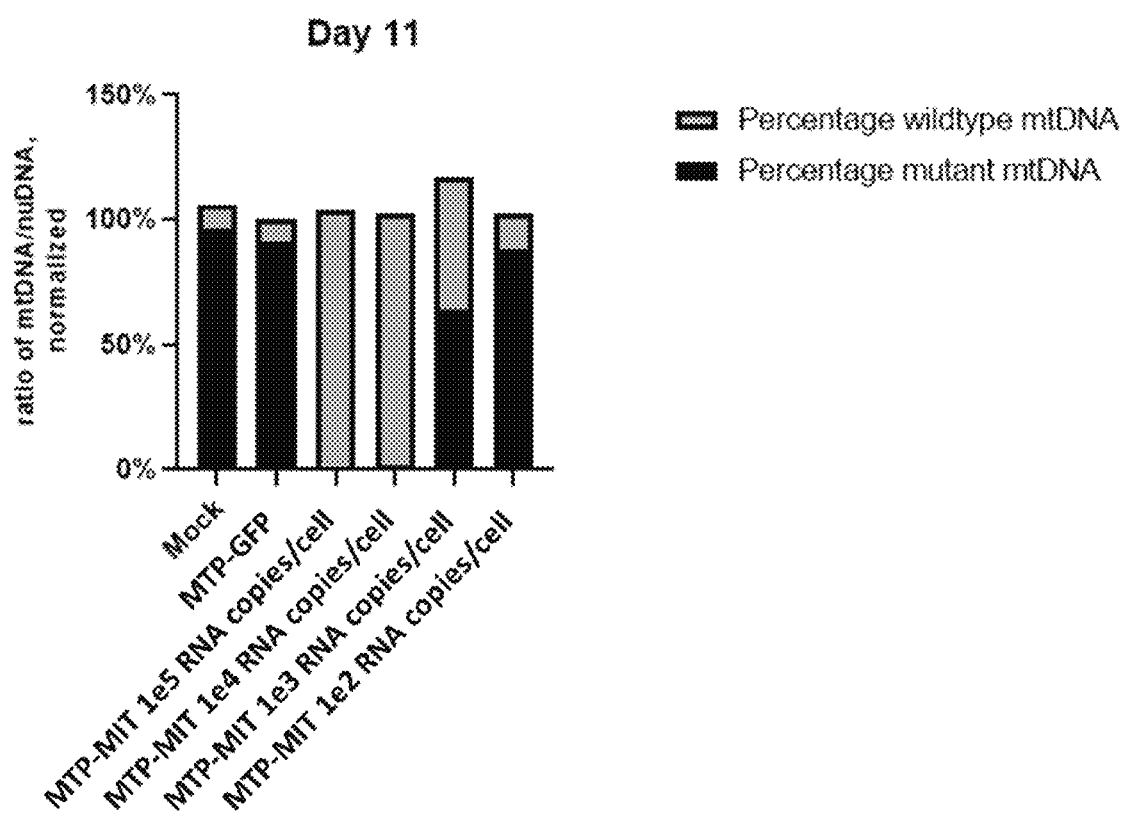
FIG. 14 shows the efficacy of the mitochondria-targeting engineered meganuclease (MTEM) MIT 25-26x.91 in a cybrid cell line that harbors the heteroplasmic MELAS mutation at day 11 post-nucleofection. These data are represented as mtDNA loss relative to the MTS-GFP cells.

As shown in FIG. 11, higher doses of the mitochondria-targeting engineered meganuclease (MTEM) resulted in a greater loss of mtDNA copies. Heteroplasmy has already begun to shift as early as day 1 post-transfection. At day 4, the cells are still recovering from the initial mtDNA reduction, especially at the high dose (1e5 RNA copies/cell) (FIG. 12). Heteroplasmy has been completely shifted (cells are 100% wildtype) in the 1e4 RNA copies/cell condition. At day 7, the cells have recovered their mtDNA copy number back to control levels across all conditions (FIG. 13). Heteroplasmy has been shifted 100% in the two highest doses (1e5 RNA copies/cell and 1e4 RNA copies/cell). Heteroplasmy has been shifted to approximately 55% mutant at a dose of 1e3 RNA copies/cell. 1e2 RNA copies/cell did not shift heteroplasmy. At day 11, the cells have recovered their mtDNA copy number back to control levels across all conditions (FIG. 14). Heteroplasmy has been shifted 100% in the two highest doses (1e5 RNA copies/cell and 1e4 RNA copies/cell). Heteroplasmy has been shifted to approximately 55% mutant at a dose of 1e3 RNA copies/cell. 1e2 RNA copies/cell did not shift heteroplasmy.

Figure 15:
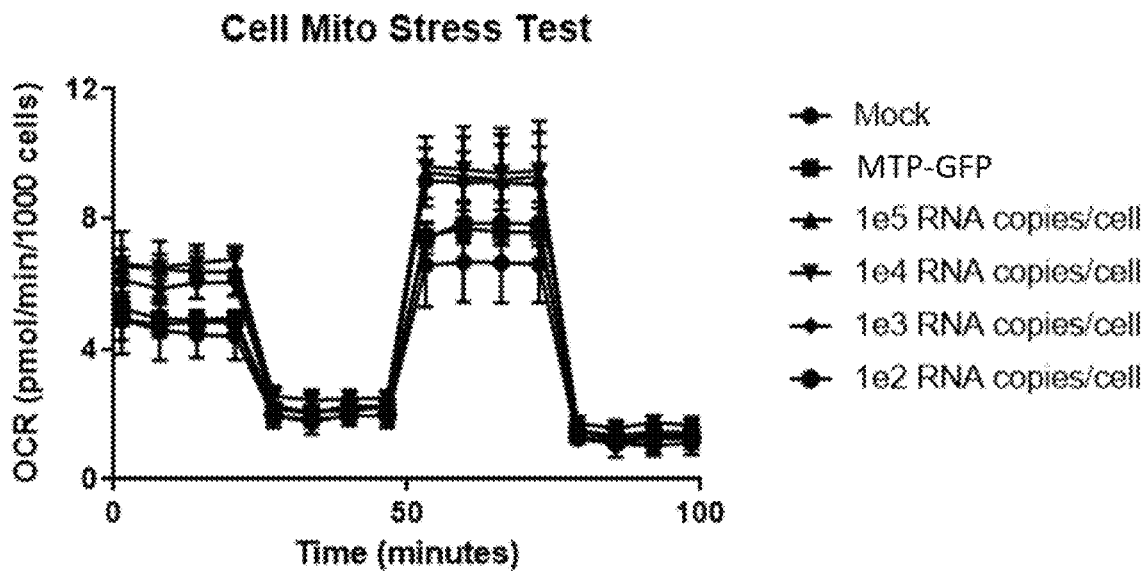
FIG. 15 shows the mitochondrial stress test of MELAS cybrid cells 11 days post-transfection with the mitochondria-targeting engineered meganuclease (MTEM) MIT 25-26x.91.

In the Cell Mito Stress Test, the MTEM-treated cells that exhibited a complete shift in heteroplasmy (1e5 RNA copies/cell) had a 53% increase in basal respiration and a 46% increase in maximal respiration above untreated cells (mock) (FIG. 15).

Figure 16:
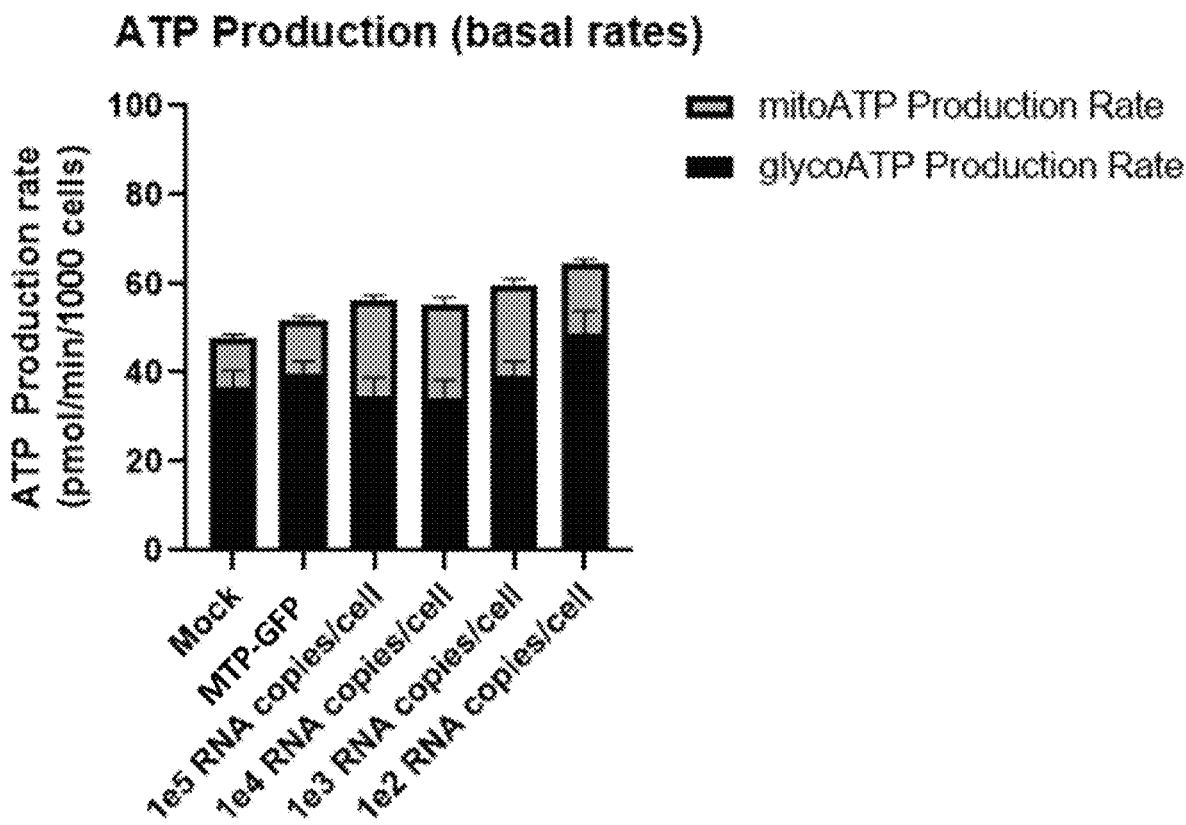
FIG. 16 shows the ATP production of MELSA cybrid cells 11 days post-transfection with the mitochondria-targeting engineered meganuclease (MTEM) MIT 25-26x.91.

In the ATP Rate Assay, the MTEM-treated cells that exhibited a complete shift in heteroplasmy (1e5 RNA copies/cell) had a 17% increase in total ATP production above untreated cells (mock) (FIG. 16).

Figure 17:
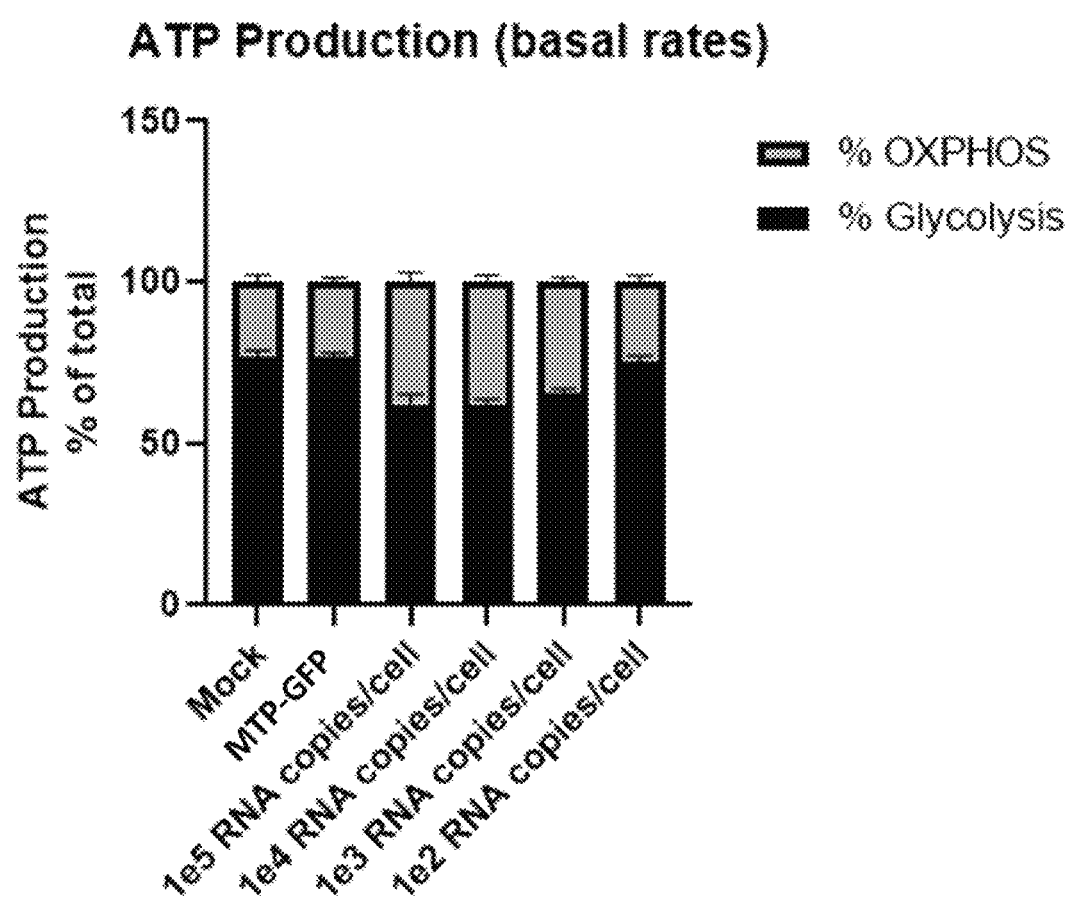
FIG. 17 shows the ATP production of MELSA cybrid cells 11 days post-transfection with the mitochondria-targeting engineered meganuclease (MTEM) MIT 25-26x.91.

In the ATP Rate Assay, the MTEM-treated cells that exhibited a complete shift in heteroplasmy (1e5 RNA copies/cell) had an 88% increase in mitoATP production above untreated cells (mock) (FIG. 17).

Figure 18:
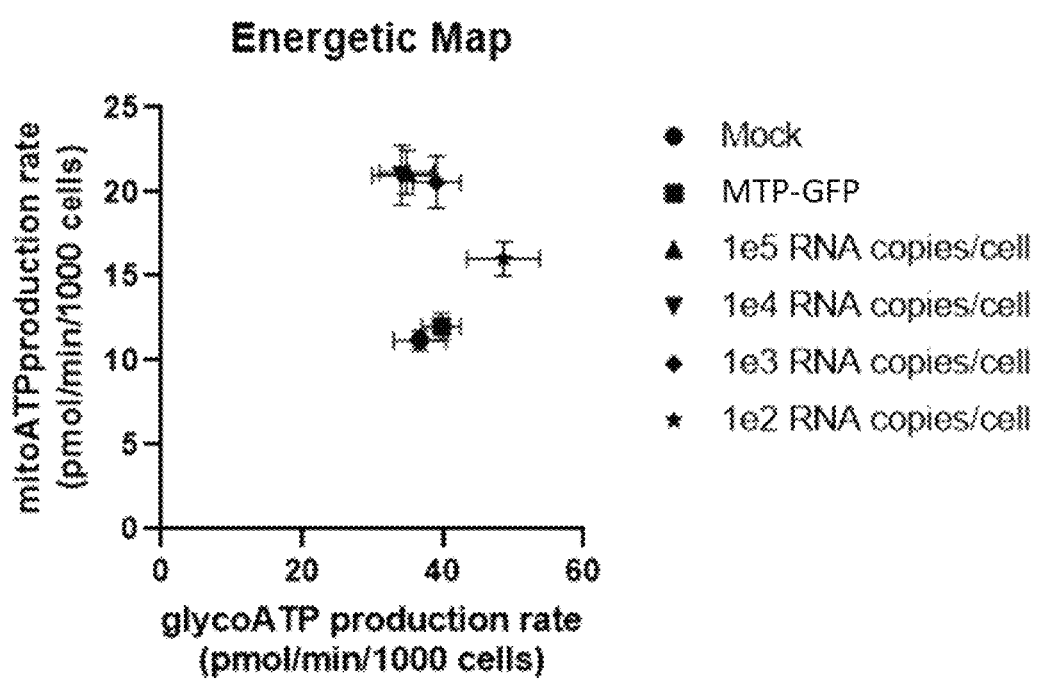
FIG. 18 shows the energetic map of MELAS cybrid cells 11 days post-transfection with the mitochondria-targeting engineered meganuclease (MTEM) MIT 25-26x.91, showing the relative contributions of glycolysis and OXPHOS on ATP production.

The relative contributions of glycolysis and OXPHOS on ATP production can be visualized in the energetic map in FIG. 18. The MTEM-treated cells that exhibited a complete shift in heteroplasmy (1e5 RNA copies/cell) showed greater ATP contributions from OXPHOS than untreated cells (mock).

Heteroplasmy was very effectively shifted in diseased cybrid cells using the MIT 25-26 meganucleases described herein. This shift resulted in significant functional improvement in oxygen consumption, ATP production, and OXPHOS ATP production. The cells treated with mitochondria-targeting engineered meganucleases are able to use oxygen to generate ATP through OXPHOS more readily than untreated cells.

Example 7: Mitochondrial Localization

The purpose of this experiment was to visualize engineered meganuclease localization when the nuclear localization signal (NLS) on the protein was replaced with a mitochondrial transit peptide (MTP).

8e5 MELAS cybrid cells were nucleofected with 1e6 RNA copies/cell engineered meganuclease mRNA using the Lonza 4D-Nucleofector™ (SF buffer, condition CA-137). Two engineered meganuclease constructs were compared: one without a targeting sequence and one with an MTP at the N-terminus of the protein. At 24 hours post-nucleofection the cells were stained with 50 nM MitoTracker™ Deep Red FM (ThermoFisher Scientific, M22426) and Hoechst 33342 (1:5000 dilution) for 30 minutes Cells were imaged using the Zeiss microscope using 63×Z-stack images.

Figure 19:
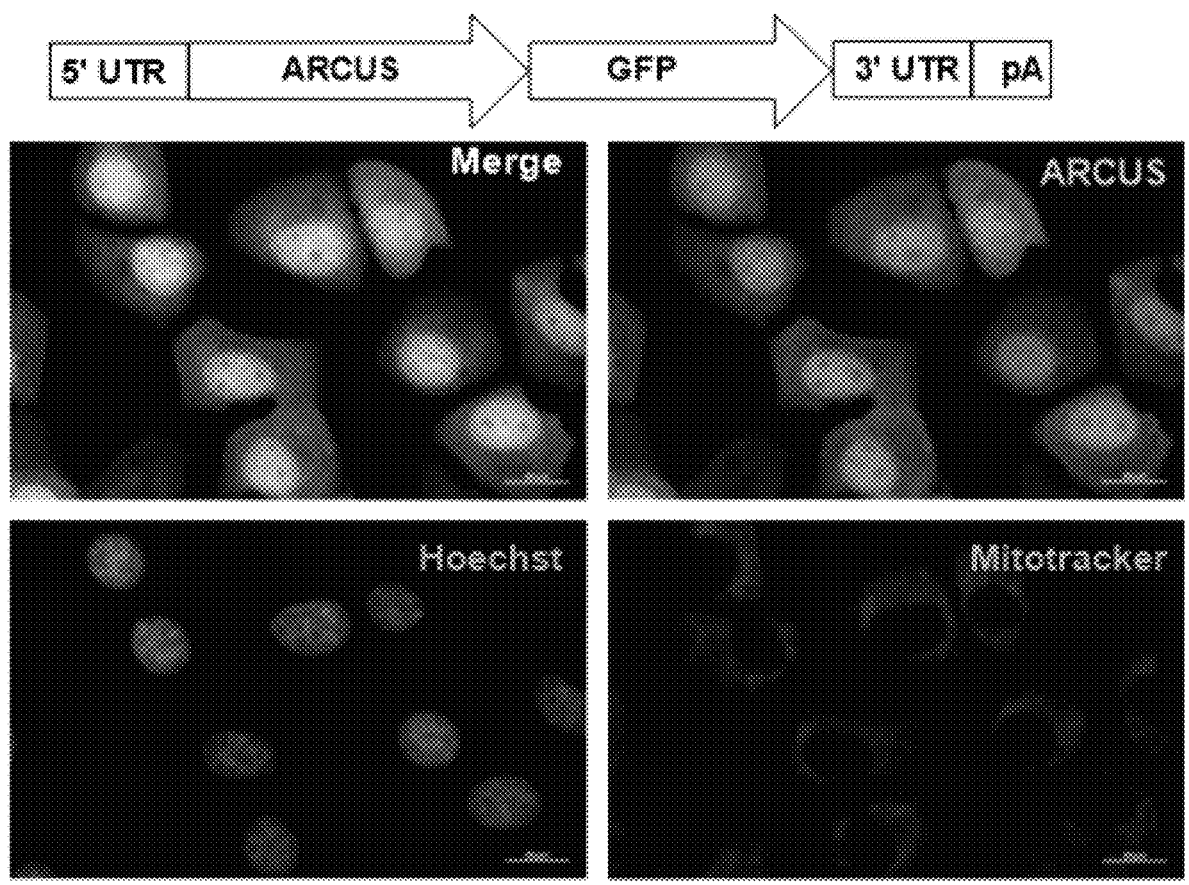
FIG. 19 is an immunofluorescent staining showing cellular localization of engineered meganuclease lacking a sub-cellular targeting sequence. Cells were transfected with a plasmid coding for an engineered meganuclease fused with a green fluorescent protein (GFP) peptide sequence. Immunocytological staining was achieved with DAPI and Mitotracker Red, which stains mitochondria. Cells were viewed under 63× magnification with a Zeiss LSM710 confocal microscope. The top left picture is an overlay of all stains. The top right picture shows the location of the engineered meganuclease. The bottom left picture shows nuclear staining with DAPI for nuclei, and the bottom right picture staining for the mitochondria.
Figure 20:
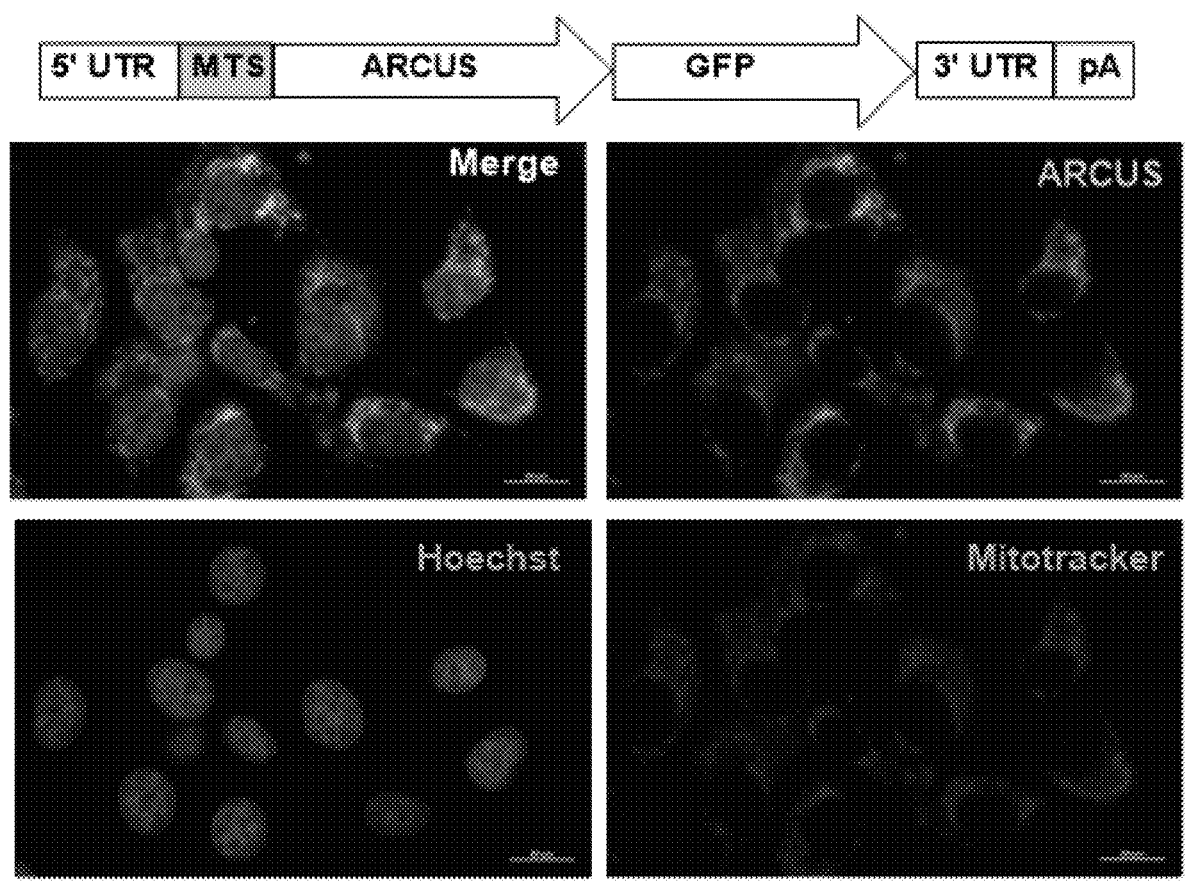
FIG. 20 is an immunofluorescent staining showing cellular localization of engineered meganuclease that contains a mitochondrial targeting peptide (MTP). Cells were transfected with a plasmid coding for an engineered meganuclease fused with the mitochondrial targeting peptide sequence (MTS) on the N-terminus and green fluorescent protein peptide (GFP) sequence on the C-terminus. Immunocytological staining was achieved with DAPI and Mitotracker Red, which stains mitochondria. Cells were viewed under 63× magnification with a Zeiss LSM710 confocal microscope. The top left picture is an overlay of all stains. The top right picture shows the location of the engineered meganuclease. The bottom left picture shows nuclear staining with DAPI for nuclei, and the bottom right picture staining for the mitochondria.

Without a targeting sequence, engineered meganuclease staining appears diffuse throughout the cytoplasm and the nucleus (FIG. 19). However, when fused with a mitochondrial transit peptide, engineered meganuclease staining appears punctate and overlays with the MitoTracker staining (FIG. 20). There does not appear to be any nuclear localization of the engineered meganuclease when attached to the MTP.

With the addition of an N-terminus MTP, engineered meganucleases are effectively localized to the mitochondria.

Example 8: Mitochondrial Targeting Meganuclease Activity and Specificity Evaluation The purpose of this experiment was to evaluate various MIT 25-26 nucleases for on-target (mutant m.3243G editing) in MELAS cells harboring the m.3243A>G mutation in mitochondrial circular DNA and to assess potential off-target editing of the nucleases for WT mitochondrial circular DNA (m.3243A activity). Accordingly, the cell lines used in this experiment contains either 100% mutant mtDNA (m.3243A>G mutation) or 100% wildtype mtDNA (m.3243A). Mitochondrial genomes are circular and linear DNA is rapidly cleared. Therefore, if a nuclease cleaves its intended on-target recognition sequence, the circular mtDNA will become linearized and eliminated by the mitochondria. The specificity of the nucleases can be assessed by determining the amount of remaining circular wild type mtDNA sequence after nuclease transfection. The amount of non-specific cleavage of the WT DNA sequence is indicative of off target activity because the WT and mutant DNA only differs by a single base pair. Because the mutant and WT mtDNA sequence only differ by a single nucleotide, it is necessary to identify an enzyme that can robustly cleave and eliminate mutant mtDNA, without disrupting WT mtDNA. Two cell lines were used for this analysis: one homoplasmic mutant (100% mutant) and one homoplasmic WT (0% mutant). Four control constructs were used: mock, MTS-GFP, a meganuclease that doesn't have recognition sequence in the mitochondrial genome MTS-APC 11-12L.330, and a nuclease activity dead meganuclease MTS-MIT 25-26x.91 KO. In the experiment the following ten MTS-MIT 25-26 nucleases were compared: MTS-MIT 25-26x. 29 (SEQ ID NO: 6), MTS-MIT 25-26x. 37 (SEQ ID NO: 7), MTS-MIT 25-26x. 73 (SEQ ID NO: 5), MTS-MIT 25-26x. 91 (SEQ ID NO: 3), MTS-MIT 25-26x. 84, MTS-MIT 25-26L. 35 (SEQ ID NO: 8), MTS-MIT 25-26L. 35 19A>S (SEQ ID NO:10), MTS-MIT 25-26x. 91 46H>W (SEQ ID NO: 12), MTS-MIT 25-26x. 91 259H>Q (SEQ ID NO: 9), and MTS-MIT 25-26x. 91 263T>R (SEQ ID NO: 11), 8e5 MELAS cybrid cells (either 100% mutant or 0% mutant) were nucleofected with 1.5e5 RNA copies/cell (142 ng) engineered meganuclease mRNA using the Lonza 4D-Nucleofector™ (SF buffer, condition CA-137). Cells were collected along a time-course (hour 6, 24, 48, and 72) for gDNA extraction. gDNA was isolated using the Macherey Nagel NucleoSpin Blood QuickPure kit. Cells were collected at one day post-nucleofection for evaluation of transfection efficiency using a Beckman Coulter CytoFlex S cytometer. Transfection efficiency exceeded 95%.

Droplet digital PCR (ddPCR) was utilized to determine mtDNA cleavage (linearized mtDNA at the MIT 25-26 binding site) and mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the ratio of linearized mtDNA molecules to circular mtDNA molecules. The number of positive droplets in assay 2 relative to the number of positive droplets in assay 3 was used to determine the mtDNA copy number in the cells.

P1:
(SEQ ID NO: 63)
TGGCAGGGCCCGGT

F1:
(SEQ ID NO: 64)
CCCAAGAACAGGGTTTGTTAAG

R1:
(SEQ ID NO: 65)
GGAATGCCATTGCGATTAG

P2:
(SEQ ID NO: 66)
AGCAGTTCTACCGTACAACCCTAACA

F2:
(SEQ ID NO: 67)
GGCAGTTGAGGTGGATTA

R2:
(SEQ ID NO: 68)
GGAATGCGGTAGTAGTTAGG

-continued

P4:
(SEQ ID NO: 69)
AACCAGACAAATCGCTCCACCAAC

F4:
(SEQ ID NO: 70)
CGGACAGGATTGACAGATT

R4:
(SEQ ID NO: 71)
CCAGAGTCTCGTTCGTTATC

Assays 1 and 2 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Figure 21:
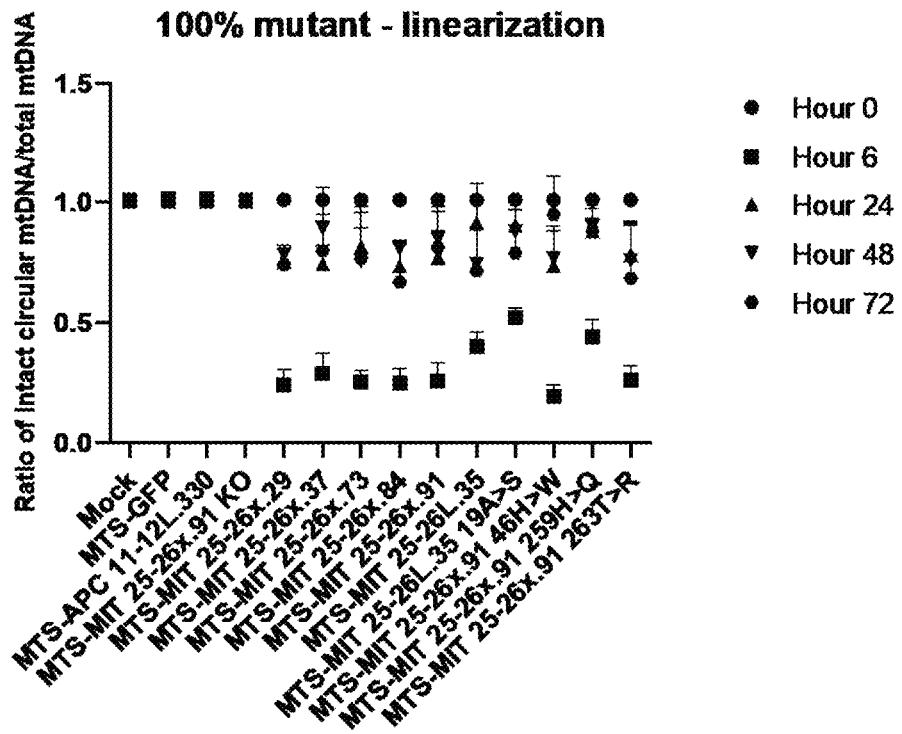
FIG. 21 provides a graph showing the ratio of circular mtDNA to total mtDNA in 100% mutant mtDNA (m.3243G) containing mitochondria for cells transfected with the indicated controls (Mock, MTS-GFP, MTS-APC 11-12L.330, and MTS-MIT 25-26x.91 KO) and test engineered meganucleases at 0, 6, 24, 48, and 72 hours post transfection.
Figure 22:
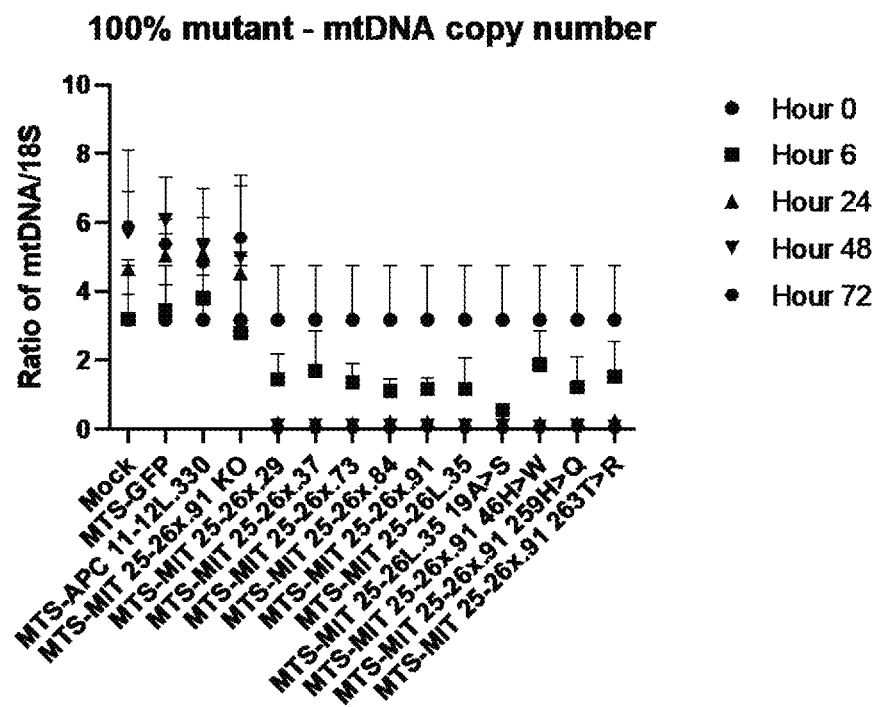
FIG. 22 provides a graph showing the ratio of total mtDNA to ribosomal 18s DNA in 100% mutant mtDNA (m.3243G) containing mitochondria for cells transfected with the indicated controls (Mock, MTS-GFP, MTS-APC 11-12L.330, and MTS-MIT 25-26x.91 KO) and test engineered meganucleases at 0, 6, 24, 48, and 72 hours post transfection.
Figure 23:
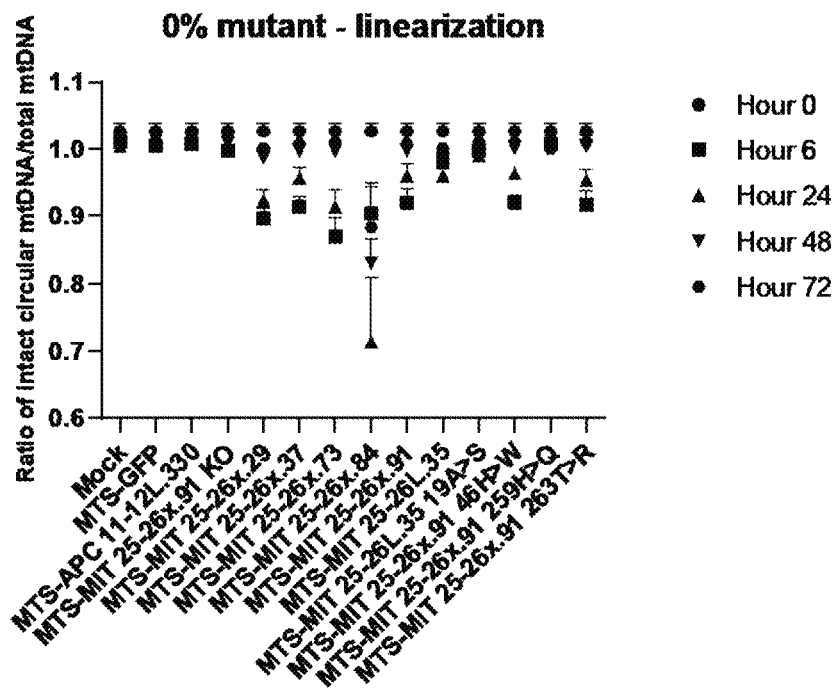
FIG. 23 provides a graph showing the ratio of circular mtDNA to total mtDNA in wild type mtDNA, containing mitochondria for cells transfected with the indicated controls (Mock, MTS-GFP, MTS-APC 11-12L.330, and MTS-MIT 25-26x.91 KO) and test engineered meganucleases at 0, 6, 24, 48, and 72 hours post transfection.
Figure 24:
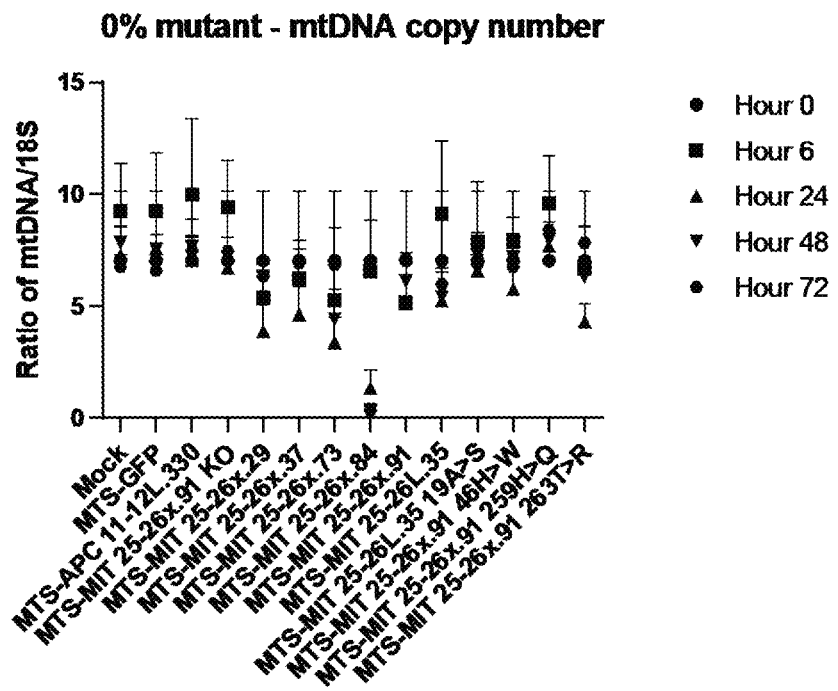
FIG. 24 provides a graph showing the ratio of total mtDNA to ribosomal 18s DNA in wild type mtDNA containing mitochondria for cells transfected with the indicated controls (Mock, MTS-GFP, MTS-APC 11-12L.330, and MTS-MIT 25-26x.91 KO) and test engineered meganucleases at 0, 6, 24, 48, and 72 hours post transfection.
Figure 25:
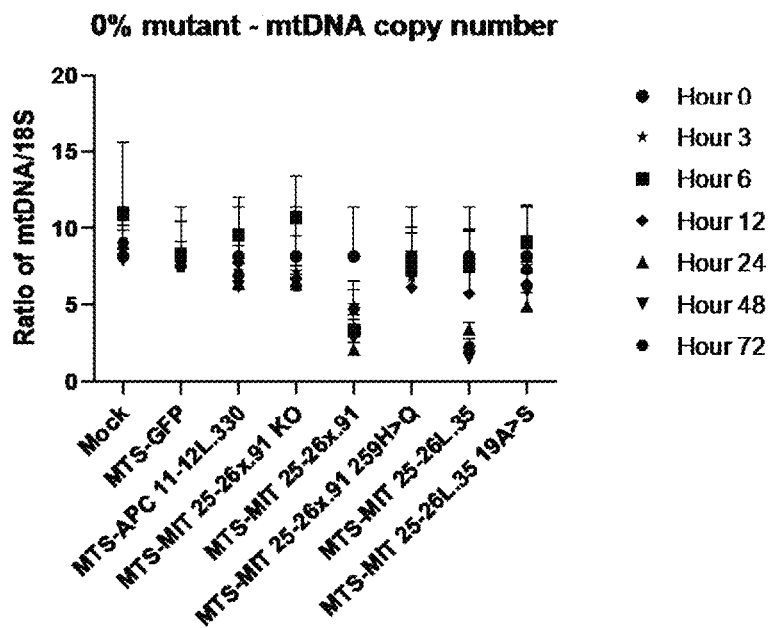
FIG. 25 provides a graph showing the ratio of total mtDNA to ribosomal 18s DNA in wild type mtDNA containing mitochondria for cells transfected with the indicated controls (Mock, MTS-GFP, MTS-APC 11-12L.330, and MTS-MIT 25-26x.91 KO) and test engineered meganucleases at 0, 3, 6, 12, 24, 48, and 72 hours post transfection.
Figure 26:
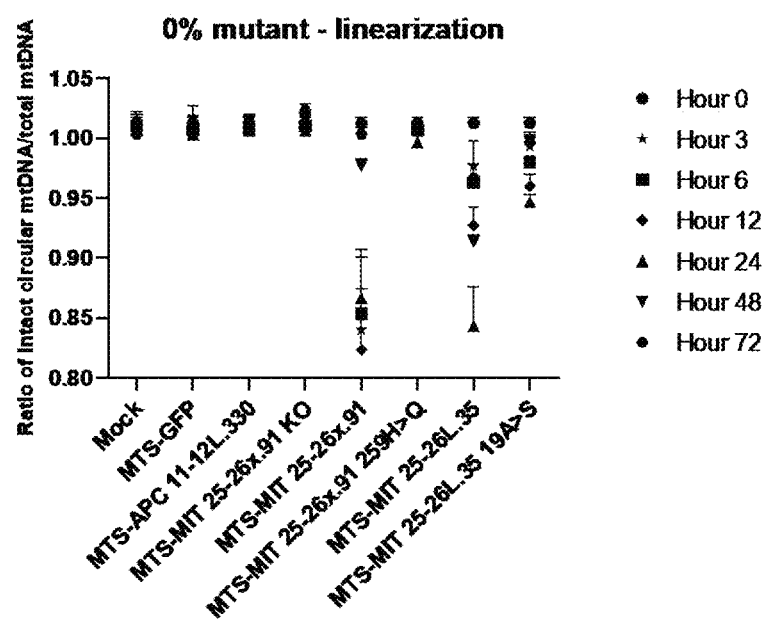
FIG. 26 provides a graph showing the ratio of circular mtDNA to total mtDNA in wild type mtDNA containing mitochondria for cells transfected with the indicated controls (Mock, MTS-GFP, MTS-APC 11-12L.330, and MTS-MIT 25-26x.91 KO) and test engineered meganucleases at 0, 3, 6, 12, 24, 48, and 72 hours post transfection.

FIG. 21 shows a marked reduction in the ratio of circular mtDNA to total mtDNA (linearized and circular) at six hours indicating robust cleavage activity of all tested nucleases for the mutant m.3243G mtDNA sequence. Immediately following cleavage of the circular DNA, the DNA is linearized and cleared by the mitochondria and only the remaining uncut or replicated circular mtDNA is detected as shown by the progressive increase in circular mtDNA after six hours. This reduction in mutant mtDNA can also be visualized by the ratio of total mtDNA to ribosomal 18s DNA sequence, which indicates that each nuclease is able to eliminate all mutant mtDNA nearly completely by 24 hours post transfection (FIG. 22). However, as shown in FIG. 23 and FIG. 24 the different nucleases varied in their specificity between mutant mtDNA and WT mtDNA. This difference in specificity is shown by the amount of WT mtDNA that was cleaved and subsequently eliminated indicating different nucleases have differing ability to discriminate against the WT m.3243A sequence. In particular, the MIT 25-26L.35 19A>S meganuclease and MIT 25-26x.91 259 H>Q nucleases demonstrated on target activity that was statistically insignificant from the four controls in their ability to both linearize and deplete WT mtDNA, indicating a high degree of specificity. In contrast the MTS 26-26x.84 nuclease was unable to sufficiently discriminate between the mutant mtDNA and WT mtDNA due to nearly all of the mtDNA being cleared by 48 hours post transfection (FIG. 24). Additional data sets indicate that MIT MTS 25-26x.91 259H>Q is the most specific nuclease because it is statistically insignificant relative to the four controls in terms of both mtDNA copy number and mtDNA linearization at all timepoints (FIGS. 25 and 26 and Tables 7 and 8).

The statistical significance at each time point for FIGS. 22-26 are shown in Tables 4-8, respectively.

TABLE 4

Statistical significance of the ratio of total mtDNA to ribosomal 18s DNA sequence in 100% mutant- mtDNA copy number cells

| Nuclease | Hour 6 | Hour 24 | Hour 48 | Hour 72 |
|---|---|---|---|---|
| MTS MIT 25-26x.29 | ** | N/A | **** | **** |
| MTS MIT 25-26x.37 | * | N/A | **** | **** |
| MTS MIT 25-26x.73 | ** | N/A | **** | **** |
| MTS MIT 25-26x.91 | *** | N/A | **** | **** |
| MTS MIT 25-26L.35 | *** | N/A | **** | **** |
| MTS MIT 25-26x.84 | *** | N/A | **** | **** |
| MTS MIT 25-26L.35 19A>S | **** | N/A | **** | **** |
| MTS MIT 25-26x.91 46H>W | * | N/A | **** | **** |
| MTS MIT 25-26x.91 259H>Q | ** | N/A | **** | **** |
| MTS MIT 25-26x.91 263T>R | ** | N/A | **** | **** |

Asterisks (*) indicate statistical significance between cells having the same number of asterisks. N/A- Statistics and 24 hours could not be computed because of two replicates

TABLE 5

Statistical significance of the ratio of intact circular mtDNA to total mtDNA in 0% mutant- mtDNA copy number cells

| Nuclease | Hour 6 | Hour 24 | Hour 48 | Hour 72 |
|---|---|---|---|---|
| MTS MIT 25-26x.29 | **** | *** | * | ns |
| MTS MIT 25-26x.37 | **** | ns | ns | ns |
| MTS MIT 25-26x.73 | **** | *** | ns | ns |
| MTS MIT 25-26x.91 | **** | ns | ns | ns |
| MTS MIT 25-26L.35 | ns | ns | ** | ns |
| MTS MIT 25-26x.84 | **** | **** | **** | **** |
| MTS MIT 25-26L.35 19A>S | ns | ns | ns | ns |
| MTS MIT 25-26x.91 46H>W | **** | ns | ns | ns |
| MTS MIT 25-26x.91 259H>Q | ns | ns | ns | ns |
| MTS MIT 25-26x.91 263T>R | **** | ns | ns | ns |

Asterisks (*) indicate statistical significance between cells having the same number of asterisks. The ns denotation indicates no statistical difference between any of the other conditions.

TABLE 6

Statistical significance of the ratio of total mtDNA to ribosomal 18s DNA sequence in 0% mutant- mtDNA copy number cells

| Nuclease | Hour 6 | Hour 24 | Hour 48 | Hour 72 |
|---|---|---|---|---|
| MTS MIT 25-26x.29 | ns | ** | ** | ns |
| MTS MIT 25-26x.37 | ns | ns | ns | ns |
| MTS MIT 25-26x.73 | * | ** | *** | ns |
| MTS MIT 25-26x.91 | * | ns | ns | ns |
| MTS MIT 25-26L.35 | ns | ns | * | ns |
| MTS MIT 25-26x.84 | ns | **** | **** | **** |
| MTS MIT 25-26L.35 19A>S | ns | ns | ns | ns |
| MTS MIT 25-26x.91 46H>W | ns | ns | ns | ns |
| MTS MIT 25-26x.91 259H>Q | ns | ns | ns | ns |
| MTS MIT 25-26x.91 263T>R | ns | * | ns | ns |

Asterisks (*) indicate statistical significance between cells having the same number of asterisks. The ns denotation indicates no statistical difference between any of the other conditions.

TABLE 7

Statistical significance of the ratio of total mtDNA to ribosomal 18s DNA sequence in 0% mutant- mtDNA copy number cells

| Nuclease | Hour 3 | Hour 6 | Hour 12 | Hour 24 | Hour 48 | Hour 72 |
|---|---|---|---|---|---|---|
| MTS MIT 25-26x.91 | ns | ** | ** | **** | **** | * |
| MTS MIT 25-26x.91 259H>Q | ns | ns | ns | ns | ns | ns |
| MTS MIT 25-26L.35 | ns | ns | ns | **** | **** | **** |
| MTS MIT 25-26L.35 19A>S | ns | ns | ns | ** | ns | ns |

Asterisks (*) indicate statistical significance between cells having the same number of asterisks. The ns denotation indicates no statistical difference between any of the other conditions.

TABLE 8

Statistical significance of the ratio of intact circular mtDNA to total mtDNA in 0% mutant- mtDNA copy number cells

| Nuclease | Hour 3 | Hour 6 | Hour 12 | Hour 24 | Hour 48 | Hour 72 |
|---|---|---|---|---|---|---|
| MTS MIT 25-26x.91 | **** | **** | **** | **** | **** | ns |
| MTS MIT 25-26x.91 259H>Q | ns | ns | ns | ns | ns | ns |
| MTS MIT 25-26L.35 | ns | **** | **** | **** | **** | **** |
| MTS MIT 25-26L.35 19A>S | ns | ** | **** | *** | ** | ns |

Asterisks (*) indicate statistical significance between cells having the same number of asterisks. The ns denotation indicates no statistical difference between any of the other conditions.

Example 9: Molecular Changes in m.3243G Mutant Cells Following Mitochondrial Targeting Meganuclease mRNA Transfection The purpose of this experiment was to show efficacy of the MIT 25-26x.91 nuclease in a cell line that harbors the heteroplasmic MELAS mutation (m.3243A>G). The cell line used is a cybrid (cytoplasmic hybrid) that contains both wildtype and mutant mtDNA. The cell line in particular is 96% mutant—that is, 96% of the mtDNA population contains the mutant allele and 6% contains the wildtype allele.

8e5 MELAS cybrid cells were nucleofected with engineered meganuclease mRNA across a dose titration using the Lonza 4D-Nucleofector™ (SF buffer, condition CA-137). The engineered meganuclease mRNA doses started at 1e5 RNA copies/cell; this translates to 8e10 RNA copies total, or 94.8 ng of RNA. The mRNA was then serially diluted 1:10 down to 1e2 RNA copies/cell. Cells were collected at one day post-nucleofection for gDNA extraction and evaluated for transfection efficiency using a Beckman Coulter CytoFlex S cytometer. Transfection efficiency exceeded 95%. gDNA was isolated using the Macherey Nagel NucleoSpin Blood QuickPure kit. The cells were carried for additional timepoints (day 4 and day 7) for gDNA extraction and functional analysis.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells. This ratio was then normalized based on the MTS-GFP (control) condition, and the resulting normalized copy number was multiplied by the heteroplasmy level to generate the data shown in FIGS. 27-29. In these graphs, the height of the bars is indicative of mtDNA loss, relative to the MTS-GFP cells. Within the bar, the relative percentage of gray corresponds to the relative percentage of wild-type mtDNA present, and the relative percentage of black corresponds to the relative percentage of mutant mtDNA present.

```
P1:
                                        (SEQ ID NO: 63)
TGGCAGGGCCCGGT

F1:
                                        (SEQ ID NO: 64)
CCCAAGAACAGGGTTTGTTAAG

R1:
                                        (SEQ ID NO: 65)
GGAATGCCATTGCGATTAG

P2:
                                        (SEQ ID NO: 66)
AGCAGTTCTACCGTACAACCCTAACA

F2:
                                        (SEQ ID NO: 67)
GGCAGTTGAGGTGGATTA

R2:
                                        (SEQ ID NO: 68)
GGAATGCGGTAGTAGTTAGG

P4:
                                        (SEQ ID NO: 69)
AACCAGACAAATCGCTCCACCAAC

F4:
                                        (SEQ ID NO: 70)
CGGACAGGATTGACAGATT

R4:
                                        (SEQ ID NO: 71)
CCAGAGTCTCGTTCGTTATC
```

Assays 1 and 2 were multiplexed in a 24 μL reaction containing 1×ddPCR Supermix for Probes (no dUTP, Bio-Rad), 250 nM of each probe, 900 nM of each primer, 20 U/μL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 μL reaction containing 1×ddPCR Supermix for Probes (no dUTP, Bio-Rad), 250 nM of each probe, 900 nM of each primer, 20 U/μL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

At day 7 post-transfection, 4e3 cells were plated into a 96 well Seahorse cell culture microplate for analysis on the Seahorse XFe96 Analyzer (Agilent). An XF Sensor Cartridge was also hydrated with 200 μL/well Seahorse XF Calibrant overnight in a non-$CO_2$ incubator. The following day (day 8), 97 mL of Seahorse Assay Medium (DMEM) was combined with 1 mL 1 mM Sodium Pyruvate, 1 mL 2 mM Glutamine, and 1 mL 10 mM Glucose. Cells were washed two times with the prepared media and then placed in a non-$CO_2$ incubator for 1 hour. One Cell Mito Stress Test Kit was reconstituted according to manufacturer directions. Solutions were made up of Oligomycin (15 uM), FCCP (5 uM), and Rotenone/Antimycin A (5 uM). For the Cell Mito Stress Test, 20 μL Oligomycin solution was added to all Port As of the hydrated cartridge, 22 μL FCCP solution was added to all Port Bs, and 24 μL of Rotenone/Antimycin A was added to all Port Cs. For the ATP Rate Assay, the same stock solutions were used. For this assay, 20 μL Oligomycin solution was added to all Port As, 22 μL of Rotenone/Antimycin A solution was added to all port Bs, and 24 μL of Seahorse Assay Medium was added to all Port Cs. The assay was run with 4 measurement cycles (03:00 mix, 00:00 wait, 03:00 measure) for baseline, Oligomycin, FCCP, and Rotenone/Antimycin A. OCR and PER values were analyzed using Wave software (Agilent). The Cell Mito Stress Test and ATP Rate Assay Reports were generated using Wave software (Agilent).

After completion of the assay, the cells were stained with Hoechst 33342 Solution (ThermoFisher, H3570) at a 1:5000 dilution in standard media. The cells were incubated at 37 C for 20 minutes and then analyzed by image cytometry using ImageXpress Pico Automated Cell Imaging System (Molecular Devices). OCR and PER values were then normalized to cell count using Wave software (Agilent).

Figure 27:
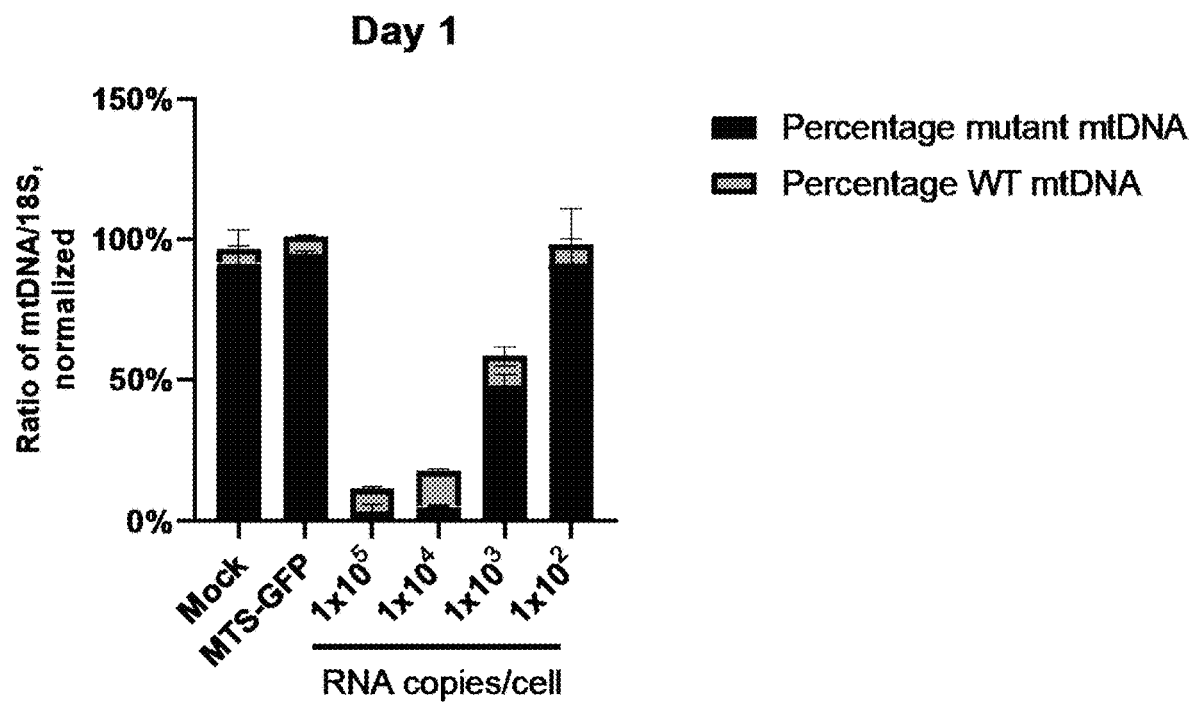
FIG. 27 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 meganuclease at Day 1 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 28:
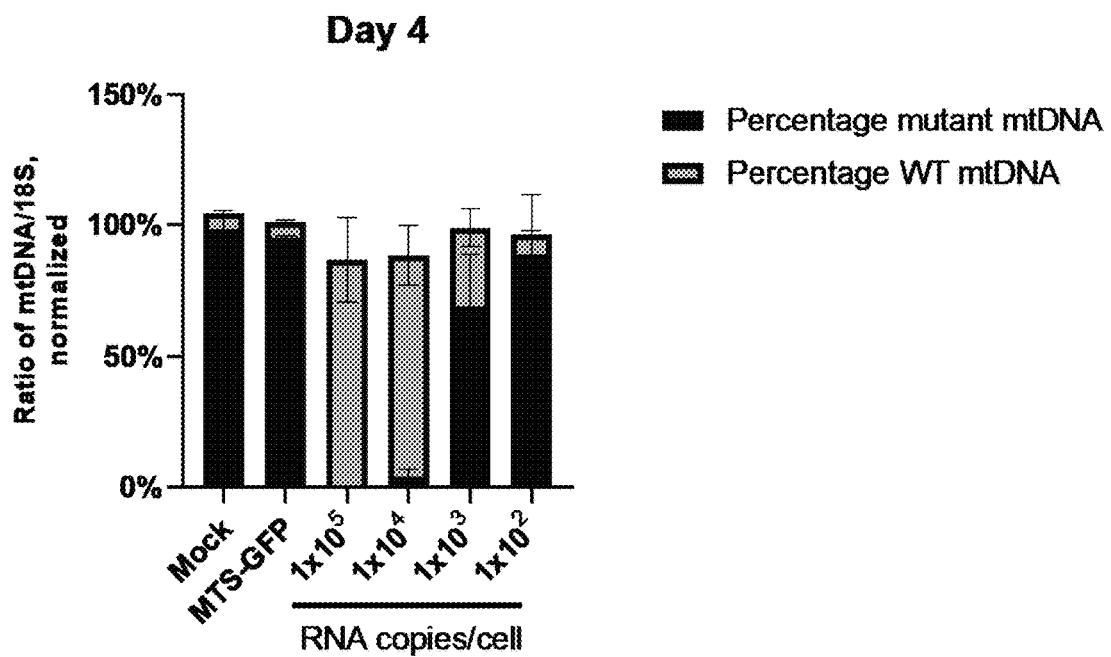
FIG. 28 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 meganuclease at Day 4 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 29:
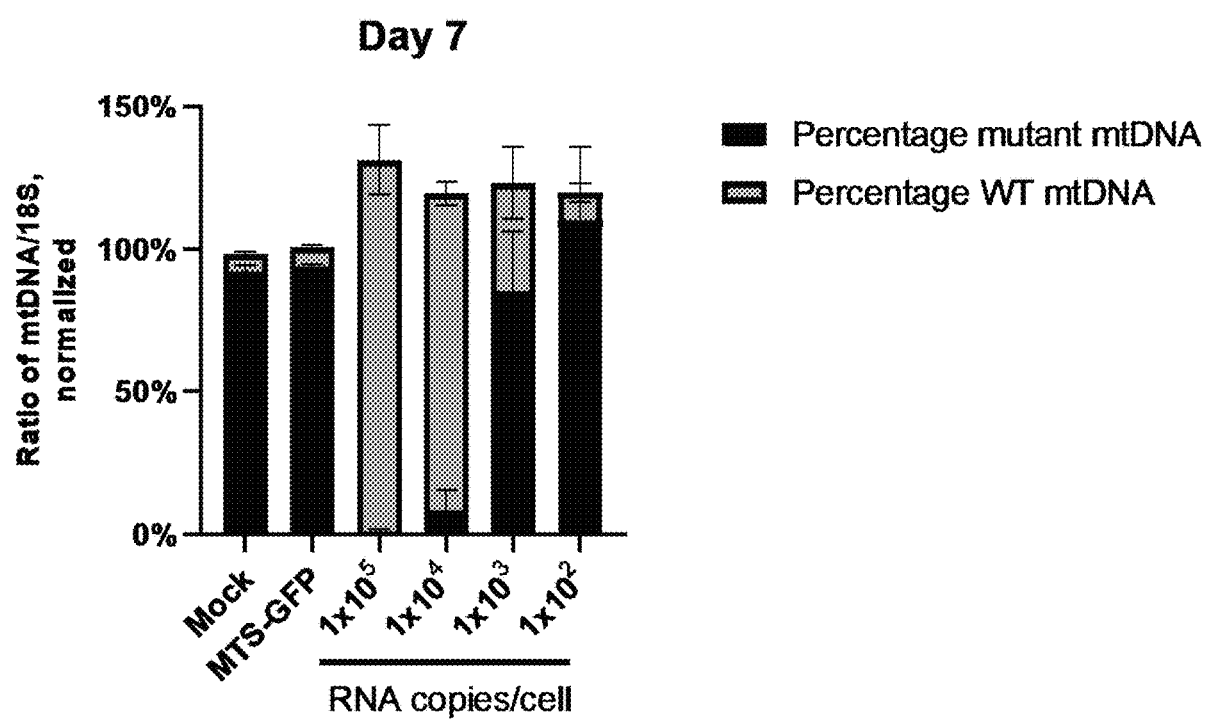
FIG. 29 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 meganuclease at Day 7 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.

As shown in FIG. 27, higher doses of the mitochondria-targeting engineered meganuclease (MTEM) resulted in a greater loss of mtDNA copies. This mtDNA reduction was statistically significant at the two highest mRNA doses at day 1 only (Table 9). The observed mtDNA depletion corresponded to the selective cleavage of mutant mtDNA. The cells treated with the three highest mRNA doses exhibited a significant loss of mutant mtDNA at all timepoints (Table 9, Table 10, Table 11). Following the elimination of the mutant mtDNA, the remaining WT mtDNA was found to repopulate the cell (FIG. 28 and FIG. 29). By day 7, there was only 0.50 mutant mtDNA remaining in the cells treated with the highest mRNA dose (FIG. 29). There was a significant increase in the amount of WT mtDNA present in the cells treated with the two highest mRNA doses at all timepoints, and the 1e3 RNA copies/cell dose at day 4 and day 7 (Table 9, Table 10, Table 11).

TABLE 9

Statistical significance in WT DNA amount at differing doses of meganuclease mRNA dose at Day 1.

| Condition | mtDNA copy number | Percent mutant mtDNA | Percent WT mtDNA |
|---|---|---|---|
| Mock | ns | ns | ns |
| 1 × $10^5$ RNA copies/cell | ** | **** | **** |
| 1 × $10^4$ RNA copies/cell | ** | **** | **** |
| 1 × $10^3$ RNA copies/cell | ns | ** | ns |
| 1 × $10^2$ RNA copies/cell | ns | ns | ns | ns: $P > 0.05$, *: $P \leq 0.05$, : $P \leq 0.01$, *: $P \leq 0.001$, ****: $P \leq 0.0001$.

TABLE 10

Statistical significance in WT DNA amount at differing doses of meganuclease mRNA dose at Day 4.

| Condition | mtDNA copy number | Percent mutant mtDNA | Percent WT mtDNA |
|---|---|---|---|
| Mock | ns | ns | ns |
| 1 × 10$^5$ RNA copies/cell | ns | **** | **** |
| 1 × 10$^4$ RNA copies/cell | ns | **** | **** |
| 1 × 10$^3$ RNA copies/cell | ns | *** | *** |
| 1 × 10$^2$ RNA copies/cell | ns | ns | ns | ns: $P > 0.05$, *: $P \leq 0.05$, : $P \leq 0.01$, *: $P \leq 0.001$, ****: $P \leq 0.0001$.

TABLE 11

Statistical significance in WT DNA amount at differing doses of meganuclease mRNA dose at Day 7.

| Condition | mtDNA copy number | Percent mutant mtDNA | Percent WT mtDNA |
|---|---|---|---|
| Mock | ns | ns | ns |
| 1 × 10$^5$ RNA copies/cell | ns | **** | **** |
| 1 × 10$^4$ RNA copies/cell | ns | **** | **** |
| 1 × 10$^3$ RNA copies/cell | ns | *** | *** |
| 1 × 10$^2$ RNA copies/cell | ns | ns | ns | ns: $P > 0.05$, *: $P \leq 0.05$, : $P \leq 0.01$, *: $P \leq 0.001$, ****: $P \leq 0.0001$.

Figure 30:
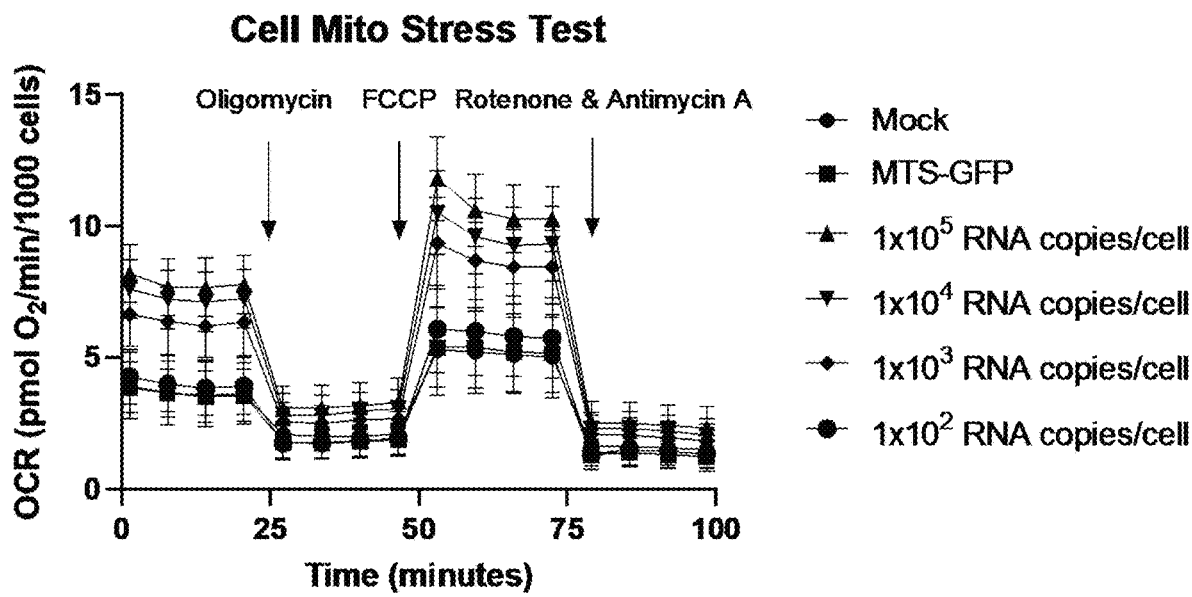
FIG. 30 is a graph showing the mitochondrial stress test of MELAS cybrid cells 11 days post-transfection with the mitochondria-targeting engineered meganuclease (MTEM) MIT 25-26x.91.

In the Cell Mito Stress Test, the MTEM-treated cells that exhibited a complete shift in heteroplasmy (1e5 RNA copies/cell) had a 2.15× increase in basal respiration and a 2.03× increase in maximal respiration above the GFP-treated cells (FIG. 30).

Figure 31:
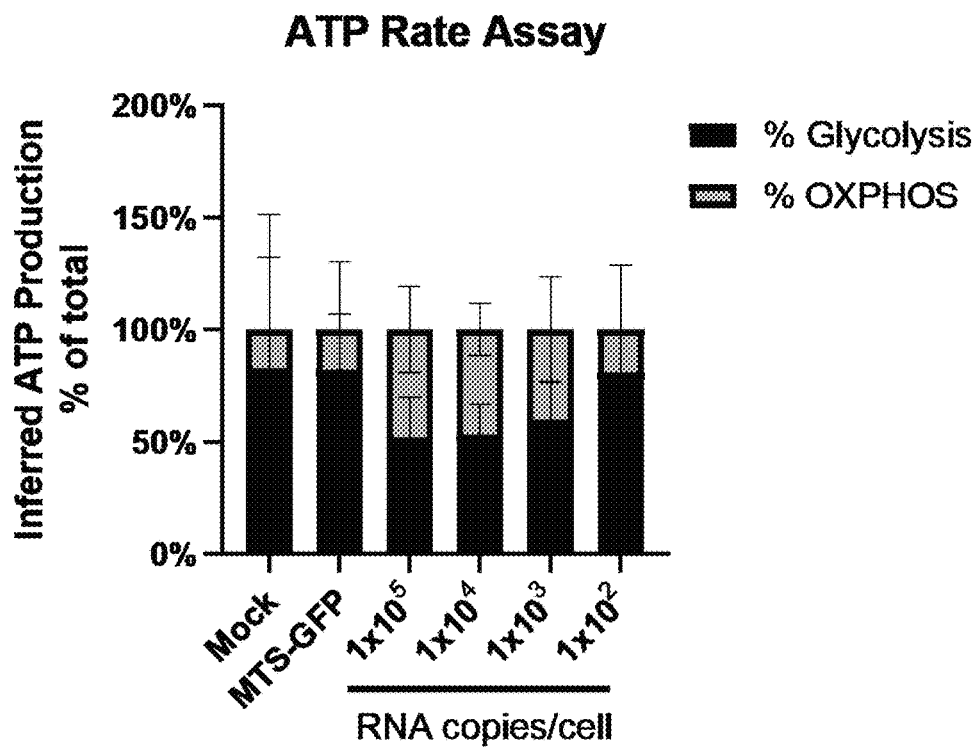
FIG. 31 shows the energetic map of MELAS cybrid cells 11 days post-transfection with the mitochondria-targeting engineered meganuclease (MTEM) MIT 25-26x.91, showing the relative contributions of glycolysis and OXPHOS on ATP production.

In the ATP Rate Assay, the MTEM-treated cells that exhibited a complete shift in heteroplasmy (1e5 RNA copies/cell) had a 2.23×increase in mitoATP production above the GFP-treated cells (FIG. 31).

Figure 32:
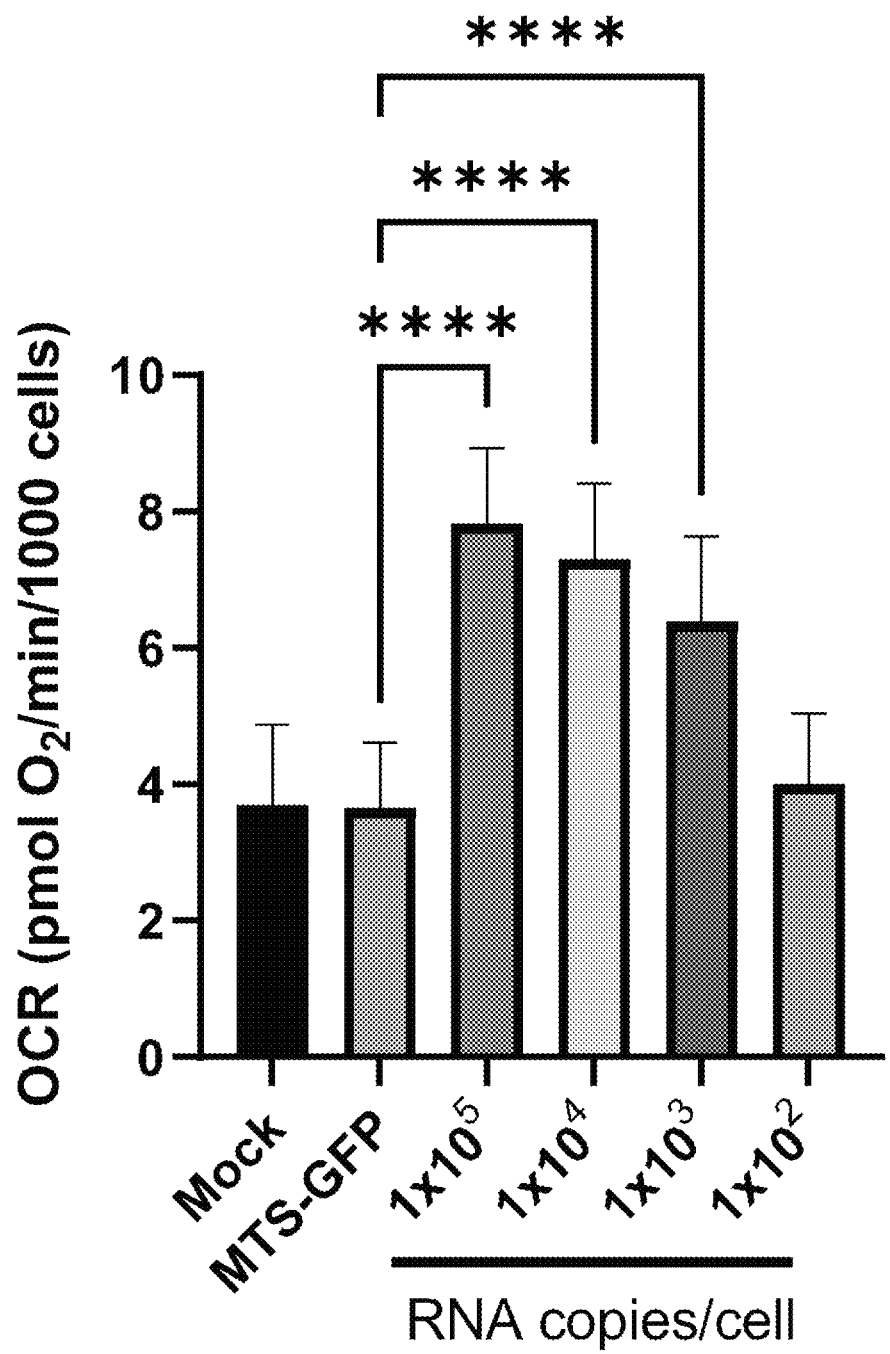
FIG. 32 shows the basal respiration rate of MELSA cybrid cells 11 days post-transfection with the mitochondria-targeting engineered meganuclease (MTEM) MIT 25-26x.91.
Figure 33:
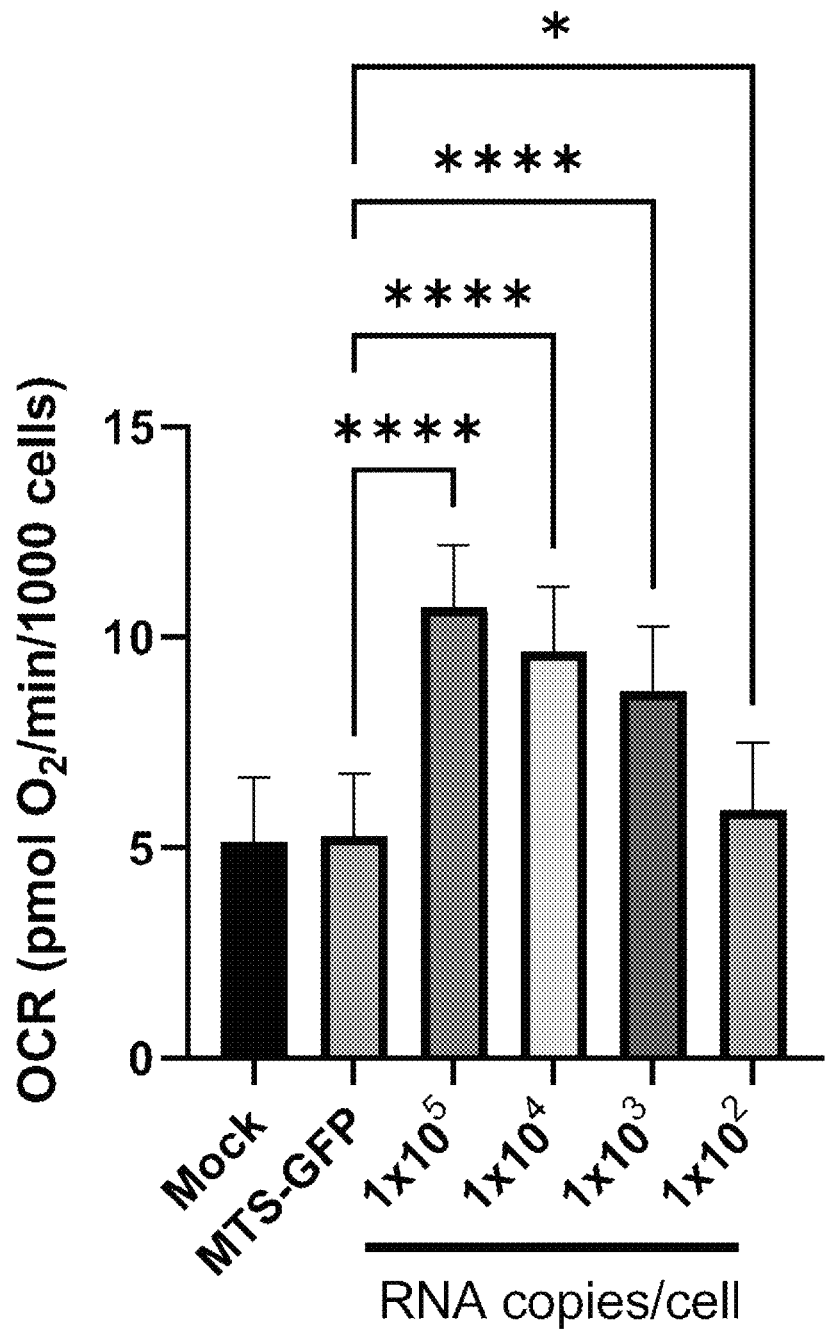
FIG. 33 shows the maximal respiration rate of MELSA cybrid cells 11 days post-transfection with the mitochondria-targeting engineered meganuclease (MTEM) MIT 25-26x.91.
Figure 34:
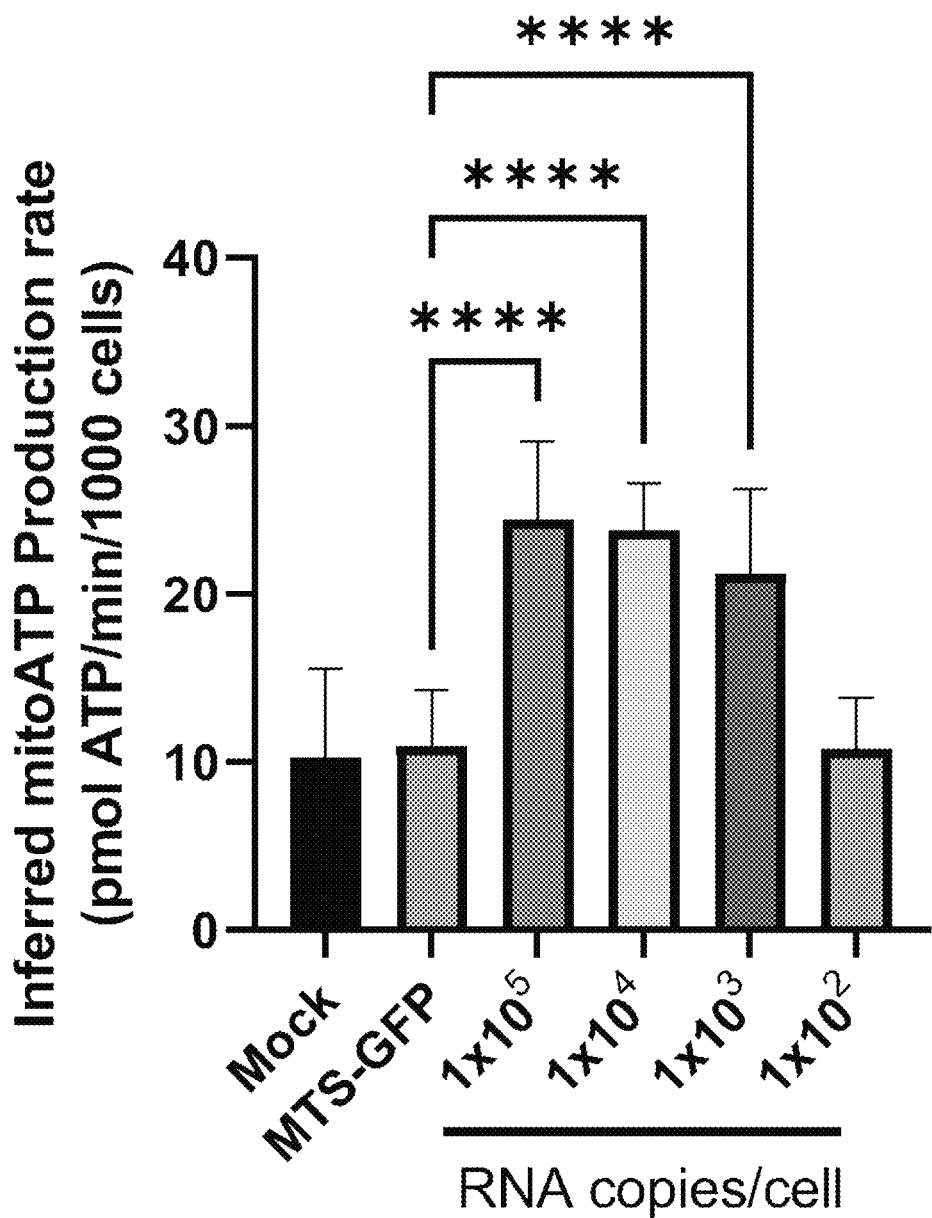
FIG. 34 shows the mitochondrial ATP production rate of MELSA cybrid cells 11 days post-transfection with the mitochondria-targeting engineered meganuclease (MTEM) MIT 25-26x.91.

Heteroplasmy was very effectively shifted in high-percentage mutant diseased cybrid cells using the MIT 25-26 meganucleases described herein. This shift resulted in significant functional improvement in basal respiration rate (FIG. 32), maximal respiration rate (FIG. 33), and mitochondrial ATP production (FIG. 34). The cells treated with mitochondria-targeting engineered meganucleases are able to use oxygen to generate ATP through oxidative phosphorylation more readily than untreated cells.

Example 10: Molecular Changes in 96% m.3243G Mutant Cells Following Mitochondrial Targeting Meganuclease mRNA Transfection The purpose of this experiment was to show efficacy of the MIT 25-26x.91 259H>Q meganuclease in a cell line that harbors the heteroplasmic MELAS mutation (m.3243A>G), as well as to determine if the transient mtDNA depletion induced by the meganuclease negatively impacted cellular respiration The cell line used is a cybrid (cytoplasmic hybrid) that contains both wildtype and mutant mtDNA. The cell line in particular is 96% mutant—that is, 96% of the mtDNA population contains the mutant allele and 6% contains the wildtype allele.

8e5 MELAS cybrid cells were nucleofected with engineered meganuclease mRNA across a dose titration using the Lonza 4D-Nucleofector™ (SF buffer, condition CA-137). The engineered meganuclease mRNA doses started at 1e5 RNA copies/cell; this translates to 8e10 RNA copies total, or 94.8 ng of RNA. The mRNA was then serially diluted 1:10 down to 1e2 RNA copies/cell. Cells were collected at days one, three, and seven post-nucleofection for gDNA extraction and Seahorse Cell Mito Stress Test evaluation. gDNA was isolated using the Macherey Nagel NucleoSpin Blood QuickPure kit.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells. This ratio was then normalized based on the MTS-GFP (control) condition, and the resulting normalized copy number was multiplied by the heteroplasmy level to generate the data shown in FIGS. 35, 37, and 39. In these graphs, the height of the bars is indicative of mtDNA loss, relative to the MTS-GFP cells. Within the bar, the relative percentage of gray corresponds to the relative percentage of wildtype mtDNA present, and the relative percentage of black corresponds to the relative percentage of mutant mtDNA present.

P1:
(SEQ ID NO: 63)
TGGCAGGGCCCGGT

F1:
(SEQ ID NO: 64)
CCCAAGAACAGGGTTTGTTAAG

R1:
(SEQ ID NO: 65)
GGAATGCCATTGCGATTAG

P2:
(SEQ ID NO: 66)
AGCAGTTCTACCGTACAACCCTAACA

F2:
(SEQ ID NO: 67)
GGCAGTTGAGGTGGATTA

R2:
(SEQ ID NO: 68)
GGAATGCGGTAGTAGTTAGG

P4:
(SEQ ID NO: 69)
AACCAGACAAATCGCTCCACCAAC

F4:
(SEQ ID NO: 70)
CGGACAGGATTGACAGATT

R4:
(SEQ ID NO: 71)
CCAGAGTCTCGTTCGTTATC

Assays 1 and 2 were multiplexed in a 24 μL reaction containing 1×ddPCR Supermix for Probes (no dUTP, Bio-Rad), 250 nM of each probe, 900 nM of each primer, 20 U/μL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98°

C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 µL reaction containing 1×ddPCR Supermix for Probes (no dUTP, BioRad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

At days 0, 2, and 6 post-transfection, 4e3 cells were plated into a 96 well Seahorse cell culture microplate for analysis on the Seahorse XFe96 Analyzer (Agilent). An XF Sensor Cartridge was also hydrated with 200 µL/well Seahorse XF Calibrant overnight in a non-$CO_2$ incubator. The following day (days 1, 3, and 7), 97 mL of Seahorse Assay Medium (DMEM) was combined with 1 mL 1 mM Sodium Pyruvate, 1 mL 2 mM Glutamine, and 1 mL 10 mM Glucose. Cells were washed two times with the prepared media and then placed in a non-$CO_2$ incubator for 1 hour. One Cell Mito Stress Test Kit was reconstituted according to manufacturer directions. Solutions were made up of Oligomycin (15 uM), FCCP (5 uM), and Rotenone/Antimycin A (5 uM). For the Cell Mito Stress Test, 20 µL Oligomycin solution was added to all Port As of the hydrated cartridge, 22 µL FCCP solution was added to all Port Bs, and 24 µL of Rotenone/Antimycin A was added to all Port Cs. The assay was run with 4 measurement cycles (03:00 mix, 00:00 wait, 03:00 measure) for baseline, Oligomycin, FCCP, and Rotenone/Antimycin A. OCR values were analyzed using Wave software (Agilent). The Cell Mito Stress Test Report was generated using Wave software (Agilent).

After completion of the assay, the cells were stained with Hoechst 33342 Solution (ThermoFisher, H3570) at a 1:5000 dilution in standard media. The cells were incubated at 37 C for 20 minutes and then analyzed by image cytometry using ImageXpress Pico Automated Cell Imaging System (Molecular Devices). OCR values were then normalized to cell count using Wave software (Agilent).

Figure 35:
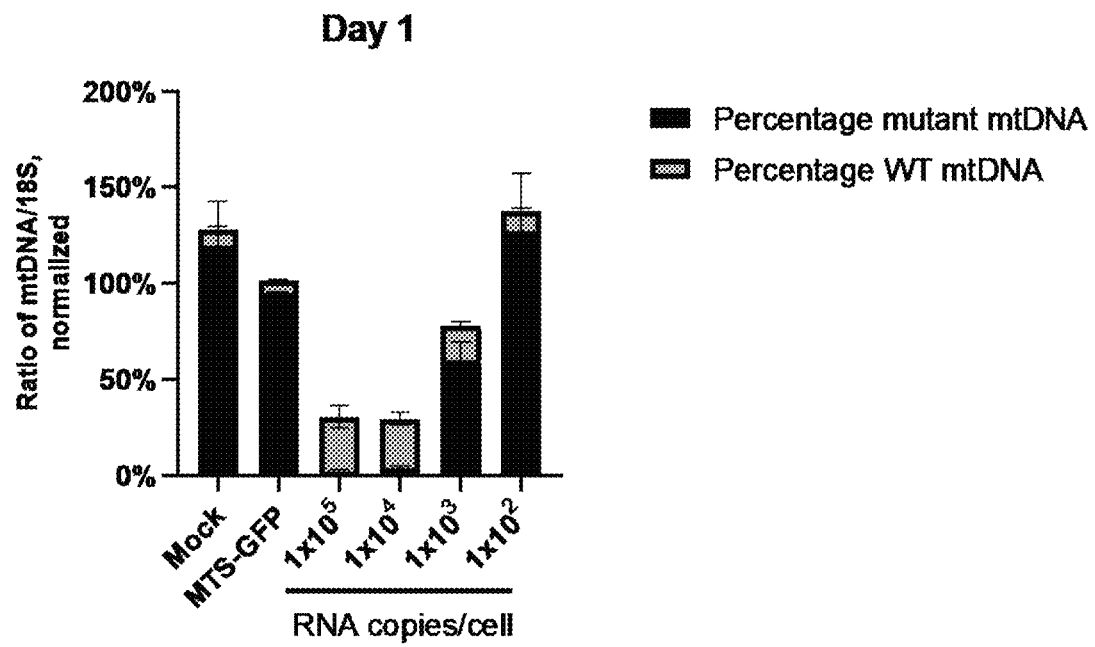
FIG. 35 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 259 H>Q meganuclease at Day 1 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 37:
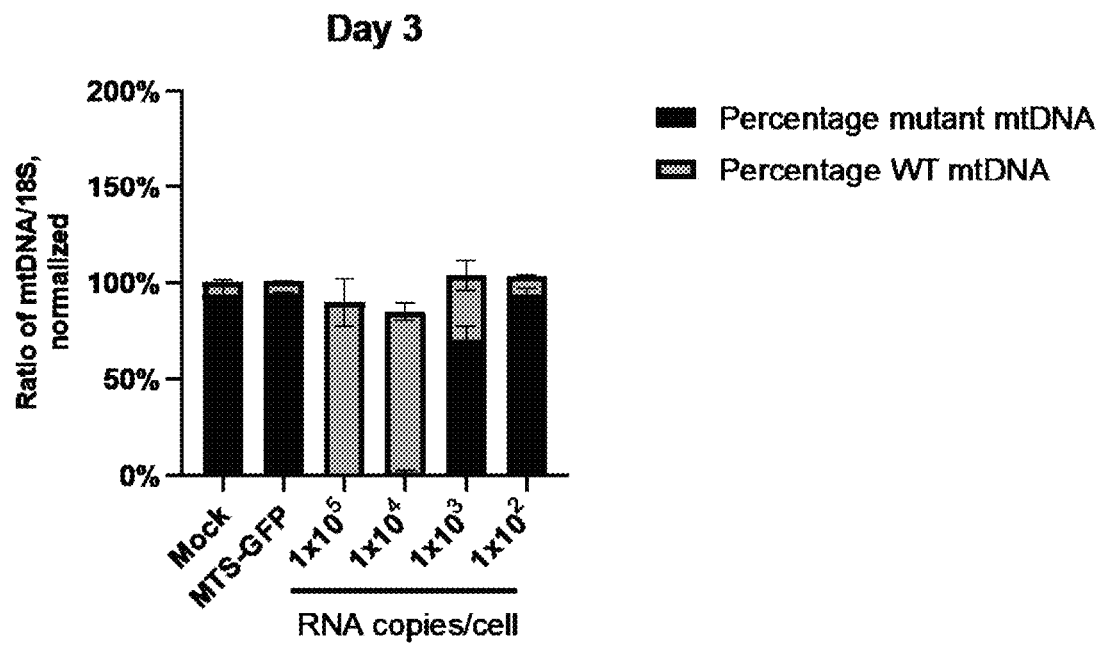
FIG. 37 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 259 H>Q meganuclease at Day 3 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 39:
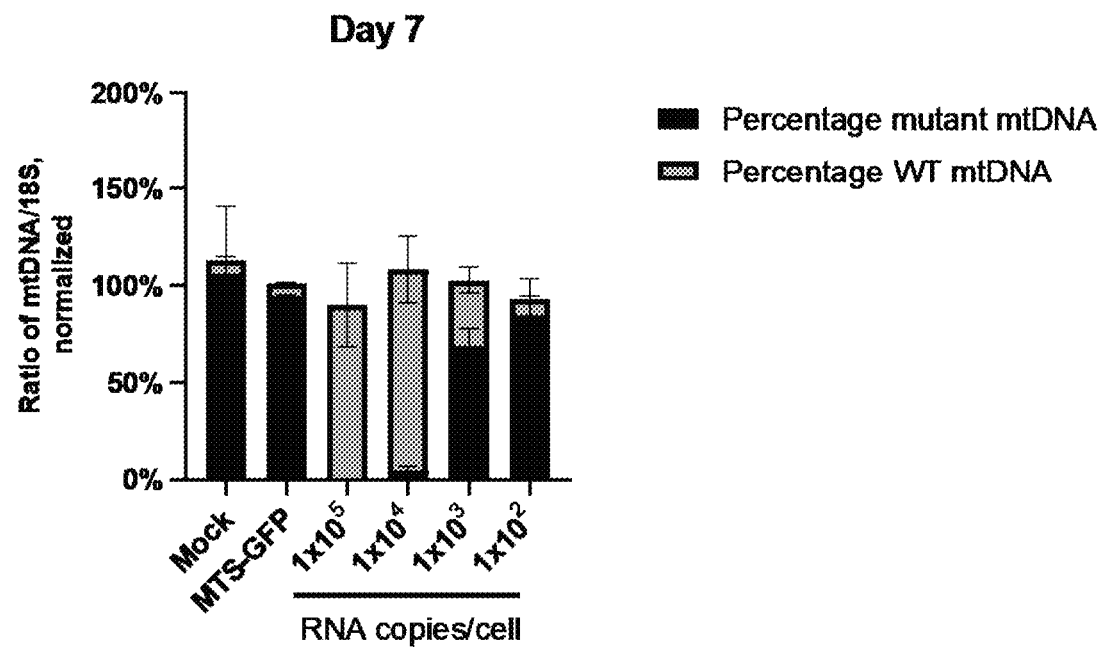
FIG. 39 provides a graph showing the ratio of total mtDNA to ribosomal 18s DNA in 96% mutant mtDNA (m.3243G) containing mitochondria for MELAS cells transfected with the indicated controls (Mock, MTS-GFP) or four different concentrations of the MIT 25-26x.91 259 H>Q meganuclease at Day 7 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.

As shown in FIG. 35, higher doses of the mitochondria-targeting engineered meganuclease (MTEM) resulted in a greater loss of mtDNA copies. This mtDNA reduction was statistically significant at the two highest mRNA doses at day 1 only (Table 12). The observed mtDNA depletion corresponded to the selective cleavage of mutant mtDNA. The cells treated with the three highest mRNA doses exhibited a significant loss of mutant mtDNA at all timepoints (Table 12, Table 13, Table 14). Following the elimination of the mutant mtDNA, the remaining WT mtDNA was found to repopulate the cell (FIG. 37 and FIG. 39). By day 7, there was only 0.3% mutant mtDNA remaining in the cells treated with the highest mRNA dose (FIG. 39). There was a significant increase in the amount of WT mtDNA present in the cells treated with the three highest mRNA doses at all timepoints, (Table 12, Table 13, Table 14).

Figure 36:
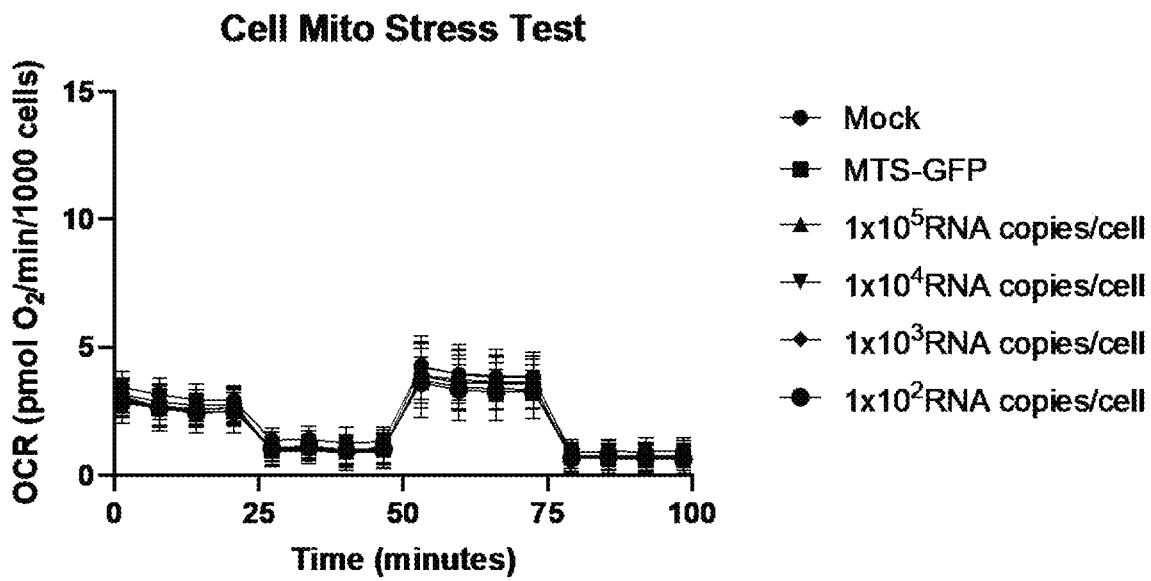
FIG. 36 is a graph showing the mitochondrial stress test of MELAS cybrid cells 1 days post-transfection with the mitochondria-targeting engineered meganuclease (MTEM) MIT 25-26x.91 259H>Q.
Figure 38:
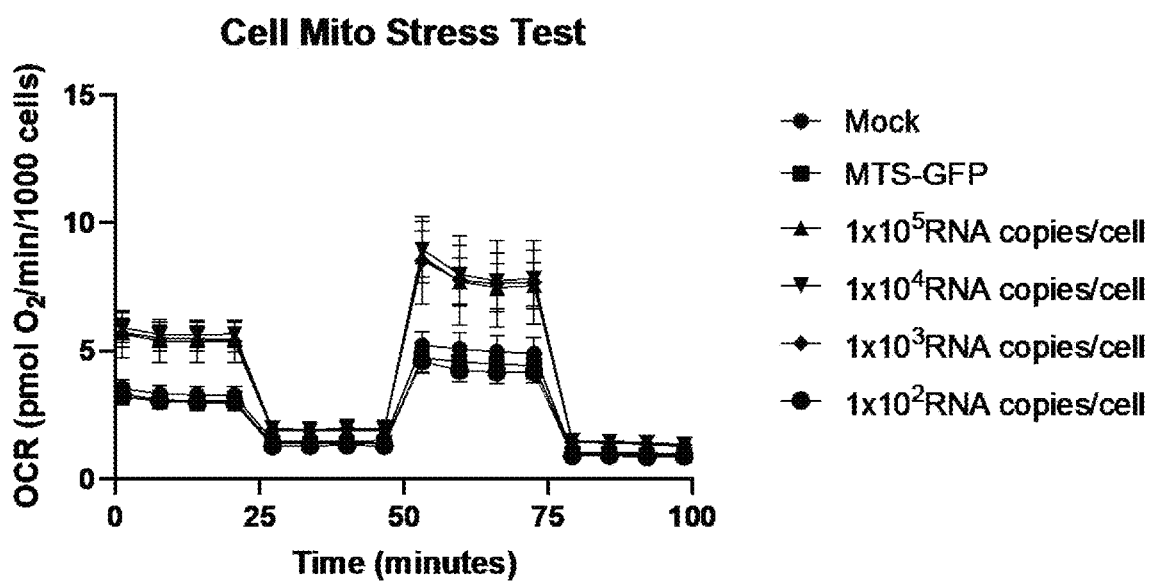
FIG. 38 is a graph showing the mitochondrial stress test of MELAS cybrid cells 3 days post-transfection with the mitochondria-targeting engineered meganuclease (MTEM) MIT 25-26x.91 259H>Q.
Figure 40:
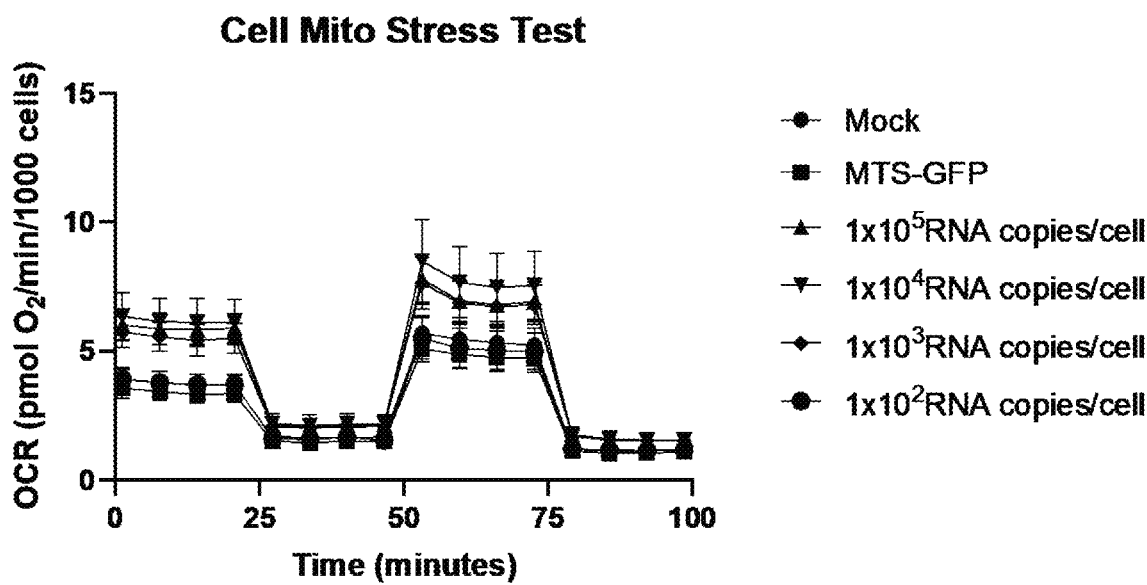
FIG. 40 is a graph showing the mitochondrial stress test of MELAS cybrid cells 7 days post-transfection with the mitochondria-targeting engineered meganuclease (MTEM) MIT 25-26x.91 259H>Q.

In the Cell Mito Stress Test at day 1, the MTEM-treated cells did not exhibit a statistically significant decrease in either basal or maximal OCR (table 12). By day 3, respiration improved significantly for cells treated with the three highest mRNA doses (table 13). By day 7, all cell populations showed a statistically significant improvement in respiration (FIGS. 36, 38, and 40, tables 12, 13, and 14)

Heteroplasmy was effectively shifted in high-percentage mutant cybrid cells using the MIT 25-26 meganuclease described herein. The induced shift resulted in a transient mtDNA depletion that did not negatively impact respiration (FIGS. 36, 38, and 40). By day 3, improvements in basal and maximal respiration were observed in treated cells (FIG. 38). The cells treated with mitochondria-targeting engineered meganucleases are able to use oxygen to generate ATP through oxidative phosphorylation more readily than untreated cells, and this process is not impacted during the transient mtDNA depletion.

TABLE 12

Statistical significance in WT DNA amount, Basal OCR, and Maximal OCR at differing doses of meganuclease mRNA dose at Day 1.

| Condition | mtDNA copy number | Percent mutant mtDNA | Percent WT mtDNA | Basal OCR | Maximal OCR |
|---|---|---|---|---|---|
| Mock | ns | ns | ns | ns | ns |
| 1 × $10^5$ RNA copies/cell | ** | **** | **** | ns | ns |
| 1 × $10^4$ RNA copies/cell | ** | **** | **** | ns | ns |
| 1 × $10^3$ RNA copies/cell | ns | **** | **** | ns | ns |
| 1 × $10^2$ RNA copies/cell | ns | ns | ns | ns | ns | ns: $P > 0.05$, *: $P \leq 0.05$, : $P \leq 0.01$, *: $P \leq 0.001$, ****: $P \leq 0.0001$.

TABLE 13

Statistical significance in WT DNA amount, Basal OCR, and Maximal OCR at differing doses of meganuclease mRNA dose at Day 3.

| Condition | mtDNA copy number | Percent mutant mtDNA | Percent WT mtDNA | Basal OCR | Maximal OCR |
|---|---|---|---|---|---|
| Mock | ns | ns | ns | ns | ns |
| 1 × $10^5$ RNA copies/cell | ns | **** | **** | **** | **** |
| 1 × $10^4$ RNA copies/cell | ns | **** | **** | **** | **** |
| 1 × $10^3$ RNA copies/cell | ns | **** | **** | **** | **** |
| 1 × $10^2$ RNA copies/cell | ns | ns | ns | ns | ns | ns: $P > 0.05$, *: $P \leq 0.05$, : $P \leq 0.01$, *: $P \leq 0.001$, ****: $P \leq 0.0001$.

TABLE 14

Statistical significance in WT DNA amount, Basal OCR, and Maximal OCR at differing doses of meganuclease mRNA dose at Day 7.

| Condition | mtDNA copy number | Percent mutant mtDNA | Percent WT mtDNA | Basal OCR | Maximal OCR |
|---|---|---|---|---|---|
| Mock | ns | ns | ns | ns | ns |
| 1 × $10^5$ RNA copies/cell | ns | **** | **** | *** | ** |
| 1 × $10^4$ RNA copies/cell | ns | **** | **** | **** | *** |
| 1 × $10^3$ RNA copies/cell | ns | *** | *** | *** | ** |
| 1 × $10^2$ RNA copies/cell | ns | ns | ns | | | ns: $P > 0.05$, *: $P \leq 0.05$, : $P \leq 0.01$, *: $P \leq 0.001$, ****: $P \leq 0.0001$.

Example 11: Meganuclease Off-Targeting Analysis by Oligo-Capture Assay

The purpose of this experiment was to determine any potential nuclear off-target sites that could be cleaved by two different MIT 25-26 nucleases: MIT 25-26x.91 259H>Q and MIT 25-26L35 19A>S. Previous data has suggested that the MTP included at the N-terminus of the protein is highly effective at achieving mitochondrial localization, but we are interested in experimentally proving that the tested engineered meganucleases do not introduce any off-target DSB within nuclear DNA.

In order to accurately determine nuclear off-target editing for a nuclease, it is necessary to have an on-target sequence as a positive control. Since the MIT 25-26 binding site is in mtDNA, there is no endogenous on-target site in nuclear DNA. Therefore, a Flp-In 293 reporter cell line was used to introduce the MIT 25-26 binding site onto the nuclear chromosome of a human cell line. 1.5e6 of these Flp-In 293 reporter cells were electroporated with 1.5 ug engineered meganuclease mRNA as well as 0.75 ug of a dsDNA oligo using the Neon transfection system (100 uL tips, condition 11). In this case, the meganuclease constructs that were used contained an NLS at the N-terminus of the protein. Two different meganucleases were used: MIT 25-26x.91 259H>Q and MIT 25-256L.35 19A>S. A control sample without meganuclease was transfected with just the dsDNA oligo. All conditions were assayed in duplicate. The co-transfection of the meganuclease mRNA with the dsDNA oligo allows for any nuclear DSB to be repaired by insertion of the oligo. The transfected cells were collected at two days post-electroporation for gDNA extraction and oligo capture analysis. The site that was cleaved can then be identified using an oligo capture assay described below.

Similar to GUIDE-seq, the oligo capture assay identifies potential off-target sites produced by the MIT 25-26 meganucleases by capturing an oligonucleotide at break sites within the cell's genomic DNA. GUIDE-seq was developed for CRISPR-Cas9 generated DNA breaks and there are a few key modifications to the chemistry and analysis in order to apply this technique to the present nucleases. Unlike CRISPR-cas9, the engineered meganucleases described herein generate a four base pair 3' overhang. To accommodate for this difference, the oligonucleotides used in oligo capture have randomized four base pair overhangs that could be compatible with the overhangs generated with the MIT 25-26 meganuclease. A higher frequency of insertion is observed due to the greater efficiency of ligating sticky ends rather than blunt ends. As described above, cells were transfected with mRNA encoding the nuclease and the double stranded DNA oligonucleotides. After two days, the genomic DNA from these cells was isolated and sonicated to shear the DNA to smaller sizes. An oligonucleotide adapter was ligated to the sheared DNA and PCR was used to amplify any DNA pieces that contain an adapter at one end and the captured oligonucleotide at the other end. The amplified DNA was purified and sequencing libraries were prepared using standard commercial kits.

Sequencing libraries were run on an Illumina MiSeq using V2 2×150 kits. The data was filtered and analyzed for valid sites that captured an oligonucleotide and a potential off-target site is predicted. Here again, the protocol needed to be adjusted from the PAM search used for CRISPR-cas9 to the MIT 25-26 meganuclease search. The software developed checks each sequence to make sure there is adapter and captured oligo flanking the sequence to verify that it is a valid read. The software also checks for PCR duplicates and removes reads that are identical to help reduce PCR bias. The sequence reads are aligned to a reference genome and grouped sequences within thousand base pair windows are scanned for a potential MIT 25-26 meganuclease site.

Each MIT 25-26 meganuclease is a linked dimer. Each monomer recognizes a nine base pair half site with a four base pair spacer in the center between the two half sites. The software looks for the closest sequence match for each half site with no allowed gaps. The middle four base pairs are not considered in the off-target selection because the MIT 25-26 meganucleases can generally tolerate a higher amount of degeneracy at these positions in the target site. The software outputs a list of potential off-target sites with the number of base mismatches in the combined half sites but not counting the middle four base pair mismatches. The software does not eliminate any off-targets based on an arbitrary mismatch filter, unlike CRISPR-Cas9 which eliminates any off-target identified with more than six base pairs mismatched. Instead, background noise generated from random capture of the oligo at fragile spots or hot spots within the genome can be reduced in two ways. First, an untreated mock sample is also run though oligo capture and windows of integration sites without the nuclease present can be subtracted from the nuclease containing samples. We have also found that running the assay in triplicate and eliminating any sites that do not repeat in at least two of the three repeats is a good way to empirically remove random integration noise.

Figure 41:
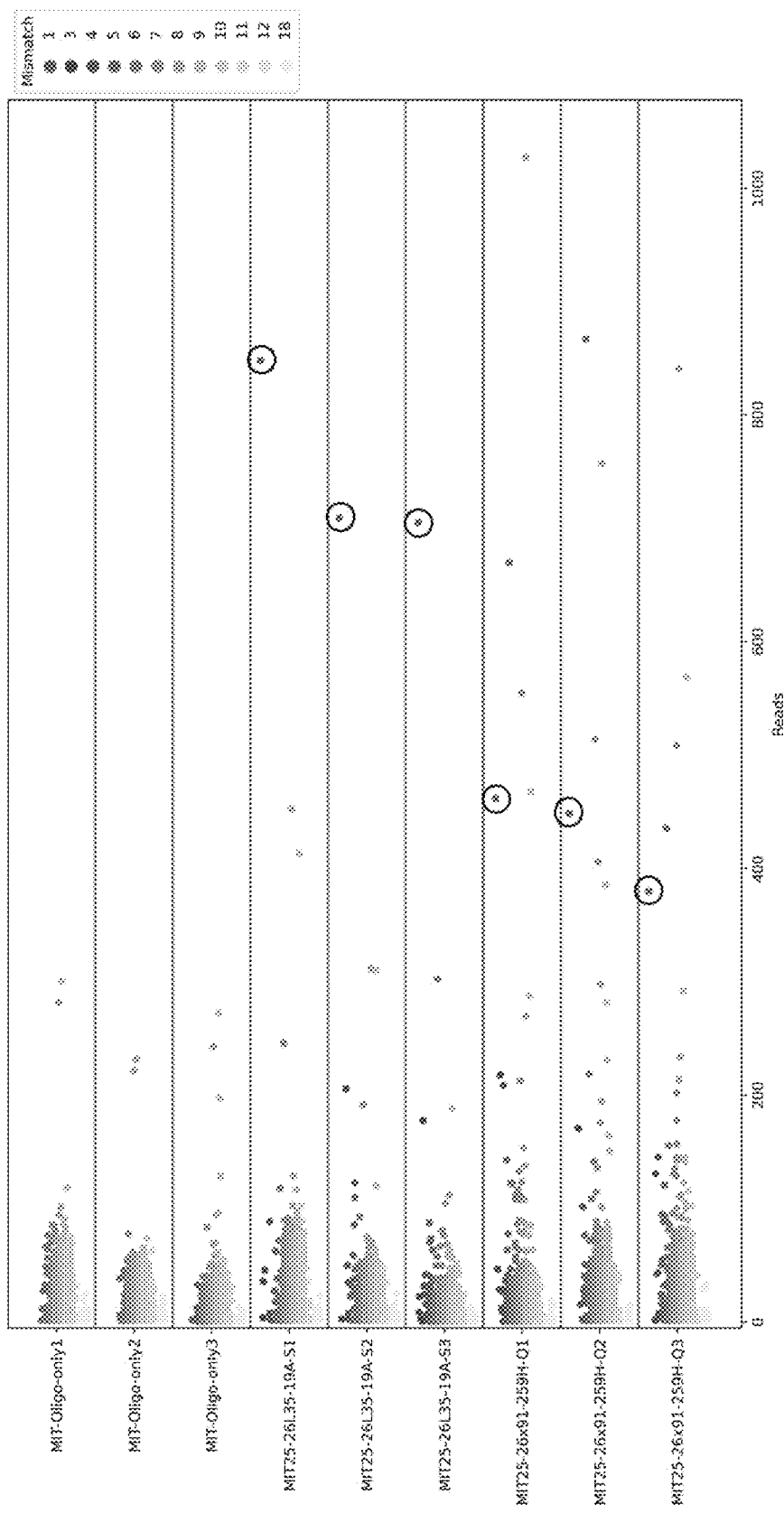
FIG. 41 is a graph depicting results from an oligo capture assay to identify off target cutting induced by the MIT 25-26L.35 19A>S and MIT 25-26x.91 259H>Q meganucleases transfected in Flp-In 293 reporter cell line. The circled dots indicate the on-target site. MT-Oligo-Only represents negative controls.

Although read count does not directly correlate with cutting frequency at a particular site, it can generally highlight off-targets that are potentially more concerning or more valid because they occur more often. One way to graphically visualize the oligo capture data as a measure of number of potentially valid off-target sites is shown in FIG. 41. Each off-target generated by a particular nuclease is plotted based on the number of unique sequence reads aligned at that site. The number of base pair mismatches between the putative off-target site and the intended site are indicated by color scale with darker colors indicating sites that are more similar to the intended target site (circled). For a nuclease with high-specificity, the intended site should have the highest read count. Better nucleases remove both the higher count sites (to the right of the graph) and the sites with high similarity (darker colored points).

Example 12: Effect of Culture in Glucose vs. Galactose on Growth Rate

The purpose of this experiment was to determine how engineered meganuclease transfection impacted cell proliferation when the cells are grown in galactose, rather than glucose-containing medium. In the presence of glucose, most cells in culture rely almost exclusively on glycolysis for ATP production, despite the abundance of oxygen and functional mitochondria. Therefore, functional outcomes of a transient mtDNA depletion cannot clearly be evaluated in cultured cells without changing the cell culture environment such that the cells must depend on mitochondrial function for ATP production. In order to do this, the cells must be transitioned from glucose-containing medium to galactose-containing medium. The oxidation of galactose to pyruvate is slower than glucose and does not produce a net gain in ATP. Thus, cells grown in galactose are forced to rely on OXPHOS for ATP production.

8e5 MELAS cybrid cells containing 96% mutant m.3243A>G mtDNA were nucleofected with engineered meganuclease mRNA using the Lonza 4D-Nucleofector™ (SF buffer, condition CA-137). The engineered meganuclease used was MIT 25-26x.91 259H>Q at a dose of 1e5 RNA copies/cell (94.8 ng mRNA). An untransfected control was used, as well as an untransfected 0% mutant cell line. Immediately following the transfection, all cells were plated into media containing 5 mM galactose. A total of 2e3 cells/well were seeded across four 96 well flat bottom plates.

Figure 42:
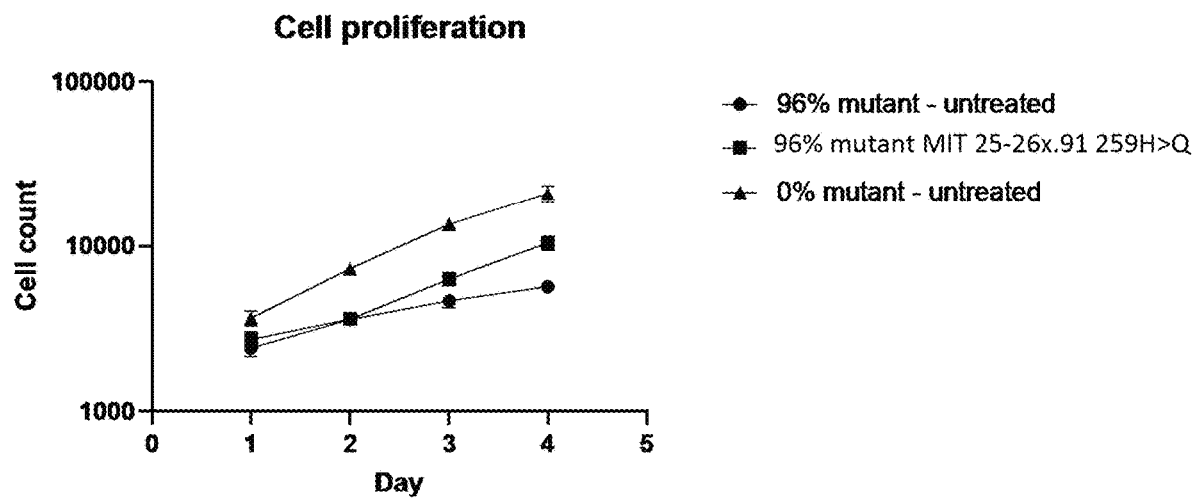
FIG. 42 is a graph showing the cell proliferation over time of either 96% mutant mtDNA (m.3243G) containing mitochondria for MELAS cells untreated, transfected with MIT 25-26x.91 259H>Q meganuclease at a dose of 1e5 RNA copies/cell or for or 0% mutant (WT cells) untreated.
Figure 43:
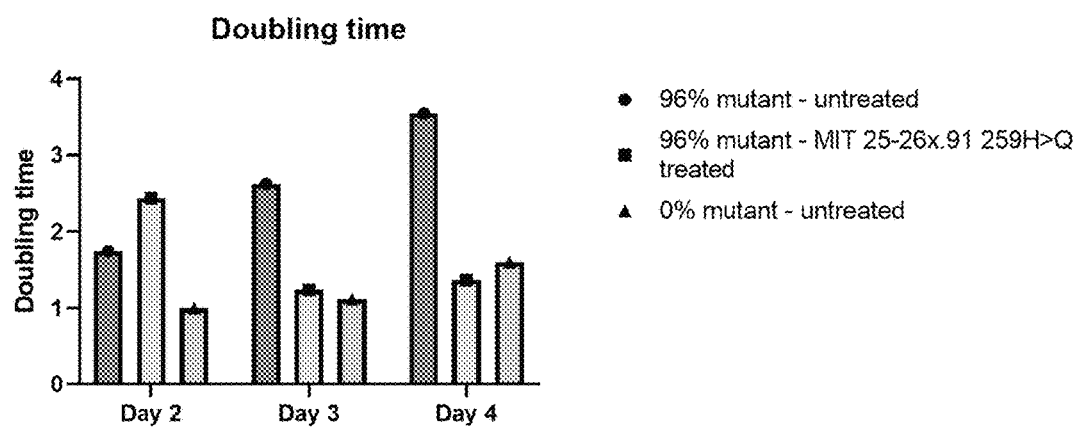
FIG. 43 is a bar graph showing the cell doubling time over D2, D3, and D4 post treatment of either 96% mutant mtDNA (m.3243G) containing mitochondria for MELAS cells untreated, transfected with MIT 25-26x.91 259H>Q meganuclease at a dose of 1e5 RNA copies/cell, or for 0% mutant (WT cells) untreated.

At day 1, 2, 3, and 4 post-transfection, one plate of cells was stained with Hoechst 33342 Solution (ThermoFisher, H3570) at a 1:10,000 dilution in galactose-containing media. The cells were incubated at 37 C for 10 minutes and then analyzed by image cytometry using ImageXpress Pico Automated Cell Imaging System (Molecular Devices) to determine the cell count (FIG. 42). By day 4, there were a total of 5,664±429 cells in the 96% mutant untreated cohort, 10,438±968 cells in the 96% mutant treated cohort, and 20,891±2,320 cells in the 0% mutant untreated cohort. The cell count data was used to determine the doubling time of each cell population (FIG. 43). At day 2, the doubling time was 1.75 days (96% mutant untreated), 2.44 days (96% mutant treated), and 1.00 days (0% mutant treated). By day 4, the doubling time was 3.55 days (96% mutant untreated), 1.37 days (96% mutant treated), and 1.60 (0% mutant untreated).

In the presence of galactose, untreated 96% mutant cybrid cells exhibit an impaired growth rate compared to 0% mutant (WT) cells. This effect is partially rescued by treatment with a mitochondrial targeted engineered meganuclease (FIG. 42).

Example 13: Effect of Meganuclease Editing on Heteroplasmy in a Mouse Xenograft Tumor Model The purpose of this experiment was to determine the efficacy of shifting m.3243A>G heteroplasmy in vivo. Unfortunately, there are no animal models currently available for this particular mutation. Since the cells utilized to study the mutation in vitro are derived from a cancer cell line, we hypothesized that we could use the cells to generate a xenograft mouse model. By generating the xenograft and then treating the mice systemically with an AAV9 encapsidated engineered meganuclease, we sought to see if heteroplasmy shifts in the tumor were possible.

Figure 44:
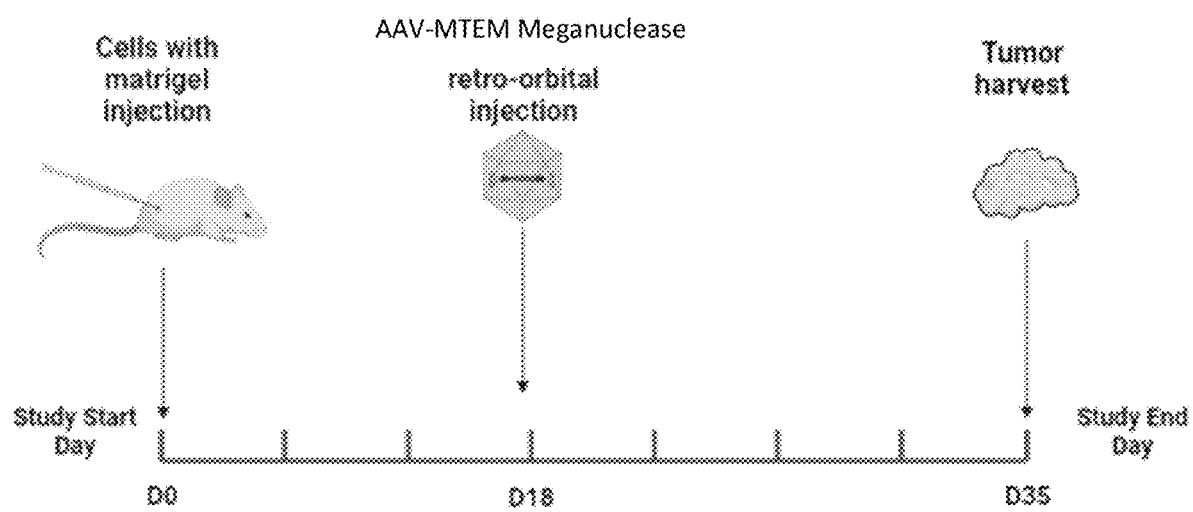
FIG. 44 provides an experimental schematic for a study showing the effect of engineered MTEM meganuclease editing on mitochondrial heteroplasmy in a mouse xenograft tumor model.
Figure 45:
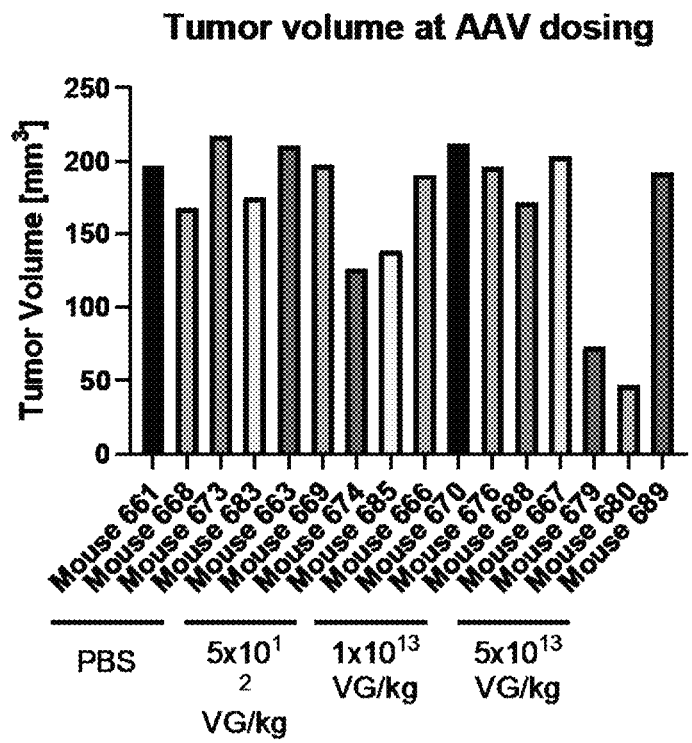
FIG. 45 provides a graph showing the tumor volume at the time of administration (D18 post cybrid introduction) of an AAV9 vector encapsidating the MIT 25-26x.91 engineered meganuclease at three different doses.

5e4 96% m.3243A>G mutant cybrid cells were mixed 1:1 with Matrigel and subcutaneously injected in a total volume of 200 uL into the right flank of nude mice. A total of 32 animals were injected. Tumor growth progression was monitored biweekly via caliper measurement. At day 18, a total of 16 animals were selected for AAV9 injection based on tumor size <~200 mm³ (FIG. 45). The meganuclease used was MIT 25-26x.91. Mice were randomly assigned to four cohorts for injection with either PBS (n=4), 5e12 VG/kg (n=4), 1e13 VG/kg (n=4), or 5e13 VG/kg (n=4). Mice were injected retro-orbitally into the right eye. Tumor growth was monitored throughout the remainder of the study and all animals were sacrificed at day 35. Four small sections (~3 mm) of tumor were harvested for gDNA isolation. A diagram of the study design is provided in FIG. 44.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells.

```
P1:
                                  (SEQ ID NO: 63)
TGGCAGGGCCCGGT

F1:
                                  (SEQ ID NO: 64)
CCCAAGAACAGGGTTTGTTAAG

R1:
                                  (SEQ ID NO: 65)
GGAATGCCATTGCGATTAG

P2:
                                  (SEQ ID NO: 66)
AGCAGTTCTACCGTACAACCCTAACA

F2:
                                  (SEQ ID NO: 67)
GGCAGTTGAGGTGGATTA

R2:
                                  (SEQ ID NO: 68)
GGAATGCGGTAGTAGTTAGG

P4:
                                  (SEQ ID NO: 69)
AACCAGACAAATCGCTCCACCAAC

F4:
                                  (SEQ ID NO: 70)
CGGACAGGATTGACAGATT

R4:
                                  (SEQ ID NO: 71)
CCAGAGTCTCGTTCGTTATC
```

Assays 1 and 2 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Figure 46:
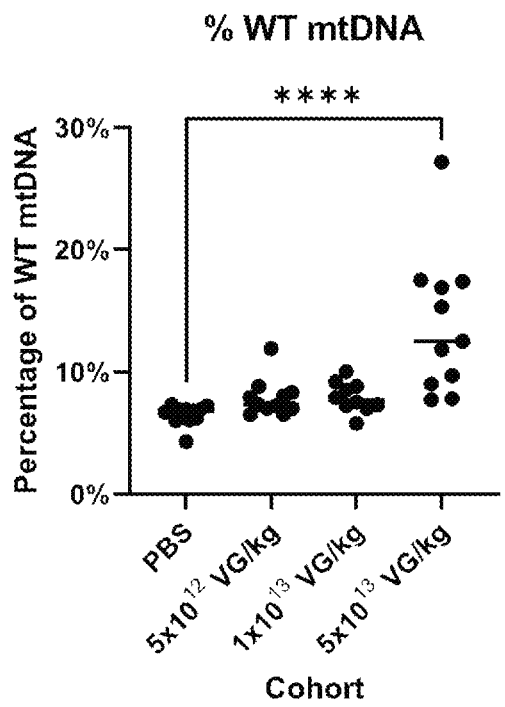
FIG. 46 provides a graph showing the percentage of WT mtDNA after administration of an AAV9 vector encapsidating the MIT 25-26x.91 engineered meganuclease at three different doses at day 35 post cybrid cell introduction and day 17 post meganuclease administration.

At the time of AAV injection, tumor volumes for the injected animals were between 47 and 217 mm³ (FIG. 45). As shown in FIG. 46, the average percentage of WT mtDNA present in the isolated tumor samples was 6.47% (PBS), 7.85% (5e12 VG/kg), 7.92% (1e13 VG/kg), and 13.89%

Figure 47:
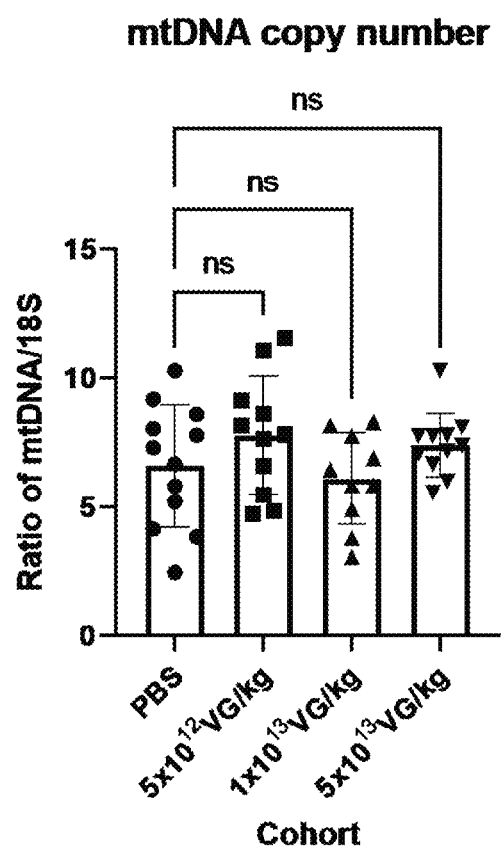
FIG. 47 provides a graph showing the percentage of WT mtDNA after administration of an AAV9 vector encapsidating the MIT 25-26x.91 engineered meganuclease at three different doses at day 35 post cybrid cell introduction and day 17 post meganuclease administration. NS indicates non-statistically significant differences between groups.

(5e13 VG/kg). As shown in FIG. 46, the percentage of WT mtDNA in the 5e13 VG/kg cohort was statistically significant relative to the PBS-treated mice. As shown in FIG. 47, the average mtDNA copy number relative to 18S rDNA was 6.61 (PBS), 7.78 (5e12 VG/kg), 6.10 (1e13 VG/kg), and 7.41 (5e13 VG/kg). None of the AAV-treated cohorts exhibited a significant change in mtDNA copy number.

Using a xenograft mouse model, AAV9 an encapsidated engineered meganuclease is capable of shifting m.3243A>G heteroplasmy in vivo.

Example 14 Molecular Changes in 85% Mutant m.3243G Mutant Cells Following Mitochondrial Targeting Meganuclease mRNA Transfection The purpose of this experiment was to show efficacy of the MIT 25-26x.91 259H>Q meganuclease in a cell line that harbors the heteroplasmic MELAS mutation (m.3243A>G), as well as to determine if the transient mtDNA depletion induced by the meganuclease negatively impacted cellular respiration The cell line used is a cybrid (cytoplasmic hybrid) that contains both wildtype and mutant mtDNA. The cell line in particular is 85% mutant—that is, 85% of the mtDNA population contains the mutant allele and 15% contains the wildtype allele. This cell line was chosen based on the slightly lower percentage of mutant mtDNA than described in example 10, which produces a more WT-like level of respiration, and therefore any negative impacts induced by the meganuclease may be detectable.

8e5 MELAS cybrid cells were nucleofected with engineered meganuclease mRNA across a dose titration using the Lonza 4D-Nucleofector™ (SF buffer, condition CA-137). The engineered meganuclease mRNA doses started at 1e5 RNA copies/cell; this translates to 8e10 RNA copies total, or 94.8 ng of RNA. The mRNA was then serially diluted 1:10 down to 1e2 RNA copies/cell. Cells were collected at days one, and three post-nucleofection for gDNA extraction and Seahorse Cell Mito Stress Test evaluation. gDNA was isolated using the Macherey Nagel NucleoSpin Blood QuickPure kit.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells. This ratio was then normalized based on the MTS-GFP (control) condition, and the resulting normalized copy number was multiplied by the heteroplasmy level to generate the data shown in FIGS. 35, 37, and 39. In these graphs, the height of the bars is indicative of mtDNA loss, relative to the MTS-GFP cells. Within the bar, the relative percentage of gray corresponds to the relative percentage of wildtype mtDNA present, and the relative percentage of black corresponds to the relative percentage of mutant mtDNA present.

P1:
TGGCAGGGCCCGGT
(SEQ ID NO: 63)

F1:
CCCAAGAACAGGGTTTGTTAAG
(SEQ ID NO: 64)

R1:
GGAATGCCATTGCGATTAG
(SEQ ID NO: 65)

P2:
AGCAGTTCTACCGTACAACCCTAACA
(SEQ ID NO: 66)

F2:
GGCAGTTGAGGTGGATTA
(SEQ ID NO: 67)

R2:
GGAATGCGGTAGTAGTTAGG
(SEQ ID NO: 68)

P4:
AACCAGACAAATCGCTCCACCAAC
(SEQ ID NO: 69)

F4:
CGGACAGGATTGACAGATT
(SEQ ID NO: 70)

R4:
CCAGAGTCTCGTTCGTTATC
(SEQ ID NO: 71)

Assays 1 and 2 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 µL reaction containing 1×ddPCR Supermix for Probes (no dUTP, Bio-Rad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

At day 0 post-transfection, 9.6e3 cells were plated into a 96 well Seahorse cell culture microplate for analysis on the Seahorse XFe96 Analyzer (Agilent). An XF Sensor Cartridge was also hydrated with 200 µL/well Seahorse XF Calibrant overnight in a non-CO$_2$ incubator. At day 2 post-transfection, 5e3 cells were plated into a 96 well Seahorse cell culture microplate for analysis on the Seahorse XFe96 Analyzer (Agilent). An XF Sensor Cartridge was also hydrated with 200 µL/well Seahorse XF Calibrant overnight in a non-CO$_2$ incubator. The following day (days 1 and 3), 97 mL of Seahorse Assay Medium (DMEM) was combined with 1 mL 1 mM Sodium Pyruvate, 1 mL 2 mM Glutamine, and 1 mL 10 mM Glucose. Cells were washed two times with the prepared media and then placed in a non-$CO_2$ incubator for 1 hour. One Cell Mito Stress Test Kit was reconstituted according to manufacturer directions. Solutions were made up of Oligomycin (15 uM), FCCP (5 uM), and Rotenone/Antimycin A (5 uM). For the Cell Mito Stress Test, 20 μL Oligomycin solution was added to all Port As of the hydrated cartridge, 22 μL FCCP solution was added to all Port Bs, and 24 μL of Rotenone/Antimycin A was added to all Port Cs. The assay was run with 4 measurement cycles (03:00 mix, 00:00 wait, 03:00 measure) for baseline, Oligomycin, FCCP, and Rotenone/Antimycin A. OCR values were analyzed using Wave software (Agilent). The Cell Mito Stress Test Report was generated using Wave software (Agilent).

After completion of the assay, the cells were stained with Hoechst 33342 Solution (ThermoFisher, H3570) at a 1:5000 dilution in standard media. The cells were incubated at 37 C for 20 minutes and then analyzed by image cytometry using ImageXpress Pico Automated Cell Imaging System (Molecular Devices). OCR values were then normalized to cell count using Wave software (Agilent).

Figure 48:
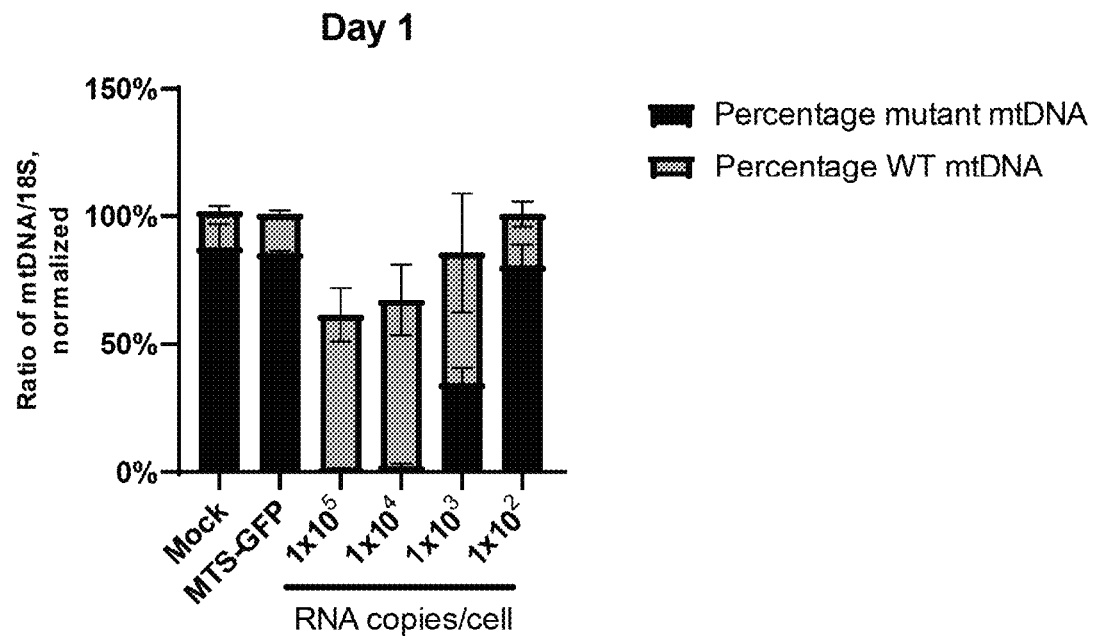
FIG. 48 provides a graph showing the ratio of total mtDNA to ribosomal 18s DNA in 85% mutant mtDNA (m.3243G) containing mitochondria for MELAS cells transfected with the indicated controls (Mock, MTS-GFP) or four different concentrations of the MIT 25-26x.91 259 H>Q meganuclease at Day 1 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 49:
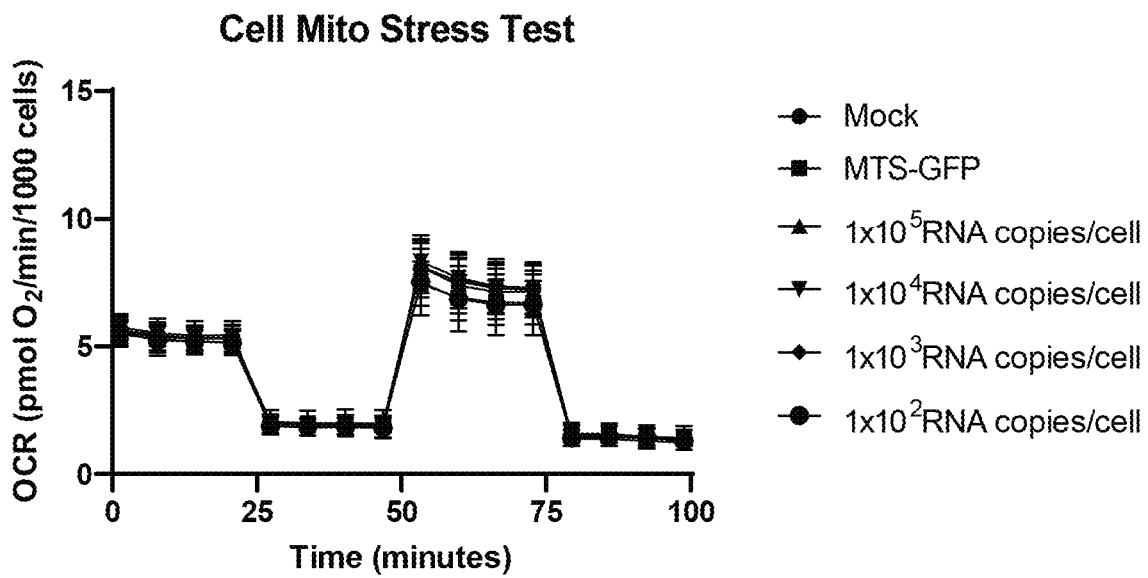
FIG. 49 is a graph showing the mitochondrial stress test of MELAS cybrid cells 1 days post-transfection with the mitochondria-targeting engineered meganuclease (MTEM) MIT 25-26x.91 259H>Q.
Figure 50:
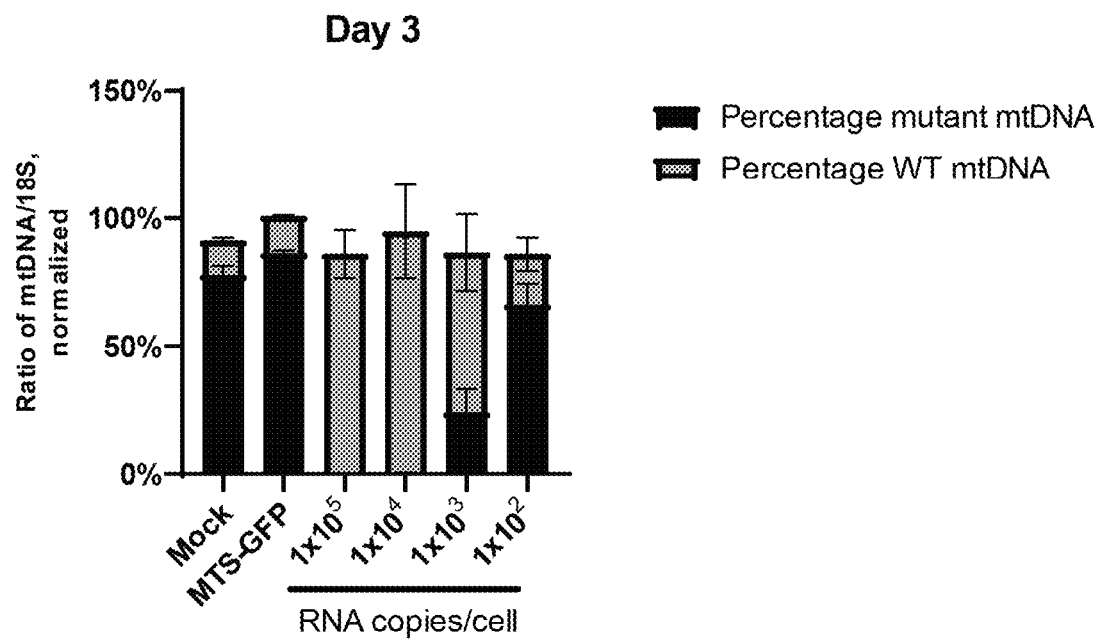
FIG. 50 provides a graph showing the ratio of total mtDNA to ribosomal 18s DNA in 85% mutant mtDNA (m.3243G) containing mitochondria for MELAS cells transfected with the indicated controls (Mock, MTS-GFP) or four different concentrations of the MIT 25-26x.91 259 H>Q meganuclease at Day 3 post transfection. The height of the bars is indicative of mtDNA, loss, normalized to the MTS-GFP transfected cells. Within the bar, the relative percentage of gray corresponds to the relative percentage of wildtype mtDNA, present, and the relative percentage of black corresponds to the relative percentage of mutant mtDNA present.
Figure 51:
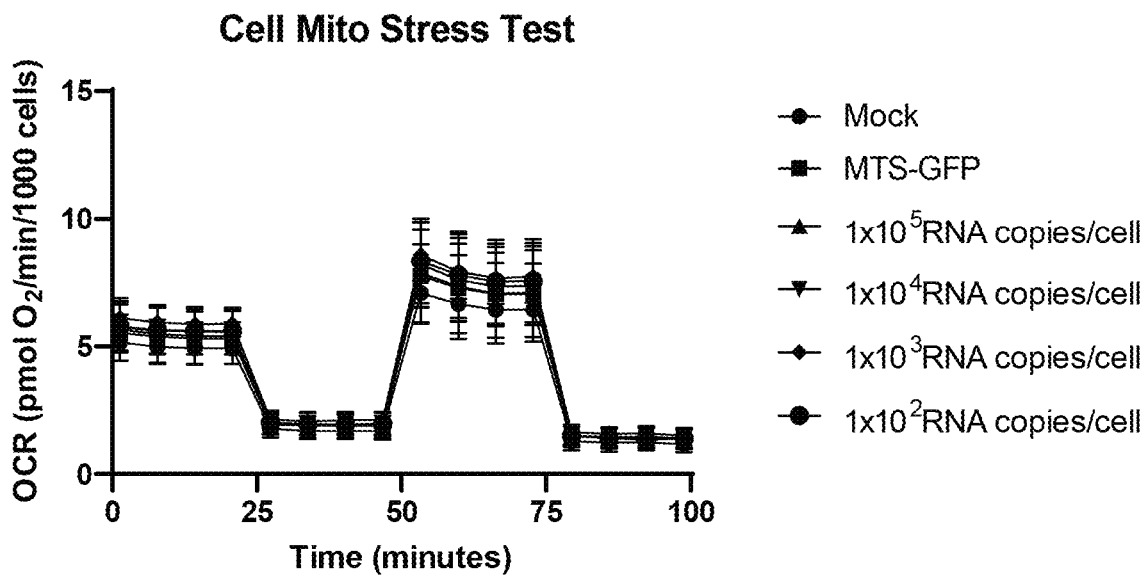
FIG. 51 is a graph showing the mitochondrial stress test of MELAS cybrid cells 3 days post-transfection with the mitochondria-targeting engineered meganuclease (MTEM) MIT 25-26x.91 259H>Q.

As shown in FIG. 48, higher doses of the mitochondria-targeting engineered meganuclease (MTEM) resulted in a greater loss of mtDNA copies. This mtDNA reduction was statistically significant at the highest mRNA dose at day 1 only (Table 15). The observed mtDNA depletion corresponded to the selective cleavage of mutant mtDNA. The cells treated with the three highest mRNA doses exhibited a significant loss of mutant mtDNA at all timepoints (Table 15 and Table 16). Following the elimination of the mutant mtDNA, the remaining WT mtDNA was found to repopulate the cell (FIG. 48 and FIG. 50). By day 3, there was only 0.2% mutant mtDNA remaining in the cells treated with the highest mRNA dose (FIG. 50). There was a significant increase in the amount of WT mtDNA present in the cells treated with the three highest mRNA doses at both timepoints, (Table 15 and Table 16).

In the Cell Mito Stress Test at day 1, the MTEM-treated cells did not exhibit a significant change in either basal or maximal OCR relative to the GFP-treated control (table 15). The same is true at day 3 (table 16). Despite the complete shift in heteroplasmy observed in the high-dose treated cells at day 3, there was no statistically significant changes to respiration indicating that the cells utilized here present with a WT-like respiration and further shifts in heteroplasmy do not confer large changes in mitochondrial function.

Heteroplasmy was effectively shifted in 85% mutant cybrid cells using the MIT 25-26 meganuclease described herein. The induced shift resulted in a transient mtDNA depletion that did not negatively impact respiration (FIGS. 48 and 50), despite the WT-like respiration present in these cells. This suggests that transient mtDNA depletions do not negatively impact cellular respiration.

TABLE 15

Statistical significance in WT DNA amount, Basal OCR, and Maximal OCR at differing doses of meganuclease mRNA dose at Day 1.

| Condition | mtDNA copy number | Percent mutant mtDNA | Percent WT mtDNA | Basal OCR | Maximal OCR |
|---|---|---|---|---|---|
| Mock | ns | ns | ns | ns | ns |
| 1 × 10$^5$ RNA copies/cell | ns | **** | **** | ns | ns |
| 1 × 10$^4$ RNA copies/cell | ns | **** | **** | ns | ns |
| 1 × 10$^3$ RNA copies/cell | ns | **** | **** | ns | ns |
| 1 × 10$^2$ RNA copies/cell | ns | ns | ns | ns | ns | ns: $P > 0.05$, *: $P \leq 0.05$, : $P \leq 0.01$, *: $P \leq 0.001$, ****: $P \leq 0.0001$.

TABLE 16

Statistical significance in WT DNA amount, Basal OCR, and Maximal OCR at differing doses of meganuclease mRNA dose at Day 3.

| Condition | mtDNA copy number | Percent mutant mtDNA | Percent WT mtDNA | Basal OCR | Maximal OCR |
|---|---|---|---|---|---|
| Mock | ns | ns | ns | ns | ns |
| 1 × 10$^5$ RNA copies/cell | ns | **** | **** | ns | ns |
| 1 × 10$^4$ RNA copies/cell | ns | **** | **** | ns | ns |
| 1 × 10$^3$ RNA copies/cell | ns | **** | **** | ns | ns |
| 1 × 10$^2$ RNA copies/cell | ns | ns | ns | ns | ns | ns: $P > 0.05$, *: $P \leq 0.05$, : $P \leq 0.01$, *: $P \leq 0.001$, ****: $P \leq 0.0001$.

Example 15 Effect of Culture in Glucose Vs. Galactose on Cellular Respiration

The purpose of this experiment was to determine how engineered meganuclease transfection impacted cellular respiration when the cells are grown in galactose, rather than glucose-containing medium. In the presence of glucose, most cells in culture rely almost exclusively on glycolysis for ATP production, despite the abundance of oxygen and functional mitochondria. Therefore, functional outcomes of a transient mtDNA depletion cannot clearly be evaluated in cultured cells without changing the cell culture environment such that the cells must depend on mitochondrial function for ATP production. In order to do this, the cells must be transitioned from glucose-containing medium to galactose-containing medium. The oxidation of galactose to pyruvate is slower than glucose and does not produce a net gain in ATP. Thus, cells grown in galactose are forced to rely on OXPHOS for ATP production.

8e5 MELAS cybrid cells containing 96% mutant m.3243A>G mtDNA were nucleofected with engineered meganuclease mRNA using the Lonza 4D-Nucleofector™ (SF buffer, condition CA-137). The engineered meganuclease used was MIT 25-26x.91 259H>Q at a dose of 1e5 RNA copies/cell (94.8 ng mRNA). An untransfected control was used, as well as an untransfected 0% mutant cell line. Immediately following the transfection, all cells were plated into media containing 5 mM galactose. Cells were collected at day one post-nucleofection for gDNA extraction and Seahorse Cell Mito Stress Test evaluation. gDNA was isolated using the Macherey Nagel NucleoSpin Blood QuickPure kit.

Droplet digital PCR (ddPCR) was utilized to determine heteroplasmy level of the mtDNA, as well as mtDNA copy number relative to nuclear DNA (nuDNA). This was accomplished using P1, F1, and R1 to generate an amplicon surrounding the binding site (assay 1), P2, F2, and R2 to generate a reference amplicon that acts as an mtDNA counter (assay 2), and P4, F4, and R4 to generate a nuclear reference amplicon that acts as an nuDNA counter (assay 3). The number of positive droplets in assay 1 relative to the number of positive droplets in assay 2 was used to determine the level of heteroplasmy in the cells. The number of positive droplets in assay 2 relative to the number of positive droplets in assay 3 was used to determine the mtDNA copy number in the cells. This ratio was then normalized based on the 96% mutant untreated control condition, and the resulting normalized copy number was multiplied by the heteroplasmy level to generate the data shown in FIG. 52. In these graphs, the height of the bars is indicative of mtDNA loss, relative to the MTS-GFP cells. Within the bar, the relative percentage of gray corresponds to the relative percentage of wildtype mtDNA present, and the relative percentage of black corresponds to the relative percentage of mutant mtDNA present.

P1:
(SEQ ID NO: 63)
TGGCAGGGCCCGGT

F1:
(SEQ ID NO: 64)
CCCAAGAACAGGGTTTGTTAAG

R1:
(SEQ ID NO: 65)
GGAATGCCATTGCGATTAG

P2:
(SEQ ID NO: 66)
AGCAGTTCTACCGTACAACCCTAACA

F2:
(SEQ ID NO: 67)
GGCAGTTGAGGTGGATTA

R2:
(SEQ ID NO: 68)
GGAATGCGGTAGTAGTTAGG

P4:
(SEQ ID NO: 69)
AACCAGACAAATCGCTCCACCAAC

F4:
(SEQ ID NO: 70)
CGGACAGGATTGACAGATT

R4:
(SEQ ID NO: 71)
CCAGAGTCTCGTTCGTTATC

Assays 1 and 2 were multiplexed in a 24 µL reaction containing 1×ddPCR Supermix for Probes (no dUTP, BioRad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

Assays 2 and 3 were multiplexed in a 24 µL reaction containing 1×ddPCR Supermix for Probes (no dUTP, BioRad), 250 nM of each probe, 900 nM of each primer, 20 U/µL Hind-III HF (NEB), and 0.225 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72 C (0.2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data.

At day 0 post-transfection, 2e3 cells/well were plated into a 96 well Seahorse cell culture microplate for analysis on the Seahorse XFe96 Analyzer (Agilent). An XF Sensor Cartridge was also hydrated with 200 µL/well Seahorse XF Calibrant overnight in a non-$CO_2$ incubator. The following day (day 1), 97 mL of Seahorse Assay Medium (DMEM) was combined with 1 mL 1 mM Sodium Pyruvate, 1 mL 2 mM Glutamine, and 10 mM Galactose. The resulting media was sterile-filtered. Cells were washed two times with the prepared media and then placed in a non-$CO_2$ incubator for 1 hour. One Cell Mito Stress Test Kit was reconstituted according to manufacturer directions. Solutions were made up of Oligomycin (15 uM), FCCP (20 uM), and Rotenone/Antimycin A (5 uM). For the Cell Mito Stress Test, 20 µL Oligomycin solution was added to all Port As of the hydrated cartridge, 22 µL FCCP solution was added to all Port Bs, and 24 µL of Rotenone/Antimycin A was added to all Port Cs. The assay was run with 4 measurement cycles (03:00 mix, 00:00 wait, 03:00 measure) for baseline, Oligomycin, FCCP, and Rotenone/Antimycin A. OCR values were analyzed using Wave software (Agilent). The Cell Mito Stress Test Report was generated using Wave software (Agilent).

After completion of the assay, the cells were stained with Hoechst 33342 Solution (ThermoFisher, H3570) at a 1:5000 dilution in standard media. The cells were incubated at 37 C for 20 minutes and then analyzed by image cytometry using ImageXpress Pico Automated Cell Imaging System (Molecular Devices). OCR values were then normalized to cell count using Wave software (Agilent).

Figure 52:
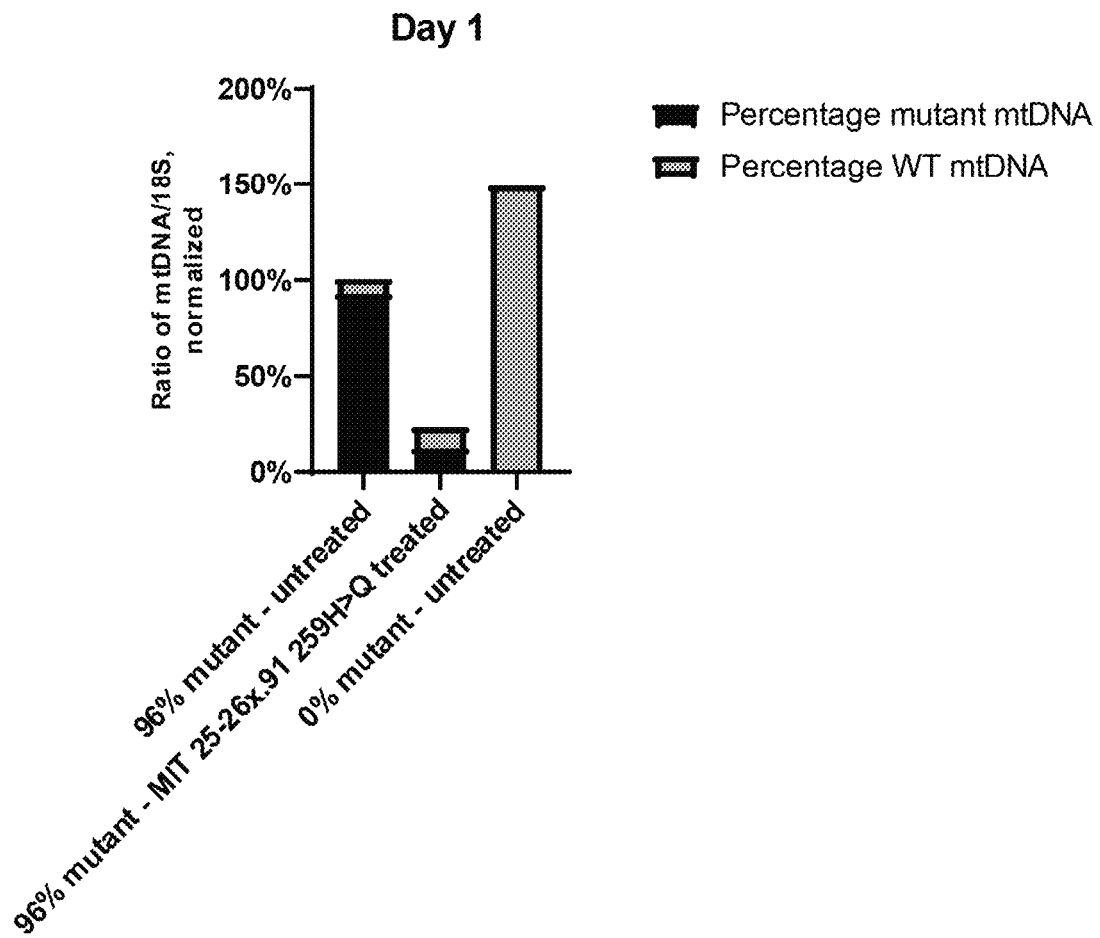
FIG. 52 provides a graph showing the ratio of total mtDNA to ribosomal 18s DNA in 96% mutant mtDNA (m.3243G) containing mitochondria MELAS cells or 0% mutant mtDNA containing WT cells at Day 1 post transfection. The mutant cells were either untreated or treated with 1e5 RNA copies/cell of the MIT 25-26x.91 259 H>Q meganuclease. The 0% mutant cells were untreated. The height of the bars is indicative of mtDNA, loss, normalized to the mutant mtDNA cells. Within the bar, the relative percentage of gray corresponds to the relative percentage of wildtype mtDNA, present, and the relative percentage of black corresponds to the relative percentage of mutant mtDNA present.

As shown in FIG. 52, the high dose used of the mitochondria-targeting engineered meganuclease (MTEM) resulted in a transient mtDNA depletion relative to the untreated controls. The MTEM-treated cells only contained 27% of the total mtDNA present in the untreated 96% mutant cells. The observed mtDNA depletion corresponded to the selective cleavage of mutant mtDNA. At day 1, 44% of the mtDNA present in the MTEM-treated cells was mutant, as opposed to 92.8% in the untreated cells.

Figure 53:
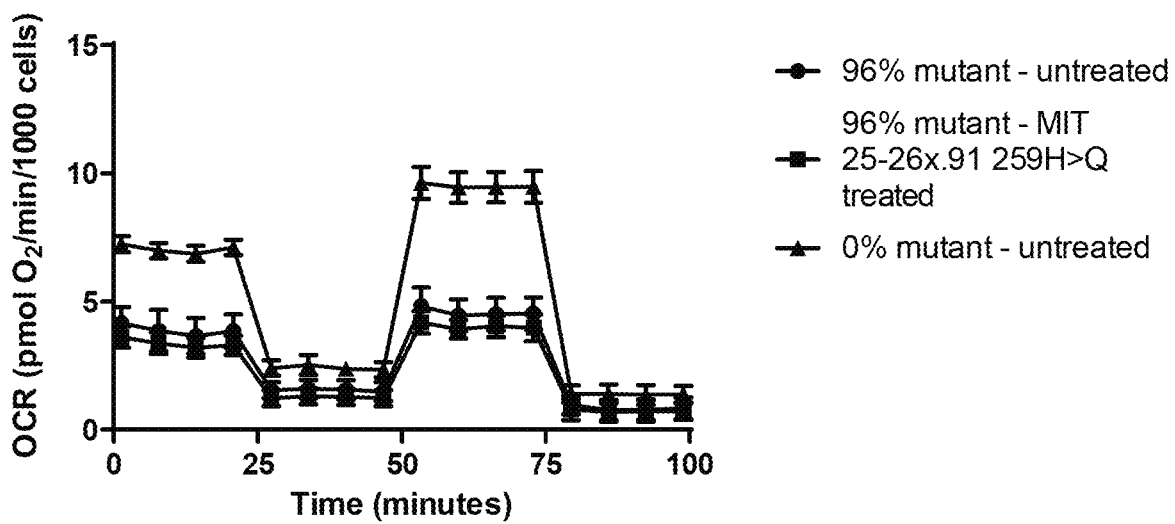
FIG. 53 is a graph showing the mitochondrial stress test of WT or MELAS cybrid cells 1 days post-transfection with the mitochondria-targeting engineered meganuclease (MTEM) MIT 25-26x.91 259H>Q.

In the Cell Mito Stress Test at day 1, the untreated 0% mutant (WT) cells exhibited high levels of basal respiration (7.5 pmol $O_2$/min/1,000 cells) and maximal respiration (10.0 pmol $O_2$/min/1,000 cells). The untreated 96% mutant cells exhibited much lower levels of respiration—4.2 pmol $O_2$/min/1,000 cells for basal respiration and 4.8 pmol $O_2$/min/1,000 cells for maximal respiration. The MTEM-treated cells have similar levels of respiration to the untreated 96% mutant cells (3.9 pmol $O_2$/min/1,000 cells for basal respiration and 4.4 pmol $O_2$/min/1,000 cells for maximal respiration), indicating that despite the reliance of these cells on OXPHOS for ATP generation and the mtDNA depletion present at this time, cellular respiration was not negatively impacted (FIG. 53).

The invention claimed is:

1. A mitochondria-targeting engineered meganuclease (MTEM) that binds and cleaves a recognition sequence consisting of SEQ ID NO: 1 in mitochondrial genomes of a eukaryotic cell, wherein said MTEM comprises an engineered meganuclease attached to a mitochondrial transit peptide (MTP), and wherein said engineered meganuclease comprises the amino acid sequence of SEQ ID NO: 9.

2. The MTEM of claim 1, wherein said MTP comprises the amino acid sequence of SEQ ID NO: 45, and wherein said MTP is attached at the N-terminus of said engineered meganuclease.

3. The MTEM of claim 2, wherein said MTEM is attached to an NES comprising the amino acid sequence of SEQ ID NO: 46, wherein said NES is attached at the C-terminus of said MTEM.

4. The MTEM of claim 1, wherein said MTEM is attached to a nuclear export sequence (NES) comprising the amino acid sequence of SEQ ID NO: 46, wherein said NES is attached at the C-terminus of said MTEM.

5. A polynucleotide comprising a nucleic acid sequence encoding an MTEM, wherein said MTEM binds and cleaves a recognition sequence consisting of SEQ ID NO: 1 in mitochondrial genomes of a eukaryotic cell, wherein said MTEM comprises an engineered meganuclease attached to an MTP, and wherein said engineered meganuclease comprises the amino acid sequence of SEQ ID NO: 9.

6. The polynucleotide of claim 5, wherein said MTP comprises the amino acid sequence of SEQ ID NO: 45, and wherein said MTP is attached at the N-terminus of said engineered meganuclease.

7. The polynucleotide of claim 6, wherein said MTEM is attached to an NES comprising the amino acid sequence of SEQ ID NO: 46, wherein said NES is attached at the C-terminus of said MTEM.

8. The polynucleotide of claim 5, wherein said MTEM is attached to an NES comprising the amino acid sequence of SEQ ID NO: 46, wherein said NES is attached at the C-terminus of said MTEM.

9. A recombinant adeno-associated virus (AAV) comprising a polynucleotide comprising a nucleic acid sequence encoding an MTEM, wherein said MTEM binds and cleaves a recognition sequence consisting of SEQ ID NO: 1 in mitochondrial genomes of a eukaryotic cell, wherein said MTEM comprises an engineered meganuclease attached to an MTP, wherein said engineered meganuclease comprises the amino acid sequence of SEQ ID NO: 9, and wherein said polynucleotide comprises a promoter operably linked to said nucleic acid sequence encoding said MTEM.

10. The recombinant AAV of claim 9, wherein said MTP comprises the amino acid sequence of SEQ ID NO: 45, and wherein said MTP is attached at the N-terminus of said engineered meganuclease.

11. The recombinant AAV of claim 10, wherein said MTEM is attached to an NES comprising the amino acid sequence of SEQ ID NO: 46, wherein said NES is attached at the C-terminus of said MTEM.

12. The recombinant AAV of claim 11, wherein said promoter is a CAG promoter.

13. The recombinant AAV of claim 10, wherein said recombinant AAV has an AAV9 capsid.

14. The recombinant AAV of claim 13, wherein said promoter is a CAG promoter.

15. The recombinant AAV of claim 10, wherein said promoter is a CAG promoter.

16. The recombinant AAV of claim 9, wherein said MTEM is attached to an NES comprising the amino acid sequence of SEQ ID NO: 46, wherein said NES is attached at the C-terminus of said MTEM.

17. The recombinant AAV of claim 16, wherein said recombinant AAV has an AAV9 capsid.

18. The recombinant AAV of claim 17, wherein said promoter is a CAG promoter.

19. The recombinant AAV of claim 16, wherein said promoter is a CAG promoter.

20. The recombinant AAV of claim 9, wherein said recombinant AAV has an AAV9 capsid.

21. The recombinant AAV of claim 11, wherein said recombinant AAV has an AAV9 capsid.

22. The recombinant AAV of claim 21, wherein said promoter is a CAG promoter.

23. The recombinant AAV of claim 20, wherein said promoter is a CAG promoter.

24. The recombinant AAV of claim 9, wherein said promoter is a CAG promoter.

\* \* \* \* \*

SEQUENCE LISTING

```
Sequence total quantity: 72
SEQ ID NO: 1                   moltype = DNA   length = 22
FEATURE                        Location/Qualifiers
source                         1..22
                               mol_type = genomic DNA
                               organism = Homo sapiens
SEQUENCE: 1
cagggcccgg taatcgcata aa                                            22

SEQ ID NO: 2                   moltype = DNA   length = 22
FEATURE                        Location/Qualifiers
source                         1..22
                               mol_type = genomic DNA
                               organism = Homo sapiens
SEQUENCE: 2
gtcccgggcc attagcgtat tt                                            22

SEQ ID NO: 3                   moltype = AA   length = 354
FEATURE                        Location/Qualifiers
REGION                         1..354
                               note = Synthesized
source                         1..354
                               mol_type = protein
                               organism = synthetic construct
SEQUENCE: 3
MNTKYNKEFL LYLAGFVDSD GSIFARIEPT QSAKFKHKLR LTFRVHQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVHD HGTISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 4                   moltype = AA   length = 354
FEATURE                        Location/Qualifiers
REGION                         1..354
                               note = Synthesized
source                         1..354
                               mol_type = protein
                               organism = synthetic construct
SEQUENCE: 4
MNTKYNKEFL LYLAGFVDAD GSIFARIEPT QSAKFKHKLR LTFRVHQKTQ RRWFLDKLVD    60
EIGVGYVYDT GSVSDYTLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVND FGSISQYRLS EIKPLYNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 5                   moltype = AA   length = 354
FEATURE                        Location/Qualifiers
REGION                         1..354
                               note = Synthesized
source                         1..354
                               mol_type = protein
                               organism = synthetic construct
SEQUENCE: 5
MNTKYNKEFL LYLAGFVDAD GSIFARIEPT QSAKFKHKLR LTFRVHQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVHD FGLISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 6                   moltype = AA   length = 354
FEATURE                        Location/Qualifiers
REGION                         1..354
                               note = Synthesized
source                         1..354
                               mol_type = protein
                               organism = synthetic construct
SEQUENCE: 6
MNTKYNKEFL LYLAGFVDAD GSIFARIEPT QSAKFKHKLR LTFRVHQKTQ RRWFLDKLVD    60
EIGVGYVYDT GSVSDYTLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEAPRAGA GSGTGYNKEF LLYLAGFVDG DGSIYACILP NQGSKFKHAL QLFFTVGQKT   240
CRRWFLDKLV DEIGVGYVHD HGLIAQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 7                   moltype = AA   length = 354
```

```
FEATURE                 Location/Qualifiers
REGION                  1..354
                        note = Synthesized
source                  1..354
                        mol_type = protein
                        organism = synthetic construct
SEQUENCE: 7
MNTKYNKEFL LYLAGFVDAD GSIFARIEPT QSAKFKHKLR LTFRVHQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVND FGPVSQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 8            moltype = AA  length = 354
FEATURE                 Location/Qualifiers
REGION                  1..354
                        note = Synthesized
source                  1..354
                        mol_type = protein
                        organism = synthetic construct
SEQUENCE: 8
MNTKYNKEFL LYLAGFVDAD GSIFARIEPT QSAKFKHKLR LTFRVWQKTQ RRWFLDKLVD    60
EIGVGYVYDE GSVSSYTLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVQD HGRISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 9            moltype = AA  length = 354
FEATURE                 Location/Qualifiers
REGION                  1..354
                        note = Synthesized
source                  1..354
                        mol_type = protein
                        organism = synthetic construct
SEQUENCE: 9
MNTKYNKEFL LYLAGFVDSD GSIFARIEPT QSAKFKHKLR LTFRVHQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVQD HGTISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 10           moltype = AA  length = 354
FEATURE                 Location/Qualifiers
REGION                  1..354
                        note = Synthesized
source                  1..354
                        mol_type = protein
                        organism = synthetic construct
SEQUENCE: 10
MNTKYNKEFL LYLAGFVDSD GSIFARIEPT QSAKFKHKLR LTFRVWQKTQ RRWFLDKLVD    60
EIGVGYVYDE GSVSSYTLSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVQD HGRISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 11           moltype = AA  length = 354
FEATURE                 Location/Qualifiers
REGION                  1..354
                        note = Synthesized
source                  1..354
                        mol_type = protein
                        organism = synthetic construct
SEQUENCE: 11
MNTKYNKEFL LYLAGFVDSD GSIFARIEPT QSAKFKHKLR LTFRVHQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVHD HGRISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 12           moltype = AA  length = 354
FEATURE                 Location/Qualifiers
REGION                  1..354
                        note = Synthesized
source                  1..354
```

```
                        mol_type = protein
                        organism = synthetic construct
SEQUENCE: 12
MNTKYNKEFL LYLAGFVDSD GSIFARIEPT QSAKFKHKLR LTFRVWQKTQ RRWFLDKLVD    60
EIGVGYVYDT GSVSDYTLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIYACILP NQGSKFKHAL QLFFTVGQKT   240
CRRWFLDKLV DEIGVGYVHD HGTISQYRLS EIKPLHNFLT QLQPFLKLKQ KQANLVLKII   300
EQLPSAKESP DKFLEVCTWV DQIAALNDSR TRKTTSETVR AVLDSLSEKK KSSP         354

SEQ ID NO: 13           moltype = AA   length = 147
FEATURE                 Location/Qualifiers
REGION                  1..147
                        note = Synthesized
source                  1..147
                        mol_type = protein
                        organism = synthetic construct
SEQUENCE: 13
KEFLLYLAGF VDSDGSIFAR IEPTQSAKFK HKLRLTFRVH QKTQRRWFLD KLVDEIGVGY    60
VYDTGSVSDY TLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 14           moltype = AA   length = 147
FEATURE                 Location/Qualifiers
REGION                  1..147
                        note = Synthesized
source                  1..147
                        mol_type = protein
                        organism = synthetic construct
SEQUENCE: 14
KEFLLYLAGF VDADGSIFAR IEPTQSAKFK HKLRLTFRVH QKTQRRWFLD KLVDEIGVGY    60
VYDTGSVSDY TLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 15           moltype = AA   length = 147
FEATURE                 Location/Qualifiers
REGION                  1..147
                        note = Synthesized
source                  1..147
                        mol_type = protein
                        organism = synthetic construct
SEQUENCE: 15
KEFLLYLAGF VDADGSIFAR IEPTQSAKFK HKLRLTFRVH QKTQRRWFLD KLVDEIGVGY    60
VYDTGSVSDY TLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 16           moltype = AA   length = 147
FEATURE                 Location/Qualifiers
REGION                  1..147
                        note = Synthesized
source                  1..147
                        mol_type = protein
                        organism = synthetic construct
SEQUENCE: 16
KEFLLYLAGF VDADGSIFAR IEPTQSAKFK HKLRLTFRVH QKTQRRWFLD KLVDEIGVGY    60
VYDTGSVSDY TLSEIKPLHN FLTQLQPFLK LKQKQANLVL KIIEQLPSAK ESPDKFLEVC   120
TWVDQIAALN DSKTRKTTSE TVRAVLD                                      147

SEQ ID NO: 17           moltype = AA   length = 147
FEATURE                 Location/Qualifiers
REGION                  1..147
                        note = Synthesized
source                  1..147
                        mol_type = protein
                        organism = synthetic construct
SEQUENCE: 17
KEFLLYLAGF VDADGSIFAR IEPTQSAKFK HKLRLTFRVH QKTQRRWFLD KLVDEIGVGY    60
VYDTGSVSDY TLSQIKPLHN FLTQLQPFLK LKQKQANLVL KIIEQLPSAK ESPDKFLEVC   120
TWVDQIAALN DSKTRKTTSE TVRAVLD                                      147

SEQ ID NO: 18           moltype = AA   length = 147
FEATURE                 Location/Qualifiers
REGION                  1..147
                        note = Synthesized
source                  1..147
                        mol_type = protein
                        organism = synthetic construct
SEQUENCE: 18
KEFLLYLAGF VDADGSIFAR IEPTQSAKFK HKLRLTFRVW QKTQRRWFLD KLVDEIGVGY    60
```

```
VYDEGSVSSY TLSEIKPLHN FLTQLQPFLK LKQKQANLVL KIIEQLPSAK ESPDKFLEVC    120
TWVDQIAALN DSKTRKTTSE TVRAVLD                                       147

SEQ ID NO: 19               moltype = AA  length = 147
FEATURE                     Location/Qualifiers
REGION                      1..147
                            note = Synthesized
source                      1..147
                            mol_type = protein
                            organism = synthetic construct
SEQUENCE: 19
KEFLLYLAGF VDSDGSIFAR IEPTQSAKFK HKLRLTFRVH QKTQRRWFLD KLVDEIGVGY     60
VYDTGSVSDY TLSQIKPLHN FLTQLQPFLK LKQKQANLVL KIIEQLPSAK ESPDKFLEVC    120
TWVDQIAALN DSKTRKTTSE TVRAVLD                                       147

SEQ ID NO: 20               moltype = AA  length = 147
FEATURE                     Location/Qualifiers
REGION                      1..147
                            note = Synthesized
source                      1..147
                            mol_type = protein
                            organism = synthetic construct
SEQUENCE: 20
KEFLLYLAGF VDSDGSIFAR IEPTQSAKFK HKLRLTFRVW QKTQRRWFLD KLVDEIGVGY     60
VYDEGSVSSY TLSEIKPLHN FLTQLQPFLK LKQKQANLVL KIIEQLPSAK ESPDKFLEVC    120
TWVDQIAALN DSKTRKTTSE TVRAVLD                                       147

SEQ ID NO: 21               moltype = AA  length = 147
FEATURE                     Location/Qualifiers
REGION                      1..147
                            note = Synthesized
source                      1..147
                            mol_type = protein
                            organism = synthetic construct
SEQUENCE: 21
KEFLLYLAGF VDSDGSIFAR IEPTQSAKFK HKLRLTFRVH QKTQRRWFLD KLVDEIGVGY     60
VYDTGSVSDY TLSQIKPLHN FLTQLQPFLK LKQKQANLVL KIIEQLPSAK ESPDKFLEVC    120
TWVDQIAALN DSKTRKTTSE TVRAVLD                                       147

SEQ ID NO: 22               moltype = AA  length = 147
FEATURE                     Location/Qualifiers
REGION                      1..147
                            note = Synthesized
source                      1..147
                            mol_type = protein
                            organism = synthetic construct
SEQUENCE: 22
KEFLLYLAGF VDSDGSIFAR IEPTQSAKFK HKLRLTFRVW QKTQRRWFLD KLVDEIGVGY     60
VYDTGSVSDY TLSQIKPLHN FLTQLQPFLK LKQKQANLVL KIIEQLPSAK ESPDKFLEVC    120
TWVDQIAALN DSKTRKTTSE TVRAVLD                                       147

SEQ ID NO: 23               moltype = AA  length = 147
FEATURE                     Location/Qualifiers
REGION                      1..147
                            note = Synthesized
source                      1..147
                            mol_type = protein
                            organism = synthetic construct
SEQUENCE: 23
KEFLLYLAGF VDGDGSIYAC ILPNQGSKFK HALQLFFTVG QKTCRRWFLD KLVDEIGVGY     60
VHDHGTISQY RLSEIKPLHN FLTQLQPFLK LKQKQANLVL KIIEQLPSAK ESPDKFLEVC    120
TWVDQIAALN DSRTRKTTSE TVRAVLD                                       147

SEQ ID NO: 24               moltype = AA  length = 147
FEATURE                     Location/Qualifiers
REGION                      1..147
                            note = Synthesized
source                      1..147
                            mol_type = protein
                            organism = synthetic construct
SEQUENCE: 24
KEFLLYLAGF VDGDGSIYAC ILPNQGSKFK HALQLFFTVG QKTCRRWFLD KLVDEIGVGY     60
VNDFGSISQY RLSEIKPLYN FLTQLQPFLK LKQKQANLVL KIIEQLPSAK ESPDKFLEVC    120
TWVDQIAALN DSRTRKTTSE TVRAVLD                                       147

SEQ ID NO: 25               moltype = AA  length = 147
FEATURE                     Location/Qualifiers
REGION                      1..147
                            note = Synthesized
```

```
                        source          1..147
                                        mol_type = protein
                                        organism = synthetic construct
SEQUENCE: 25
KEFLLYLAGF VDGDGSIYAC ILPNQGSKFK HALQLFFTVG QKTCRRWFLD KLVDEIGVGY    60
VHDFGLISQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 26           moltype = AA   length = 147
FEATURE                 Location/Qualifiers
REGION                  1..147
                        note = Synthesized
source                  1..147
                        mol_type = protein
                        organism = synthetic construct
SEQUENCE: 26
KEFLLYLAGF VDGDGSIYAC ILPNQGSKFK HALQLFFTVG QKTCRRWFLD KLVDEIGVGY    60
VHDHGLIAQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 27           moltype = AA   length = 147
FEATURE                 Location/Qualifiers
REGION                  1..147
                        note = Synthesized
source                  1..147
                        mol_type = protein
                        organism = synthetic construct
SEQUENCE: 27
KEFLLYLAGF VDGDGSIYAC ILPNQGSKFK HALQLFFTVG QKTCRRWFLD KLVDEIGVGY    60
VNDFGPVSQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 28           moltype = AA   length = 147
FEATURE                 Location/Qualifiers
REGION                  1..147
                        note = Synthesized
source                  1..147
                        mol_type = protein
                        organism = synthetic construct
SEQUENCE: 28
KEFLLYLAGF VDGDGSIYAC ILPNQGSKFK HALQLFFTVG QKTCRRWFLD KLVDEIGVGY    60
VQDHGRISQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 29           moltype = AA   length = 147
FEATURE                 Location/Qualifiers
REGION                  1..147
                        note = Synthesized
source                  1..147
                        mol_type = protein
                        organism = synthetic construct
SEQUENCE: 29
KEFLLYLAGF VDGDGSIYAC ILPNQGSKFK HALQLFFTVG QKTCRRWFLD KLVDEIGVGY    60
VQDHGTISQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 30           moltype = AA   length = 147
FEATURE                 Location/Qualifiers
REGION                  1..147
                        note = Synthesized
source                  1..147
                        mol_type = protein
                        organism = synthetic construct
SEQUENCE: 30
KEFLLYLAGF VDGDGSIYAC ILPNQGSKFK HALQLFFTVG QKTCRRWFLD KLVDEIGVGY    60
VQDHGRISQY RLSEIKPLHN FLTQLQPFLK LKQKQANLVL KIIEQLPSAK ESPDKFLEVC   120
TWVDQIAALN DSRTRKTTSE TVRAVLD                                       147

SEQ ID NO: 31           moltype = AA   length = 147
FEATURE                 Location/Qualifiers
REGION                  1..147
                        note = Synthesized
source                  1..147
                        mol_type = protein
                        organism = synthetic construct
SEQUENCE: 31
KEFLLYLAGF VDGDGSIYAC ILPNQGSKFK HALQLFFTVG QKTCRRWFLD KLVDEIGVGY    60
VHDHGRISQY RLSEIKPLHN FLTQLQPFLK LKQKQANLVL KIIEQLPSAK ESPDKFLEVC   120
TWVDQIAALN DSRTRKTTSE TVRAVLD                                       147
```

```
SEQ ID NO: 32            moltype = AA   length = 147
FEATURE                  Location/Qualifiers
REGION                   1..147
                         note = Synthesized
source                   1..147
                         mol_type = protein
                         organism = synthetic construct
SEQUENCE: 32
KEFLLYLAGF VDGDGSIYAC ILPNQGSKFK HALQLFFTVG QKTCRRWFLD KLVDEIGVGY   60
VHDHGTISQY RLSEIKPLHN FLTQLQPFLK LKQKQANLVL KIIEQLPSAK ESPDKFLEVC  120
TWVDQIAALN DSRTRKTTSE TVRAVLD                                     147

SEQ ID NO: 33            moltype = DNA   length = 1062
FEATURE                  Location/Qualifiers
misc_feature             1..1062
                         note = Synthesized
source                   1..1062
                         mol_type = other DNA
                         organism = synthetic construct
SEQUENCE: 33
atgaatacaa aatataataa agagttctta ctctacttag cagggtttgt agactctgac    60
ggttccatct ttgcccgtat cgagcctact caaagtgcta agttcaagca caagctgagg  120
ctcacgttcc gggtccatca gaagacacag cgccgttggt tcctcgacaa gctggtggac  180
gagatcggtg tgggttacgt gtatgacact ggcagcgtct ccgattacac tctgtcccag  240
atcaagcctt tgcataattt tttaaacaca ctacaacctt ttctaaaact aaaacaaaaa  300
caagcaaatt tagttttaaa aattattgaa caacttccg cagcaaaaga tccccggac   360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctatgcctg tatccttcct  660
aatcaaggga gtaagttcaa gcacgctctg cagctctttt tcacggtcgg ccagaagaca  720
tgccgccgtt ggttcctcga caagctggtg gacgagatcg gtgtgggtta cgtgcacgac  780
cacggcacta tctcgcagta ccgcctgtcc gagatcaagc ctctgcacaa cttcctgacc  840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                    1062

SEQ ID NO: 34            moltype = DNA   length = 1062
FEATURE                  Location/Qualifiers
misc_feature             1..1062
                         note = Synthesized
source                   1..1062
                         mol_type = other DNA
                         organism = synthetic construct
SEQUENCE: 34
atgaatacaa aatataataa agagttctta ctctacttag cagggtttgt agacgctgac    60
ggttccatct ttgcccgtat cgagcctact caaagtgcta agttcaagca caagctgagg  120
ctcacgttcc gggtccatca gaagacacag cgccgttggt tcctcgacaa gctggtggac  180
gagatcggtg tgggttacgt gtatgacact ggcagcgtct ccgattacac tctgtccag   240
atcaagcctt tgcataattt tttaaacaca ctacaaacct ttctaaaact aaaacaaaaa  300
caagcaaatt tagttttaaa aattattgaa caacttccgt cagcaaaaga tccccggac   360
aaattcttag aagtttgtac atgggtggat caaattgcag ctctgaatga ttcgaagacg  420
cgtaaaacaa cttctgaaac cgttcgtgct gtgctagaca gtttaccagg atccgtggga  480
ggtctatcgc catctcaggc atccagcgcc gcatcctcgg cttcctcaag cccgggttca  540
gggatctccg aagcactcag agctggagca ggttccggca ctggatacaa caaggaattc  600
ctgctctacc tggcgggctt cgtcgacggg gacggctcca tctatgcctg tatccttcct  660
aatcaaggga gtaagttcaa gcacgctctg cagctctttt tcacggtcgg ccagaagaca  720
tgccgccgtt ggttcctcga caagctggtg gacgagatcg gtgtgggtta cgtgaacgac  780
ttcgctcta tctcgcagta ccgcctgtcc gagatcaagc tctgtacaa cttcctgacc    840
cagctccagc ccttcctgaa gctcaagcag aagcaggcca acctcgtgct gaagatcatc  900
gagcagctgc cctccgccaa ggaatccccg gacaagttcc tggaggtgtg cacctgggtg  960
gaccagatcg ccgctctgaa cgactccagg acccgcaaga ccacttccga aaccgtccgc 1020
gccgttctag acagtctctc cgagaagaag aagtcgtccc cc                    1062

SEQ ID NO: 35            moltype = DNA   length = 1062
FEATURE                  Location/Qualifiers
misc_feature             1..1062
                         note = Synthesized
source                   1..1062
                         mol_type = other DNA
                         organism = synthetic construct
SEQUENCE: 35
atgaatacaa aatataataa agagttctta ctctacttag cagggtttgt agacgctgac    60
ggttccatct ttgcccgtat cgagcctact caaagtgcta agttcaagca caagctgagg  120
ctcacgttcc gggtccatca gaagacacag cgccgttggt tcctcgacaa gctggtggac  180
gagatcggtg tgggttacgt gtatgacact ggcagcgtct ccgattacac tctgtccag   240
```

```
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgcctg tatccttcct   660
aatcaaggga gtaagttcaa gcacgctctg cagctctttt tcacggtcgg ccagaagaca   720
tgccgccgtt ggttcctcga caagctggtg gacgagatcg gtgtgggtta cgtgcacgac   780
ttcggcctga tctcgcagta ccgcctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                    1062

SEQ ID NO: 36          moltype = DNA   length = 1062
FEATURE                Location/Qualifiers
misc_feature           1..1062
                       note = Synthesized
source                 1..1062
                       mol_type = other DNA
                       organism = synthetic construct
SEQUENCE: 36
atgaatacaa aatataataa agagttctta ctctacttag cagggtttgt agacgctgac    60
ggttccatct ttgcccgtat cgagcctact caaagtgcta agttcaagca caagctgagg   120
ctcacgttcc gggtccatca gaagacacag cgccgttggt tcctcgacaa gctggtggac   180
gagatcggtg tgggttacgt gtatgacact ggcagcgtct ccgattacac tctgtccgga   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcacccag agctggagca ggttccggca ctggatacaa caaggaattc   600
ctgctctacc tggcgggctt cgtcgacggg gacggctcca tctatgcctg tatccttcct   660
aatcaaggga gtaagttcaa gcacgctctg cagctctttt tcacggtcgg ccagaagaca   720
tgccgccgtt ggttcctcga caagctggtg gacgagatcg gtgtgggtta cgtgcacgac   780
cacggcctta tcgcgcagta ccgcctgtcc gagatcaagc tctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                    1062

SEQ ID NO: 37          moltype = DNA   length = 1062
FEATURE                Location/Qualifiers
misc_feature           1..1062
                       note = Synthesized
source                 1..1062
                       mol_type = other DNA
                       organism = synthetic construct
SEQUENCE: 37
atgaatacaa aatataataa agagttctta ctctacttag cagggtttgt agacgctgac    60
ggttccatct ttgcccgtat cgagcctact caaagtgcta agttcaagca caagctgagg   120
ctcacgttcc gggtccatca gaagacacag cgccgttggt tcctcgacaa gctggtggac   180
gagatcggtg tgggttacgt gtatgacact ggcagcgtct ccgattacac tctgtccgga   240
atcaagcctt tgcataattt tttaacacaa ctacaacctt ttctaaaact aaaacaaaaa   300
caagcaaatt tagttttaaa aattattgaa caacttccgt cagcaaaaga atccccggac   360
aaattcttag aagtttgtac atgggtggat caaattgcag ctctgaatga ttcgaagacg   420
cgtaaaacaa cttctgaaac tgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgcctg tatccttcct   660
aatcaaggga gtaagttcaa gcacgctctg cagctctttt tcacggtcgg ccagaagaca   720
tgccgccgtt ggttcctcga caagctggtg gacgagatcg gtgtgggtta cgtgaacgac   780
ttcggcctg tctcgcagta ccgcctgtcc gagatcaagc tctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                    1062

SEQ ID NO: 38          moltype = DNA   length = 1062
FEATURE                Location/Qualifiers
misc_feature           1..1062
                       note = Synthesized
source                 1..1062
                       mol_type = other DNA
                       organism = synthetic construct
SEQUENCE: 38
atgaatacaa aatataataa agagttctta ctctacttag cagggtttgt agacgctgac    60
ggttccatct ttgcccgtat cgagcctact caaagtgcta agttcaagca caagctgagg   120
```

```
ctcacgttcc gggtctggca gaagacacag cgccgttggt tcctcgacaa gctggtggac    180
gagatcggtg tgggttacgt gtatgacgag ggcagcgtct cctcttacac tctgtccgag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctatgcctg tatccttcct    660
aatcaaggga gtaagttcaa gcacgctctg cagctattct tcacggtcgg ccagaagaca    720
tgccgccgtt ggttcctcga caagctggtg gacgagatcg gtgtgggtta cgtgcaggac    780
cacggcagga tctcgcagta ccgcctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc    1062

SEQ ID NO: 39          moltype = DNA  length = 1062
FEATURE                Location/Qualifiers
misc_feature           1..1062
                       note = Synthesized
source                 1..1062
                       mol_type = other DNA
                       organism = synthetic construct
SEQUENCE: 39
atgaatacaa aatataataa agagttctta ctctacttag cagggtttgt agactctgac    60
ggttccatct ttgcccgtat cgagcctact caaagtgcta agttcaagca caagctgagg    120
ctcacgttcc gggtccatca gaagacacag cgccgttggt tcctcgacaa gctggtggac    180
gagatcggtg tgggttacgt gtatgacact ggcagcgtct ccgattacac tctgtcccag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctatgcctg tatccttcct    660
aatcaaggga gtaagttcaa gcacgctctg cagctcttt tcacggtcgg ccagaagaca    720
tgccgccgtt ggttcctcga caagctggtg gacgagatcg gtgtgggtta cgtgcaggac    780
cacggcacta tctcgcagta ccgcctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc    1062

SEQ ID NO: 40          moltype = DNA  length = 1062
FEATURE                Location/Qualifiers
misc_feature           1..1062
                       note = Synthesized
source                 1..1062
                       mol_type = other DNA
                       organism = synthetic construct
SEQUENCE: 40
atgaatacaa aatataataa agagttctta ctctacttag cagggtttgt agactctgac    60
ggttccatct ttgcccgtat cgagcctact caaagtgcta agttcaagca caagctgagg    120
ctcacgttcc gggtctggca gaagacacag cgccgttggt tcctcgacaa gctggtggac    180
gagatcggtg tgggttacgt gtatgacgag ggcagcgtct cctcttacac tctgtccgag    240
atcaagcctt tgcataattt tttaacacaa ctacaacctt ttctaaaact aaaacaaaaa    300
caagcaaatt tagtttttaaa aattattgaa caacttccgt cagcaaaaga atccccggac    360
aaattcttag aagtttgtac atgggtggat caaattgcag ctctgaatga ttcgaagacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctatgcctg tatccttcct    660
aatcaaggga gtaagttcaa gcacgctctg cagctattct tcacggtcgg ccagaagaca    720
tgccgccgtt ggttcctcga caagctggtg gacgagatcg gtgtgggtta cgtgcaggac    780
cacggcagga tctcgcagta ccgcctgtcc gagatcaagc tctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccagg acccgcaaga ccacttccga aaccgtccgc    1020
gccgttctag acagtctctc cgagaagaag aagtcgtccc cc    1062

SEQ ID NO: 41          moltype = DNA  length = 1062
FEATURE                Location/Qualifiers
misc_feature           1..1062
                       note = Synthesized
source                 1..1062
                       mol_type = other DNA
                       organism = synthetic construct
SEQUENCE: 41
```

```
atgaatacaa aatataataa agagttctta ctctacttag cagggtttgt agactctgac    60
ggttccatct ttgcccgtat cgagcctact caaagtgcta agttcaagca caagctgagg   120
ctcacgttcc gggtccatca gaagacacag cgccgttggt tcctcgacaa gctggtggac   180
gagatcggtg tgggttacgt gtatgacact ggcagcgtct ccgattacac tctgtcccag   240
atcaagcctt tgcataattt tttaacacaa ctacaacctt ttctaaaact aaaacaaaaa   300
caagcaaatt tagtttttaaa aattattgaa caacttccgt cagcaaaaga tccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgcctg tatccttcct   660
aatcaaggga gtaagttcaa gcacgctctg cagctctttt tcacggtcgg ccagaagaca   720
tgccgccgtt ggttcctcga caagctggtg acgagatcg gtgtgggtta cgtgcacgac   780
cacggcagga tctcgcagta ccgcctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 42             moltype = DNA  length = 1062
FEATURE                   Location/Qualifiers
misc_feature              1..1062
                          note = Synthesized
source                    1..1062
                          mol_type = other DNA
                          organism = synthetic construct
SEQUENCE: 42
atgaatacaa aatataataa agagttctta ctctacttag cagggtttgt agactctgac    60
ggttccatct ttgcccgtat cgagcctact caaagtgcta agttcaagca caagctgagg   120
ctcacgttcc gggtccatgca gaagacacag cgccgttggt tcctcgacaa gctggtggac   180
gagatcggtg tgggttacgt gtatgacact ggcagcgtct ccgattacac tctgtcccag   240
atcaagcctt tgcataattt tttaacacaa ctacaacctt ttctaaaact aaaacaaaaa   300
caagcaaatt tagttttaaa aattattgaa caacttccgt cagcaaaaga tccccggac   360
aaattcttag aagtttgtac atgggtggat caaattgcag ctctgaatga ttcgaagacg   420
cgtaaaacaa cttctgaaac cgttcgtgct gtgctagaca gtttaccagg atccgtggga   480
ggtctatcgc catctcaggc atccagcgcc gcatcctcgg cttcctcaag cccgggttca   540
gggatctccg aagcactcag agctggagca ggttccggca ctggatacaa caaggaattc   600
ctgctctacc tggcgggctt cgtcgacggg gacggctcca tctatgcctg tatccttcct   660
aatcaaggga gtaagttcaa gcacgctctg cagctctttt tcacggtcgg ccagaagaca   720
tgccgccgtt ggttcctcga caagctggtg acgagatcg gtgtgggtta cgtgcacgac   780
cacggcacta tctcgcagta ccgcctgtcc gagatcaagc ctctgcacaa cttcctgacc   840
cagctccagc ccttcctgaa gctcaagcag aagcaggcca acctcgtgct gaagatcatc   900
gagcagctgc cctccgccaa ggaatccccg gacaagttcc tggaggtgtg cacctgggtg   960
gaccagatcg ccgctctgaa cgactccagg acccgcaaga ccacttccga aaccgtccgc  1020
gccgttctag acagtctctc cgagaagaag aagtcgtccc cc                     1062

SEQ ID NO: 43             moltype = AA  length = 35
FEATURE                   Location/Qualifiers
source                    1..35
                          mol_type = protein
                          organism = Homo sapiens
SEQUENCE: 43
MSVLTPLLLR GLTGSARRLP VPRAKIHSLP PEGKL                                35

SEQ ID NO: 44             moltype = AA  length = 63
FEATURE                   Location/Qualifiers
source                    1..63
                          mol_type = protein
                          organism = Neurospora crassa
SEQUENCE: 44
MASTRVLASR LASQMAASAK VARPAVRVAQ VSKRTIQTGS PLQTLKRTQM TSIVNATTRQ    60
AFQ                                                                   63

SEQ ID NO: 45             moltype = AA  length = 98
FEATURE                   Location/Qualifiers
REGION                    1..98
                          note = Synthesized
source                    1..98
                          mol_type = protein
                          organism = synthetic construct
SEQUENCE: 45
MSVLTPLLLR GLTGSARRLP VPRAKIHSLP PEGKLMASTR VLASRLASQM AASAKVARPA    60
VRVAQVSKRT IQTGSPLQTL KRTQMTSIVN ATTRQAFQ                             98

SEQ ID NO: 46             moltype = AA  length = 18
FEATURE                   Location/Qualifiers
source                    1..18
                          mol_type = protein
                          organism = Mouse parovirus NS2
```

```
SEQUENCE: 46
VDEMTKKFGT LTIHDTEK                                                    18

SEQ ID NO: 47           moltype = AA   length = 10
FEATURE                 Location/Qualifiers
REGION                  1..10
                        note = Synthesized
source                  1..10
                        mol_type = protein
                        organism = synthetic construct
SEQUENCE: 47
LGAGLGALGL                                                             10

SEQ ID NO: 48           moltype = AA   length = 163
FEATURE                 Location/Qualifiers
source                  1..163
                        mol_type = protein
                        organism = Chlamydomonas reinhardtii
SEQUENCE: 48
MNTKYNKEFL LYLAGFVDGD GSIIAQIKPN QSYKFKHQLS LAFQVTQKTQ RRWFLDKLVD       60
EIGVGYVRDR GSVSDYILSE IKPLHNFLTQ LQPFLKLKQK QANLVLKIIW RLPSAKESPD      120
KFLEVCTWVD QIAALNDSKT RKTTSETVRA VLDSLSEKKK SSP                        163

SEQ ID NO: 49           moltype = DNA   length = 20
FEATURE                 Location/Qualifiers
misc_feature            1..20
                        note = Synthesized
source                  1..20
                        mol_type = other DNA
                        organism = synthetic construct
SEQUENCE: 49
agccccgggt actccttgtt                                                  20

SEQ ID NO: 50           moltype = DNA   length = 18
FEATURE                 Location/Qualifiers
misc_feature            1..18
                        note = Synthesized
source                  1..18
                        mol_type = other DNA
                        organism = synthetic construct
SEQUENCE: 50
ttccttgcag gaacagag                                                    18

SEQ ID NO: 51           moltype = DNA   length = 17
FEATURE                 Location/Qualifiers
misc_feature            1..17
                        note = Synthesized
source                  1..17
                        mol_type = other DNA
                        organism = synthetic construct
SEQUENCE: 51
ctgcttgacc acccatt                                                     17

SEQ ID NO: 52           moltype = DNA   length = 19
FEATURE                 Location/Qualifiers
misc_feature            1..19
                        note = Synthesized
source                  1..19
                        mol_type = other DNA
                        organism = synthetic construct
SEQUENCE: 52
ccagcaggcc aggtacacc                                                   19

SEQ ID NO: 53           moltype = DNA   length = 16
FEATURE                 Location/Qualifiers
misc_feature            1..16
                        note = Synthesized
source                  1..16
                        mol_type = other DNA
                        organism = synthetic construct
SEQUENCE: 53
accgccaagg atgcac                                                      16

SEQ ID NO: 54           moltype = DNA   length = 16
FEATURE                 Location/Qualifiers
misc_feature            1..16
                        note = Synthesized
source                  1..16
                        mol_type = other DNA
```

```
                              organism = synthetic construct
SEQUENCE: 54
gcgggtggga atggag                                                            16

SEQ ID NO: 55             moltype = DNA   length = 27
FEATURE                   Location/Qualifiers
misc_feature              1..27
                          note = Synthesized
source                    1..27
                          mol_type = other DNA
                          organism = synthetic construct
SEQUENCE: 55
gctggctagc gtttaaactt aagcttg                                                27

SEQ ID NO: 56             moltype = DNA   length = 34
FEATURE                   Location/Qualifiers
misc_feature              1..34
                          note = Synthesized
source                    1..34
                          mol_type = other DNA
                          organism = synthetic construct
SEQUENCE: 56
gggtatgttg ttaagaagag gaattgaacc tctg                                        34

SEQ ID NO: 57             moltype = DNA   length = 31
FEATURE                   Location/Qualifiers
misc_feature              1..31
                          note = Synthesized
source                    1..31
                          mol_type = other DNA
                          organism = synthetic construct
SEQUENCE: 57
tgtgagtgca tataatgaaa tgggatgaca g                                           31

SEQ ID NO: 58             moltype = DNA   length = 29
FEATURE                   Location/Qualifiers
misc_feature              1..29
                          note = Synthesized
source                    1..29
                          mol_type = other DNA
                          organism = synthetic construct
SEQUENCE: 58
cagtccccac ctcttaagtt tcaaatgac                                              29

SEQ ID NO: 59             moltype = DNA   length = 20
FEATURE                   Location/Qualifiers
misc_feature              1..20
                          note = Synthesized
source                    1..20
                          mol_type = other DNA
                          organism = synthetic construct
SEQUENCE: 59
ccgcaagccc cttggtactg                                                        20

SEQ ID NO: 60             moltype = DNA   length = 23
FEATURE                   Location/Qualifiers
misc_feature              1..23
                          note = Synthesized
source                    1..23
                          mol_type = other DNA
                          organism = synthetic construct
SEQUENCE: 60
gtctgcactc aaggaaggag ctc                                                    23

SEQ ID NO: 61             moltype = DNA   length = 32
FEATURE                   Location/Qualifiers
misc_feature              1..32
                          note = Synthesized
source                    1..32
                          mol_type = other DNA
                          organism = synthetic construct
SEQUENCE: 61
gaccttatgc tgaggaaaag ctgtcattct ag                                          32

SEQ ID NO: 62             moltype = DNA   length = 32
FEATURE                   Location/Qualifiers
misc_feature              1..32
                          note = Synthesized
source                    1..32
```

```
                        mol_type = other DNA
                        organism = synthetic construct
SEQUENCE: 62
ggccatttat ttcagagttt agatcgctat gc                                32

SEQ ID NO: 63           moltype = DNA   length = 14
FEATURE                 Location/Qualifiers
misc_feature            1..14
                        note = Synthesized
source                  1..14
                        mol_type = other DNA
                        organism = synthetic construct
SEQUENCE: 63
tggcagggcc cggt                                                    14

SEQ ID NO: 64           moltype = DNA   length = 22
FEATURE                 Location/Qualifiers
misc_feature            1..22
                        note = Synthesized
source                  1..22
                        mol_type = other DNA
                        organism = synthetic construct
SEQUENCE: 64
cccaagaaca gggtttgtta ag                                           22

SEQ ID NO: 65           moltype = DNA   length = 19
FEATURE                 Location/Qualifiers
misc_feature            1..19
                        note = Synthesized
source                  1..19
                        mol_type = other DNA
                        organism = synthetic construct
SEQUENCE: 65
ggaatgccat tgcgattag                                               19

SEQ ID NO: 66           moltype = DNA   length = 26
FEATURE                 Location/Qualifiers
misc_feature            1..26
                        note = Synthesized
source                  1..26
                        mol_type = other DNA
                        organism = synthetic construct
SEQUENCE: 66
agcagttcta ccgtacaacc ctaaca                                       26

SEQ ID NO: 67           moltype = DNA   length = 18
FEATURE                 Location/Qualifiers
misc_feature            1..18
                        note = Synthesized
source                  1..18
                        mol_type = other DNA
                        organism = synthetic construct
SEQUENCE: 67
ggcagttgag gtggatta                                                18

SEQ ID NO: 68           moltype = DNA   length = 20
FEATURE                 Location/Qualifiers
misc_feature            1..20
                        note = Synthesized
source                  1..20
                        mol_type = other DNA
                        organism = synthetic construct
SEQUENCE: 68
ggaatgcggt agtagttagg                                              20

SEQ ID NO: 69           moltype = DNA   length = 24
FEATURE                 Location/Qualifiers
misc_feature            1..24
                        note = Synthesized
source                  1..24
                        mol_type = other DNA
                        organism = synthetic construct
SEQUENCE: 69
aaccagacaa atcgctccac caac                                         24

SEQ ID NO: 70           moltype = DNA   length = 19
FEATURE                 Location/Qualifiers
misc_feature            1..19
                        note = Synthesized
```

```
source          1..19
                mol_type = other DNA
                organism = synthetic construct
SEQUENCE: 70
cggacaggat tgacagatt                                              19

SEQ ID NO: 71   moltype = DNA  length = 20
FEATURE         Location/Qualifiers
misc_feature    1..20
                note = Synthesized
source          1..20
                mol_type = other DNA
                organism = synthetic construct
SEQUENCE: 71
ccagagtctc gttcgttatc                                             20

SEQ ID NO: 72   moltype = DNA  length = 15
FEATURE         Location/Qualifiers
misc_feature    1..15
                note = Synthesized
source          1..15
                mol_type = other DNA
                organism = synthetic construct
SEQUENCE: 72
accgggctct gccat                                                  15
```